(12) United States Patent
Bleicher et al.

(10) Patent No.: US 8,703,768 B2
(45) Date of Patent: Apr. 22, 2014

(54) NITROGEN CONTAINING HETEROARYL COMPOUNDS

(75) Inventors: Konrad Bleicher, Freiburg (DE);
Alexander Flohr, Loerrach (DE);
Katrin Groebke Zbinden, Liestal (CH);
Felix Gruber, Gelterkinden (CH);
Matthias Koerner, Grenzach-Wyhlen (DE); Bernd Kuhn, Reinach BL (CH);
Jens-Uwe Peters, Grenzach-Wyhlen (DE); Rosa Maria Rodriguez-Sarmiento, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 10 days.

(21) Appl. No.: 13/151,301

(22) Filed: Jun. 2, 2011

(65) Prior Publication Data
US 2011/0306589 A1   Dec. 15, 2011

(30) Foreign Application Priority Data
Jun. 9, 2010   (EP) .................................... 10165427

(51) Int. Cl.
| C07D 239/42 | (2006.01) |
| A01N 43/54 | (2006.01) |
| A61K 31/5355 | (2006.01) |
| C07D 403/14 | (2006.01) |
| A61K 31/497 | (2006.01) |
| A61P 25/18 | (2006.01) |

(52) U.S. Cl.
USPC .................. 514/236.5; 514/256; 514/252.11; 514/255.05; 544/322; 544/122; 544/296; 544/295

(58) Field of Classification Search
USPC .................. 544/322, 122, 296, 295; 514/256, 514/236.5, 252.11, 255.05
See application file for complete search history.

(56) References Cited

U.S. PATENT DOCUMENTS

| 2006/0199828 A1 | 9/2006 | Jaeschke et al. |
| 2006/0199960 A1 | 9/2006 | Jaeschke et al. |

FOREIGN PATENT DOCUMENTS

| WO | 2000/66566 | 11/2000 |
| WO | 02/28847 | 4/2002 |
| WO | WO2005/012485 | 2/2005 |
| WO | 2005/021500 | 3/2005 |
| WO | 2007/061360 | 5/2007 |
| WO | 2008/106692 | 9/2008 |
| WO | 2009/026241 | 2/2009 |
| WO | 2011/089132 | 7/2011 |

OTHER PUBLICATIONS

Fujishige et al., "J. Biol. Chem." 274:18438-18445 (1999).
Conti et al., "Prog. Nucleic Acid Res. Mol. Biol." 63:1-38 (1999).
Siuciak et al., "Neuropharmacology" 51(2):374-385 (2006).
Rodefer et al., "Eur. J. Neuroscience" 2:1070-1076 ( 2005).
Vandenberg et al., "Expert Opinion on Therapeutic Targets" 5(4):507-518 ( 2001).
Loughney et al., "Gene" 234(1):109-117 ( 1999).
Graybiel, A. M., "Curr. Biol." 10:R509-R511 ( 2000).
Siuciak et al., "Neuropharmacology" 51(2):386-396 ( 2006).
Sharma et al., "Psychiatry" 174( SUPPL 28):44-51 ( 1999).
Soderling et al., "Current Opinion Cell Biol." 12:174-179 ( 2000).
Lewis et al., "Neuron" 28:325-333 ( 2000).
Coskran et al., "J. Histochem. Cytochem." 54(11):1205-1213 ( 2006).
Seeger et al., "Brain Research" 985:113-126 ( 2003).
Sano, H., "J. Neurochem." 105:546-556 ( 2008).
Manallack et al., "J. Med. Chem." 48(10):3449-3462 ( 2005).
Soderling et al., "Proc. Natl. Acad. Sci. USA" 96(12):7071-7076 ( 1999).
Fujishige et al., "Eur. J. Biochem." 266(3):1118-1127 ( 1999).
Javitt et al., "Biol. Psychiatry" 45:668-679 ( 1999).
Beavo et al., "Physiol. Review" 75:725-748 ( 1995).
Nakazato et al., "Expert Opinion on Therapeutic Patents" 10(1):75-98 ( 2000).
Mizutani et al., Bioorganic & Medicinal Chemistry Letters 18:6041-6045 ( 2008).
Peng et al., Heterocycles 65(10):2321-2327 ( 2005).
Budesinsky et al., Collection Czech. Chem. Commun. 45(2):539-547 ( 1980).
Neilsen et al., J. Heterocyclic Chem. 24:1621-1628 ( 1987).
Fawcett et al., PNAS 97(7):3702-3707 ( 2000).
Hassaneen et al., Z. Naturforsch 59:1132-1136 ( 2004).
(*European Search Report for PCT/EP2011/059234 Sep. 12, 2011*).
The Columbian Office Action, issued on Oct. 2, 2013, in the corresponding Columbian application No. 12-192.367.

*Primary Examiner* — James O Wilson
*Assistant Examiner* — Cecilia M Jaisle

(57) ABSTRACT

The invention is concerned with novel nitrogen-containing heteroaryl compounds of formula (I)

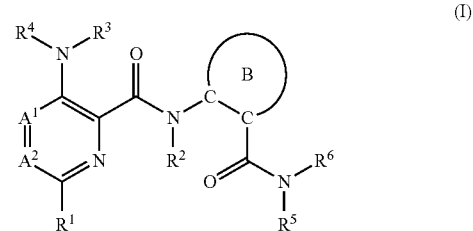

wherein $A^1$, $A^2$,

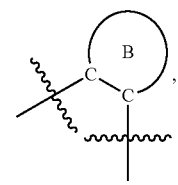

$R^1$, $R^2$, $R^3$, $R^4$, $R^5$ and $R^6$ are as defined in the description and in the claims, as well as physiologically acceptable salts and esters thereof. These compounds inhibit PDE10A and can be used as therapeutics.

55 Claims, No Drawings

NITROGEN CONTAINING HETEROARYL COMPOUNDS

PRIORITY TO RELATED APPLICATION(S)

This application claims the benefit of European Patent Application No. 10165427.5, filed Jun. 9, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron,* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry,* 174(suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry,* 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididymal sperm (Coskran T. M, et al., *J. Histochem. Cytochem.* 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel nitrogen-containing heteroaryl compounds of formula (I)

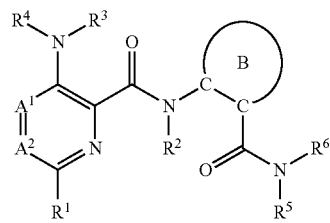

(I)

wherein
$A^1$ is selected from the group consisting of CH and N;
$A^2$ is selected from the group consisting of $CR^{19}$ and N, provided that $A^1$ and $A^2$ are not N simultaneously;

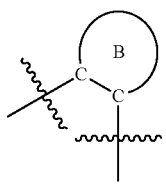

is aryl or heteroaryl, wherein said aryl and said heteroaryl are optionally substituted by 1 to 3 substituents independently selected from the group consisting of lower alkyl, lower alkoxy, lower hydroxyalkyl, lower haloalkyl, lower-alkoxy-lower-alkyl, lower alkyl-C(O)—, —C(O)—N($R^8$)$_2$, —N($R^8$)—C(O)-lower alkyl, cyano, halogen, $R^9$ and amino, and wherein said lower alkyl is optionally substituted by oxo, —C(O)OH, lower alkoxy-C(O)— or $R^7$, and wherein said lower alkoxy is optionally substituted by hydroxyl, lower alkoxy or —C(O)—N($R^8$)$_2$, and wherein said amino is optionally substituted by 1 or 2 substituents independently selected from the group consisting of lower alkyl, lower hydroxyalkyl, lower-alkoxy-lower-alkyl and lower alkyl-C(O)—;

$R^1$ is lower alkyl, lower alkoxy, lower hydroxyalkyl, lower haloalkyl, lower-alkoxy-lower-alkyl, lower alkyl-C(O)—, —O-lower haloalkyl, cyano, halogen, $R^7$ or amino, wherein said lower alkyl is optionally substituted by $R^7$, and wherein said amino is optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is aryl or heteroaryl, wherein said aryl and said heteroaryl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino, and wherein said amino is optionally substituted by 1 or 2 substituents independently selected from the group consisting of lower alkyl and lower-alkoxy-lower-alkyl;

$R^5$ and $R^6$ are independently hydrogen, lower alkyl, lower alkoxy, lower haloalkyl, lower cyanoalkyl, lower hydroxyalkyl, lower-alkoxy-lower-alkyl, cycloalkyl or heterocyclyl, wherein said lower alkyl is optionally substituted by oxo, $R^7$ or —N($R^8$)$_2$, and wherein said lower haloalkyl is optionally substituted by hydroxyl, and wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano, —C(O)-lower alkoxy and —N($R^8$)$_2$, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino, and wherein said amino is optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl;

$R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl; and $R^{19}$ is hydrogen or tetrahydrofuran-2-yl;

or pharmaceutically acceptable salts thereof.

Further, the invention provides a process for the manufacture of the above compounds, pharmaceutical compositions which contain such compounds as well as the processes for the production of pharmaceutical compositions.

Compounds of the present invention are PDE10A inhibitors. They can be used to treat diseases of the central nervous system and of other PDE10A expressing tissues. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

Compounds of the invention also can be used as anti-inflammatories. Compounds of the invention are useful for the treatment of Alzheimer's disease, Huntington's disease, Parkinson's disease, multiple sclerosis, stroke or spinal cord injury.

Compounds of the invention also are useful for the treatment of solid tumors and hematological malignancies such as renal cell carcinoma or breast cancer.

DETAILED DESCRIPTION OF THE INVENTION

Unless otherwise indicated, the following definitions are set forth to illustrate and define the meaning and scope of the various terms used to describe the invention herein.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

In this specification the term "lower" is used to mean a group consisting of one to seven, more specifically of one to four carbon atom(s).

The term "halogen" refers to fluorine, chlorine, bromine and iodine, more specifically fluorine, chlorine and bromine.

The term "alkyl" refers to a branched or straight-chain monovalent saturated aliphatic hydrocarbon radical of one to twenty carbon atoms, more specifically one to sixteen carbon atoms, yet more specifically one to ten carbon atoms.

The term "lower alkyl", alone or in combination with other groups, refers to a branched or straight-chain monovalent alkyl radical of one to seven carbon atoms, more specifically one to four carbon atoms. This term is further exemplified by such radicals as methyl, ethyl, n-propyl, isopropyl, n-butyl, s-butyl, t-butyl and the like.

The term "cycloalkyl" refers to a monovalent carbocyclic radical of 3 to 10 carbon atoms, more specifically 3 to 6 carbon atoms, such as cyclopropyl, cyclobutyl, cyclopentyl or cyclohexyl.

The term "lower haloalkyl" refers to lower alkyl groups which are mono- or multiply substituted with halogen, particularly fluoro. Examples of lower haloalkyl groups are e.g. —$CFH_2$, —$CF_2H$, —$CF_3$, $CF_3CH_2$—, $CF_3(CH_2)_2$—, $(CF_3)_2$CH— and $CF_2H$—$CH_2$—.

The term "alkoxy" refers to the group R'—O—, wherein R' is an alkyl. The term "lower alkoxy" refers to the group R'—O—, wherein R' is a lower alkyl.

The term "lower-alkoxy-lower-alkyl" refers to lower alkyl groups which are mono- or multiply substituted with lower alkoxy. Examples of lower-alkoxy-lower-alkyl groups are e.g. —$CH_2$—O—$CH_3$, —$CH_2$—$CH_2$—O—$CH_3$ and —$CH_2$—O—$CH_2$—$CH_3$.

The term "lower hydroxyalkyl" refers to a lower alkyl group as defined above, which is substituted by 1 to 3 hydroxyl groups. Examples of lower hydroxyalkyl groups are e.g. hydroxy-methyl, 2-hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "lower cyanoalkyl" refers to a lower alkyl group as defined above, which is substituted by 1 to 3 cyano groups. Examples of lower cyanoalkyl groups are e.g. cyanomethyl and cyanoethyl.

The term "amino" refers to a monovalent group that has a nitrogen atom with two hydrogen atoms (represented by —$NH_2$).

The term "oxo" when referring to substituents on heterocyclyl means that an oxygen atom is attached to the heterocyclyl ring. Thereby, the "oxo" may either replace two hydrogen atoms on a carbon atom, or it may simply be attached to sulfur, so that the sulfur exists in oxidized form, i.e. bearing one or two oxygens.

The term "heterocyclyl" refers to a monovalent saturated 4- to 6-membered monocyclic ring containing one, two or three ring heteroatoms independently selected from N, O and S, the remaining ring atoms being carbon atoms, wherein the point of attachment can be through either a carbon atom or a heteroatom. Examples of heterocyclyl are e.g. morpholinyl and piperidinyl.

The term "spiro-heterocyclyl" refers to a monovalent saturated 7- to 11-membered bicyclic moiety with the rings connected through one atom, containing one, two or three ring heteroatoms independently selected from N, O and S, the remaining ring atoms being carbon atoms, wherein the point of attachment can be through either a carbon atom or a heteroatom.

The term "aryl" refers to a monovalent aromatic hydrocarbon ring. The aryl group more specifically includes 6 to 10 carbon atoms. Examples of aryl groups are e.g. phenyl.

The term "heteroaryl" refers to an aromatic 5- or 6-membered monocyclic ring or at least partially aromatic 9- or 10-membered bicyclic ring which comprises 1, 2 or 3 atoms independently selected from nitrogen, oxygen and/or sulphur, such as pyrimidinyl.

The term "bicyclic ring" or 'bicyclic moiety" refers to two rings, wherein the two rings are fused or spiro linked. Each ring is independently aromatic or non-aromatic. In certain embodiments, both rings are aromatic. In certain embodiments, both rings are non-aromatic. In certain embodiments, one ring is aromatic and one ring is non-aromatic.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as formic acid, methanesulphonic acid, p-toluenesulphonic acid, acetic acid, lactic acid, trifluoroacetic acid, citric acid, fumaric acid, maleic acid, tartaric acid, succinic acid or salicylic acid, more specifically formic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammonium salt. The term "pharmaceutically acceptable salts" also refers to such salts. Particular salts are those obtained by the addition of an acid.

The term "pharmaceutically acceptable esters" embraces derivatives of the compounds of formula (I), in which a carboxy group has been converted to an ester. Lower alkyl, lower hydroxyalkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. Particular esters are methyl, ethyl, propyl, butyl and benzyl esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

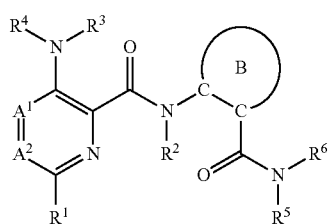

wherein
$A^1$ is selected from the group consisting of CH and N;
$A^2$ is selected from the group consisting of $CR^{19}$ and N, provided that $A^1$ and $A^2$ are not N simultaneously;

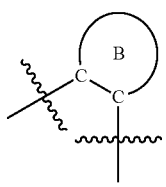

is aryl or heteroaryl, wherein said aryl and said heteroaryl are optionally substituted by 1 to 3 substituents independently selected from the group consisting of lower alkyl, lower alkoxy, lower hydroxyalkyl, lower haloalkyl, lower-alkoxy-lower-alkyl, lower alkyl-C(O)—, —C(O)—N(R$^8$)$_2$, —N(R$^8$)—C(O)-lower alkyl, cyano, halogen, R$^9$ and amino, and wherein said lower alkyl is optionally substituted by oxo, —C(O)OH, lower alkoxy-C(O)— or R$^7$, and wherein said lower alkoxy is optionally substituted by hydroxyl, lower alkoxy or —C(O)—N(R$^8$)$_2$, and wherein said amino is optionally substituted by 1 or 2 substituents independently selected from the group consisting of lower alkyl, lower hydroxyalkyl, lower-alkoxy-lower-alkyl and lower alkyl-C(O)—;

$R^1$ is lower alkyl, lower alkoxy, lower hydroxyalkyl, lower haloalkyl, lower-alkoxy-lower-alkyl, lower alkyl-C(O)—, —O-lower haloalkyl, cyano, halogen, R$^7$ or amino, wherein said lower alkyl is optionally substituted by R$^7$, and wherein said amino is optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is aryl or heteroaryl, wherein said aryl and said heteroaryl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C (O)—, cyano and amino, and wherein said amino is optionally substituted by 1 or 2 substituents independently selected from the group consisting of lower alkyl and lower-alkoxy-lower-alkyl;

$R^5$ and $R^6$ are independently hydrogen, lower alkyl, lower alkoxy, lower haloalkyl, lower cyanoalkyl, lower hydroxyalkyl, lower-alkoxy-lower-alkyl, cycloalkyl or heterocyclyl, wherein said lower alkyl is optionally substituted by oxo, R$^7$ or —N(R$^8$)$_2$, and wherein said lower haloalkyl is optionally substituted by hydroxyl, and wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano, —C(O)-lower alkoxy and —N(R$^8$)$_2$, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino, and wherein said amino is optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl;

$R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl;

$R^{19}$ is hydrogen or tetrahydrofuran-2-yl;

or pharmaceutically acceptable salts thereof.

Another embodiment of the present invention relates to compounds of formula (I)

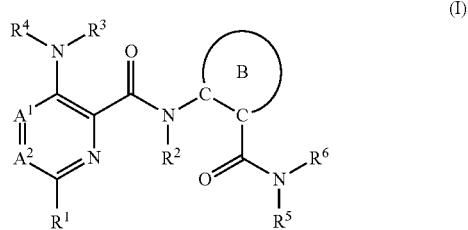

wherein

A¹ and A² are independently selected from the group consisting of CH and N, provided that A¹ and A² are not N simultaneously;

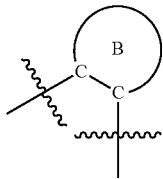

is aryl or heteroaryl, wherein said aryl and said heteroaryl are optionally substituted by 1 or 2 substituents independently selected from the group consisting of lower alkyl optionally substituted by oxo or $R^7$, lower alkoxy, lower hydroxyalkyl, lower haloalkyl, lower-alkoxy-lower-alkyl, lower alkyl-C(O)—, —C(O)—N($R^8$)$_2$, —N($R^8$)—C(O)-lower alkyl, cyano, halogen, $R^9$ and amino optionally substituted by 1 or 2 substituents independently selected from the group consisting of lower alkyl, lower hydroxyalkyl and lower-alkoxy-lower-alkyl;

$R^1$ is lower alkyl optionally substituted by $R^7$, lower alkoxy, lower hydroxyalkyl, lower haloalkyl, lower-alkoxy-lower-alkyl, lower alkyl-C(O)—, cyano, halogen, $R^7$ or amino optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is heteroaryl optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino optionally substituted by 1 or 2 substituents independently selected from the group consisting of lower alkyl and lower-alkoxy-lower-alkyl;

$R^5$ and $R^6$ are independently hydrogen, lower alkyl optionally substituted by oxo or $R^7$, lower haloalkyl, lower cyanoalkyl, lower hydroxyalkyl, lower-alkoxy-lower-alkyl, cycloalkyl or heterocyclyl, wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano and amino optionally substituted by 1 or 2 substituents independently selected from the group consisting of lower alkyl and lower-alkoxy-lower-alkyl, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl;

$R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl;

or pharmaceutically acceptable salts thereof.

The compounds of formula (I) can have one or more asymmetric C atoms and can therefore exist as an enantiomeric mixture, mixture of stereoisomers or as optically pure compounds. The compounds of formula (I) include all diastereomers, tautomers, racemates and mixtures thereof.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

A particular embodiment of the present invention relates to compounds of formula (I) as described above, wherein

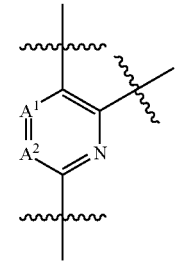

is selected from the group consisting of:

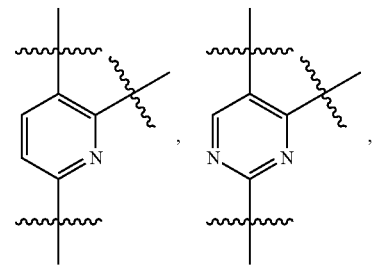

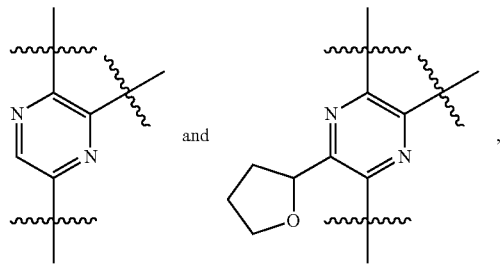

more specifically the group consisting of:

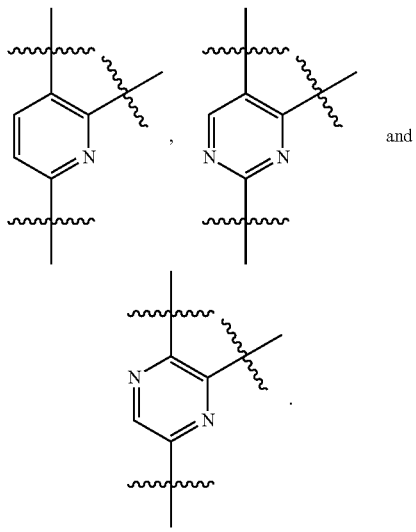

Another particular embodiment of the present invention relates to compounds of formula (I) as described above, wherein $R^2$ and $R^3$ are hydrogen.

A particular embodiment of the present invention relates to compounds of formula (I) as described above, wherein $R^4$ is 3-fluoro-phenyl, 4-fluoro-phenyl, pyridin-3-yl, 5-fluoro-pyridin-3-yl, pyrimidin-5-yl or pyrazin-2-yl, more specifically pyridin-3-yl, 5-fluoro-pyridin-3-yl or pyrimidin-5-yl.

Yet another particular embodiment of the present invention relates to compounds of formula (I) as described above, wherein $R^4$ is pyrimidinyl, more specifically pyrimidin-5-yl.

A particular embodiment of the present invention relates to compounds of formula (I) as described above, wherein

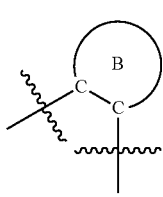

is selected from the group (1) consisting of:

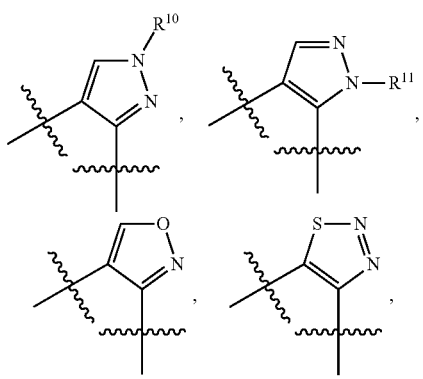

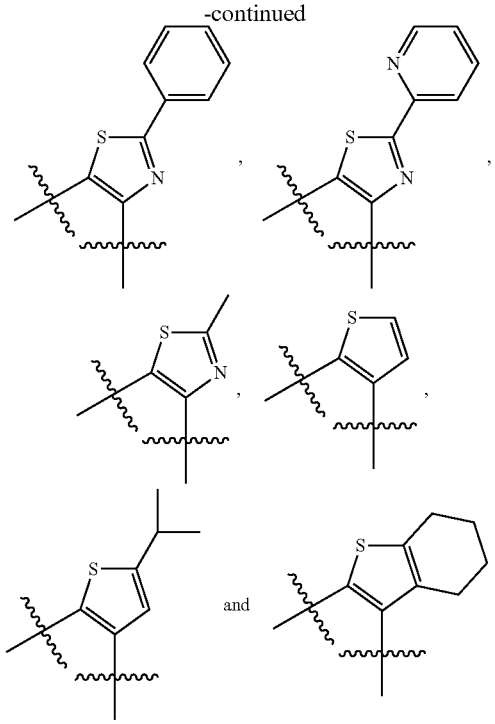

more specifically the group consisting of:

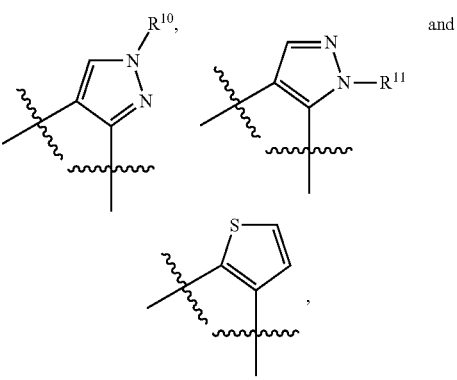

wherein
$R^{10}$ is lower alkyl, lower-alkoxy-lower-alkyl, lower haloalkyl, aryl or heteroaryl, wherein said lower alkyl is optionally substituted by cycloalkyl, more specifically methyl, ethyl, cyclopropylmethyl, 2-methoxy-ethyl, 2,2,2-trifluoro-ethyl, 3,3,3-trifluoro-propyl, phenyl or pyridin-2-yl, yet more specifically methyl; and
$R^{11}$ is lower alkyl, lower-alkoxy-lower-alkyl, lower haloalkyl, lower hydroxyalkyl or heterocyclyl, wherein said lower alkyl is optionally substituted by cycloalkyl or heterocyclyl, more specifically methyl, ethyl, isopropyl, isobutyl, cyclopropylmethyl, oxetan-2-ylmethyl, tetrahydro-furan-2-ylmethyl, tetrahydro-furan-3-ylmethyl, 2-methoxy-ethyl, 2-hydroxy-ethyl, 2,2,2-trifluoro-ethyl, 3,3,3-trifluoro-propyl or tetrahydro-furan-3-yl, yet more specifically methyl or 2-methoxy-ethyl.

Another particular embodiment of the present invention relates to compounds of formula (I) as described above, wherein

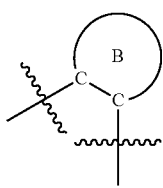

is selected from the group (1') consisting of:

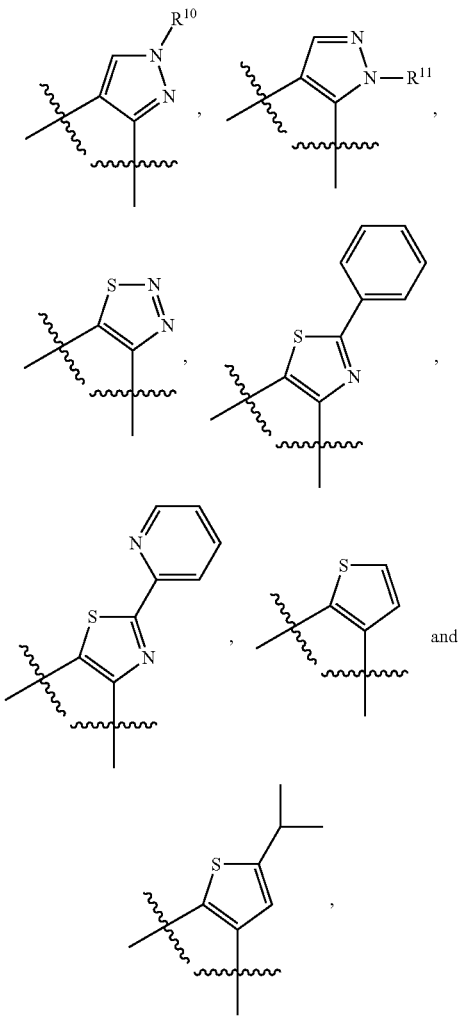

more specifically the group consisting of:

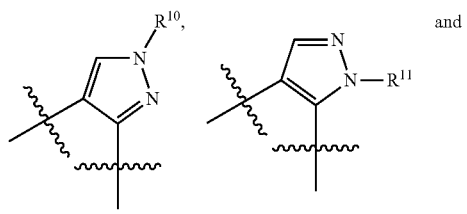

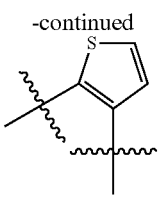

wherein $R^{10}$ is lower alkyl optionally substituted by cycloalkyl, lower-alkoxy-lower-alkyl, lower haloalkyl, aryl or heteroaryl, more specifically methyl, ethyl, cyclopropylmethyl, 2-methoxy-ethyl, 2,2,2-trifluoro-ethyl, 3,3,3-trifluoro-propyl, phenyl or pyridin-2-yl, yet more specifically methyl; and $R^{11}$ is lower alkyl optionally substituted by cycloalkyl, lower-alkoxy-lower-alkyl or lower haloalkyl, more specifically methyl, cyclopropylmethyl, 2-methoxy-ethyl or 3,3,3-trifluoro-propyl, yet more specifically methyl or 2-methoxy-ethyl.

The chemical structures of

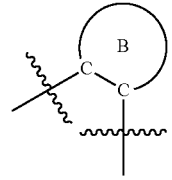

described above and hereunder are attached to the amide nitrogen in formula (I) at their left side and attached to the amide carbon in formula (I) at their right side.

Another particular embodiment of the present invention relates to compounds of formula (I) as described above, wherein

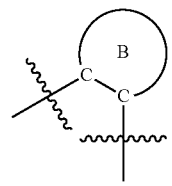

is selected from the group (1) as described above, and wherein $R^1$ is halogen, lower alkyl, lower alkoxy, lower hydroxyalkyl, lower-alkoxy-lower-alkyl, —C(O)-lower alkyl, —O-lower haloalkyl, cycloalkyl, heterocyclyl or amino, and wherein said heterocyclyl is optionally substituted by lower alkyl, and wherein said amino is substituted by 1 or 2 substituents independently selected from the group consisting of lower alkyl and lower-alkoxy-lower-alkyl, more specifically chloro, methyl, 1-hydroxy-ethyl, 1-hydroxy-1-methyl-ethyl, isopropyl, isobutyl, tert-butyl, methoxymethyl, methoxy, 2,2,2-trifluoro-ethoxy, acetyl, cyclopropyl, cyclobutyl, cyclohexyl, tetrahydrofuran-2-yl, tetrahydrofuran-3-yl, azetidin-1-yl, pyrrolidin-1-yl, morpholin-4-yl, 4-methyl-piperazin-1-yl, ethyl-methyl-amino or 2-methoxy-ethylamino, yet more specifically 1-hydroxy-1-methyl-ethyl, isopropyl, isobutyl, tert-butyl, cyclopropyl, tetrahydrofuran-3-yl or morpholin-4-yl.

Yet another particular embodiment of the present invention relates to compounds of formula (I) as described above, wherein

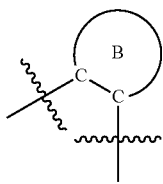

is selected from the group (1') as described above, and wherein $R^1$ is lower alkyl, lower hydroxyalkyl, lower-alkoxy-lower-alkyl, cycloalkyl or heterocyclyl, more specifically methyl, 1-hydroxy-ethyl, isopropyl, isobutyl, tert-butyl, methoxymethyl, cyclopropyl, cyclohexyl, tetrahydrofuran-2-yl or tetrahydrofuran-3-yl, yet more specifically isopropyl, isobutyl or cyclopropyl.

Another particular embodiment of the present invention relates to compounds of formula (I) as described above, wherein

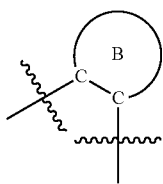

is selected from the group (1) as described above, and wherein $R^5$ and $R^6$ are independently hydrogen, lower alkyl, lower hydroxyalkyl, lower alkoxy, lower haloalkyl, lower-alkoxy-lower-alkyl, cycloalkyl or heterocyclyl, wherein said lower alkyl is optionally substituted by dimethylamino or heterocyclyl, and wherein said lower haloalkyl is optionally substituted by hydroxyl, and wherein said cycloalkyl is optionally substituted by hydroxyl, and wherein said heterocyclyl is optionally substituted by lower alkyl or —C(O)-lower alkoxy, more specifically hydrogen, methyl, tetrahydrofuran-2-yl-methyl, ethyl, 2-methoxy-1-methyl-ethyl, 2-hydroxy-ethyl, 2-fluoro-ethyl, 2-hydroxy-1,1-dimethyl-ethyl, 2,2-difluoro-ethyl, 2,2,2-trifluoro-ethyl, 2,2,2-trifluoro-1-methyl-ethyl, 2-dimethylamino-ethyl, propyl, isopropyl, 2,3-dihydroxy-propyl, 3-hydroxy-propyl, 2-hydroxy-2-methyl-propyl, 3-hydroxy-2-methyl-propyl, 3-hydroxy-2,2-dimethyl-propyl, 2,2-difluoro-propyl, 3,3,3-trifluoro-2-hydroxy-propyl, 2-methoxy-2-methyl-propyl, butyl, isobutyl, 3-hydroxy-3-methyl-butyl, methoxy, cyclopropyl, cyclobutyl, cyclopentyl, 2-hydroxy-cyclopentyl, cyclohexyl, oxetan-3-yl, 3-methyl-oxetan-3-yl, tetrahydro-furan-3-yl, tetrahydro-pyran-4-yl, 1-methyl-azetidin-3-yl, pyrrolidin-3-yl, 1-methyl-pyrrolidin-3-yl, 1-(tert-butoxycarbonyl)pyrrolidin-3-yl, 1-methyl-piperidin-3-yl or 1-methyl-piperidin-4-yl, yet more specifically hydrogen, methyl, ethyl, 2,2-difluoro-ethyl, 2-hydroxy-2-methyl-propyl, 2-hydroxy-cyclopentyl, 1-methyl-azetidin-3-yl, 3-methyl-oxetan-3-yl or tetrahydro-furan-3-yl, or $R^5$ and $R^6$, together with the nitrogen atom to which they are attached, form an azetidine, pyrrolidine, piperidine, morpholine, piperazine, isoxazolidine or 2-oxa-6-aza-sprio[3.3]heptane ring, wherein each of said azetidine, pyrrolidine, piperidine, morpholine, piperazine, isoxazolidine or 2-oxa-6-aza-spiro[3.3]heptane ring is optionally substituted by 1 or 2 substituents independently selected from the group consisting of hydroxyl, halogen, lower alkyl, lower hydroxyalkyl, lower alkoxy, oxo and amino, and wherein said amino is substituted by 2 lower alkyl; $R^5$ and $R^6$ more specifically forming an optionally substituted heterocyclyl or spiro-heterocyclyl ring selected from the group consisting of azetidin-1-yl, 3-hydroxy-azetidin-1-yl, 3-fluoro-azetidin-1-yl, 3,3-difluoro-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, piperidin-1-yl, 2-methyl-piperidin-1-yl, isoxazolidin-2-yl, morpholin-4-yl, 3-oxo-piperazin-1-yl and 2-oxa-6-aza-spiro[3.3]heptan-6-yl, yet more specifically azetidin-1-yl, isoxazolidin-2-yl or morpholin-4-yl.

Yet another particular embodiment of the present invention relates to compounds of formula (I) as described above, wherein

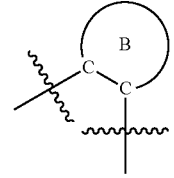

is selected from the group (1') as described above, and wherein $R^5$ and $R^6$ are independently hydrogen, lower alkyl optionally substituted by heterocyclyl, lower hydroxyalkyl, lower-alkoxy-lower-alkyl or cycloalkyl, more specifically hydrogen, methyl, tetrahydrofuran-2-yl-methyl, 2-methoxy-1-methyl-ethyl, 2-hydroxy-ethyl, isopropyl, 2,3-dihydroxy-propyl, 3-hydroxy-propyl, 2-hydroxy-2-methyl-propyl, cyclopropyl, cyclobutyl, cyclopentyl or cyclohexyl, yet more specifically hydrogen, methyl or 2-hydroxy-2-methyl-propyl, or $R^5$ and $R^6$, together with the nitrogen atom to which they are attached, form an azetidine, pyrrolidine, piperidine, morpholine, piperazine or 2-oxa-6-aza-spiro[3.3]heptane ring, wherein each of said azetidine, pyrrolidine, piperidine, morpholine, piperazine or 2-oxa-6-aza-spiro[3.3]heptane ring is optionally substituted by 1 or 2 substituents independently selected from the group consisting of hydroxyl, halogen, lower alkyl, lower hydroxyalkyl, lower alkoxy, oxo and amino substituted by 2 lower alkyl; $R^5$ and $R^6$ more specifically forming an optionally substituted heterocyclyl or spiro-heterocyclyl ring selected from the group consisting of azetidin-1-yl, 3-hydroxy-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, piperidin-1-yl, morpholin-4-yl, 3-oxo-piperazin-1-yl and 2-oxa-aza-spiro[3.3]heptan-6-yl, yet more specifically morpholin-4-yl.

Particular compounds of formula (I), wherein

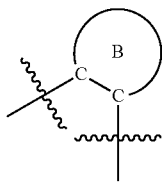

is selected from the group (1) as described above, are those selected from the group consisting of:
- 6-Cyclopropyl-3-(pyrimidin-5-ylamino)-pyridine-2-carboxylic acid (3-dimethylcarbamoyl-1-methyl-1H-pyrazol-4-yl)-amide,
- 6-Cyclopropyl-3-(pyrimidin-5-ylamino)-pyridine-2-carboxylic acid (1-methyl-3-methylcarbamoyl-1H-pyrazol-4-yl)-amide,
- 6-Cyclopropyl-3-(pyrimidin-5-ylamino)-pyridine-2-carboxylic acid (3-carbamoyl-1-methyl-1H-pyrazol-4-yl)-amide,
- 6-Cyclopropyl-3-(pyrimidin-5-ylamino)-pyridine-2-carboxylic acid [3-dimethylcarbamoyl-1-(2-methoxy-ethyl)-1H-pyrazol-4-yl]-amide,
- 6-Cyclopropyl-3-(pyrimidin-5-ylamino)-pyrazine-2-carboxylic acid (1-methyl-3-methylcarbamoyl-1H-pyrazol-4-yl)-amide,
- 6-Cyclopropyl-3-(pyrimidin-5-ylamino)-pyridine-2-carboxylic acid [5-dimethylcarbamoyl-1-(2-methoxy-ethyl)-1H-pyrazol-4-yl]-amide,
- 6-Cyclopropyl-3-(pyrimidin-5-ylamino)-pyridine-2-carboxylic acid [3-dimethylcarbamoyl-1-(2,2,2-trifluoro-ethyl)-1H-pyrazol-4-yl]-amide,
- 6-Cyclopropyl-3-(pyrimidin-5-ylamino)-pyridine-2-carboxylic acid [3-methylcarbamoyl-1-(2,2,2-trifluoro-ethyl)-1H-pyrazol-4-yl]-amide,
- 6-Cyclopropyl-3-(pyrimidin-5-ylamino)-pyridine-2-carboxylic acid [3-methylcarbamoyl-1-(3,3,3-trifluoro-propyl)-1H-pyrazol-4-yl]-amide,
- 6-Cyclopropyl-3-(pyrimidin-5-ylamino)-pyridine-2-carboxylic acid [5-methylcarbamoyl-1-(3,3,3-trifluoro-propyl)-1H-pyrazol-4-yl]-amide,
- 6-Cyclopropyl-3-(pyrimidin-5-ylamino)-pyridine-2-carboxylic acid [1-(2-methoxy-ethyl)-5-methylcarbamoyl-1H-pyrazol-4-yl]-amide,
- 6-Cyclopropyl-3-(pyrimidin-5-ylamino)-pyridine-2-carboxylic acid (1-cyclopropylmethyl-3-methylcarbamoyl-1H-pyrazol-4-yl)-amide,
- 6-Cyclopropyl-3-(pyrimidin-5-ylamino)-pyridine-2-carboxylic acid (1-cyclopropylmethyl-5-methylcarbamoyl-1H-pyrazol-4-yl)-amide,
- 6-Cyclopropyl-3-(pyrimidin-5-ylamino)-pyridine-2-carboxylic acid [1-methyl-3-(morpholine-4-carbonyl)-1-pyrazol-4-yl]-amide,
- 6-Cyclopropyl-3-(pyrimidin-5-ylamino)-pyridine-2-carboxylic acid [3-(cyclopropyl-methyl-carbamoyl)-1-methyl-1H-pyrazol-4-yl]-amide,
- 6-Cyclopropyl-3-(pyrimidin-5-ylamino)-pyridine-2-carboxylic acid [1-methyl-3-(piperidine-1-carbonyl)-1H-pyrazol-4-yl]-amide,
- 6-Cyclopropyl-3-(pyrimidin-5-ylamino)-pyridine-2-carboxylic acid [3-(cyclohexyl-methyl-carbamoyl)-1-methyl-1H-pyrazol-4-yl]-amide,
- 6-Cyclopropyl-3-(pyrimidin-5-ylamino)-pyridine-2-carboxylic acid [1-(2-methoxy-ethyl)-3-methylcarbamoyl-1H-pyrazol-4-yl]-amide,
- 6-Cyclopropyl-3-(pyrimidin-5-ylamino)-pyridine-2-carboxylic acid [3-(cyclopentyl-methyl-carbamoyl)-1-methyl-1H-pyrazol-4-yl]-amide,
- 6-Cyclopropyl-3-(pyrimidin-5-ylamino)-pyridine-2-carboxylic acid [3-(isopropyl-methyl-carbamoyl)-1-methyl-1H-pyrazol-4-yl]-amide,
- 6-Cyclopropyl-3-(pyrimidin-5-ylamino)-pyridine-2-carboxylic acid [1-methyl-3-(pyrrolidine-1-carbonyl)-1H-pyrazol-4-yl]-amide,
- 6-Cyclopropyl-3-(pyrimidin-5-ylamino)-pyridine-2-carboxylic acid (3-methylcarbamoyl-1-phenyl-1H-pyrazol-4-yl)-amide,
- 6-Methoxymethyl-3-(pyrimidin-5-ylamino)-pyridine-2-carboxylic acid [1-(2-methoxy-ethyl)-5-methylcarbamoyl-1H-pyrazol-4-yl]-amide,
- 6-Cyclopropyl-N-[1-methyl-3-(2-methyl-pyrrolidine-1-carbonyl)-1H-pyrazol-4-yl]-3-(pyrimidin-5-ylamino)-pyridine-2-carboximidic acid,
- N-(3-Cyclohexylcarbamoyl-1-methyl-1H-pyrazol-4-yl)-6-cyclopropyl-3-(pyrimidin-5-ylamino)-pyridine-2-carboximidic acid,
- N-[3-(Azetidine-1-carbonyl)-1-methyl-1H-pyrazol-4-yl]-6-cyclopropyl-3-(pyrimidin-5-ylamino)-pyridine-2-carboximidic acid,
- 6-Cyclopropyl-N-(3-cyclopropylcarbamoyl-1-methyl-1H-pyrazol-4-yl)-3-(pyrimidin-5-ylamino)-pyridine-2-carboximidic acid,
- 6-Cyclopropyl-N-[3-(3,3-dimethyl-pyrrolidine-1-carbonyl)-1-methyl-1H-pyrazol-4-yl]-3-(pyrimidin-5-ylamino)-pyridine-2-carboximidic acid,
- N-(3-Cyclobutylcarbamoyl-1-methyl-1H-pyrazol-4-yl)-6-cyclopropyl-3-(pyrimidin-5-ylamino)-pyridine-2-carboximidic acid,
- N-(3-Cyclopentylcarbamoyl-1-methyl-1H-pyrazol-4-yl)-6-cyclopropyl-3-(pyrimidin-5-ylamino)-pyridine-2-carboximidic acid,
- 6-Cyclopropyl-N-[3-(2,5-dimethyl-pyrrolidine-1-carbonyl)-1-methyl-1H-pyrazol-4-yl]-3-(pyrimidin-5-ylamino)-pyridine-2-carboximidic acid,
- 6-Cyclopropyl-N-[3-(3,3-difluoro-pyrrolidine-1-carbonyl)-1-methyl-1H-pyrazol-4-yl]-3-(pyrimidin-5-ylamino)-pyridine-2-carboximidic acid,
- 6-Cyclopropyl-N-[3-(3-dimethylamino-pyrrolidine-1-carbonyl)-1-methyl-1H-pyrazol-4-yl]-3-(pyrimidin-5-ylamino)-pyridine-2-carboximidic acid,
- 6-Cyclopropyl-N-{3-[(3-hydroxy-propyl)-methyl-carbamoyl]-1-methyl-1H-pyrazol-4-yl}-3-(pyrimidin-5-ylamino)-pyridine-2-carboxamidic acid,
- 6-Cyclopropyl-N-[3-(2-hydroxy-ethylcarbamoyl)-1-methyl-1H-pyrazol-4-yl]-3-(pyrimidin-5-ylamino)-pyridine-2-carboximidic acid,
- 6-Cyclopropyl-N-{3-[(2-hydroxy-ethyl)-methyl-carbamoyl]-1-methyl-1H-pyrazol-4-yl}-3-(pyrimidin-5-ylamino)-pyridine-2-carboximidic acid,
- 6-Cyclopropyl-N-[3-(2-methoxy-1-methyl-ethylcarbamoyl)-1-methyl-1H-pyrazol-4-yl]-3-(pyrimidin-5-ylamino)-pyridine-2-carboximidic acid,
- 6-Cyclopropyl-N-[3-(2,3-dihydroxy-propylcarbamoyl)-1-methyl-1H-pyrazol-4-yl]-3-(pyrimidin-5-ylamino)-pyridine-2-carboximidic acid,
- 6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid,
- 6-Cyclopropyl-N-[3-(3-hydroxy-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(2-hydroxy-1-methyl-ethylcarbamoyl)-1-methyl-1H-pyrazol-4-yl]-3-(pyrimidin-5-ylamino)-pyridine-2-carboximidic acid, 6-Cyclopropyl-N-{3-[(2,3-dihydroxy-propyl)-methyl-carbamoyl]-1-methyl-1H-pyrazol-4-yl}-3-(pyrimidin-5-ylamino)-pyridine-2-carboximidic acid, 6-Cyclopropyl-N-[3-(5-hydroxy-3,6-dihydro-2H-pyrazine-1-carbonyl)-1-methyl-1H-pyrazol-4-yl]-3-(pyrimidin-5-ylamino)-pyridine-2-carboximidic acid, 6-Cyclopropyl-N-[3-(3-methoxy-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(2-hydroxymethyl-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3-hydroxy-azetidine-1-carbonyl)-1-methyl-1H-pyrazol-4-yl]-3-(pyrimidin-5-ylamino)-pyridine-2-carboximidic acid, 6-Cyclopropyl-N-[1-methyl-3-(2-oxa-6-aza-spiro[3.3]heptane-6-carbonyl)-1H-pyrazol-4-yl]-3-(pyrimidin-5-ylamino)-pyridine-2-carboximidic acid, 6-Cyclopropyl-N-[3-(2,2-dimethyl-pyrrolidine-1-carbonyl)-1-methyl-1H-pyrazol-4-yl]-3-(pyrimidin-5-ylamino)-pyridine-2-carboximidic acid, 6-Cyclopropyl-3-(pyrimidin-5-ylamino)-pyridine-2-carboxylic acid (4-methylcarbamoyl-[1,2,3]thiadiazol-5-yl)-amide, 6-Cyclopropyl-3-(pyrimidin-5-ylamino)-pyridine-2-carboxylic acid (4-methylcarbamoyl-2-phenyl-thiazol-5-yl)-amide, 6-Cyclopropyl-3-(pyrimidin-5-ylamino)-pyridine-2-carboxylic acid (4-methylcarbamoyl-2-pyridin-2-yl-thiazol-5-yl)-amide, 6-Cyclopropyl-3-(pyrimidin-5-ylamino)-pyridine-2-carboxylic acid (3-dimethylcarbamoyl-1-pyridin-2-yl-1H-pyrazol-4-yl)-amide, 2-Isopropyl-5-(pyrimidin-5-ylamino)-pyrimidine-4-carboxylic acid (1-methyl-3-methylcarbamoyl-1H-pyrazol-4-yl)-amide, 2-Cyclopropyl-5-(pyrimidin-5-ylamino)-pyrimidine-4-carboxylic acid (1-methyl-3-methylcarbamoyl-1H-pyrazol-4-yl)-amide, 2-tert-Butyl-5-(pyrimidin-5-ylamino)-pyrimidine-4-carboxylic acid (1-methyl-3-methylcarbamoyl-1H-pyrazol-4-yl)-amide, 2-Isobutyl-5-(pyrimidin-5-ylamino)-pyrimidine-4-carboxylic acid (1-methyl-3-methylcarbamoyl-1H-pyrazol-4-yl)-amide, 2-Cyclohexyl-5-(pyrimidin-5-ylamino)-pyrimidine-4-carboxylic acid (1-methyl-3-methylcarbamoyl-1H-pyrazol-4-yl)-amide, 6-Cyclopropyl-3-(pyrimidin-5-ylamino)-pyridine-2-carboxylic acid (3-cyclopropylcarbamoyl-thiophen-2-yl)-amide, 6-Cyclopropyl-3-(pyrimidin-5-ylamino)-pyridine-2-carboxylic acid [3-(morpholine-4-carbonyl)-thiophen-2-yl]-amide, 6-Cyclopropyl-3-(pyrimidin-5-ylamino)-pyridine-2-carboxylic acid [5-isopropyl-3-(morpholine-4-carbonyl)-thiophen-2-yl]-amide, 6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide, N-(1-methyl-3-(methylcarbamoyl)-1H-pyrazol-4-yl)-3-(pyrimidin-5-ylamino)-6-(tetrahydrofuran-2-yl)pyrazine-2-carboxamide, N-(1-methyl-3-(methylcarbamoyl)-1H-pyrazol-4-yl)-3-(pyrimidin-5-ylamino)-6-(tetrahydrofuran-3-yl)pyrazine-2-carboxamide, N-(1-methyl-3-(methylcarbamoyl)-1H-pyrazol-4-yl)-3-(pyrimidin-5-ylamino)-6-(tetrahydrofuran-2-yl)picolinamide, 6-isobutyl-N-(1-methyl-3-(methylcarbamoyl)-1H-pyrazol-4-yl)-3-(pyrimidin-5-ylamino)pyrazine-2-carboxamide, 6-cyclopropyl-N-(1-ethyl-3-(methylcarbamoyl)-1H-pyrazol-4-yl)-3-(pyrimidin-5-ylamino)pyrazine-2-carboxamide, 6-cyclopropyl-N-(1-ethyl-3-((tetrahydrofuran-2-yl)methylcarbamoyl)-1H-pyrazol-4-yl)-3-(pyrimidin-5-ylamino)pyrazine-2-carboxamide, 6-cyclopropyl-N-(1-methyl-3-((tetrahydrofuran-2-yl)methylcarbamoyl)-1H-pyrazol-4-yl)-3-(pyrimidin-5-ylamino)pyrazine-2-carboxamide, 6-cyclopropyl-N-(3-((2-hydroxy-2-methylpropyl)(methyl)carbamoyl)-1-methyl-1H-pyrazol-4-yl)-3-(pyrimidin-5-ylamino)pyrazine-2-carboxamide, N-(3-(2-hydroxy-2-methylpropylcarbamoyl)-1-methyl-1H-pyrazol-4-yl)-2-methyl-5-(pyrimidin-5-ylamino)pyrimidine-4-carboxamide, 6-(1-Hydroxy-ethyl)-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide, 2-(2-Methoxy-ethylamino)-5-(pyrimidin-5-ylamino)-pyrimidine-4-carboxylic acid (1-methyl-3-methylcarbamoyl-1H-pyrazol-4-yl)-amide, 3-(Pyrimidin-5-ylamino)-6-(tetrahydro-furan-3-yl)-pyridine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (2-methyl-4-methylcarbamoyl-thiazol-5-yl)-amide, 6-Isopropyl-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [1-ethyl-5-(2-hydroxy-2-methyl-propylcarbamoyl)-1H-pyrazol-4-yl]-amide, 6-Cyclopropyl-3-(pyrimidin-5-ylamino)-pyrazine-2-carboxylic acid (1-ethyl-5-methylcarbamoyl-1H-pyrazol-4-yl)-amide, 6-Cyclopropyl-3-(pyrimidin-5-ylamino)-pyrazine-2-carboxylic acid [5-(2-hydroxy-2-methyl-propylcarbamoyl)-1-isobutyl-1H-pyrazol-4-yl]-amide, 6-Cyclopropyl-3-(pyrimidin-5-ylamino)-pyrazine-2-carboxylic acid [1-methyl-5-(oxetan-3-ylcarbamoyl)-1H-pyrazol-4-yl]-amide, 6-Cyclopropyl-3-(pyrimidin-5-ylamino)-pyrazine-2-carboxylic acid [1-methyl-5-(3-methyl-oxetan-3-ylcarbamoyl)-1H-pyrazol-4-yl]-amide, 6-Cyclopropyl-3-(pyrimidin-5-ylamino)-pyrazine-2-carboxylic acid (1-isobutyl-5-methylcarbamoyl-1H-pyrazol-4-yl)-amide, 6-Cyclopropyl-3-(pyrimidin-5-ylamino)-pyrazine-2-carboxylic acid [5-(2-hydroxy-2-methyl-propylcarbamoyl)-1-isopropyl-1H-pyrazol-4-yl]-amide, 6-Cyclopropyl-3-(pyrimidin-5-ylamino)-pyrazine-2-carboxylic acid (1-isopropyl-5-methylcarbamoyl-1H-pyrazol-4-yl)-amide,
6-Cyclopropyl-3-(pyrimidin-5-ylamino)-pyrazine-2-carboxylic acid [5-(3-hydroxy-3-methyl-butylcarbamoyl)-1-methyl-1H-pyrazol-4-yl]-amide,
6-Cyclopropyl-3-(pyrimidin-5-ylamino)-pyrazine-2-carboxylic acid [1-methyl-5-(tetrahydro-furan-3-ylcarbamoyl)-1H-pyrazol-4-yl]-amide,
6-Cyclopropyl-3-(pyrimidin-5-ylamino)-pyrazine-2-carboxylic acid [5-(3-hydroxy-2,2-dimethyl-propylcarbamoyl)-1-methyl-1H-pyrazol-4-yl]-amide,
6-Cyclopropyl-3-(pyrimidin-5-ylamino)-pyrazine-2-carboxylic acid [5-(3,3-difluoro-azetidine-1-carbonyl)-1-methyl-1H-pyrazol-4-yl]-amide,
6-Cyclopropyl-3-(pyrimidin-5-ylamino)-pyrazine-2-carboxylic acid [1-methyl-5-(2,2,2-trifluoro-ethylcarbamoyl)-1H-pyrazol-4-yl]-amide,
6-Cyclopropyl-3-(pyrimidin-5-ylamino)-pyrazine-2-carboxylic acid [5-(2,2-difluoro-ethylcarbamoyl)-1-methyl-1H-pyrazol-4-yl]-amide,
6-Cyclopropyl-3-(pyrimidin-5-ylamino)-pyrazine-2-carboxylic acid [1-methyl-5-(3,3,3-trifluoro-2-hydroxy-propylcarbamoyl)-1H-pyrazol-4-yl]-amide,
6-Cyclopropyl-3-(pyrimidin-5-ylamino)-pyrazine-2-carboxylic acid [1-(2-methoxy-ethyl)-5-methylcarbamoyl-1H-pyrazol-4-yl]-amide,
6-Cyclopropyl-3-(pyrimidin-5-ylamino)-pyridine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(3-hydroxy-2-methyl-propylcarbamoyl)-1-methyl-1H-pyrazol-4-yl]-amide,
6-Cyclopropyl-3-(pyrimidin-5-ylamino)-pyrazine-2-carboxylic acid (5-carbamoyl-1-methyl-1H-pyrazol-4-yl)-amide,
6-Cyclopropyl-3-(pyrimidin-5-ylamino)-pyrazine-2-carboxylic acid [5-(2-methoxy-2-methyl-propylcarbamoyl)-1-methyl-1H-pyrazol-4-yl]-amide,
6-Cyclopropyl-3-(pyrimidin-5-ylamino)-pyrazine-2-carboxylic acid [5-(2-hydroxy-1,1-dimethyl-ethylcarbamoyl)-1-methyl-1H-pyrazol-4-yl]-amide,
6-Cyclopropyl-3-(pyrimidin-5-ylamino)-pyrazine-2-carboxylic acid {5-[(2-hydroxy-2-methyl-propyl)-methylcarbamoyl]-1-methyl-1H-pyrazol-4-yl}-amide,
2-tert-Butyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(azetidine-1-carbonyl)-1-methyl-1H-pyrazol-4-yl]-amide,
6-Cyclopropyl-3-(pyrimidin-5-ylamino)-pyrazine-2-carboxylic acid [1-methyl-5-(pyrrolidine-1-carbonyl)-1H-pyrazol-4-yl]-amide,
6-Cyclopropyl-3-(pyrimidin-5-ylamino)-pyrazine-2-carboxylic acid (5-dimethylcarbamoyl-1-methyl-1H-pyrazol-4-yl)-amide,
3-(Pyrimidin-5-ylamino)-6-(tetrahydro-furan-3-yl)-pyrazine-2-carboxylic acid (1-methyl-5-methylcarbamoyl-1H-pyrazol-4-yl)-amide,
2-Isopropyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-5-(tetrahydro-furan-2-yl)-pyrazine-2-carboxylic acid [5-(2-fluoro-ethylcarbamoyl)-1-methyl-1H-pyrazol-4-yl]-amide,
6-Cyclopropyl-3-(pyrimidin-5-ylamino)-pyrazine-2-carboxylic acid (3-cyclopropylcarbamoyl-isoxazol-4-yl)-amide,
6-Cyclopropyl-3-(pyrimidin-5-ylamino)-pyrazine-2-carboxylic acid [1-methyl-5-(2,2,2-trifluoro-1-methyl-ethylcarbamoyl)-1H-pyrazol-4-yl]-amide,
6-Cyclopropyl-3-(pyrimidin-5-ylamino)-pyrazine-2-carboxylic acid [5-(2,2-difluoro-propylcarbamoyl)-1-methyl-1H-pyrazol-4-yl]-amide,
6-Chloro-3-(pyrimidin-5-ylamino)-pyridine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (5-isobutylcarbamoyl-1-methyl-1H-pyrazol-4-yl)-amide,
6-Cyclopropyl-3-(pyrimidin-5-ylamino)-pyrazine-2-carboxylic acid [1-methyl-5-(piperidine-1-carbonyl)-1H-pyrazol-4-yl]-amide,
6-Cyclopropyl-3-(pyrimidin-5-ylamino)-pyrazine-2-carboxylic acid (5-dimethylcarbamoyl-1-ethyl-1H-pyrazol-4-yl)-amide,
6-Cyclopropyl-3-(pyrimidin-5-ylamino)-pyrazine-2-carboxylic acid [1-ethyl-5-(morpholine-4-carbonyl)-1-pyrazol-4-yl]-amide,
6-Cyclopropyl-3-(pyrimidin-5-ylamino)-pyrazine-2-carboxylic acid [5-(2-fluoro-ethylcarbamoyl)-1-methyl-1H-pyrazol-4-yl]-amide,
6-Cyclopropyl-3-(pyrimidin-5-ylamino)-pyrazine-2-carboxylic acid [5-(2-hydroxy-2-methyl-propylcarbamoyl)-1-(3,3,3-trifluoro-propyl)-1H-pyrazol-4-yl]-amide,
6-Cyclopropyl-3-(pyrimidin-5-ylamino)-pyrazine-2-carboxylic acid [5-methylcarbamoyl-1-(3,3,3-trifluoro-propyl)-1H-pyrazol-4-yl]-amide,
6-Cyclopropyl-3-(pyrimidin-5-ylamino)-pyrazine-2-carboxylic acid [5-(3-fluoro-azetidine-1-carbonyl)-1-methyl-1H-pyrazol-4-yl]-amide,
6-Cyclopropyl-3-(pyrimidin-5-ylamino)-pyrazine-2-carboxylic acid [5-(2-hydroxy-2-methyl-propylcarbamoyl)-1-(2,2,2-trifluoro-ethyl)-1H-pyrazol-4-yl]-amide,
6-Cyclopropyl-3-(pyrimidin-5-ylamino)-pyrazine-2-carboxylic acid [5-methylcarbamoyl-1-(2,2,2-trifluoro-ethyl)-1H-pyrazol-4-yl]-amide,
6-Cyclopropyl-3-(pyrimidin-5-ylamino)-pyrazine-2-carboxylic acid [1-methyl-5-(morpholine-4-carbonyl)-1-pyrazol-4-yl]-amide,
6-Acetyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (3-ethylcarbamoyl-4,5,6,7-tetrahydro-benzo[b]thiophen-2-yl)-amide,
2-Isopropyl-5-(pyridin-3-ylamino)-pyrimidine-4-carboxylic acid (1-methyl-5-methylcarbamoyl-1H-pyrazol-4-yl)-amide,
6-(1-Hydroxy-ethyl)-3-(pyrimidin-5-ylamino)-pyrazine-2-carboxylic acid (1-methyl-5-methylcarbamoyl-1H-pyrazol-4-yl)-amide,
5-(3-Fluoro-phenylamino)-2-isopropyl-pyrimidine-4-carboxylic acid (1-methyl-5-methylcarbamoyl-1H-pyrazol-4-yl)-amide,
6-Methoxymethyl-3-(pyrimidin-5-ylamino)-pyridine-2-carboxylic acid (1-methyl-5-methylcarbamoyl-1H-pyrazol-4-yl)-amide,
5-(5-Fluoro-pyridin-3-ylamino)-2-isopropyl-pyrimidine-4-carboxylic acid (1-methyl-5-methylcarbamoyl-1H-pyrazol-4-yl)-amide, 5-(4-Fluoro-phenylamino)-2-isopropyl-pyrimidine-4-carboxylic acid (1-methyl-5-methylcarbamoyl-1H-pyrazol-4-yl)-amide,
2-Cyclobutyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (5-ethylcarbamoyl-1-methyl-1H-pyrazol-4-yl)-amide,
6-Cyclopropyl-3-(pyrazin-2-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (1-ethyl-5-ethylcarbamoyl-1H-pyrazol-4-yl)-amide,
6-Cyclopropyl-3-(pyrimidin-5-ylamino)-pyrazine-2-carboxylic acid (1-ethyl-5-isobutylcarbamoyl-1H-pyrazol-4-yl)-amide,
6-Cyclopropyl-3-(pyrimidin-5-ylamino)-pyrazine-2-carboxylic acid [5-(ethyl-methyl-carbamoyl)-1-methyl-1H-pyrazol-4-yl]-amide,
6-Cyclopropyl-3-(pyridin-3-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (5-dipropylcarbamoyl-1-methyl-1H-pyrazol-4-yl)-amide,
6-Cyclopropyl-3-(pyrimidin-5-ylamino)-pyrazine-2-carboxylic acid [5-(butyl-methyl-carbamoyl)-1-methyl-1H-pyrazol-4-yl]-amide,
6-Cyclopropyl-3-(pyrimidin-5-ylamino)-pyrazine-2-carboxylic acid {5-[(2-hydroxy-ethyl)-methyl-carbamoyl]-1-methyl-1H-pyrazol-4-yl}-amide,
6-Cyclopropyl-3-(pyrimidin-5-ylamino)-pyrazine-2-carboxylic acid [5-(isopropyl-methyl-carbamoyl)-1-methyl-1H-pyrazol-4-yl]-amide,
6-Cyclopropyl-3-(pyrimidin-5-ylamino)-pyrazine-2-carboxylic acid (5-diethylcarbamoyl-1-methyl-1H-pyrazol-4-yl)-amide,
6-Cyclopropyl-3-(pyrimidin-5-ylamino)-pyrazine-2-carboxylic acid [1-methyl-5-(methyl-propyl-carbamoyl)-1H-pyrazol-4-yl]-amide,
6-Cyclopropyl-3-(pyrimidin-5-ylamino)-pyrazine-2-carboxylic acid {5-[ethyl-(2-hydroxy-ethyl)-carbamoyl]-1-methyl-1H-pyrazol-4-yl}-amide,
6-Cyclopropyl-3-(pyrimidin-5-ylamino)-pyrazine-2-carboxylic acid {1-methyl-5-[methyl-(tetrahydro-pyran-4-yl)-carbamoyl]-1H-pyrazol-4-yl}-amide,
6-Cyclopropyl-3-(pyrimidin-5-ylamino)-pyrazine-2-carboxylic acid {1-methyl-5-[(tetrahydro-furan-2-ylmethyl)-carbamoyl]-1H-pyrazol-4-yl}-amide,
6-Cyclopropyl-3-(pyrimidin-5-ylamino)-pyrazine-2-carboxylic acid {1-ethyl-5-[(tetrahydro-furan-2-ylmethyl)-carbamoyl]-1H-pyrazol-4-yl}-amide,
6-Cyclopropyl-3-(pyridin-3-ylamino)-pyrazine-2-carboxylic acid [5-(azetidine-1-carbonyl)-1-methyl-1H-pyrazol-4-yl]-amide,
6-Cyclopropyl-3-(pyrimidin-5-ylamino)-pyrazine-2-carboxylic acid [1-methyl-5-(2-methyl-piperidine-1-carbonyl)-1H-pyrazol-4-yl]-amide,
3-[(4-{[6-Cyclopropyl-3-(pyrimidin-5-ylamino)-pyrazine-2-carbonyl]-amino}-2-methyl-2H-pyrazole-3-carbonyl)-amino]-pyrrolidine-1-carboxylic acid tert-butyl ester,
6-Cyclopropyl-3-(pyrimidin-5-ylamino)-pyrazine-2-carboxylic acid {1-methyl-5-[methyl-(2,2,2-trifluoro-ethyl)-carbamoyl]-1H-pyrazol-4-yl}-amide,
6-Cyclopropyl-3-(pyrimidin-5-ylamino)-pyrazine-2-carboxylic acid [5-(cyclopropyl-methyl-carbamoyl)-1-methyl-1H-pyrazol-4-yl]-amide,
6-Cyclopropyl-3-(pyrimidin-5-ylamino)-pyrazine-2-carboxylic acid [1-methyl-5-(2-methyl-pyrrolidine-1-carbonyl)-1H-pyrazol-4-yl]-amide,
6-Cyclopropyl-3-(pyrimidin-5-ylamino)-pyrazine-2-carboxylic acid [1-methyl-5-(methyl-oxetan-3-yl-carbamoyl)-1H-pyrazol-4-yl]-amide,
6-Cyclopropyl-3-(pyrimidin-5-ylamino)-pyrazine-2-carboxylic acid [1-methyl-5-(1-methyl-piperidin-3-ylcarbamoyl)-1H-pyrazol-4-yl]-amide,
6-Cyclopropyl-3-(pyrimidin-5-ylamino)-pyrazine-2-carboxylic acid [1-methyl-5-(1-methyl-piperidin-4-ylcarbamoyl)-1H-pyrazol-4-yl]-amide,
6-Cyclopropyl-3-(pyrimidin-5-ylamino)-pyrazine-2-carboxylic acid [5-methylcarbamoyl-1-(tetrahydro-furan-2-ylmethyl)-1H-pyrazol-4-yl]-amide,
6-Cyclopropyl-3-(pyrimidin-5-ylamino)-pyrazine-2-carboxylic acid [5-(2-hydroxy-2-methyl-propylcarbamoyl)-1-(tetrahydro-furan-2-ylmethyl)-1H-pyrazol-4-yl]-amide,
6-Cyclopropyl-3-(pyrimidin-5-ylamino)-pyrazine-2-carboxylic acid {5-[(2-fluoro-ethyl)-methyl-carbamoyl]-1-methyl-1H-pyrazol-4-yl}-amide,
6-Cyclopropyl-3-(pyrimidin-5-ylamino)-pyrazine-2-carboxylic acid {1-methyl-5-[methyl-(1-methyl-pyrrolidin-3-yl)-carbamoyl]-1H-pyrazol-4-yl}-amide,
6-Cyclopropyl-3-(pyrimidin-5-ylamino)-pyrazine-2-carboxylic acid [5-methylcarbamoyl-1-(tetrahydro-furan-3-yl)-1H-pyrazol-4-yl]-amide,
6-Cyclopropyl-3-(pyrimidin-5-ylamino)-pyrazine-2-carboxylic acid [1-methyl-5-(pyrrolidin-3-ylcarbamoyl)-1H-pyrazol-4-yl]-amide,
6-Cyclopropyl-3-(pyrimidin-5-ylamino)-pyrazine-2-carboxylic acid (1-methyl-5-{[(S)-1-(tetrahydro-furan-2-yl)methyl]-carbamoyl}-1H-pyrazol-4-yl)-amide,
6-Cyclopropyl-3-(pyrimidin-5-ylamino)-pyrazine-2-carboxylic acid (1-methyl-5-{[(R)-1-(tetrahydro-furan-2-yl)methyl]-carbamoyl}-1H-pyrazol-4-yl)-amide,
6-Cyclopropyl-3-(pyrimidin-5-ylamino)-pyrazine-2-carboxylic acid {1-methyl-5-[methyl-(tetrahydro-furan-2-ylmethyl)-carbamoyl]-1H-pyrazol-4-yl}-amide,
6-Methoxy-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-(2-hydroxy-ethyl)-5-methylcarbamoyl-1H-pyrazol-4-yl]-amide,
3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide,
3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid {1-methyl-5-[(S)-(tetrahydro-furan-3-yl)carbamoyl]-1H-pyrazol-4-yl}-amide,
6-Cyclopropyl-3-(pyrimidin-5-ylamino)-pyrazine-2-carboxylic acid {1-methyl-5-[(R)-(tetrahydro-furan-3-yl)carbamoyl]-1H-pyrazol-4-yl}-amide,
6-Cyclopropyl-3-(pyrimidin-5-ylamino)-pyrazine-2-carboxylic acid (5-methylcarbamoyl-1-oxetan-2-ylmethyl-1H-pyrazol-4-yl)-amide,
6-Cyclopropyl-3-(pyrimidin-5-ylamino)-pyrazine-2-carboxylic acid [5-(2-hydroxy-2-methyl-propylcarbamoyl)-1-oxetan-2-ylmethyl-1H-pyrazol-4-yl]-amide, 6-Cyclopropyl-3-(pyrimidin-5-ylamino)-pyrazine-2-carboxylic acid [5-methylcarbamoyl-1-(tetrahydro-furan-3-ylmethyl)-1H-pyrazol-4-yl]-amide,
6-Cyclopropyl-3-(pyrimidin-5-ylamino)-pyrazine-2-carboxylic acid [5-(2-hydroxy-2-methyl-propylcarbamoyl)-1-(tetrahydro-furan-3-ylmethyl)-1H-pyrazol-4-yl]-amide,
3-(Pyrimidin-5-ylamino)-6-pyrrolidin-1-yl-pyrazine-2-carboxylic acid (1-methyl-5-methylcarbamoyl-1H-pyrazol-4-yl)-amide,
6-Morpholin-4-yl-3-(pyrimidin-5-ylamino)-pyrazine-2-carboxylic acid (1-methyl-5-methylcarbamoyl-1H-pyrazol-4-yl)-amide,
6-Azetidin-1-yl-3-(pyrimidin-5-ylamino)-pyrazine-2-carboxylic acid (1-methyl-5-methylcarbamoyl-1H-pyrazol-4-yl)-amide,
6-(Ethyl-methyl-amino)-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(2-dimethylamino-ethylcarbamoyl)-1-methyl-1H-pyrazol-4-yl]-amide,
2-Cyclopropyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-methyl-5-(1-methyl-azetidin-3-ylcarbamoyl)-1H-pyrazol-4-yl]-amide,
2-Isobutyl-5-(pyrimidin-5-ylamino)-pyrimidine-4-carboxylic acid (1-methyl-5-methylcarbamoyl-1H-pyrazol-4-yl)-amide,
4-Methyl-5'-(pyrimidin-5-ylamino)-3,4,5,6-tetrahydro-2H-[1,2]bipyrazinyl-6'-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(methoxy-methyl-carbamoyl)-1-methyl-1H-pyrazol-4-yl]-amide,
6-Cyclopropyl-3-(pyrimidin-5-ylamino)-pyrazine-2-carboxylic acid [5-(isoxazolidine-2-carbonyl)-1-methyl-1H-pyrazol-4-yl]-amide,
6-Cyclopropyl-3-(pyrimidin-5-ylamino)-pyrazine-2-carboxylic acid [5-(2-hydroxy-cyclopentylcarbamoyl)-1-methyl-1H-pyrazol-4-yl]-amide,
5-(Pyrimidin-5-ylamino)-2-(2,2,2-trifluoro-ethoxy)-pyrimidine-4-carboxylic acid (1-methyl-5-methylcarbamoyl-1H-pyrazol-4-yl)-amide,
3-(Pyrimidin-5-ylamino)-6-(2,2,2-trifluoro-ethoxy)-pyrazine-2-carboxylic acid (1-methyl-5-methylcarbamoyl-1H-pyrazol-4-yl)-amide,
2-(1-Hydroxy-1-methyl-ethyl)-5-(pyrimidin-5-ylamino)-pyrimidine-4-carboxylic acid (1-methyl-5-methylcarbamoyl-1H-pyrazol-4-yl)-amide, and
6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide,
or pharmaceutically acceptable salts thereof
Particular compounds of formula (I), wherein

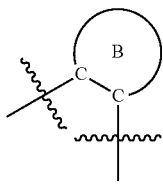

is selected from the group (1) as described above, are those selected from the group consisting of:
6-Cyclopropyl-3-(pyrimidin-5-ylamino)-pyridine-2-carboxylic acid (1-methyl-3-methylcarbamoyl-1H-pyrazol-4-yl)-amide,
6-Cyclopropyl-3-(pyrimidin-5-ylamino)-pyrazine-2-carboxylic acid (1-methyl-3-methylcarbamoyl-1H-pyrazol-4-yl)-amide,
6-Cyclopropyl-3-(pyrimidin-5-ylamino)-pyridine-2-carboxylic acid [1-(2-methoxy-ethyl)-5-methylcarbamoyl-1H-pyrazol-4-yl]-amide,
6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid,
2-Isopropyl-5-(pyrimidin-5-ylamino)-pyrimidine-4-carboxylic acid (1-methyl-3-methylcarbamoyl-1H-pyrazol-4-yl)-amide,
2-Isobutyl-5-(pyrimidin-5-ylamino)-pyrimidine-4-carboxylic acid (1-methyl-3-methylcarbamoyl-1H-pyrazol-4-yl)-amide,
6-Cyclopropyl-3-(pyrimidin-5-ylamino)-pyridine-2-carboxylic acid [3-(morpholine-4-carbonyl)-thiophen-2-yl]-amide,
6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide,
6-isobutyl-N-(1-methyl-3-(methylcarbamoyl)-1H-pyrazol-4-yl)-3-(pyrimidin-5-ylamino)pyrazine-2-carboxamide,
6-Cyclopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide,
6-Isopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-methyl-5-(3-methyl-oxetan-3-ylcarbamoyl)-1H-pyrazol-4-yl]-amide,
6-Cyclopropyl-3-(pyrimidin-5-ylamino)-pyrazine-2-carboxylic acid [5-(2,2-difluoro-ethylcarbamoyl)-1-methyl-1H-pyrazol-4-yl]-amide,
2-tert-Butyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(azetidine-1-carbonyl)-1-methyl-1H-pyrazol-4-yl]-amide,
3-(Pyrimidin-5-ylamino)-6-(tetrahydro-furan-3-yl)-pyrazine-2-carboxylic acid (1-methyl-5-methylcarbamoyl-1H-pyrazol-4-yl)-amide,
2-Isopropyl-5-(pyrimidin-5-ylamino)-pyrimidine-4-carboxylic acid (1-methyl-5-methylcarbamoyl-1H-pyrazol-4-yl)-amide,
2-Isopropyl-5-(pyridin-3-ylamino)-pyrimidine-4-carboxylic acid (1-methyl-5-methylcarbamoyl-1H-pyrazol-4-yl)-amide,
5-(5-Fluoro-pyridin-3-ylamino)-2-isopropyl-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid (5-ethylcarbamoyl-1-methyl-1H-pyrazol-4-yl)-amide,
6-Cyclopropyl-3-(pyrimidin-5-ylamino)-pyrazine-2-carboxylic acid [5-(ethyl-methyl-carbamoyl)-1-methyl-1H-pyrazol-4-yl]-amide, 3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide, 3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid {1-methyl-5-[(S)-(tetrahydro-furan-3-yl)carbamoyl]-1H-pyrazol-4-yl}-amide, 6-Cyclopropyl-3-(pyrimidin-5-ylamino)-pyrazine-2-carboxylic acid {1-methyl-5-[(R)-(tetrahydro-furan-3-yl)carbamoyl]-1H-pyrazol-4-yl}-amide, 6-Morpholin-4-yl-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [1-methyl-5-(1-methyl-azetidin-3-ylcarbamoyl)-1H-pyrazol-4-yl]-amide, 6-Cyclopropyl-3-(pyrimidin-5-ylamino)-pyrazine-2-carboxylic acid [5-(isoxazolidine-2-carbonyl)-1-methyl-1H-pyrazol-4-yl]-amide, 6-Cyclopropyl-3-(pyrimidin-5-ylamino)-pyrazine-2-carboxylic acid [5-(2-hydroxy-cyclopentylcarbamoyl)-1-methyl-1H-pyrazol-4-yl]-amide, and 6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide, or pharmaceutically acceptable salts thereof Particular compounds of formula (I), wherein

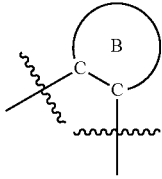

is selected from the group (1') as described above, are those selected from the group consisting of:

6-Cyclopropyl-3-(pyrimidin-5-ylamino)-pyridine-2-carboxylic acid (3-dimethylcarbamoyl-1-methyl-1H-pyrazol-4-yl)-amide, 6-Cyclopropyl-3-(pyrimidin-5-ylamino)-pyridine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid (3-carbamoyl-1-methyl-1H-pyrazol-4-yl)-amide, 6-Cyclopropyl-3-(pyrimidin-5-ylamino)-pyridine-2-carboxylic acid [3-dimethylcarbamoyl-1-(2-methoxy-ethyl)-1H-pyrazol-4-yl]-amide, 6-Cyclopropyl-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid [5-dimethylcarbamoyl-1-(2-methoxy-ethyl)-1H-pyrazol-4-yl]-amide, 6-Cyclopropyl-3-(pyrimidin-5-ylamino)-pyridine-2-carboxylic acid [3-dimethylcarbamoyl-1-(2,2,2-trifluoro-ethyl)-1H-pyrazol-4-yl]-amide, 6-Cyclopropyl-3-(pyrimidin-5-ylamino)-pyridine-2-carboxylic acid [3-methylcarbamoyl-1-(2,2,2-trifluoro-ethyl)-1H-pyrazol-4-yl]-amide, 6-Cyclopropyl-3-(pyrimidin-5-ylamino)-pyridine-2-carboxylic acid [3-methylcarbamoyl-1-(3,3,3-trifluoro-propyl)-1H-pyrazol-4-yl]-amide, 6-Cyclopropyl-3-(pyrimidin-5-ylamino)-pyridine-2-carboxylic acid [5-methylcarbamoyl-1-(3,3,3-trifluoro-propyl)-1H-pyrazol-4-yl]-amide, 6-Cyclopropyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-3-(pyrimidin-5-ylamino)-pyridine-2-carboxylic acid (1-cyclopropylmethyl-3-methylcarbamoyl-1H-pyrazol-4-yl)-amide, 6-Cyclopropyl-3-(pyrimidin-5-ylamino)-pyridine-2-carboxylic acid (1-cyclopropylmethyl-5-methylcarbamoyl-1H-pyrazol-4-yl)-amide, 6-Cyclopropyl-3-(pyrimidin-5-ylamino)-pyridine-2-carboxylic acid [1-methyl-3-(morpholine-4-carbonyl)-1-pyrazol-4-yl]-amide, 6-Cyclopropyl-3-(pyrimidin-5-ylamino)-pyridine-2-carboxylic acid [3-(cyclopropyl-methyl-carbamoyl)-1-methyl-1H-pyrazol-4-yl]-amide, 6-Cyclopropyl-3-(pyrimidin-5-ylamino)-pyridine-2-carboxylic acid [1-methyl-3-(piperidine-1-carbonyl)-1H-pyrazol-4-yl]-amide, 6-Cyclopropyl-3-(pyrimidin-5-ylamino)-pyridine-2-carboxylic acid [3-(cyclohexyl-methyl-carbamoyl)-1-methyl-1H-pyrazol-4-yl]-amide, 6-Cyclopropyl-3-(pyrimidin-5-ylamino)-pyridine-2-carboxylic acid [1-(2-methoxy-ethyl)-3-methylcarbamoyl-1H-pyrazol-4-yl]-amide, 6-Cyclopropyl-3-(pyrimidin-5-ylamino)-pyridine-2-carboxylic acid [3-(cyclopentyl-methyl-carbamoyl)-1-methyl-1H-pyrazol-4-yl]-amide, 6-Cyclopropyl-3-(pyrimidin-5-ylamino)-pyridine-2-carboxylic acid [3-(isopropyl-methyl-carbamoyl)-1-methyl-1H-pyrazol-4-yl]-amide, 6-Cyclopropyl-3-(pyrimidin-5-ylamino)-pyridine-2-carboxylic acid [1-methyl-3-(pyrrolidine-1-carbonyl)-1H-pyrazol-4-yl]-amide, 6-Cyclopropyl-3-(pyrimidin-5-ylamino)-pyridine-2-carboxylic acid (3-methylcarbamoyl-1-phenyl-1H-pyrazol-4-yl)-amide, 6-Methoxymethyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-N-[1-methyl-3-(2-methyl-pyrrolidine-1-carbonyl)-1H-pyrazol-4-yl]-3-(pyrimidin-5-ylamino)-pyridine-2-carboximidic acid, N-(3-Cyclohexylcarbamoyl-1-methyl-1H-pyrazol-4-yl)-6-cyclopropyl-3-(pyrimidin-5-ylamino)-pyridine-2-carboximidic acid, N-[3-(Azetidine-1-carbonyl)-1-methyl-1H-pyrazol-4-yl]-6-cyclopropyl-3-(pyrimidin-5-ylamino)-pyridine-2-carboximidic acid, 6-Cyclopropyl-N-(3-cyclopropylcarbamoyl-1-methyl-1H-pyrazol-4-yl)-3-(pyrimidin-5-ylamino)-pyridine-2-carboximidic acid, 6-Cyclopropyl-N-[3-(3,3-dimethyl-pyrrolidine-1-carbonyl)-1-methyl-1H-pyrazol-4-yl]-3-(pyrimidin-5-ylamino)-pyridine-2-carboximidic acid, N-(3-Cyclobutylcarbamoyl-1-methyl-1H-pyrazol-4-yl)-6-cyclopropyl-3-(pyrimidin-5-ylamino)-pyridine-2-carboximidic acid, N-(3-Cyclopentylcarbamoyl-1-methyl-1H-pyrazol-4-yl)-6-cyclopropyl-3-(pyrimidin-5-ylamino)-pyridine-2-carboximidic acid, 6-Cyclopropyl-N-[3-(2,5-dimethyl-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3,3-difluoro-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3-dimethylamino-pyrrolidine-1-carbonyl)-1-methyl-1H-pyrazol-4-yl]-3-(pyrimidin-5-ylamino)-pyridine-2-carboximidic acid, 6-Cyclopropyl-N-{3-[(3-hydroxy-propyl)-methyl-carbamoyl]-1-methyl-1H-pyrazol-4-yl}-3-(pyrimidin-5-ylamino)-pyridine-2-carboximidic acid, 6-Cyclopropyl-N-[3-(2-hydroxy-ethylcarbamoyl)-1-methyl-1H-pyrazol-4-yl]-3-(pyrimidin-5-ylamino)-pyridine-2-carboximidic acid, 6-Cyclopropyl-N-{3-[(2-hydroxy-ethyl)-methyl-carbamoyl]-1-methyl-1H-pyrazol-4-yl}-3-(pyrimidin-5-ylamino)-pyridine-2-carboximidic acid, 6-Cyclopropyl-N-[3-(2-methoxy-1-methyl-ethylcarbamoyl)-1-methyl-1H-pyrazol-4-yl]-3-(pyrimidin-5-ylamino)-pyridine-2-carboximidic acid, 6-Cyclopropyl-N-[3-(2,3-dihydroxy-propylcarbamoyl)-1-methyl-1H-pyrazol-4-yl]-3-(pyrimidin-5-ylamino)-pyridine-2-carboximidic acid, 6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid, 6-Cyclopropyl-N-[3-(3-hydroxy-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(2-hydroxy-1-methyl-ethylcarbamoyl)-1-methyl-1H-pyrazol-4-yl]-3-(pyrimidin-5-ylamino)-pyridine-2-carboximidic acid, 6-Cyclopropyl-N-{3-[(2,3-dihydroxy-propyl)-methyl-carbamoyl]-1-methyl-1H-pyrazol-4-yl}-3-(pyrimidin-5-ylamino)-pyridine-2-carboximidic acid, 6-Cyclopropyl-N-[3-(5-hydroxy-3,6-dihydro-2H-pyrazine-1-carbonyl)-1-methyl-1H-pyrazol-4-yl]-3-(pyrimidin-5-ylamino)-pyridine-2-carboximidic acid, 6-Cyclopropyl-N-[3-(3-methoxy-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(2-hydroxymethyl-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3-hydroxy-azetidine-1-carbonyl)-1-methyl-1H-pyrazol-4-yl]-3-(pyrimidin-5-ylamino)-pyridine-2-carboximidic acid, 6-Cyclopropyl-N-[1-methyl-3-(2-oxa-6-aza-spiro[3.3]heptane-6-carbonyl)-1H-pyrazol-4-yl]-3-(pyrimidin-5-ylamino)-pyridine-2-carboximidic acid, 6-Cyclopropyl-N-[3-(2,2-dimethyl-pyrrolidine-1-carbonyl)-1-methyl-1H-pyrazol-4-yl]-3-(pyrimidin-5-ylamino)-pyridine-2-carboximidic acid, 6-Cyclopropyl-3-(pyrimidin-5-ylamino)-pyridine-2-carboxylic acid (3-dimethylcarbamoyl-1-pyridin-2-yl-1H-pyrazol-4-yl)-amide, 2-Isopropyl-5-(pyrimidin-5-ylamino)-pyrimidine-4-carboxylic acid (1-methyl-3-methylcarbamoyl-1H-pyrazol-4-yl)-amide, 2-Cyclopropyl-5-(pyrimidin-5-ylamino)-pyrimidine-4-carboxylic acid (1-methyl-3-methylcarbamoyl-1H-pyrazol-4-yl)-amide, 2-tert-Butyl-5-(pyrimidin-5-ylamino)-pyrimidine-4-carboxylic acid (1-methyl-3-methylcarbamoyl-1H-pyrazol-4-yl)-amide, 2-Isobutyl-5-(pyrimidin-5-ylamino)-pyrimidine-4-carboxylic acid (1-methyl-3-methylcarbamoyl-1H-pyrazol-4-yl)-amide, 2-Cyclohexyl-5-(pyrimidin-5-ylamino)-pyrimidine-4-carboxylic acid (1-methyl-3-methylcarbamoyl-1H-pyrazol-4-yl)-amide, 6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide, N-(1-methyl-3-(methylcarbamoyl)-1H-pyrazol-4-yl)-3-(pyrimidin-5-ylamino)-6-(tetrahydrofuran-2-yl)pyrazine-2-carboxamide, N-(1-methyl-3-(methylcarbamoyl)-1H-pyrazol-4-yl)-3-(pyrimidin-5-ylamino)-6-(tetrahydrofuran-3-yl)pyrazine-2-carboxamide, N-(1-methyl-3-(methylcarbamoyl)-1H-pyrazol-4-yl)-3-(pyrimidin-5-ylamino)-6-(tetrahydrofuran-2-yl)picolinamide, 6-isobutyl-N-(1-methyl-3-(methylcarbamoyl)-1H-pyrazol-4-yl)-3-(pyrimidin-5-ylamino)pyrazine-2-carboxamide, 6-cyclopropyl-N-(1-ethyl-3-(methylcarbamoyl)-1H-pyrazol-4-yl)-3-(pyrimidin-5-ylamino)pyrazine-2-carboxamide, 6-cyclopropyl-N-(1-ethyl-3-((tetrahydro furan-2-yl)methylcarbamoyl)-1H-pyrazol-4-yl)-3-(pyrimidin-5-ylamino)pyrazine-2-carboxamide, 6-cyclopropyl-N-(1-methyl-3-((tetrahydro furan-2-yl)methylcarbamoyl)-1H-pyrazol-4-yl)-3-(pyrimidin-5-ylamino)pyrazine-2-carboxamide, 6-cyclopropyl-N-(3-((2-hydroxy-2-methylpropyl)(methyl)carbamoyl)-1-methyl-1H-pyrazol-4-yl)-3-(pyrimidin-5-ylamino)pyrazine-2-carboxamide, N-(3-(2-hydroxy-2-methylpropylcarbamoyl)-1-methyl-1H-pyrazol-4-yl)-2-methyl-5-(pyrimidin-5-ylamino)pyrimidine-4-carboxamide, 6-(1-Hydroxy-ethyl)-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide, or pharmaceutically acceptable salts thereof Particular compounds of formula (I), wherein

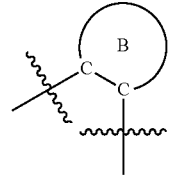

is selected from the group (1') as described above, are those selected from the group consisting of:

6-Cyclopropyl-3-(pyrimidin-5-ylamino)-pyridine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid,
2-Isopropyl-5-(pyrimidin-5-ylamino)-pyrimidine-4-carboxylic acid (1-methyl-3-methylcarbamoyl-1H-pyrazol-4-yl)-amide,
2-Isobutyl-5-(pyrimidin-5-ylamino)-pyrimidine-4-carboxylic acid (1-methyl-3-methylcarbamoyl-1H-pyrazol-4-yl)-amide,
6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide,
6-isobutyl-N-(1-methyl-3-(methylcarbamoyl)-1H-pyrazol-4-yl)-3-(pyrimidin-5-ylamino)pyrazine-2-carboxamide,
6-Cyclopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide,
or pharmaceutically acceptable salts thereof.
Particular compounds of formula (I), wherein

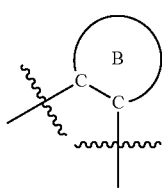

is selected from the group (1') as described above, are those selected from the group consisting of:
6-Cyclopropyl-3-(pyrimidin-5-ylamino)-pyridine-2-carboxylic acid (4-methylcarbamoyl-[1,2,3]thiadiazol-5-yl)-amide,
6-Cyclopropyl-3-(pyrimidin-5-ylamino)-pyridine-2-carboxylic acid (4-methylcarbamoyl-2-phenyl-thiazol-5-yl)-amide,
6-Cyclopropyl-3-(pyrimidin-5-ylamino)-pyridine-2-carboxylic acid (4-methylcarbamoyl-2-pyridin-2-yl-thiazol-5-yl)-amide,
6-Cyclopropyl-3-(pyrimidin-5-ylamino)-pyridine-2-carboxylic acid (3-cyclopropylcarbamoyl-thiophen-2-yl)-amide,
6-Cyclopropyl-3-(pyrimidin-5-ylamino)-pyridine-2-carboxylic acid [3-(morpholine-4-carbonyl)-thiophen-2-yl]-amide, and
6-Cyclopropyl-3-(pyrimidin-5-ylamino)-pyridine-2-carboxylic acid [5-isopropyl-3-(morpholine-4-carbonyl)-thiophen-2-yl]-amide,
or pharmaceutically acceptable salts thereof
Particular compounds of formula (I), wherein

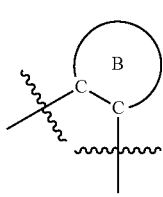

is selected from the group (1') as described above, are those selected from the group consisting of:
6-Cyclopropyl-3-(pyrimidin-5-ylamino)-pyridine-2-carboxylic acid [3-(morpholine-4-carbonyl)-thiophen-2-yl]-amide,
or pharmaceutically acceptable salts thereof.

A particular embodiment of the present invention relates to compounds of formula (I) as described above, wherein

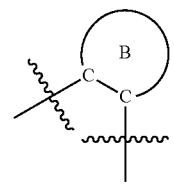

is selected from the group (2) consisting of:

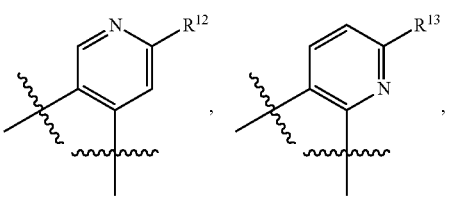

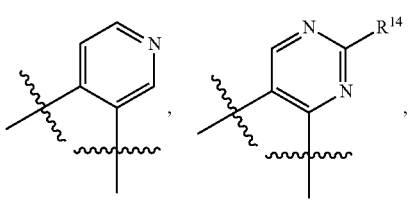

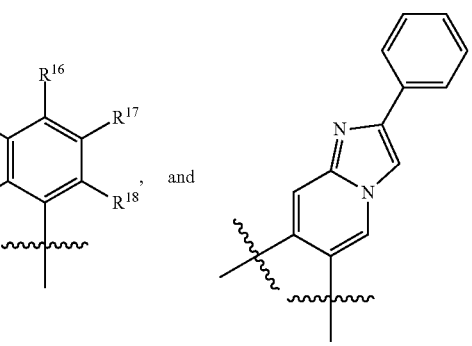

more specifically the group consisting of:

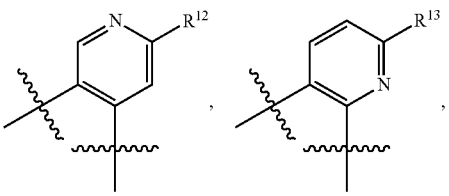

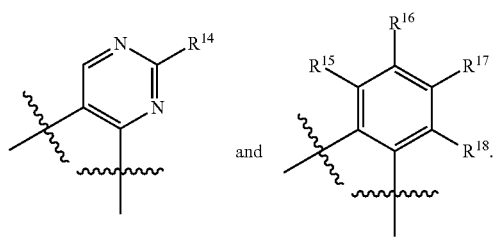

wherein

R[12] is hydrogen or halogen, more specifically hydrogen;

R[13] is hydrogen, lower alkyl, lower-alkoxy-lower-alkyl, cycloalkyl or tetrahydrofuranyl, more specifically hydrogen, methyl or cyclopropyl;

R[14] is hydrogen or lower alkyl, more specifically hydrogen;

R[15] is hydrogen or halogen, more specifically hydrogen;

R[16] is hydrogen, halogen or diethylaminocarbonyl, more specifically fluoro;

R[17] is hydrogen, halogen, lower alkyl, lower alkoxy, lower haloalkyl, cyano, 2-hydroxy-ethoxy, 2-methoxy-ethoxy, 2-hydroxy-2-methyl-propoxy, 2-(hydroxycarbonyl)ethyl, 2-ethoxycarbonyl-ethyl, methylcarbamoylmethoxy or acetylamino, more specifically fluoro; and R[18] is hydrogen, halogen, lower alkyl or lower alkoxy, more specifically hydrogen.

Another particular embodiment of the present invention relates to compounds of formula (I) as described above, wherein

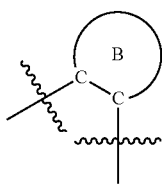

is selected from the group (2') consisting of:

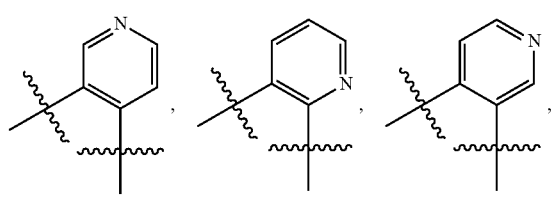

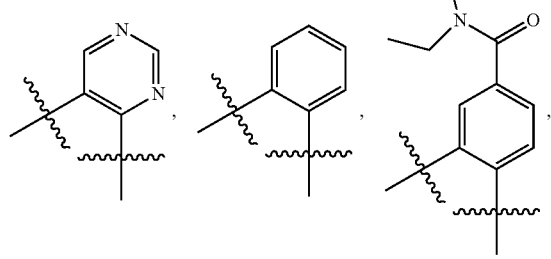

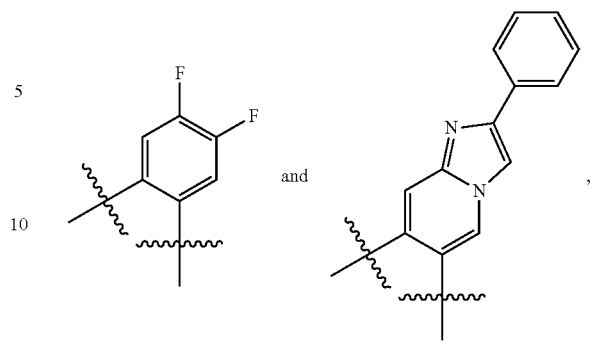

more specifically the group consisting of:

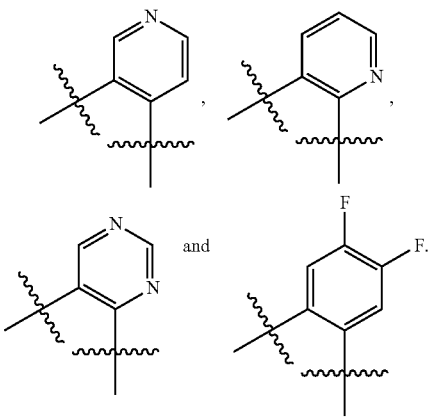

A particular embodiment of the present invention relates to compounds of formula (I) as described above, wherein

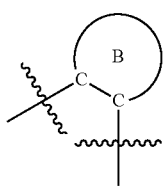

is selected from the group (2) as described above, and wherein R[1] is lower alkyl or cycloalkyl, more specifically isopropyl, isobutyl, tert-butyl or cyclopropyl, yet more specifically isopropyl, tert-butyl or cyclopropyl.

Another particular embodiment of the present invention relates to compounds of formula (I) as described above, wherein

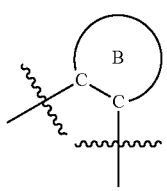

is selected from the group (2') as described above, and wherein $R^1$ is lower alkyl or cycloalkyl, more specifically isopropyl, tert-butyl or cyclopropyl, yet more specifically cyclopropyl.

A particular embodiment of the present invention relates to compounds of formula (I) as described above, wherein

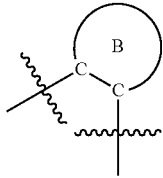

is selected from the group (2) as described above, and wherein $R^5$ and $R^6$ are independently hydrogen, lower alkyl, lower hydroxyalkyl, lower haloalkyl, lower-alkoxy-lower-alkyl, cycloalkyl or heterocyclyl, wherein said lower alkyl is optionally substituted by heterocyclyl, and wherein said heterocyclyl is optionally substituted by lower alkyl, more specifically hydrogen, methyl, tetrahydrofuran-2-yl-methyl, ethyl, 2-hydroxy-1-methyl-ethyl, 2-hydroxy-1,1-dimethyl-ethyl, 2-methoxyethyl, 2-methoxy-1-methyl-ethyl, 2-hydroxy-ethyl, 2-isopropoxy-ethyl, 2,2,2,-trifluoro-ethyl, isopropyl, 2,3-dihydroxy-propyl, 3-hydroxy-propyl, 2-hydroxy-2-methyl-propyl, 2-methoxy-2-methyl-propyl, 3-methoxy-2,2-dimethyl-propyl, cyclopropyl, cyclobutyl, cyclopentyl, cyclohexyl, tetrahydrofuran-3-yl, oxetan-3-yl, 3-methyl-oxetan-3-yl or tetrahydro-pyran-4-yl, yet more specifically hydrogen, methyl, 2-methoxy-1-methyl-ethyl, 2-hydroxy-2-methyl-propyl, 2-methoxy-2-methyl-propyl or cyclopropyl, or $R^5$ and $R^6$, together with the nitrogen atom to which they are attached, form an azetidine, pyrrolidine, piperidine, piperazine or 2-oxa-6-aza-spiro[3.3]heptane ring, wherein each of said azetidine, pyrrolidine, piperazine or 2-oxa-6-aza-spiro[3.3]heptane ring is optionally substituted by 1 or 2 substituents independently selected from the group consisting of hydroxyl, halogen, lower alkyl, lower hydroxyalkyl, lower alkoxy, oxo and amino, and wherein said amino is substituted by 2 lower alkyl; $R^5$ and $R^6$ more specifically forming an optionally substituted heterocyclyl or spiro-heterocyclyl ring selected from the group consisting of azetidin-1-yl, 3-hydroxy-azetidin-1-yl, 3,3-difluoro-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, piperidin-1-yl, 2-methyl-piperidin-1-yl, 3-oxo-piperazin-1-yl, 3-methyl-morpholin-4-yl and 2-oxa-6-aza-spiro[3.3]heptan-6-yl.

Yet another particular embodiment of the present invention relates to compounds of formula (I) as described above, wherein

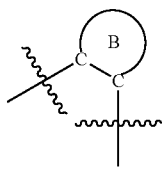

is selected from the group (2') as described above, and wherein $R^5$ and $R^6$ are independently hydrogen, lower alkyl optionally substituted by heterocyclyl, lower hydroxyalkyl, lower-alkoxy-lower-alkyl, cycloalkyl or heterocyclyl optionally substituted by lower alkyl, more specifically hydrogen, methyl, tetrahydrofuran-2-yl-methyl, 2-hydroxy-1-methyl-ethyl, 2-hydroxy-1,1-dimethyl-ethyl, 2-methoxyethyl, 2-methoxy-1-methyl-ethyl, 2-hydroxy-ethyl, 2-isopropoxy-ethyl, 2,3-dihydroxy-propyl, 3-hydroxy-propyl, 2-hydroxy-2-methyl-propyl, 2-methoxy-2-methyl-propyl, 3-methoxy-2,2-dimethyl-propyl, cyclopropyl, cyclobutyl, cyclopentyl, cyclohexyl, tetrahydrofuran-3-yl, oxetan-3-yl or 3-methyl-oxetan-3-yl, yet more specifically hydrogen, 2-methoxy-1-methyl-ethyl, 2-hydroxy-2-methyl-propyl, 2-methoxy-2-methyl-propyl or cyclopropyl, or $R^5$ and $R^6$, together with the nitrogen atom to which they are attached, form an azetidine, pyrrolidine, piperazine or 2-oxa-6-aza-spiro[3.3]heptane ring, wherein each of said azetidine, pyrrolidine, piperazine or 2-oxa-6-aza-spiro [3.3]heptane ring is optionally substituted by 1 or 2 substituents independently selected from the group consisting of hydroxyl, halogen, lower alkyl, lower hydroxyalkyl, lower alkoxy, oxo and amino substituted by 2 lower alkyl; $R^5$ and $R^6$ more specifically forming an optionally substituted heterocyclyl or spiro-heterocyclyl ring selected from the group consisting of azetidin-1-yl, 3-hydroxy-azetidin-1-yl, 3,3-difluoro-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, 3-oxo-piperazin-1-yl and 2-oxa-6-aza-spiro[3.3]heptan-6-yl.

Particular compounds of formula (I), wherein

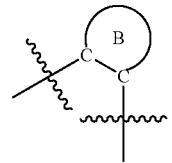

is selected from the group (2) as described above, are those selected from the group consisting of:
6-Cyclopropyl-3-(pyrimidin-5-ylamino)-pyridine-2-carboxylic acid [4-(pyrrolidine-1-carbonyl)-pyridin-3-yl]-amide,
6-Cyclopropyl-3-(pyrimidin-5-ylamino)-pyridine-2-carboxylic acid (4-dimethylcarbamoyl-pyridin-3-yl)-amide,
6-Cyclopropyl-3-(pyrimidin-5-ylamino)-pyridine-2-carboxylic acid (4-methylcarbamoyl-pyridin-3-yl)-amide,
6-Cyclopropyl-3-(pyrimidin-5-ylamino)-pyridine-2-carboxylic acid (2-methylcarbamoyl-phenyl)-amide,
6-Cyclopropyl-N-[4-(3-dimethylamino-pyrrolidine-1-carbonyl)-pyridin-3-yl]-3-(pyrimidin-5-ylamino)-pyridine-2-carboximidic acid,
6-Cyclopropyl-N-[4-(2-methyl-pyrrolidine-1-carbonyl)-pyridin-3-yl]-3-(pyrimidin-5-ylamino)-pyridine-2-carboximidic acid,
6-Cyclopropyl-N-[4-(3,3-difluoro-pyrrolidine-1-carbonyl)-pyridin-3-yl]-3-(pyrimidin-5-ylamino)-pyridine-2-carboximidic acid,
6-Cyclopropyl-N-(4-cyclopropylcarbamoyl-pyridin-3-yl)-3-(pyrimidin-5-ylamino)-pyridine-2-carboximidic acid,
N-(4-Cyclobutylcarbamoyl-pyridin-3-yl)-6-cyclopropyl-3-(pyrimidin-5-ylamino)-pyridine-2-carboximidic acid, 6-Cyclopropyl-N-[4-(2,5-dimethyl-pyrrolidine-1-carbonyl)-pyridin-3-yl]-3-(pyrimidin-5-ylamino)-pyridine-2-carboximidic acid,
6-Cyclopropyl-N-[4-(5-hydroxy-3,6-dihydro-2H-pyrazine-1-carbonyl)-pyridin-3-yl]-3-(pyrimidin-5-ylamino)-pyridine-2-carboximidic acid,
N-(4-Cyclopentylcarbamoyl-pyridin-3-yl)-6-cyclopropyl-3-(pyrimidin-5-ylamino)-pyridine-2-carboximidic acid,
6-Cyclopropyl-N-[4-(3-methoxy-pyrrolidine-1-carbonyl)-pyridin-3-yl]-3-(pyrimidin-5-ylamino)-pyridine-2-carboximidic acid,
6-Cyclopropyl-N-[4-(3,3-dimethyl-pyrrolidine-1-carbonyl)-pyridin-3-yl]-3-(pyrimidin-5-ylamino)-pyridine-2-carboximidic acid,
6-Cyclopropyl-N-[4-(2-hydroxy-1-methyl-ethylcarbamoyl)-pyridin-3-yl]-3-(pyrimidin-5-ylamino)-pyridine-2-carboximidic acid,
N-[4-(Azetidine-1-carbonyl)-pyridin-3-yl]-6-cyclopropyl-3-(pyrimidin-5-ylamino)-pyridine-2-carboximidic acid,
6-Cyclopropyl-N-[4-(2-hydroxy-ethylcarbamoyl)-pyridin-3-yl]-3-(pyrimidin-5-ylamino)-pyridine-2-carboximidic acid,
6-Cyclopropyl-N-[4-(2,3-dihydroxy-propylcarbamoyl)-pyridin-3-yl]-3-(pyrimidin-5-ylamino)-pyridine-2-carboximidic acid,
6-Cyclopropyl-N-[4-(2-hydroxy-2-methyl-propylcarbamoyl)-pyridin-3-yl]-3-(pyrimidin-5-ylamino)-pyridine-2-carboximidic acid,
6-Cyclopropyl-N-{4-[(3-hydroxy-propyl)-methyl-carbamoyl]-pyridin-3-yl}-3-(pyrimidin-5-ylamino)-pyridine-2-carboximidic acid,
6-Cyclopropyl-N-[4-(2-methoxy-1-methyl-ethylcarbamoyl)-pyridin-3-yl]-3-(pyrimidin-5-ylamino)-pyridine-2-carboximidic acid,
6-Cyclopropyl-N-{4-[(2-hydroxy-ethyl)-methyl-carbamoyl]-pyridin-3-yl}-3-(pyrimidin-5-ylamino)-pyridine-2-carboximidic acid,
N-(4-Cyclohexylcarbamoyl-pyridin-3-yl)-6-cyclopropyl-3-(pyrimidin-5-ylamino)-pyridine-2-carboximidic acid,
6-Cyclopropyl-N-[4-(3,3-difluoro-azetidine-1-carbonyl)-pyridin-3-yl]-3-(pyrimidin-5-ylamino)-pyridine-2-carboximidic acid,
6-Cyclopropyl-N-[4-(2-hydroxymethyl-pyrrolidine-1-carbonyl)-pyridin-3-yl]-3-(pyrimidin-5-ylamino)-pyridine-2-carboximidic acid,
7-{[6-Cyclopropyl-3-(pyrimidin-5-ylamino)-pyridine-2-carbonyl]-amino}-2-phenyl-imidazo[1,2-a]pyridine-6-carboxylic acid methylamide,
6-Cyclopropyl-N-[4-(3-hydroxy-azetidine-1-carbonyl)-pyridin-3-yl]-3-(pyrimidin-5-ylamino)-pyridine-2-carboximidic acid,
6-Cyclopropyl-N-[4-(2,2-dimethyl-pyrrolidine-1-carbonyl)-pyridin-3-yl]-3-(pyrimidin-5-ylamino)-pyridine-2-carboximidic acid,
6-Cyclopropyl-N-{4-[(2,3-dihydroxy-propyl)-methyl-carbamoyl]-pyridin-3-yl}-3-(pyrimidin-5-ylamino)-pyridine-2-carboximidic acid,
6-Cyclopropyl-N-[4-(3-hydroxy-pyrrolidine-1-carbonyl)-pyridin-3-yl]-3-(pyrimidin-5-ylamino)-pyridine-2-carboximidic acid,
6-Cyclopropyl-N-[4-(2-oxa-6-aza-spiro[3.3]heptane-6-carbonyl)-pyridin-3-yl]-3-(pyrimidin-5-ylamino)-pyridine-2-carboximidic acid,
2-Isopropyl-5-(pyrimidin-5-ylamino)-pyrimidine-4-carboxylic acid [4-(2-hydroxy-2-methyl-propylcarbamoyl)-pyridin-3-yl]-amide,
2-tert-Butyl-5-(pyrimidin-5-ylamino)-pyrimidine-4-carboxylic acid [4-(2-hydroxy-2-methyl-propylcarbamoyl)-pyridin-3-yl]-amide,
2-(2-tert-butyl-5-(pyrimidin-5-ylamino)pyrimidine-4-carboxamido)-N4,N4-diethyl-N1-methylterephthalamide,
5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide,
6-Cyclopropyl-3-(pyrimidin-5-ylamino)-pyrazine-2-carboxylic acid [2-(2-hydroxy-2-methyl-propylcarbamoyl)-pyridin-3-yl]-amide,
6-Cyclopropyl-3-(pyrimidin-5-ylamino)-pyrazine-2-carboxylic acid [4-(2-isopropoxy-ethylcarbamoyl)-pyridin-3-yl]-amide,
6-Cyclopropyl-3-(pyrimidin-5-ylamino)-pyrazine-2-carboxylic acid [4-(tetrahydro-furan-3-ylcarbamoyl)-pyridin-3-yl]-amide,
6-Cyclopropyl-3-(pyrimidin-5-ylamino)-pyrazine-2-carboxylic acid {4-[(tetrahydro-furan-2-ylmethyl)-carbamoyl]-pyridin-3-yl}-amide,
6-Cyclopropyl-3-(pyrimidin-5-ylamino)-pyrazine-2-carboxylic acid [4-(2-hydroxy-2-methyl-propylcarbamoyl)-pyridin-3-yl]-amide,
6-Cyclopropyl-3-(pyrimidin-5-ylamino)-pyrazine-2-carboxylic acid [4-(oxetan-3-ylcarbamoyl)-pyridin-3-yl]-amide,
6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide,
6-Cyclopropyl-3-(pyrimidin-5-ylamino)-pyrazine-2-carboxylic acid [4-(2-methoxy-2-methyl-propylcarbamoyl)-pyridin-3-yl]-amide,
6-Cyclopropyl-3-(pyrimidin-5-ylamino)-pyrazine-2-carboxylic acid [4-(3-methoxy-2,2-dimethyl-propylcarbamoyl)-pyridin-3-yl]-amide,
6-cyclopropyl-N-(2-((2-methoxyethyl)(methyl)carbamoyl)pyridin-3-yl)-3-(pyrimidin-5-ylamino)pyrazine-2-carboxamide,
5-(6-cyclopropyl-3-(pyrimidin-5-ylamino)pyrazine-2-carboxamido)-N-(2-methoxyethyl)-N-methylpyrimidine-4-carboxamide,
6-cyclopropyl-N-(3-(2-hydroxy-2-methylpropylcarbamoyl)pyridin-4-yl)-3-(pyrimidin-5-ylamino)pyrazine-2-carboxamide,
6-Cyclopropyl-3-(pyrimidin-5-ylamino)-pyrazine-2-carboxylic acid [4-(3-methyl-oxetan-3-ylcarbamoyl)-pyridin-3-yl]-amide,
5-(6-cyclopropyl-3-(pyrimidin-5-ylamino)pyrazine-2-carboxamido)-N-(2-hydroxy-2-methylpropyl)-N-methylpyrimidine-4-carboxamide,
6-cyclopropyl-N-(2-((2-hydroxy-2-methylpropyl)(methyl)carbamoyl)pyridin-3-yl)-3-(pyrimidin-5-ylamino)pyrazine-2-carboxamide,
6-Cyclopropyl-3-(pyrimidin-5-ylamino)-pyrazine-2-carboxylic acid (4-methylcarbamoyl-pyridin-3-yl)-amide,
6-Cyclopropyl-3-(pyrimidin-5-ylamino)-pyrazine-2-carboxylic acid [4-(2-hydroxy-1,1-dimethyl-ethylcarbamoyl)-pyridin-3-yl]-amide,
6-Cyclopropyl-3-(pyrimidin-5-ylamino)-pyrazine-2-carboxylic acid (2-methylcarbamoyl-pyridin-3-yl)-amide,
6-Cyclopropyl-3-(pyrimidin-5-ylamino)-pyrazine-2-carboxylic acid (2-dimethylcarbamoyl-pyridin-3-yl)-amide,
6-Cyclopropyl-3-(pyrimidin-5-ylamino)-pyrazine-2-carboxylic acid (6-cyclopropyl-2-methylcarbamoyl-pyridin-3-yl)-amide, 6-Cyclopropyl-3-(pyrimidin-5-ylamino)-pyrazine-2-carboxylic acid [6-cyclopropyl-2-(2-hydroxy-2-methyl-propylcarbamoyl)-pyridin-3-yl]-amide,
6-Cyclopropyl-3-(pyrimidin-5-ylamino)-pyrazine-2-carboxylic acid [2-methylcarbamoyl-6-(tetrahydro-furan-2-yl)-pyridin-3-yl]-amide,
6-Cyclopropyl-3-(pyrimidin-5-ylamino)-pyrazine-2-carboxylic acid [2-(2-hydroxy-2-methyl-propylcarbamoyl)-6-(tetrahydro-furan-2-yl)-pyridin-3-yl]-amide,
6-Cyclopropyl-3-(pyrimidin-5-ylamino)-pyrazine-2-carboxylic acid (6-ethyl-2-methylcarbamoyl-pyridin-3-yl)-amide,
6-Cyclopropyl-3-(pyrimidin-5-ylamino)-pyrazine-2-carboxylic acid [6-ethyl-2-(2-hydroxy-2-methyl-propylcarbamoyl)-pyridin-3-yl]-amide,
6-Cyclopropyl-3-(pyrimidin-5-ylamino)-pyrazine-2-carboxylic acid (6-methyl-2-methylcarbamoyl-pyridin-3-yl)-amide,
6-Cyclopropyl-3-(pyrimidin-5-ylamino)-pyrazine-2-carboxylic acid [2-(2-hydroxy-2-methyl-propylcarbamoyl)-6-methyl-pyridin-3-yl]-amide,
6-Cyclopropyl-3-(pyrimidin-5-ylamino)-pyrazine-2-carboxylic acid (3-methoxy-2-methylcarbamoyl-phenyl)-amide,
6-Cyclopropyl-3-(pyrimidin-5-ylamino)-pyrazine-2-carboxylic acid [2-(azetidine-1-carbonyl)-pyridin-3-yl]-amide,
6-Cyclopropyl-3-(pyrimidin-5-ylamino)-pyrazine-2-carboxylic acid [2-(piperidine-1-carbonyl)-pyridin-3-yl]-amide,
6-Cyclopropyl-3-(pyrimidin-5-ylamino)-pyrazine-2-carboxylic acid (3-chloro-2-methylcarbamoyl-phenyl)-amide,
6-Cyclopropyl-3-(pyrimidin-5-ylamino)-pyrazine-2-carboxylic acid [2-(pyrrolidine-1-carbonyl)-pyridin-3-yl]-amide,
6-Cyclopropyl-3-(pyrimidin-5-ylamino)-pyrazine-2-carboxylic acid [2-(ethyl-methyl-carbamoyl)-pyridin-3-yl]-amide,
5-{[6-Cyclopropyl-3-(pyrimidin-5-ylamino)-pyrazine-2-carbonyl]-amino}-pyrimidine-4-carboxylic acid ethyl-methyl-amide,
5-{[6-Cyclopropyl-3-(pyrimidin-5-ylamino)-pyrazine-2-carbonyl]-amino}-pyrimidine-4-carboxylic acid dimethylamide,
6-Cyclopropyl-3-(pyrimidin-5-ylamino)-pyrazine-2-carboxylic acid (2-dimethylcarbamoyl-3-methoxy-phenyl)-amide,
6-Cyclopropyl-3-(pyrimidin-5-ylamino)-pyrazine-2-carboxylic acid [2-(2-hydroxy-2-methyl-propylcarbamoyl)-4-isopropyl-phenyl]-amide,
6-Cyclopropyl-3-(pyrimidin-5-ylamino)-pyrazine-2-carboxylic acid (4-isopropyl-2-methylcarbamoyl-phenyl)-amide,
6-Cyclopropyl-3-(pyrimidin-5-ylamino)-pyrazine-2-carboxylic acid (6-methoxymethyl-2-methylcarbamoyl-pyridin-3-yl)-amide,
6-Cyclopropyl-3-(pyrimidin-5-ylamino)-pyrazine-2-carboxylic acid [2-(2-hydroxy-2-methyl-propylcarbamoyl)-6-methoxymethyl-pyridin-3-yl]-amide,
6-Cyclopropyl-3-(pyrimidin-5-ylamino)-pyrazine-2-carboxylic acid [4-(azetidine-1-carbonyl)-pyrimidin-5-yl]-amide,
6-Cyclopropyl-3-(pyrimidin-5-ylamino)-pyrazine-2-carboxylic acid [4-(piperidine-1-carbonyl)-pyrimidin-5-yl]-amide,
6-Cyclopropyl-3-(pyrimidin-5-ylamino)-pyrazine-2-carboxylic acid [2-(2-hydroxy-2-methyl-propylcarbamoyl)-4-(2-methoxy-ethoxy)-phenyl]-amide,
6-Cyclopropyl-3-(pyrimidin-5-ylamino)-pyrazine-2-carboxylic acid [4-(2-methoxy-ethoxy)-2-methylcarbamoyl-phenyl]-amide,
6-Cyclopropyl-3-(pyrimidin-5-ylamino)-pyrazine-2-carboxylic acid [4-(2-hydroxy-ethoxy)-2-(2-hydroxy-2-methyl-propylcarbamoyl)-phenyl]-amide,
6-Cyclopropyl-3-(pyrimidin-5-ylamino)-pyrazine-2-carboxylic acid [4-(2-hydroxy-ethoxy)-2-methylcarbamoyl-phenyl]-amide,
5-{[6-Cyclopropyl-3-(pyrimidin-5-ylamino)-pyrazine-2-carbonyl]-amino}-pyrimidine-4-carboxylic acid methylamide,
6-Cyclopropyl-3-(pyrimidin-5-ylamino)-pyrazine-2-carboxylic acid [4-(pyrrolidine-1-carbonyl)-pyrimidin-5-yl]-amide,
6-Cyclopropyl-3-(pyrimidin-5-ylamino)-pyrazine-2-carboxylic acid (2-ethylcarbamoyl-pyridin-3-yl)-amide,
6-Cyclopropyl-3-(pyrimidin-5-ylamino)-pyrazine-2-carboxylic acid (2-isopropylcarbamoyl-pyridin-3-yl)-amide,
6-Cyclopropyl-3-(pyrimidin-5-ylamino)-pyrazine-2-carboxylic acid (3-methyl-2-methylcarbamoyl-phenyl)-amide,
6-Cyclopropyl-3-(pyrimidin-5-ylamino)-pyrazine-2-carboxylic acid (4-methoxy-2-methylcarbamoyl-phenyl)-amide,
6-Cyclopropyl-3-(pyrimidin-5-ylamino)-pyrazine-2-carboxylic acid {2-[methyl-(tetrahydro-pyran-4-yl)-carbamoyl]-pyridin-3-yl}-amide,
6-Cyclopropyl-3-(pyrimidin-5-ylamino)-pyrazine-2-carboxylic acid {2-[methyl-(2,2,2-trifluoro-ethyl)-carbamoyl]-pyridin-3-yl}-amide,
6-Cyclopropyl-3-(pyrimidin-5-ylamino)-pyrazine-2-carboxylic acid [2-(cyclopropyl-methyl-carbamoyl)-pyridin-3-yl]-amide,
6-Cyclopropyl-3-(pyrimidin-5-ylamino)-pyrazine-2-carboxylic acid [2-(2-methyl-pyrrolidine-1-carbonyl)-pyridin-3-yl]-amide,
6-Cyclopropyl-3-(pyrimidin-5-ylamino)-pyrazine-2-carboxylic acid [2-(2-methyl-piperidine-1-carbonyl)-pyridin-3-yl]-amide,
6-Cyclopropyl-3-(pyrimidin-5-ylamino)-pyrazine-2-carboxylic acid [2-(3-methyl-morpholine-4-carbonyl)-pyridin-3-yl]-amide,
6-Cyclopropyl-3-(pyrimidin-5-ylamino)-pyrazine-2-carboxylic acid (6-chloro-4-methylcarbamoyl-pyridin-3-yl)-amide,
6-Cyclopropyl-3-(pyrimidin-5-ylamino)-pyrazine-2-carboxylic acid [6-chloro-4-(2-hydroxy-2-methyl-propylcarbamoyl)-pyridin-3-yl]-amide,
6-Cyclopropyl-3-(pyrimidin-5-ylamino)-pyrazine-2-carboxylic acid (4-cyano-2-methylcarbamoyl-phenyl)-amide,
6-Cyclopropyl-3-(pyrimidin-5-ylamino)-pyrazine-2-carboxylic acid [4-cyano-2-(2-hydroxy-2-methyl-propylcarbamoyl-phenyl]-amide,
6-Cyclopropyl-3-(pyrimidin-5-ylamino)-pyrazine-2-carboxylic acid (3,4-dimethyl-2-methylcarbamoyl-phenyl)-amide,
6-Cyclopropyl-3-(pyrimidin-5-ylamino)-pyrazine-2-carboxylic acid (6-cyclopropyl-2-dimethylcarbamoyl-pyridin-3-yl)-amide,
6-Cyclopropyl-3-(pyrimidin-5-ylamino)-pyrazine-2-carboxylic acid (2-dimethylcarbamoyl-6-methyl-pyridin-3-yl)-amide, 6-Cyclopropyl-3-(pyrimidin-5-ylamino)-pyrazine-2-carboxylic acid {2-[(2-hydroxy-ethyl)-methyl-carbamoyl]-pyridin-3-yl}-amide,
6-Cyclopropyl-3-(pyrimidin-5-ylamino)-pyrazine-2-carboxylic acid {2-[ethyl-(2-hydroxy-ethyl)-carbamoyl]-pyridin-3-yl}-amide,
6-Cyclopropyl-3-(pyrimidin-5-ylamino)-pyrazine-2-carboxylic acid [2-(2-hydroxy-ethylcarbamoyl)-pyridin-3-yl]-amide,
6-Cyclopropyl-3-(pyrimidin-5-ylamino)-pyrazine-2-carboxylic acid [2-(azetidine-1-carbonyl)-6-cyclopropyl-pyridin-3-yl]-amide,
6-Cyclopropyl-3-(pyrimidin-5-ylamino)-pyrazine-2-carboxylic acid [2-(2-hydroxy-1,1-dimethyl-ethylcarbamoyl)-pyridin-3-yl]-amide,
6-Cyclopropyl-3-(pyrimidin-5-ylamino)-pyrazine-2-carboxylic acid (4-acetylamino-2-methylcarbamoyl-phenyl)-amide,
6-Cyclopropyl-3-(pyrimidin-5-ylamino)-pyrazine-2-carboxylic acid [2-(3-methyl-oxetan-3-ylcarbonyl)-pyridin-3-yl]-amide,
6-Cyclopropyl-3-(pyrimidin-5-ylamino)-pyrazine-2-carboxylic acid {2-[methyl-(tetrahydrofuran-2-ylmethyl)-carbamoyl]-pyridin-3-yl}-amide,
6-Cyclopropyl-3-(pyrimidin-5-ylamino)-pyrazine-2-carboxylic acid [2-(oxetan-3-ylcarbamoyl)-pyridin-3-yl]-amide,
6-Cyclopropyl-3-(pyrimidin-5-ylamino)-pyrazine-2-carboxylic acid [2-(azetidine-1-carbonyl)-6-methyl-pyridin-3-yl]-amide,
5-{[6-Cyclopropyl-3-(pyrimidin-5-ylamino)-pyrazine-2-carbonyl]-amino}-2-methyl-pyrimidine-4-carboxylic acid (2-hydroxy-2-methyl-propyl)-amide,
6-Cyclopropyl-3-(pyrimidin-5-ylamino)-pyrazine-2-carboxylic acid (2-dimethylcarbamoyl-4,5-difluoro-phenyl)-amide,
5-{[6-Cyclopropyl-3-(pyrimidin-5-ylamino)-pyrazine-2-carbonyl]-amino}-2-methyl-pyrimidine-4-carboxylic acid methylamide,
6-Cyclopropyl-3-(pyrimidin-5-ylamino)-pyrazine-2-carboxylic acid (4,5-difluoro-2-methylcarbamoyl-phenyl)-amide,
6-Cyclopropyl-3-(pyrimidin-5-ylamino)-pyrazine-2-carboxylic acid (2-fluoro-6-methylcarbamoyl-phenyl)-amide,
6-Cyclopropyl-3-(pyrimidin-5-ylamino)-pyrazine-2-carboxylic acid [2-(azetidine-1-carbonyl)-4,5-difluoro-phenyl]-amide,
6-Cyclopropyl-3-(pyrimidin-5-ylamino)-pyrazine-2-carboxylic acid (5-fluoro-2-methylcarbamoyl-phenyl)-amide,
6-Cyclopropyl-3-(pyrimidin-5-ylamino)-pyrazine-2-carboxylic acid [2-fluoro-6-(2-hydroxy-2-methyl-propylcarbamoyl)-phenyl]-amide,
6-Cyclopropyl-3-(pyrimidin-5-ylamino)-pyrazine-2-carboxylic acid (2-dimethylcarbamoyl-5-fluoro-phenyl)-amide,
6-Cyclopropyl-3-(pyrimidin-5-ylamino)-pyrazine-2-carboxylic acid [2-(2-hydroxy-2-methyl-propylcarbamoyl)-4-trifluoromethyl-phenyl]-amide,
6-Cyclopropyl-3-(pyrimidin-5-ylamino)-pyrazine-2-carboxylic acid (2-methylcarbamoyl-4-trifluoromethyl-phenyl)-amide,
6-Cyclopropyl-3-(pyrimidin-5-ylamino)-pyrazine-2-carboxylic acid (2-dimethylcarbamoyl-4-fluoro-phenyl)-amide,
6-Cyclopropyl-3-(pyrimidin-5-ylamino)-pyrazine-2-carboxylic acid (3,5-difluoro-2-methylcarbamoyl-phenyl)-amide,
6-Cyclopropyl-3-(pyrimidin-5-ylamino)-pyrazine-2-carboxylic acid (2-dimethylcarbamoyl-3,5-difluoro-phenyl)-amide,
6-Cyclopropyl-3-(pyrimidin-5-ylamino)-pyrazine-2-carboxylic acid [5-fluoro-2-(2-hydroxy-2-methyl-propylcarbamoyl)-phenyl]-amide,
6-Cyclopropyl-3-(pyrimidin-5-ylamino)-pyrazine-2-carboxylic acid [2-(azetidine-1-carbonyl)-5-fluoro-phenyl]-amide,
6-Cyclopropyl-3-(pyrimidin-5-ylamino)-pyrazine-2-carboxylic acid (2-dimethylcarbamoyl-6-fluoro-phenyl)-amide,
6-Cyclopropyl-3-(pyrimidin-5-ylamino)-pyrazine-2-carboxylic acid [2-(azetidine-1-carbonyl)-4-fluoro-phenyl]-amide,
6-Cyclopropyl-3-(pyrimidin-5-ylamino)-pyrazine-2-carboxylic acid [4-fluoro-2-(2-hydroxy-2-methyl-propylcarbamoyl)-phenyl]-amide,
6-Cyclopropyl-3-(pyrimidin-5-ylamino)-pyrazine-2-carboxylic acid (3-fluoro-2-methylcarbamoyl-phenyl)-amide,
6-Cyclopropyl-3-(pyrimidin-5-ylamino)-pyrazine-2-carboxylic acid (2-dimethylcarbamoyl-3-fluoro-phenyl)-amide,
6-Cyclopropyl-3-(pyrimidin-5-ylamino)-pyrazine-2-carboxylic acid [2-(azetidine-1-carbonyl)-3-fluoro-phenyl]-amide,
6-Cyclopropyl-3-(pyrimidin-5-ylamino)-pyrazine-2-carboxylic acid [3-fluoro-2-(2-hydroxy-2-methyl-propylcarbamoyl)-phenyl]-amide,
6-Cyclopropyl-3-(pyrimidin-5-ylamino)-pyrazine-2-carboxylic acid (4-fluoro-2-methylcarbamoyl-phenyl)-amide,
6-Cyclopropyl-3-(pyrimidin-5-ylamino)-pyrazine-2-carboxylic acid (2-dimethylcarbamoyl-3,4-difluoro-phenyl)-amide,
6-Cyclopropyl-3-(pyrimidin-5-ylamino)-pyrazine-2-carboxylic acid (3,4-difluoro-2-methylcarbamoyl-phenyl)-amide,
6-Cyclopropyl-3-(pyrimidin-5-ylamino)-pyrazine-2-carboxylic acid [3,4-difluoro-2-(2-hydroxy-2-methyl-propylcarbamoyl)-phenyl]-amide,
6-Cyclopropyl-3-(pyrimidin-5-ylamino)-pyrazine-2-carboxylic acid [2-(azetidine-1-carbonyl)-3,4-difluoro-phenyl]-amide,
6-Cyclopropyl-3-(pyrimidin-5-ylamino)-pyrazine-2-carboxylic acid [6-(azetidine-1-carbonyl)-2,3-difluoro-phenyl]-amide,
3-(4-{[6-Cyclopropyl-3-(pyrimidin-5-ylamino)-pyrazine-2-carbonyl]-amino}-3-methylcarbamoyl-phenyl)-propionic acid ethyl ester,
6-Cyclopropyl-3-(pyrimidin-5-ylamino)-pyrazine-2-carboxylic acid (2-methylcarbamoyl-4-methylcarbamoyl-methoxy-phenyl)-amide,
6-Cyclopropyl-3-(pyrimidin-5-ylamino)-pyrazine-2-carboxylic acid [2-(azetidine-1-carbonyl)-3,5-difluoro-phenyl]-amide,
6-Cyclopropyl-3-(pyrimidin-5-ylamino)-pyrazine-2-carboxylic acid [3,5-difluoro-2-(2-hydroxy-2-methyl-propylcarbamoyl)-phenyl]-amide,
6-Cyclopropyl-3-(pyrimidin-5-ylamino)-pyrazine-2-carboxylic acid (6-dimethylcarbamoyl-2,3-difluoro-phenyl)-amide, 6-Cyclopropyl-3-(pyrimidin-5-ylamino)-pyrazine-2-carboxylic acid [2,3-difluoro-6-(2-hydroxy-2-methyl-propylcarbamoyl)-phenyl]-amide, 6-Cyclopropyl-3-(pyrimidin-5-ylamino)-pyrazine-2-carboxylic acid (2,3-difluoro-6-methylcarbamoyl-phenyl)-amide, 3-(4-{[6-Cyclopropyl-3-(pyrimidin-5-ylamino)-pyrazine-2-carbonyl]-amino}-3-methylcarbamoyl-phenyl)-propionic acid, 2-Isopropyl-5-(pyrimidin-5-ylamino)-pyrimidine-4-carboxylic acid [2-(2-hydroxy-2-methyl-propylcarbamoyl)-pyridin-3-yl]-amide, 2-tert-Butyl-5-(pyrimidin-5-ylamino)-pyrimidine-4-carboxylic acid [2-(2-hydroxy-2-methyl-propylcarbamoyl)-pyridin-3-yl]-amide, 2-Isobutyl-5-(pyrimidin-5-ylamino)-pyrimidine-4-carboxylic acid [2-(2-hydroxy-2-methyl-propylcarbamoyl)-pyridin-3-yl]-amide, and 6-Cyclopropyl-3-(pyrimidin-5-ylamino)-pyrazine-2-carboxylic acid [4-(2-hydroxy-2-methyl-propoxy)-2-methylcarbamoyl-phenyl]-amide, or pharmaceutically acceptable salts thereof.

Yet particular compounds of formula (I), wherein

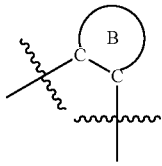

is selected from the group (2) as described above, are those selected from the group consisting of:

6-Cyclopropyl-N-(4-cyclopropylcarbamoyl-pyridin-3-yl)-3-(pyrimidin-5-ylamino)-pyridine-2-carboximidic acid, 6-Cyclopropyl-N-[4-(2-hydroxy-2-methyl-propylcarbamoyl)-pyridin-3-yl]-3-(pyrimidin-5-ylamino)-pyridine-2-carboximidic acid, 6-Cyclopropyl-N-[4-(2-methoxy-1-methyl-ethylcarbamoyl)-pyridin-3-yl]-3-(pyrimidin-5-ylamino)-pyridine-2-carboximidic acid, 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide, 6-Cyclopropyl-3-(pyrimidin-5-ylamino)-pyrazine-2-carboxylic acid [2-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-hydroxy-2-methyl-propylcarbamoyl)-pyridin-3-yl]-amide, 6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide, 6-Cyclopropyl-3-(pyrimidin-5-ylamino)-pyrazine-2-carboxylic acid [4-(2-methoxy-2-methyl-propylcarbamoyl)-pyridin-3-yl]-amide, 6-cyclopropyl-N-(2-((2-hydroxy-2-methylpropyl)(methyl)carbamoyl)pyridin-3-yl)-3-(pyrimidin-5-ylamino)pyrazine-2-carboxamide, 6-Cyclopropyl-3-(pyrimidin-5-ylamino)-pyrazine-2-carboxylic acid (6-cyclopropyl-2-methylcarbamoyl-pyridin-3-yl)-amide, 6-Cyclopropyl-3-(pyrimidin-5-ylamino)-pyrazine-2-carboxylic acid [2-(2-hydroxy-2-methyl-propylcarbamoyl)-6-methyl-pyridin-3-yl]-amide, 2-Isopropyl-5-(pyrimidin-5-ylamino)-pyrimidine-4-carboxylic acid [2-(2-hydroxy-2-methyl-propylcarbamoyl)-pyridin-3-yl]-amide, and 2-tert-Butyl-5-(pyrimidin-5-ylamino)-pyrimidine-4-carboxylic acid [2-(2-hydroxy-2-methyl-propylcarbamoyl)-pyridin-3-yl]-amide, or pharmaceutically acceptable salts thereof.

Particular compounds of formula (I), wherein

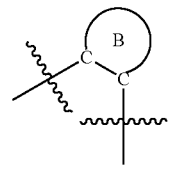

is selected from the group (2') as described above, are those selected from the group consisting of:

6-Cyclopropyl-3-(pyrimidin-5-ylamino)-pyridine-2-carboxylic acid [4-(pyrrolidine-1-carbonyl)-pyridin-3-yl]-amide, 6-Cyclopropyl-3-(pyrimidin-5-ylamino)-pyridine-2-carboxylic acid (4-dimethylcarbamoyl-pyridin-3-yl)-amide, 6-Cyclopropyl-3-(pyrimidin-5-ylamino)-pyridine-2-carboxylic acid (4-methylcarbamoyl-pyridin-3-yl)-amide, 6-Cyclopropyl-N-[4-(3-dimethylamino-pyrrolidine-1-carbonyl)-pyridin-3-yl]-3-(pyrimidin-5-ylamino)-pyridine-2-carboximidic acid, 6-Cyclopropyl-N-[4-(2-methyl-pyrrolidine-1-carbonyl)-pyridin-3-yl]-3-(pyrimidin-5-ylamino)-pyridine-2-carboximidic acid, 6-Cyclopropyl-N-[4-(3,3-difluoro-pyrrolidine-1-carbonyl)-pyridin-3-yl]-3-(pyrimidin-5-ylamino)-pyridine-2-carboximidic acid, 6-Cyclopropyl-N-(4-cyclopropylcarbamoyl-pyridin-3-yl)-3-(pyrimidin-5-ylamino)-pyridine-2-carboximidic acid, N-(4-Cyclobutylcarbamoyl-pyridin-3-yl)-6-cyclopropyl-3-(pyrimidin-5-ylamino)-pyridine-2-carboximidic acid, 6-Cyclopropyl-N-[4-(2,5-dimethyl-pyrrolidine-1-carbonyl)-pyridin-3-yl]-3-(pyrimidin-5-ylamino)-pyridine-2-carboximidic acid, 6-Cyclopropyl-N-[4-(5-hydroxy-3,6-dihydro-2H-pyrazine-1-carbonyl)-pyridin-3-yl]-3-(pyrimidin-5-ylamino)-pyridine-2-carboximidic acid, N-(4-Cyclopentylcarbamoyl-pyridin-3-yl)-6-cyclopropyl-3-(pyrimidin-5-ylamino)-pyridine-2-carboximidic acid, 6-Cyclopropyl-N-[4-(3-methoxy-pyrrolidine-1-carbonyl)-pyridin-3-yl]-3-(pyrimidin-5-ylamino)-pyridine-2-carboximidic acid, 6-Cyclopropyl-N-[4-(3,3-dimethyl-pyrrolidine-1-carbonyl)-pyridin-3-yl]-3-(pyrimidin-5-ylamino)-pyridine-2-carboximidic acid, 6-Cyclopropyl-N-[4-(2-hydroxy-1-methyl-ethylcarbamoyl)-pyridin-3-yl]-3-(pyrimidin-5-ylamino)-pyridine-2-carboximidic acid, N-[4-(Azetidine-1-carbonyl)-pyridin-3-yl]-6-cyclopropyl-3-(pyrimidin-5-ylamino)-pyridine-2-carboximidic acid, 6-Cyclopropyl-N-[4-(2-hydroxy-ethylcarbamoyl)-pyridin-3-yl]-3-(pyrimidin-5-ylamino)-pyridine-2-carboximidic acid, 6-Cyclopropyl-N-[4-(2,3-dihydroxy-propylcarbamoyl)-pyridin-3-yl]-3-(pyrimidin-5-ylamino)-pyridine-2-carboximidic acid, 6-Cyclopropyl-N-[4-(2-hydroxy-2-methyl-propylcarbamoyl)-pyridin-3-yl]-3-(pyrimidin-5-ylamino)-pyridine-2-carboximidic acid, 6-Cyclopropyl-N-{4-[(3-hydroxy-propyl)-methyl-carbamoyl]-pyridin-3-yl}-3-(pyrimidin-5-ylamino)-pyridine-2-carboximidic acid, 6-Cyclopropyl-N-[4-(2-methoxy-1-methyl-ethylcarbamoyl)-pyridin-3-yl]-3-(pyrimidin-5-ylamino)-pyridine-2-carboximidic acid, 6-Cyclopropyl-N-{4-[(2-hydroxy-ethyl)-methyl-carbamoyl]-pyridin-3-yl}-3-(pyrimidin-5-ylamino)-pyridine-2-carboximidic acid, N-(4-Cyclohexylcarbamoyl-pyridin-3-yl)-6-cyclopropyl-3-(pyrimidin-5-ylamino)-pyridine-2-carboximidic acid, 6-Cyclopropyl-N-[4-(3,3-difluoro-azetidine-1-carbonyl)-pyridin-3-yl]-3-(pyrimidin-5-ylamino)-pyridine-2-carboximidic acid, 6-Cyclopropyl-N-[4-(2-hydroxymethyl-pyrrolidine-1-carbonyl)-pyridin-3-yl]-3-(pyrimidin-5-ylamino)-pyridine-2-carboximidic acid, 6-Cyclopropyl-N-[4-(3-hydroxy-azetidine-1-carbonyl)-pyridin-3-yl]-3-(pyrimidin-5-ylamino)-pyridine-2-carboximidic acid, 6-Cyclopropyl-N-[4-(2,2-dimethyl-pyrrolidine-1-carbonyl)-pyridin-3-yl]-3-(pyrimidin-5-ylamino)-pyridine-2-carboximidic acid, 6-Cyclopropyl-N-{4-[(2,3-dihydroxy-propyl)-methyl-carbamoyl]-pyridin-3-yl}-3-(pyrimidin-5-ylamino)-pyridine-2-carboximidic acid, 6-Cyclopropyl-N-[4-(3-hydroxy-pyrrolidine-1-carbonyl)-pyridin-3-yl]-3-(pyrimidin-5-ylamino)-pyridine-2-carboximidic acid, 6-Cyclopropyl-N-[4-(2-oxa-6-aza-spiro[3.3]heptane-6-carbonyl)-pyridin-3-yl]-3-(pyrimidin-5-ylamino)-pyridine-2-carboximidic acid, 2-Isopropyl-5-(pyrimidin-5-ylamino)-pyrimidine-4-carboxylic acid [4-(2-hydroxy-2-methyl-propylcarbamoyl)-pyridin-3-yl]-amide, 2-tert-Butyl-5-(pyrimidin-5-ylamino)-pyrimidine-4-carboxylic acid [4-(2-hydroxy-2-methyl-propylcarbamoyl)-pyridin-3-yl]-amide, 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide, 6-Cyclopropyl-3-(pyrimidin-5-ylamino)-pyrazine-2-carboxylic acid [2-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-isopropoxy-ethylcarbamoyl)-pyridin-3-yl]-amide, 6-Cyclopropyl-3-(pyrimidin-5-ylamino)-pyrazine-2-carboxylic acid [4-(tetrahydro-furan-3-ylcarbamoyl)-pyridin-3-yl]-amide, 6-Cyclopropyl-3-(pyrimidin-5-ylamino)-pyrazine-2-carboxylic acid {4-[(tetrahydro-furan-2-ylmethyl)-carbamoyl]-pyridin-3-yl}-amide, 6-Cyclopropyl-3-(pyrimidin-5-ylamino)-pyrazine-2-carboxylic acid [4-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(oxetan-3-ylcarbamoyl)-pyridin-3-yl]-amide, 6-Cyclopropyl-3-(pyrimidin-5-ylamino)-pyrazine-2-carboxylic acid [4-(2-methoxy-2-methyl-propylcarbamoyl)-pyridin-3-yl]-amide, 6-Cyclopropyl-3-(pyrimidin-5-ylamino)-pyrazine-2-carboxylic acid [4-(3-methoxy-2,2-dimethyl-propylcarbamoyl)-pyridin-3-yl]-amide, 6-Cyclopropyl-N-(2-((2-methoxyethyl)(methyl)carbamoyl)pyridin-3-yl)-3-(pyrimidin-5-ylamino)pyrazine-2-carboxamide, 5-(6-cyclopropyl-3-(pyrimidin-5-ylamino)pyrazine-2-carboxamido)-N-(2-methoxyethyl)-N-methylpyrimidine-4-carboxamide, 6-cyclopropyl-N-(3-(2-hydroxy-2-methylpropylcarbamoyl)pyridin-4-yl)-3-(pyrimidin-5-ylamino)pyrazine-2-carboxamide, 6-Cyclopropyl-3-(pyrimidin-5-ylamino)-pyrazine-2-carboxylic acid [4-(3-methyl-oxetan-3-ylcarbamoyl)-pyridin-3-yl]-amide, 5-(6-cyclopropyl-3-(pyrimidin-5-ylamino)pyrazine-2-carboxamido)-N-(2-hydroxy-2-methylpropyl)-N-methylpyrimidine-4-carboxamide, 6-cyclopropyl-N-(2-((hydroxy-2-methylpropyl)(methyl)carbamoyl)pyridin-3-yl)-3-(pyrimidin-5-ylamino)pyrazine-2-carboxamide, 6-Cyclopropyl-3-(pyrimidin-5-ylamino)-pyrazine-2-carboxylic acid (4-methylcarbamoyl-pyridin-3-yl)-amide, 6-Cyclopropyl-3-(pyrimidin-5-ylamino)-pyrazine-2-carboxylic acid [4-(2-hydroxy-1,1-dimethyl-ethylcarbamoyl)-pyridin-3-yl]-amide, or pharmaceutically acceptable salts thereof.

Yet particular compounds of formula (I), wherein

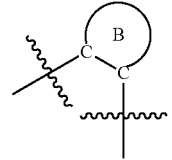

is selected from the group (2') as described above, are those selected from the group consisting of:

6-Cyclopropyl-N-(4-cyclopropylcarbamoyl-pyridin-3-yl)-3-(pyrimidin-5-ylamino)-pyridine-2-carboximidic acid, 6-Cyclopropyl-N-[4-(2-hydroxy-2-methyl-propylcarbamoyl)-pyridin-3-yl]-3-(pyrimidin-5-ylamino)-pyridine-2-carboximidic acid, 6-Cyclopropyl-N-[4-(2-methoxy-1-methyl-ethylcarbamoyl)-pyridin-3-yl]-3-(pyrimidin-5-ylamino)-pyridine-2-carboximidic acid, 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide, 6-Cyclopropyl-3-(pyrimidin-5-ylamino)-pyrazine-2-carboxylic acid [2-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-methoxy-2-methyl-propylcarbamoyl)-pyridin-3-yl]-amide, or pharmaceutically acceptable salts thereof.

Particular compounds of formula (I), wherein

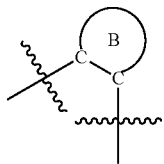

is selected from the group (2') as described above, are those selected from the group consisting of:
6-Cyclopropyl-3-(pyrimidin-5-ylamino)-pyridine-2-carboxylic acid (2-methylcarbamoyl-phenyl)-amide,
2-(2-tert-butyl-5-(pyrimidin-5-ylamino)pyrimidine-4-carboxamido)-N4,N4-diethyl-N-1-methylterephthalamide,
6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide,
or pharmaceutically acceptable salts thereof Yet particular compounds of formula (I), wherein

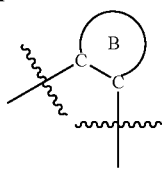

is selected from the group (2') as described above, are those selected from the group consisting of:
6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide,
or pharmaceutically acceptable salts thereof Particular compounds of formula (I), wherein

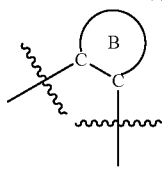

is selected from the group (2') as described above, are those selected from the group consisting of:
7-{[6-Cyclopropyl-3-(pyrimidin-5-ylamino)-pyridine-2-carbonyl]-amino}-2-phenyl-imidazo[1,2-a]pyridine-6-carboxylic acid methylamide,
or pharmaceutically acceptable salts thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises:
reacting a compound of formula (1)

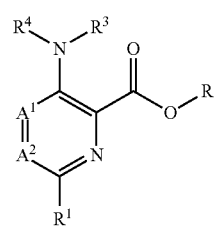

(1)

with a compound of formula (2)

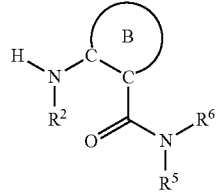

(2)

wherein $A^1$, $A^2$,

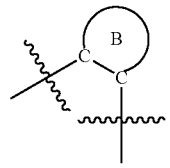

$R^1$, $R^2$, $R^3$, $R^4$, $R^5$ and $R^6$ are as defined above and R is hydrogen or lower alkyl, and if desired, converting the compounds into pharmaceutically acceptable salts thereof.

The reaction described above can be carried out under conditions as described in the description and examples or under conditions well known to the person skilled in the art.

The compounds of formula (1) and (2) can be prepared by methods known in the art or as described below or in analogy thereto.

The present invention also relates to compounds of formula (I) as defined above, when prepared by a process as described above.

Compounds of general formula (I) wherein $A^1$=CH or N and $A^2$=$CR^{19}$ can be prepared as outlined in schemes 1 and 2 and in general procedures 1, 2a, 2b and 2c.

Scheme 1

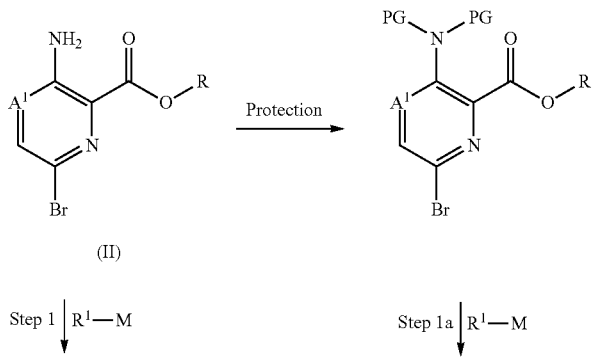

-continued
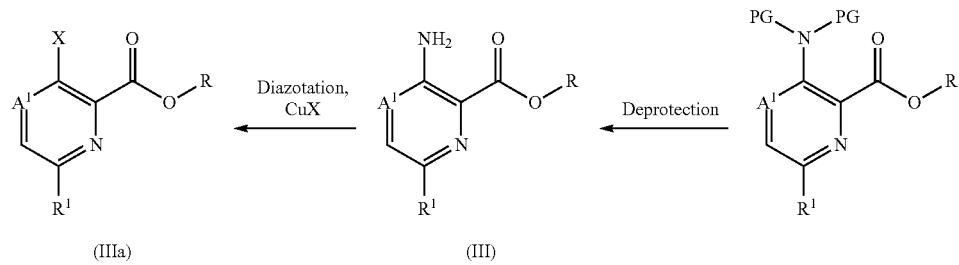
(IIIa) (III)
Step 2 | R⁴—X
opt. R³—X
Step 2a | R⁴—NH₂, opt. R³—X
or R⁴—N(H)—R³
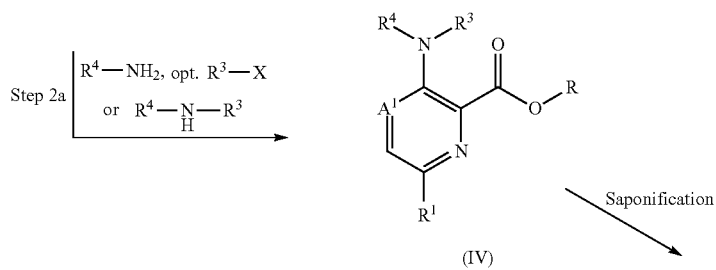
(IV)
Saponification
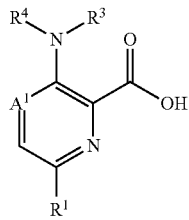
(IVa)
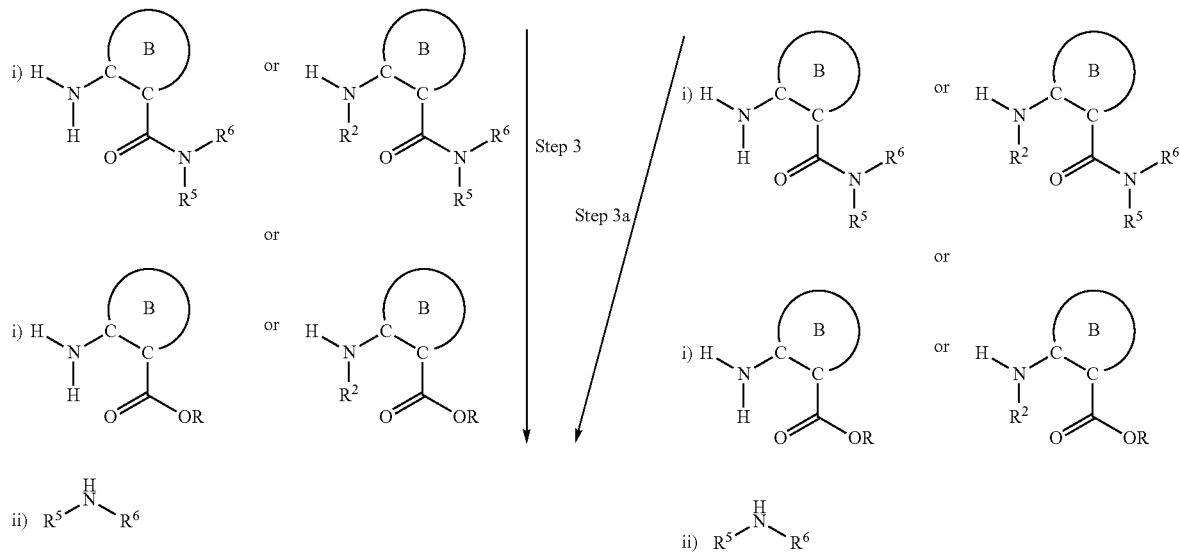

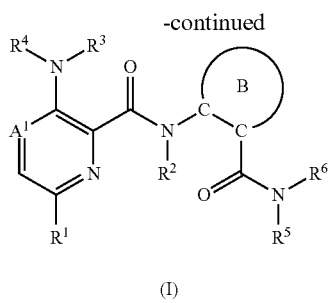

(I)

General Procedure 1

Step 1:

Compounds of formula (II) wherein R=lower alkyl are commercially available or can be prepared starting from pyridine-2,3-dicarboxylic acid according to US 2006/0199960 (for $A^1$ and $A^2$=CH) or starting from alkyl 3-amino-2-pyrazinecarboxylate or 3-amino-2-pyrazinecarboxylic acid according to e.g. Heterocycles 2005, 65, 2321 or WO 2007/061360 (for $A^1$=N and $A^2$=CH).

Compounds of formula (II) can be converted to a compound of formula (III) by a Pd-catalyzed coupling reaction with an organometallic reagent $R^1$-M (e.g. organoboronic acid or organoboronic acid ester) using a Pd-catalyst (e.g. $Pd_2dba_3$) and a base (e.g. potassium phosphate) in an organic solvent (e.g. dioxane), by treatment of a compound of formula (II) with an alcohol (e.g. methanol) and a base (e.g. sodium hydride or cesium carbonate) in an organic solvent (e.g. methanol or DMSO), or by a Cu-catalyzed coupling reaction with an amine using a copper source (e.g. copper bromide), a ligand (e.g. BINOL) and a base (e.g. cesium carbonate) in an organic solvent (e.g. DMF). Compounds of formula (III) can be isolated and purified by conventional methods.

Compounds of formula (II) wherein R=H are commercially available or can be prepared according to WO 2008/106692 and subsequently be transformed to compounds of formula (II) wherein R=lower alkyl by standard methods of ester formation known to those skilled in the art.

Step 1a:

Compounds of formula (II) wherein R=lower alkyl can also be converted to a compound of formula (III) according to the methods described in US 2006/0199960 by i) protection of the amino group with a suitable protective group (e.g. Boc) using e.g. di-tert-butyl-dicarbonate in the presence of an organic or inorganic base (e.g. DMAP or triethylamine) in an organic solvent, ii) Pd-catalyzed coupling reaction with an organometallic reagent $R^1$-M (e.g. organozinc reagent or organotin reagent) using a Pd-catalyst (e.g. $Pd(PPh_3)_4$) and a base (e.g. potassium carbonate) in an organic solvent (e.g. dioxane), treatment of a compound of formula (II) with an alcohol (e.g. methanol) and a base (e.g. sodium hydride or cesium carbonate) in an organic solvent (e.g. methanol or DMSO), or a Cu-catalyzed coupling reaction with an amine using a copper source (e.g. copper bromide), a ligand (e.g. BINOL) and a base (e.g. cesium carbonate) in an organic solvent (e.g. DMF) and iii) deprotection of the amino group using e.g. an organic or inorganic acid (e.g. HCl or trifluoroacetic acid) in an organic solvent. Compounds of formula (III) can be isolated and purified by conventional methods.

Step 2:

A compound of formula (IV) wherein $R^3$=H can be obtained by e.g. a Pd-catalyzed arylation of the amino group of compounds of formula (III) using aryl halides or heteroaryl halides (e.g. 5-bromopyrimidine) $R^4$—X, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). A compound of formula (IV) wherein $R^3$=lower alkyl can be obtained by e.g. Pd-catalyzed arylation as described before and subsequent alkylation using an alkyl halide (e.g. methyl iodide) or alkyl triflate $R^3$—X and a base (e.g. NaH) in an organic solvent (e.g. DMF). Compounds of formula (IV) can be isolated and purified by conventional methods.

Step 2a:

Compounds of formula (IIIa) wherein R=lower alkyl can be prepared according to US 2006/0199960. Alternatively, compounds of formula (III) can be converted to a compound of formula (IIIa) wherein X=halogen by diazotation using e.g. sodium nitrite or tert-butyl nitrite and subsequent substitution using a suitable copper halide. A compound of formula (IV) wherein $R^3$=H can be obtained by e.g. a Pd-catalyzed amination of compounds of formula (IIIa) using arylamines or heteroarylamines (e.g. 5-aminopyrimidine) $R^4$—$NH_2$, a Pd-catalyst (e.g. $PdOAc_2$), a suitable ligand (e.g. 4,5-bis(diphenyl-phosphino)-9,9-dimethylxanthene) and a base (e.g. potassium carbonate) in an organic solvent (e.g. toluene, o-xylene). A compound of formula (IV) wherein $R^3$=lower alkyl can be obtained by e.g. a Pd-catalyzed amination as described before using arylamines or heteroarylamines $R^4$—NH—$R^3$ or by e.g. Pd-catalyzed amination as described before using arylamines or heteroarylamines $R^4$—$NH_2$ and subsequent alkylation with alkyl halides or alkyl triflates $R^3$—X as described above. Compounds of formula (IV) can be isolated and purified by conventional methods.

Step 3:

A compound of formula (IV) can be converted to compounds of formula (I) by direct aminolysis of the ester group using aminoaryl carboxylic acid amides or aminoheteroaryl carboxylic acid amides

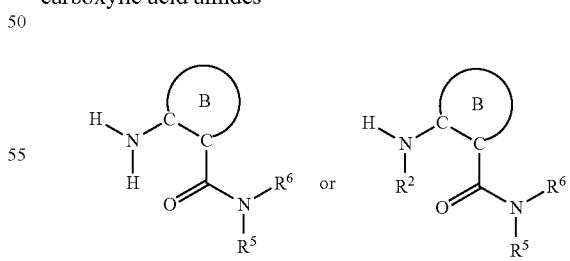

and a Lewis acid (e.g. trimethylaluminium or dimethylaluminium chloride) in an organic solvent (e.g. toluene or dioxane).

A compound of formula (IV) can also be converted to compounds of formula (I) by direct aminolysis of the ester group as described above using aminoaryl carboxylates or aminoheteroaryl carboxylates

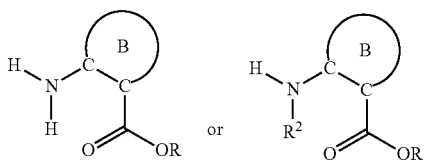

wherein R=H or lower alkyl. The thus formed intermediate can be subsequently converted to compounds of formula (I) by either direct aminolysis of the ester group as described above using amines R⁵—NH—R⁶ or by amide bond formation of the free carboxylate using amines R⁵—NH—R⁶, a coupling reagent (e.g. propylphosphonic acid anhydride, HATU, TBTU) and an organic base (e.g. N,N-diisopropylethylamine, N-methyl-morpholine or triethylamine) in an organic solvent (e.g. DMF, ethyl acetate, THF). Compounds of formula (I) can be isolated and purified by conventional methods.

Aminoaryl carboxylic acid amides or aminoheteroaryl carboxylic acid amides

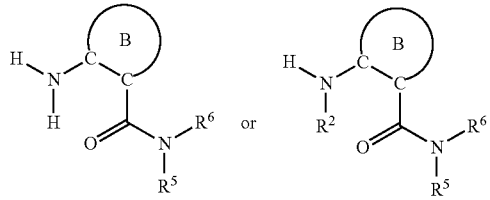

as well as aminoaryl carboxylates or aminoheteroaryl carboxylates

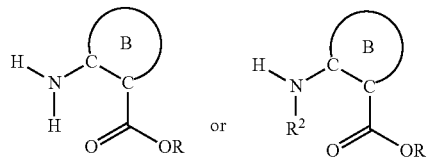

wherein R=H or lower alkyl are commercially available or can be prepared by standard methods known to those skilled in the art and as described at the respective examples.

Step 3a:

Alternatively, the ester group of a compound of formula (IV) can be saponified to its free acid (IVa) using an inorganic base (e.g. lithium hydroxide, sodium hydroxide) in an organic solvent (e.g. ethanol, dioxane, THF) or a mixture thereof. A compound of formula (IVa) can then be converted to compounds of formula (I) by amide bond formation as described above using aminoaryl carboxylic acid amides or aminoheteroaryl carboxylic acid amides

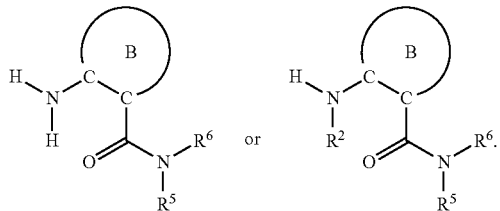

A compound of formula (IVa) can also be converted to compounds of formula (I) by amide bond formation as described above using aminoaryl carboxylates or aminoheteroaryl carboxylates

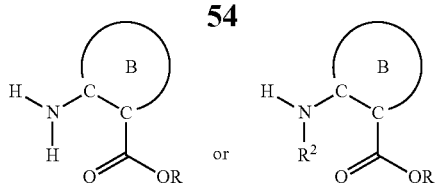

wherein R=H or lower alkyl. The thus formed intermediate can subsequently be converted to compounds of formula (I) by either direct aminolysis of the ester group as described above or by amide bond formation of the free carboxylate as described above using amines R⁵—NH—R⁶. Compounds of formula (I) can be isolated and purified by conventional methods.

Compounds of formula (I) can also be prepared according to the methods outlined above by reversing the order of reaction steps 2/2a and 3/3a.

Compounds of formula (I) wherein A¹=CH or N and A²=CH that can not be synthesized as outlined in scheme 1 and in general procedure 1 can be prepared from intermediates of formula (IIIb), (IIIc) or (IIId) as outlined in scheme 2 and in general procedures 2a, 2b and 2c.

Scheme 2

General Procedure 2a:

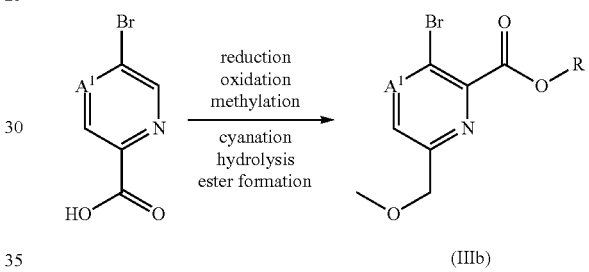

General Procedure 2b:

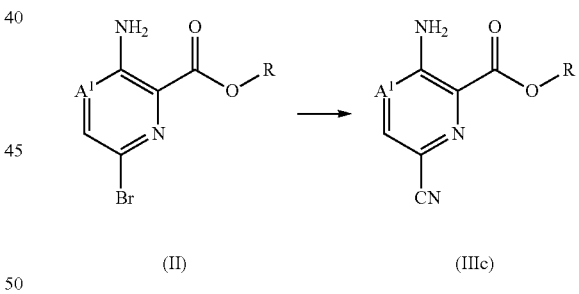

General Procedure 2c:

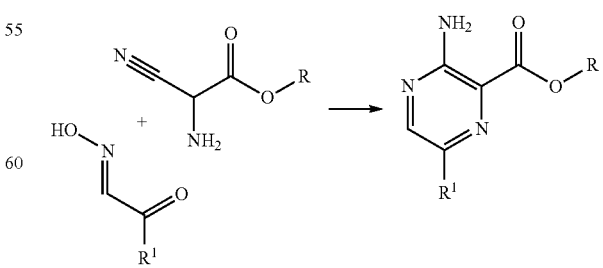

General Procedure 2a

Starting from commercially available 5-bromopyridine-2-carboxylic acid or 5-bromopyrazine-2-carboxylic acid, an intermediate of formula (IIIb) can be prepared by:
i) reduction of carboxylate using a reducing agent (e.g. sodium borohydride, borane-dimethylsulphide) in an organic solvent (e.g. THF)
ii) oxidation of pyridine to pyridine-N-oxide using an oxidizing reagent (e.g. m-chlorobenzoic acid) in an organic solvent (e.g. dichloromethane)
iii) alkylation of hydroxyl group using an alkylating reagent (e.g. methyl iodide) and a suitable inorganic base (e.g. sodium hydride) in an organic solvent (e.g. THF or dioxane)
iv) cyanation of pyridinium-N-oxide using e.g. cyanotrimethylsilane, a suitable base (e.g. triethylamine) in an organic solvent (e.g. acetonitrile or DMF)
v) hydrolysis of nitrile to liberate the free acid using a strong inorganic base (e.g. potassium hydroxide) in an organic solvent (e.g. methanol or ethanol)
vi) ester formation of acid group using e.g. an alcohol in the presence of a strong acid, an alkylhalide in the presence of a base or special alkylating reagents (e.g. trimethylsilyl-diazomethane).

Intermediates of formula (IIIb) can be further converted to compounds of general formula (I) by the general procedures described above.

General Procedure 2b

Starting from compounds of formula (II) wherein R=lower alkyl, intermediates of formula (IIIc) can be prepared by replacement of the bromine by a nitrile group using e.g. copper (I) cyanide in an organic solvent as e.g. DMF. These intermediates can either be converted to compounds of general formula (I) by the general methods described above. Or the nitrile group can be further converted to e.g. a carboxylic acid (via hydrolysis), an alkyl carboxylate (via hydrolysis and ester formation), an alcohol (via hydrolysis and reduction), a ketone (via hydrolysis, activation as e.g. Weinreb amide and alkylation with e.g. a Grignard reagent), or an amino group (via hydrolysis and Curtius reaction) which can be further substituted by e.g. alkyl groups on the stage of either the different intermediates or the final products. These intermediates can be further converted to compounds of general formula (I) by the general procedures described above.

General Procedure 2c

Compounds of formula (IIId) wherein R=lower alkyl can be prepared starting from an aminocyanoacetic acid ester and an appropriate α-ketoaldehyde oxime according to J. Heterocycl. Chem. 1987, 24, 1621 or US 2006/199828.

Compounds of general formula (I) wherein $A^1$ is CH and $A^2$ is N can be prepared as outlined in schemes 3 and 4 and in general procedures 3 and 4.

Scheme 3

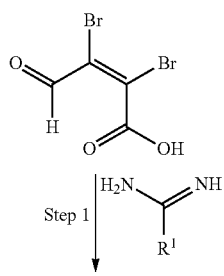

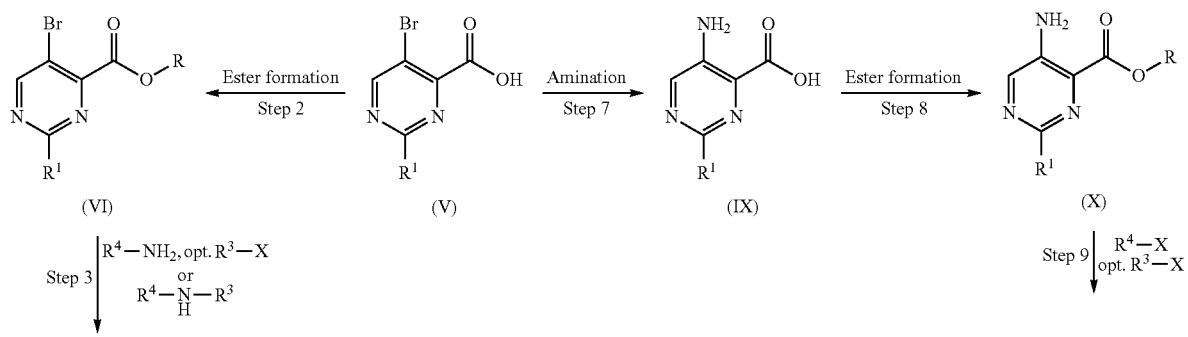

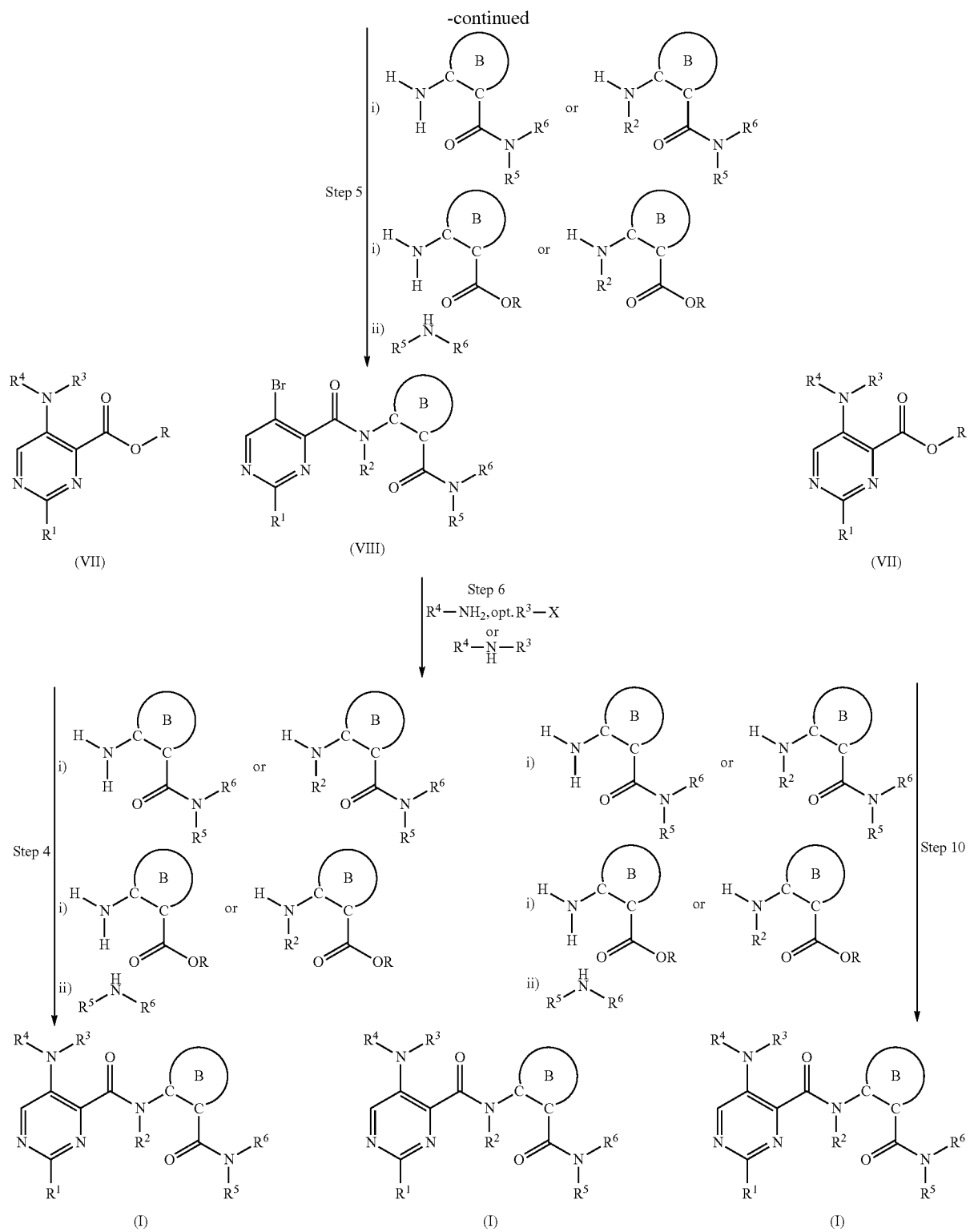

General Procedure 3

Step 1:

Compounds of formula (V) are commercially available or can be prepared according to the general methods described in e.g. WO 2000/066566 or WO 2005/021500 by condensation of e.g. mucobromic acid with a suitable amidine containing residue $R^1$ in the presence of an organic base (e.g. sodium ethylate) in an organic solvent (e.g. ethanol) at ambient or elevated temperatures.

Step 2:

A compound of formula (V) can be converted to compounds of formula (VI) wherein R=lower alkyl by formation of an ester using e.g. an alcohol in the presence of a strong acid, an alcohol in the presence of an acid chloride-forming reagent (e.g. thionyl chloride), an alkylhalide in the presence of a base or special alkylating reagents (e.g. trimethylsilyl-diazomethane). Compounds of formula (VI) can be isolated and purified by conventional methods.

Step 3:

A compound of formula (VII) wherein $R^3$=H can be obtained by e.g. a Pd-catalyzed amination of compounds of formula (VI) as described above using arylamines or heteroarylamines (e.g. 5-aminopyrimidine) $R^4$—$NH_2$. A compound of formula (VII) wherein $R^3$=lower alkyl can be obtained by e.g. a Pd-catalyzed amination as described above using arylamines or heteroarylamines $R^4$—NH—$R^3$ or by e.g. a Pd-catalyzed amination of compounds of formula (VI) as described above using arylamines or heteroarylamines $R^4$—$NH_2$ and subsequent alkylation with alkyl halides or alkyl triflates $R^3$—X as described above. Compounds of formula (VII) can be isolated and purified by conventional methods.

Step 4:

A compound of formula (VII) can be converted to compounds of formula (I) by direct aminolysis of the ester group as described above using aminoaryl carboxylic acid amides or aminoheteroaryl carboxylic acid amides

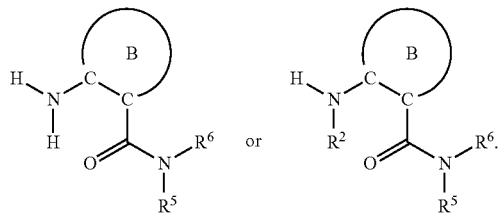

and a Lewis acid (e.g. trimethylaluminium or dimethylaluminium chloride) in an organic solvent (e.g. toluene or dioxane).

A compound of formula (VII) can also be converted to compounds of formula (I) by direct aminolysis of the ester group as described above using aminoaryl carboxylates or aminoheteroaryl carboxylates

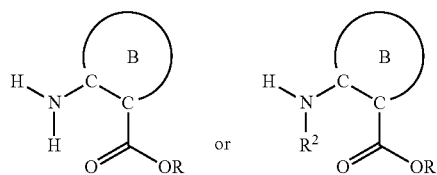

wherein R=H or lower alkyl. The thus formed intermediate can subsequently be converted to compounds of formula (I) by either direct aminolysis of the ester group as described above or by amide bond formation of the free carboxylate as described above using amines $R^5$—NH—$R^6$.

Alternatively, a compound of formula (VII) can be saponified to its free acid as described above. The free acid of a compound of formula (VII) can then be converted to compounds of formula (I) by amide bond formation as described above using aminoaryl carboxylic acid amides or aminoheteroaryl carboxylic acid amides

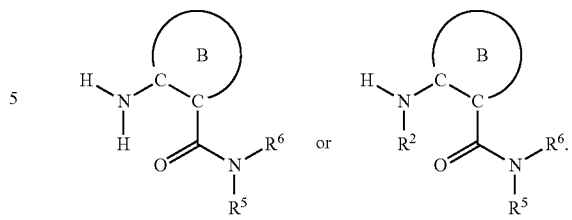

The free acid of a compound of formula (VII) can also be converted to compounds of formula (I) by amide bond formation as described above using aminoaryl carboxylates or aminoheteroaryl carboxylates

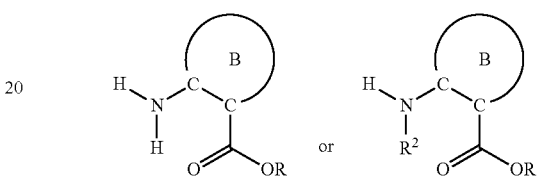

wherein R=H or lower alkyl, and subsequent a) direct aminolysis of the ester group as described above or b) amide bond formation of the free carboxylate as described above using amines $R^5$—NH—$R^6$. Compounds of formula (I) can be isolated and purified by conventional methods.

Step 5:

A compound of formula (V) can be converted to compounds of formula (VIII) according to the methods described in step 4 for the conversion of acids of formula (VII).

Step 6:

A compound of formula (VIII) can be converted to compounds of formula (I) according to the method described in step 3 for the formation of compounds of formula (VII).

Step 7:

A compound of formula (V) can be converted to compounds of formula (IX) by amination of the bromide using an ammonia source (e.g. ammonium hydroxide) in the presence of a transition metal (e.g. copper (II) sulfate) in a solvent like water. Compounds of formula (IX) can be isolated and purified by conventional methods.

Step 8:

A compound of formula (IX) can be converted to compounds of formula (X) according to the method described in step 2 for the formation of compounds of formula (VI).

Step 9:

A compound of formula (X) can be converted to compounds of formula (VII) according to the methods described in step 3 for the formation of compounds of formula (VII) using aryl halides or heteroaryl halides (e.g. 5-bromopyrimidine) $R^4$—X and optionally alkyl halides or alkyl triflates $R^3$—X.

Step 10:

A compound of formula (XI) can be converted to compounds of formula (I) according to the methods described in step 4 for the conversion of compounds of formula (VII).

Compounds of formula (VI) wherein $A^1$ is CH and $A^2$ is N and R=H or lower alkyl that can not be synthesized as outlined in scheme 3 and in general procedure 3 can be prepared e.g from commercially available intermediates of formula (VIa) as outlined in scheme 4 and in general procedure 4.

Scheme 4

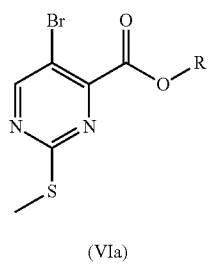

(VIa)

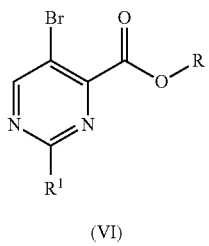

(VI)

General Procedure 4

Starting from commercially available 5-bromo-2-methylthio-pyrimidine-4-carboxylates of formula (VIa), intermediates of formula VI wherein $R^1$ is alkoxy or optionally substituted amine can be prepared by:
  i) oxidation of the methylthio group using an oxidizing reagent (e.g. 3-chloroperbenzoic acid) in an organic solvent (e.g. dichloromethane) to form a methylsulphonyl group
  ii) nucleophilic substitution of the methylsulphonyl group by oxygen or nitrogen nucleophiles (e.g. alkylamine or alkylalcohol) in an organic solvent (e.g. dichloromethane) to yield intermediates (VI).

These intermediates can be further converted to compounds of general formula (I) by the general procedures described above.

Certain substituents on the groups $R^1$, $R^2$, $R^3$, $R^4$ and $R^5$ may not be inert to the conditions of the synthesis sequences described above and may require protection by standard protecting groups known in the art. For instance, an amino or hydroxyl group may be protected as an acetyl or tert.-butoxycarbonyl derivative. Alternatively, some substituents may be derived from others at the end of the reaction sequence. For instance, a compound of formula I may be synthesized bearing a nitro-, an ethoxycarbonyl, an ether, a sulfonic acid substituent on the groups $R^1$, $R^2$, $R^3$, $R^4$ and $R^5$, which substituents are finally converted to an amino- (e.g. by reduction of a nitro group or cleavage of a suitable amino protective group (e.g. removal of a Boc group with TFA)), alkylamino- (e.g. by reductive amination of an amino group), dialkylamino- (e.g. by alkylation of an amino group, reduction of an appropriate acylamino group with lithium aluminum hydride or Eschweiler-Clarke reaction with an appropriate amino or alkylamino group), acylamino- (by amide formation from an amino group e.g. with appropriate acyl halides or with appropriate carboxylic acids after their activation with CDI, EDC etc.), alkylsulfonylamino (e.g. by reaction of an amino group with sulfonyl chlorides), arylsulfonylamino substituent (e.g. by reaction of an amino group with sulfonyl chlorides), hydroxyl- (by cleavage of a suitable hydroxy protective group (e.g. hydrogenolytic removal of a benzyl ether or oxidative cleavage of a p-methoxy benzyl ether), ether- (e.g. by Williamson's ether synthesis from a hydroxyl group) or to a carboxamide substituent (e.g. by amide formation from a carboxylic acid group with appropriate amines after activation of the carboxylic acid group with CDI, EDC etc. or conversion to an acyl chloride), or to a sulfonamide substituent by standard procedures.

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxane or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another embodiment, the invention relates to a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also relates to the use of compounds as described above for the preparation of medicaments for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

Prevention and/or treatment of schizophrenia is a particular indication. Yet particular indication is prevention and/or treatment of positive, negative and/or cognitive symptoms associated with schizophrenia.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. # A-7906), 50 nM cGMP (Sigma, cat. # G6129) and 50 nM [$^3$H]-cGMP (GE Healthcare, cat. # TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A activity by 50%). Non-specific activity was tested without the enzyme. The reaction was initiated by the addition of the substrate solution (cGMP and [$^3$H]-cGMP) and allowed to progress for 20 minutes at room temperature. The reaction was terminated by adding 25 µl of YSi-SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an $IC_{50}$ value below 10 µM, more specifically below 5 µM, yet more specifically below 1 µM. The following table shows data for some examples.

| Example | PDE10A inhibition $IC_{50}$ [µmol/l] |
|---|---|
| 1 | 0.0315 |
| 2 | 0.0046 |
| 3 | 0.0075 |
| 4 | 0.1245 |
| 5 | 0.0052 |
| 6 | 0.0126 |
| 7 | 0.3356 |
| 8 | 0.1396 |
| 9 | 0.149 |
| 10 | 0.2024 |
| 11 | 0.0012 |
| 12 | 0.4952 |

| Example | PDE10A inhibition IC$_{50}$ [µmol/l] |
|---|---|
| 13 | 0.2557 |
| 14 | 0.0114 |
| 15 | 0.0107 |
| 16 | 0.0076 |
| 17 | 0.0126 |
| 18 | 0.091 |
| 19 | 0.0087 |
| 20 | 0.0221 |
| 21 | 0.007 |
| 22 | 0.0187 |
| 23 | 0.0878 |
| 24 | 0.0137 |
| 25 | 1.8646 |
| 26 | 0.0283 |
| 27 | 0.0114 |
| 28 | 0.006 |
| 29 | 0.0013 |
| 30 | 0.0342 |
| 31 | 0.0031 |
| 32 | 0.0073 |
| 33 | 0.0031 |
| 34 | 0.0045 |
| 35 | 0.0457 |
| 36 | 0.0032 |
| 37 | 0.0181 |
| 38 | 0.0072 |
| 39 | 0.0082 |
| 40 | 0.0075 |
| 41 | 0.0069 |
| 42 | 0.0081 |
| 43 | 0.0031 |
| 44 | 0.0274 |
| 45 | 0.0171 |
| 46 | 0.0193 |
| 47 | 0.0132 |
| 48 | 0.0083 |
| 49 | 0.0039 |
| 50 | 0.0317 |
| 51 | 0.058 |
| 52 | 0.0082 |
| 53 | 0.0737 |
| 54 | 0.025 |
| 55 | 0.115 |
| 56 | 0.0657 |
| 57 | 0.0021 |
| 58 | 0.0011 |
| 59 | 0.0844 |
| 60 | 0.2316 |
| 61 | 0.0013 |
| 62 | 0.0939 |
| 63 | 0.087 |
| 64 | 1.1056 |
| 65 | 0.0014 |
| 66 | 0.0478 |
| 67 | 0.0042 |
| 68 | 0.0033 |
| 69 | 0.0041 |
| 70 | 0.0021 |
| 71 | 0.0564 |
| 72 | 0.0042 |
| 73 | 0.0189 |
| 74 | 0.0073 |
| 75 | 0.0088 |
| 76 | 0.0079 |
| 77 | 0.0034 |
| 78 | 0.002 |
| 79 | 0.0296 |
| 80 | 0.1049 |
| 81 | 0.0004 |
| 82 | 0.0585 |
| 83 | 0.0055 |
| 84 | 0.0019 |
| 85 | 0.0245 |
| 86 | 0.2153 |
| 87 | 0.1796 |
| 88 | 0.5713 |
| 89 | 0.0005 |
| 90 | 0.0004 |
| 91 | 0.0275 |
| 92 | 0.0064 |
| 93 | 0.0043 |
| 94 | 0.3915 |
| 95 | 0.0018 |
| 96 | 0.096 |
| 97 | 0.0011 |
| 98 | 0.0004 |
| 99 | 0.0026 |
| 100 | 0.0025 |
| 101 | 0.0015 |
| 102 | 0.0163 |
| 103 | 0.0587 |
| 104 | 0.0113 |
| 105 | 0.0011 |
| 106 | 0.0026 |
| 107 | 0.1174 |
| 108 | 0.0397 |
| 109 | 0.0189 |
| 110 | 0.0006 |
| 111 | 0.015 |
| 112 | 0.0796 |
| 113 | 0.0016 |
| 114 | 0.0011 |
| 115 | 0.1709 |
| 116 | 0.0045 |
| 117 | 0.0268 |
| 118 | 0.0897 |
| 119 | 0.0045 |
| 120 | 0.0004 |
| 121 | 0.0058 |
| 122 | 0.0453 |
| 123 | 0.0096 |
| 124 | 0.0021 |
| 125 | 0.0056 |
| 126 | 0.122 |
| 127 | 0.0085 |
| 128 | 0.0013 |
| 129 | 0.006 |
| 131 | 0.0014 |
| 132 | 0.0169 |
| 133 | 0.0067 |
| 134 | 0.0215 |
| 135 | 0.0066 |
| 136 | 0.0036 |
| 137 | 0.0587 |
| 138 | 0.0249 |
| 139 | 0.0116 |
| 140 | 0.003 |
| 141 | 0.0035 |
| 142 | 0.0011 |
| 143 | 0.0233 |
| 144 | 0.0021 |
| 145 | 0.0029 |
| 146 | 0.0017 |
| 147 | 0.0012 |
| 148 | 0.0144 |
| 149 | 0.0015 |
| 150 | 0.0085 |
| 151 | 0.0027 |
| 152 | 0.0034 |
| 153 | 0.0161 |
| 154 | 0.0025 |
| 155 | 0.0127 |
| 156 | 0.0112 |
| 157 | 0.0322 |
| 158 | 0.0008 |
| 159 | 0.0004 |
| 160 | 0.0029 |
| 161 | 0.0128 |
| 162 | 0.1243 |
| 163 | 0.0062 |
| 164 | 0.0052 |
| 165 | 0.0022 |
| 166 | 0.3352 |
| 167 | 0.0044 |

-continued

| Example | PDE10A inhibition IC$_{50}$ [µmol/l] |
|---|---|
| 168 | 0.0329 |
| 169 | 0.0223 |
| 170 | 0.0889 |
| 171 | 0.0028 |
| 172 | 0.0129 |
| 173 | 0.0195 |
| 174 | 0.0148 |
| 175 | 0.025 |
| 176 | 0.027 |
| 177 | 0.0002 |
| 178 | 0.0001 |
| 179 | 0.1484 |
| 180 | 0.0055 |
| 181 | 0.0004 |
| 182 | 0.0035 |
| 183 | 0.0003 |
| 184 | 0.1618 |
| 185 | 2.6868 |
| 186 | 0.0082 |
| 187 | 0.0638 |
| 188 | 0.0517 |
| 189 | 0.1438 |
| 190 | 0.024 |
| 191 | 0.4701 |
| 192 | 0.0031 |
| 193 | 0.0117 |
| 194 | 0.0055 |
| 195 | 0.0164 |
| 196 | 0.022 |
| 197 | 0.0039 |
| 198 | 0.0025 |
| 199 | 0.0062 |
| 200 | 0.4256 |
| 201 | 0.0115 |
| 202 | 0.0038 |
| 203 | 0.0338 |
| 204 | 0.0525 |
| 205 | 0.0901 |
| 206 | 0.0122 |
| 207 | 0.0011 |
| 208 | 0.0013 |
| 209 | 0.0037 |
| 210 | 0.0005 |
| 211 | 2.6545 |
| 212 | 0.0812 |
| 213 | 0.0007 |
| 214 | 0.001 |
| 215 | 0.0005 |
| 216 | 0.0008 |
| 217 | 0.0113 |
| 218 | 0.0052 |
| 219 | 0.0523 |
| 220 | 0.0023 |
| 221 | 0.0049 |
| 222 | 0.0425 |
| 223 | 0.0184 |
| 224 | 0.0181 |
| 225 | 0.0005 |
| 226 | 0.0543 |
| 227 | 0.0641 |
| 228 | 0.038 |
| 229 | 0.0126 |
| 230 | 0.1179 |
| 231 | 0.0417 |
| 232 | 0.004 |
| 233 | 0.0249 |
| 234 | 0.0773 |
| 235 | 0.034 |
| 236 | 0.0068 |
| 237 | 0.0934 |
| 238 | 0.0523 |
| 239 | 0.0477 |
| 240 | 0.1908 |
| 241 | 0.0286 |
| 242 | 0.0693 |
| 243 | 0.0014 |
| 244 | 0.0002 |

-continued

| Example | PDE10A inhibition IC$_{50}$ [µmol/l] |
|---|---|
| 245 | 0.0359 |
| 246 | 0.4252 |
| 247 | 0.29 |
| 248 | 0.0081 |
| 249 | 0.0268 |
| 250 | 0.0159 |
| 251 | 0.1371 |
| 252 | 0.0058 |
| 253 | 0.0159 |
| 254 | 0.0317 |
| 255 | 0.0029 |
| 256 | 0.0033 |
| 257 | 0.0671 |
| 258 | 0.1758 |
| 259 | 0.0018 |
| 260 | 0.0016 |
| 261 | 0.0035 |
| 262 | 0.0007 |
| 263 | 0.0543 |
| 264 | 0.0032 |
| 265 | 0.0206 |
| 266 | 0.012 |
| 267 | 0.007 |
| 268 | 0.0149 |
| 269 | 0.0127 |
| 270 | 0.0533 |
| 271 | 0.0004 |
| 272 | 0.0085 |
| 273 | 0.0003 |
| 274 | 0.0004 |
| 275 | 0.0004 |
| 276 | 0.0122 |
| 277 | 0.0027 |
| 278 | 0.0019 |
| 279 | 0.0069 |
| 280 | 0.0035 |
| 281 | 0.0006 |
| 282 | 0.002 |
| 283 | 0.0011 |
| 284 | 0.028 |
| 285 | 0.0193 |
| 286 | 0.0432 |
| 287 | 0.0151 |
| 288 | 0.0008 |
| 289 | 0.024 |
| 290 | 0.0028 |
| 291 | 0.0312 |
| 292 | 0.0007 |
| 293 | 0.006 |
| 294 | 0.0193 |
| 295 | 0.0023 |
| 296 | 0.0039 |
| 297 | 0.0041 |
| 298 | 0.0078 |
| 299 | 0.0003 |
| 300 | 0.0167 |
| 301 | 0.0004 |
| 302 | 0.001 |
| 303 | 0.368 |
| 304 | 0.1434 |
| 305 | 0.0045 |
| 306 | 0.0014 |
| 307 | 0.0686 |
| 308 | 0.0009 |
| 309 | 0.0011 |
| 310 | 0.0098 |
| 311 | 0.0205 |
| 312 | 0.0008 |
| 313 | 0.052 |
| 314 | 0.0343 |
| 315 | 0.0111 |
| 316 | 0.0241 |
| 317 | 0.0027 |
| 318 | 0.0046 |
| 319 | 0.0155 |
| 320 | 0.0863 |
| 321 | 0.0006 |

-continued

| Example | PDE10A inhibition IC$_{50}$ [µmol/l] |
|---|---|
| 322 | 0.0017 |
| 323 | 0.0359 |
| 324 | 0.0011 |
| 325 | 0.3353 |
| 326 | 0.0027 |
| 327 | 0.0018 |
| 328 | 0.0004 |
| 329 | 0.0029 |
| 330 | 0.0011 |
| 331 | 0.0031 |
| 332 | 0.0128 |
| 333 | 0.6908 |
| 334 | 0.0022 |
| 335 | 0.0008 |
| 336 | 0.0053 |
| 337 | 0.1262 |
| 338 | 0.0021 |
| 339 | 0.0493 |
| 340 | 0.2504 |
| 341 | 0.028 |

The compounds of formula (I) and/or their pharmaceutically acceptable salts can be used as therapeutics, e.g. in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils.

The production of the pharmaceutical compositions can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula (I) can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 0.1-500 mg, more specifically 1-200 mg, of a compound of formula (I).

The following examples serve to illustrate the present invention in more detail. They are, however, not intended to limit its scope in any manner.

EXAMPLES

A. Intermediates

A-1: 6-Cyclopropyl-3-(pyrimidin-5-ylamino)-pyridine-2-carboxylic acid ethyl ester

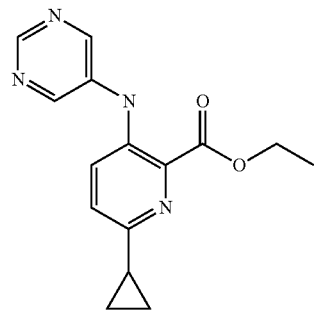 [SMILES: CCOC(=O)c1nc(C2CC2)ccc1Nc1cncnc1]

Step 1:
3-Amino-6-cyclopropyl-pyridine-2-carboxylic acid ethyl ester

To a solution of 3-amino-6-bromo-pyridine-2-carboxylic acid ethyl ester (prepared according to US 2006/199960; 1.0 g, 4.08 mmol), potassium phosphate (3.03 g, 14.3 mmol), tricyclohexylphosphine (0.228 g, 0.82 mmol) and water (1.25 ml) in toluene (25 ml) was added cyclopropylboronic acid (0.91 g, 10.6 mmol) and palladium (II) acetate (90 mg, 0.4 mmol). The resulting suspension was stirred at 100° C. for 24 hours. After solvent evaporation, the title compound was obtained after silica gel chromatography using a heptane/ethyl acetate gradient as yellow solid (0.374 g, 44%).
MS: M=207.0 (M+H)$^+$ Step 2: 6-Cyclopropyl-3-(pyrimidin-5-ylamino)-pyridine-2-carboxylic acid ethyl ester A suspension of 3-amino-6-cyclopropylpyridine-2-carboxylic acid ethyl ester (763 mg, 3.7 mmol), 5-bromopyrimidine (823 mg, 5.2 mmol), water (140 µl, 7.8 mmol) and potassium carbonate (920 mg, 6.7 mmol) in o-xylene (10 ml) was evacuated and vented with argon. Palladium(II) acetate (33 mg, 0.15 mmol) and 4,5-bis(diphenylphosphino)-9,9-dimethylxanthene (xantphos; 107 mg, 0.18 mmol) were consecutively added under inert gas atmosphere and the reaction mixture was heated to 140° C. and stirred overnight. After cooling-down to ambient temperature, the reaction mixture was diluted with dichloromethane (15 ml) and filtrated. The filtrate was concentrated in vacuo and the product was purified by silica gel chromatography using a heptane/ethyl acetate gradient to yield the title compound (796 mg, 75.7%) as light yellow solid.

MS: M=285.3 (M+H)$^+$

A-2: 6-Cyclopropyl-3-(pyrimidin-5-ylamino)-pyridine-2-carboxylic acid

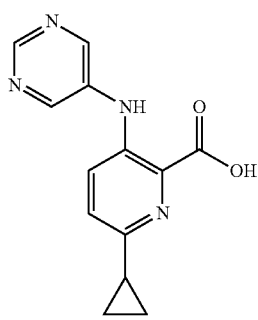 [SMILES: O=C(O)c1nc(C2CC2)ccc1Nc1cncnc1]

A suspension of 6-cyclopropyl-3-(pyrimidin-5-ylamino)-pyridine-2-carboxylic acid ethyl ester (1.85 g, 6.5 mmol) from example A-1 in EtOH (15 ml) was treated with 1N NaOH (13 ml). The reaction mixture was stirred at rt overnight. The compact suspension was brought to pH 6 by addition of 1N HCl. The solid was collected by filtration, washed with EtOH and dried to give the product (1.29 g, 77%) as off-white solid.

MS: M=255.0 (M–H)$^-$

A-3: 6-Methoxymethyl-3-(pyrimidin-5-ylamino)-pyridine-2-carboxylic acid methyl ester

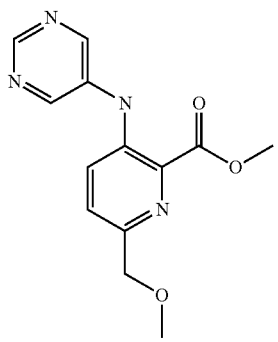 [SMILES: COCc1ccc(Nc2cncnc2)c(C(=O)OC)n1]

Step 1: 5-Bromo-pyridin-2-yl-methanol

To a solution of 5-bromopyridin-2-carboxylic acid (8 g, 42.1 mmol) in THF (100 ml) was added borane-dimethylsulphide (16 ml, 168.30 mmol) dropwise at 0° C. After warming-up to ambient temperature stirring was continued for 24 hours. The solution was cooled again to 0° C., quenched with MeOH and refluxed for 1 h. Solvents were removed and the residue was treated with water. The aqueous phase was extracted with ethyl acetate and the combined organic layers were washed with water and brine, dried, filtered and concentrated under reduced pressure to afford 4.76 g (64%) of the title compound.

MS: M=188.0 & 190.0 (M+H)$^+$

Step 2: 5-Bromo-2-hydroxymethyl-pyridine-1-oxide

5-Bromo-pyridin-2-yl-methanol (6.0 g, 31.9 mmol) was dissolved in dichloromethane (80 ml) and cooled to 0° C. A solution of 3-chloroperbenzoic acid (8.26 g, 47.9 mmol) in dichloromethane (20 ml) was slowly added, the ice bath was removed after completion of the addition, and the reaction mixture was stirred at ambient temperature for 1 h. The solvent was removed and the crude product was purified by silica gel chromatography using ethyl acetate to yield 3.68 g (56%) of the title compound.

MS: M=204.0 & 206.2 (M+H)$^+$

Step 3: 5-Bromo-2-methoxymethyl-pyridine-1-oxide

To a solution of 5-bromo-2-hydroxymethyl-pyridine-1-oxide (6.43 g, 31.5 mmol) in THF (200 ml) was added sodium hydride (1.51 g, 63.1 mmol) at 0° C., and then the reaction mixture was stirred at ambient temperature for 1 h. After cooling to 0° C., methyl iodide (2.90 ml, 46.6 mmol) was added. The temperature was raised to ambient temperature and the reaction mixture was heated to 70° C. for 1 h. After cooling to 0° C. the reaction mixture was quenched with MeOH. The solvents were removed, and the crude product was purified by silica gel chromatography using an ethyl acetate/hexane eluent to yield 4.8 g (70%) of the title compound.

MS: M=218.2 & 220.2 (M+H)$^+$

Step 4: 3-Bromo-6-methoxymethyl-pyridine-2-carbonitrile

A solution of 5-bromo-2-methoxymethyl-pyridine-1-oxide (5.0 g, 22.7 mmol), triethylamine (12.7 ml, 91 mmol) and trimethylsilyl cyanide (9.1 ml, 68.2 mmol) in acetonitrile (10 ml) was heated in a sealed tube to 120° C. for 18 hours. After completion of the reaction, water was added to the reaction mixture and acetonitrile was removed. The crude material was extracted with ethyl acetate. The combined organic layers were washed with water and brine, dried, filtered, and evaporated. The crude product was purified by silica gel chromatography using an ethyl acetate/hexane eluent to yield 3.0 g (58%) of the title compound.

MS: M=229.2 (M+H)$^+$

Step 5: 3-Bromo-6-methoxymethyl-pyridine-2-carboxylic acid

To a solution of 3-bromo-6-methoxymethyl-pyridine-2-carbonitrile (300 mg, 1.32 mmol) in MeOH (6 ml) was added a solution of potassium hydroxide (1.48 g, 26.43 mmol) in water (4 ml). The mixture was refluxed for 3 hours. MeOH was removed in vacuo, the aqueous solution was neutralized with conc. HCl under cooling, and the mixture was extracted with ethyl acetate. The combined organic layers were washed with water and brine, dried, filtered and evaporated. The obtained product (276 mg, 85%) was used in the next step without any further purification.

MS: M=246.2 & 248.2 (M+H)$^+$

Step 6:
3-Bromo-6-methoxymethyl-pyridine-2-carboxylic acid methyl ester

To a solution of 3-bromo-6-methoxymethyl-pyridine-2-carboxylic acid (200 mg, 0.81 mmol) in benzene (4 ml) and MeOH (1 ml) was slowly added trimethylsilyl-diazomethane (0.41 ml, 0.81 mmol) at ambient temperature, and the reaction mixture was stirred for 2 hours. The solvents were removed and the residue was extracted with ethyl acetate. The combined organic layers were washed with water and brine, dried, filtered, and evaporated. The crude product was purified by silica gel chromatography using an ethyl acetate/hexane eluent to yield 158 mg (75%) of the title compound as light yellow oil.
MS: M=260.0 & 262.0 (M+H)$^+$

Step 7: 6-Methoxymethyl-3-(pyrimidin-5-ylamino)-pyridine-2-carboxylic acid methyl ester According to the method described in step 2 of example A-1 and using 5-aminopyrimidine instead of 5-bromopyrimidine, the title compound was obtained as off-white solid in 75% yield.
MS: M=275.2 (M+H)$^+$

A-4: 2-Isopropyl-5-(pyrimidin-5-ylamino)-pyrimidine-4-carboxylic acid methyl ester

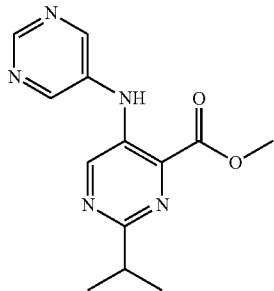 [SMILES: COC(=O)c1nc(C(C)C)ncc1Nc1cncnc1]

Step 1:
5-Bromo-2-isopropyl-pyrimidine-4-carboxylic acid

To a stirred suspension of isobutyramidine hydrochloride (6.47 g, 47.5 mmol) at rt in EtOH (30 ml) under an argon atmosphere was added NaOEt solution (21 ml, 21% in EtOH) over min. The suspension was heated to 50° C. and a solution of mucobromic acid (5.7 g, 22.1 mmol) in EtOH (24 ml) was added dropwise over 5 min at 50° C. An additional portion of NaOEt solution (12 ml, 21% in EtOH) was added dropwise over 5 min. The mixture was then cooled to rt. The solids were filtered off, and the cake was washed with plenty of ethanol. The filtrate was concentrated to leave the crude product as a light brown solid. The crude material was triturated in 2 N HCl (100 ml). The product was collected by filtration, washed with plenty of H$_2$O and plenty of n-heptane and dried to give the product (2.09 g, 73%) as beige solid.
MS: M=244.9 (M–H)$^-$

Step 2:
5-Bromo-2-isopropyl-pyrimidine-4-carboxylic acid methyl ester

To a stirred, cooled (0° C.) solution of 5-bromo-2-isopropyl-pyrimidine-4-carboxylic acid (3 g, 12.2 mmol) in methanol (50 ml) under an argon atmosphere was added dropwise thionyl chloride (4.37 g, 2.68 ml, 36.7 mmol). When the addition was complete, the mixture was allowed to warm to rt and stirring at rt was continued for 17 h. The orange mixture was concentrated to leave a paste which was taken up in EtOAc (50 ml)/saturated aqueous Na$_2$CO$_3$ solution (50 ml). The aqueous phase was extracted with EtOAc. The combined organic layers were washed with H$_2$O and brine, dried over MgSO$_4$, filtered and concentrated to leave the product (2.98 g, 94%) as a light brown oil which was used in the next reaction step without further purification.
MS: M=260.9 (M+H)$^+$

Step 3: 2-Isopropyl-5-(pyrimidin-5-ylamino)-pyrimidine-4-carboxylic acid methyl ester According to the method described in step 2 of example A-1 and using 5-aminopyrimidine instead of 5-bromopyrimidine, the title compound was obtained as yellow solid (76%).
MS: M=272.1 (M–H)$^-$

A-5: 2-Cyclopropyl-5-(pyrimidin-5-ylamino)-pyrimidine-4-carboxylic acid methyl ester

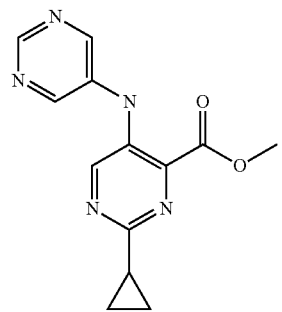 [SMILES: COC(=O)c1nc(C2CC2)ncc1Nc1cncnc1]

According to the methods described in example A-4, the title compound was obtained as yellow solid starting from cyclopropanecarboxamidine hydrochloride.
MS: M=270.1 (M–H)$^-$

A-6: 2-tert-Butyl-5-(pyrimidin-5-ylamino)-pyrimidine-4-carboxylic acid methyl ester

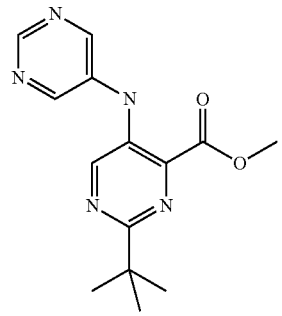 [SMILES: COC(=O)c1nc(C(C)(C)C)ncc1Nc1cncnc1]

According to the methods described in example A-4, the title compound was obtained as waxy solid starting from 2,2-dimethyl-propionamidine hydrochloride.
MS: M=288.1 (M+H)$^+$

A-7: 2-Isobutyl-5-(pyrimidin-5-ylamino)-pyrimidine-4-carboxylic acid methyl ester

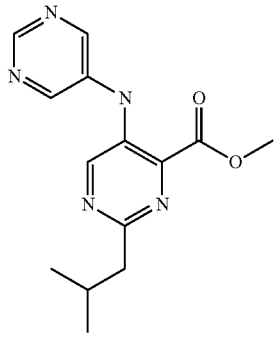 [SMILES: COC(=O)c1nc(CC(C)C)ncc1Nc1cncnc1]

According to the methods described in example A-4, the title compound was obtained as viscous oil starting from 3-methyl-butyramidine hydrochloride.
MS: M=288.1 (M+H)$^+$

A-8: 2-Cyclohexyl-5-(pyrimidin-5-ylamino)-pyrimidine-4-carboxylic acid methyl ester

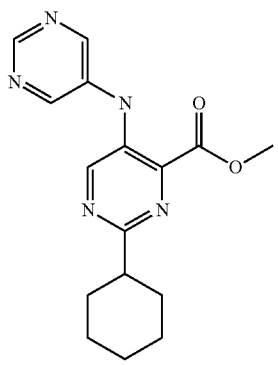 [SMILES: COC(=O)c1nc(C2CCCCC2)ncc1Nc1cncnc1]

According to the methods described in example A-4, the title compound was obtained as waxy solid starting from cyclohexanecarboxamidine.
MS: M=314.1 (M+H)$^+$

A-9: 2-tert-Butyl-5-(pyrimidin-5-ylamino)-pyrimidine-4-carboxylic acid

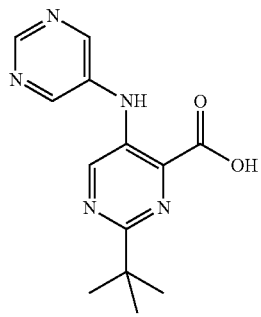 [SMILES: CC(C)(C)c1ncc(Nc2cncnc2)c(C(=O)O)n1]

According to the method described in example A-2, the title compound was obtained as light brown solid starting from A-6.
MS: M=272.1 (M–H)$^-$

A-10: 6-Cyclopropyl-3-(pyrimidin-5-ylamino)-pyrazine-2-carboxylic acid methyl ester

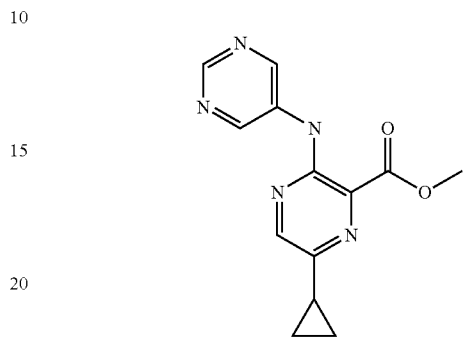

Step 1: Methyl 3-(bis(tert-butoxycarbonyl)amino)-6-bromopyrazine-2-carboxylate To a stirred mixture of methyl 3-amino-6-bromopyrazine-2-carboxylate (13.22 g, 57.0 mmol) and 4-dimethylaminopyridine (348 mg, 2.85 mmol) at rt in dichloroethane (175 ml) under an argon atmosphere was added dropwise a solution of di-tert-butyl dicarbonate (25.5 g, 117 mmol) in dichloroethane (75 ml) within 30 min. The mixture was heated to 75° C. and stirring at that temperature was continued for 18 h. The mixture was concentrated to leave a light brown syrup. Trituration in cyclohexane (150 ml) gave a precipitate. The suspension was stirred at rt for 2 h. The solid was collected by filtration, washed with cyclohexane and dried. The filtrate was concentrated and the residue was triturated in cyclohexane (50 ml). The suspension was stirred at rt for 2 h. The solid was collected by filtration, washed with cyclohexane and dried. The two crops of solids thus obtained were combined to give the title compound (23.2 g, 94%) as off-white solid.
MS: M=434.2 (M+H)$^+$

Step 2: 3-Amino-6-cyclopropylpyrazine-2-carboxylic acid methyl ester

Preparation of ZnCl$_2$ stock solution: 13.63 g zinc chloride (0.1 mol) was added a first portion of THF (20 ml). After the vigorous reaction had calmed down, the mixture was gently heated using a hair dryer for about 2 min. Then, under a stream of argon was added the rest of THF (80 ml) in one portion to give a colorless solution which was kept under argon.

To a stirred solution of bromocyclopropane (5.0 g, 41.3 mmol) at –78° C. in THF (30 ml) under an argon atmosphere was added n-BuLi solution in hexane (25.8 ml, 41.3 mmol). The temperature was kept below –70° C. during the addition. Stirring at –78° C. was then continued for 1 h. The above described ZnCl$_2$ solution (50 ml) was added dropwise at –78° C. Again, the temperature was kept below –70° C. during the addition. When the addition was complete, the reaction mixture was slowly allowed to reach r.t.

To a stirred suspension of methyl 3-(bis(tert-butoxycarbonyl)amino)-6-bromopyrazine-2-carboxylate (7 g, 16.2 mmol) at 0° C. in THF (50 ml) under an argon atmosphere was added dropwise the cyclopropylzinc(II) chloride solution described above. When the addition was complete, tetrakis(triphenlyphosphine)palladium(0) (187 mg, 162 µmol) was added in one portion and the ice bath was removed. The mixture was allowed to warm to rt and stirring at rt was continued for overnight. The mixture was treated with 0.5 N HCl (100 ml). The aqueous phase was extracted with EtOAc (50 ml). The combined organics were washed with brine (100 ml), dried (MgSO$_4$), filtered and concentrated to leave a dark brown syrup. The product thus obtained after filtration through silica gel using a n-heptane/ethyl acetate gradient as eluent is a mixture of 3-tert-butoxycarbonylamino-6-cyclopropyl-pyrazine-2-carboxylic acid methyl ester and 3-(bis(tert-butoxycarbonyl)amino)-6-cyclopropyl-pyrazine-2-carboxylic acid methyl ester (3.1 g, 59%). Off-white solid.

To a stirred solution of this mixture at rt in dichloromethane (30 ml) under an argon atmosphere was added trifluoroacetic acid (7.2 ml). The reaction was stirred at rt for 18 h, then diluted with CH$_2$Cl$_2$ (20 ml) and washed with saturated aqueous Na$_2$CO$_3$ (50 ml). The aqueous phase was back extracted with CH$_2$Cl$_2$ (25 ml). The combined organics were washed with brine (30 ml), dried (MgSO$_4$), filtered and concentrated to leave an orange sticky solid. This residue was triturated in cyclohexane (15 ml). The suspension was stirred at rt. for 1 h. The product was collected by filtration, washed with cyclohexane and dried to give the title compound (1.5 g, 83%) as yellow solid.

MS: M=194.2 (M+H)$^+$

Step 3: 6-Cyclopropyl-3-(pyrimidin-5-ylamino)-pyrazine-2-carboxylic acid methyl ester According to the method described in step 2 of example A-1 the product was obtained as yellow solid (2.5 g, 82%).
MS: M=272.2 (M+H)$^+$ A-11: 6-Cyclopropyl-3-(pyrimidin-5-ylamino)-pyrazine-2-carboxylic acid

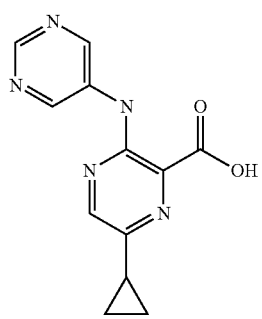 [SMILES: O=C(O)c1nc(C2CC2)cnc1Nc1cncnc1]

A solution of 6-cyclopropyl-3-(pyrimidin-5-ylamino)-pyrazine-2-carboxylic acid methyl ester (150 mg, 550 µmol) in THF (9 ml) and MeOH (1.8 ml) was cooled at 0° C. and treated with LiOH (1.66 ml, 1N aqueous solution). The ice bath was removed after 10 min and the reaction mixture was stirred at ambient temperature for 2 hrs. The reaction mixture was acidified with HCl (1.66 ml, 1N aqueous solution), diluted with water and extracted with dichloromethane. The combined organic layers were dried and concentrated in vacuo to yield a yellow solid. The aqueous phase was also concentrated in vacuo and the residue was triturated with ethyl acetate and sucked off to yield identical yellow solid (according to analytics). The solid material was combined to yield the product (75 mg, 52%)

MS: M=258.2 (M+H)$^+$

A-12: 6-Isobutyl-3-(pyrimidin-5-ylamino)-pyrazine-2-carboxylic acid methyl ester

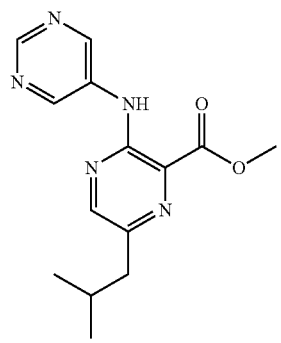 [SMILES: COC(=O)c1nc(CC(C)C)cnc1Nc1cncnc1]

Step 1: 3-(Bis(tert-butoxycarbonyl)amino)-6-bromopyrazine-2-carboxylic acid methyl ester To a mixture of 3-amino-6-bromopyrazine-2-carboxylic acid methyl ester (200 mg, 862 mmol) and DMAP (5.27 mg, 43.1 µmol) in dichloroethane (5 mL) was added dropwise a solution of di-tert-butyl dicarbonate (564 mg, 600 µL, 2.59 mmol) in dichloroethane (2.00 mL) at room temperature. The mixture was stirred at 75° C. for 16 h and then concentrated in vacuo. The product was obtained after silica gel chromatography using a heptane/ethyl acetate gradient as colorless oil (350 mg, 94%; crystallized after few hours).

MS: M=332.0 (M+H—C$_5$H$_9$O$_2$)$^+$

Step 2: 3-(Bis(tert-butoxycarbonyl)amino)-6-isobutylpyrazine-2-carboxylic acid methyl ester According to the method described in example A-1, step 1 and starting from 3-(bis(tert-butoxycarbonyl)amino)-6-bromopyrazine-2-carboxylic acid methyl ester, the product was obtained as light yellow oil (195 mg, 66%).

MS: M=410.2 (M+H)$^+$

Step 3: 3-Amino-6-isobutylpyrazine-2-carboxylic acid methyl ester

To a solution of 3-(bis(tert-butoxycarbonyl)amino)-6-isobutylpyrazine-2-carboxylic acid methyl ester (201 mg, 442 µmol) in dichloromethane (4 mL) was added trifluoroacetic acid (511 µL, 6.63 mmol) at room temperature. The mixture was stirred at ambient temperature for 3 h and the volatiles were evaporated. The residue was dissolved in dichloromethane (50 mL) and extracted with sodium carbonate. The aqueous phase was washed with dichloromethane and the organic layers were dried and evaporated. The product was obtained after silica gel chromatography using a heptane/ethyl acetate gradient as light yellow solid (88 mg, 95%).

MS: M=210.2 (M+H)$^+$

Step 4: 6-Isobutyl-3-(pyrimidin-5-ylamino)-pyrazine-2-carboxylic acid methyl ester According to the method described in step 2 of example A-1 and starting from 3-amino-6-isobutylpyrazine-2-carboxylic acid methyl ester, the product was obtained as light yellow solid (84 mg, 73%).

MS: M=288.2 (M+H)$^+$

A-13: 2-Methyl-5-(pyrimidin-5-ylamino)-pyrimidine-4-carboxylic acid

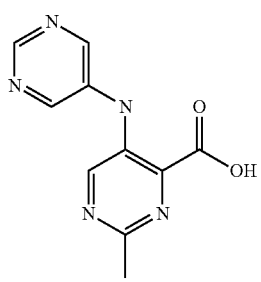 [SMILES: Cc1ncc(Nc2cncnc2)c(C(=O)O)n1]

Step 1: 2-Methyl-5-(pyrimidin-5-ylamino)-pyrimidine-4-carboxylic acid methyl ester A suspension of 5-bromo-2-methylpyrimidine-4-carboxylic acid methyl ester (89.1 mg, 386 μmol), 5-aminopyrimidine (55.0 mg, 578 μmo) and potassium phosphate tribasic (115 mg, 540 μmol) in toluene (3 mL) was evacuated and flushed with argon. 4,5-Bis(diphenylphosphino)-9,9-dimethylxanthene (Xantphos; 73.6 mg, 127 μmol) and tris(dibenzylideneacetone)-dipalladium(0) chloroform adduct (39.9 mg, 38.6 μmol) were added and the reaction mixture was stirred at 120° C. for 16 h. The reaction mixture was poured into ethyl acetate (50 mL) and extracted with water. The organic phase was washed brine and the aqueous layers were back-extracted with ethyl acetate. The organic layers were dried and the solvent was removed. The product was obtained after silica gel chromatography using a heptane/ethyl acetate gradient as light yellow solid (55 mg, 58%).

MS: M=246.2 (M+H)$^+$

Step 2: 2-Methyl-5-(pyrimidin-5-ylamino)-pyrimidine-4-carboxylic acid

According to the method described in example A-11 and starting from 2-methyl-5-(pyrimidin-5-ylamino)-pyrimidine-4-carboxylic acid methyl ester, the product was obtained as light yellow solid (51 mg, 97%).

MS: M=230.2 (M–H)$^-$

A-14: 6-Acetyl-3-(pyrimidin-5-amino)-pyrazine-2-carboxylic acid

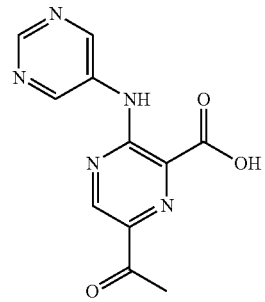 [SMILES: CC(=O)c1cnc(Nc2cncnc2)c(C(=O)O)n1]

Step 1: 6-Acetyl-3-tert-butoxycarbonylamino-pyrazine-2-carboxylic acid methyl ester To a stirred solution of an 1:4 mixture of methyl 3-(bis(tert-butoxycarbonyl)amino)-6-bromopyrazine-2-carboxylate and methyl 6-bromo-3-(tert-butoxycarbonylamino)pyrazine-2-carboxylate (ca. 4.1 g, 11.6 mmol) at rt in toluene (55 ml) under an argon atmosphere were added bis(triphenylpohsphine)palladium(II) chloride (81.1 mg, 0.12 mmol) and 1-ethoxyvinyl tri-N-butyltin (3.0 g, 2.8 ml, 12.7 mmol). The clear yellow solution was heated to reflux and stirring was continued for 18 h. The mixture was cooled to 0° C. 1 N HCl (55 ml) was added dropwise within 15 min. The biphasic mixture was stirred vigourously for 22 h, slowly warming up to rt. The layers were separated. The organic layer was diluted with 150 ml EtOAc (150 ml). Then, a 10% aqueous ammonium fluoride solution (150 ml) was added. The biphasic mixture was then stirred at rt for 5 h and then filtered. The organic phase of the filtrate was washed with 50 ml brine, dried (MgSO4), filtered and concentrated. The product was purified by silica gel chromatography using a n-heptane/ethyl acetate gradient. The product-containing fractions were concentrated. The residue was triturated with n-heptane/cyclohexane 9:1 (20 ml). The suspension was stirred for 2 hrs. The solid was filtrated, washed with n-heptane and dried to give the title compound (1.54 g, 45%) as off-white solid.

MS: M=296.2 (M+H)$^+$

Step 2: 6-Acetyl-3-amino-pyrazine-2-carboxylic acid methyl ester

To a stirred solution of 6-acetyl-3-tert-butoxycarbonylamino-pyrazine-2-carboxylic acid methyl ester (500 mg, 1.69 mmol) at rt in dioxane (10 ml) under an argon atmosphere was added 4 M HCl solution in dioxane (4.23 ml, 16.9 mmol) in one portion. The reaction mixture was stirred overnight, then concentrated. The residue was triturated with Et$_2$O, filtrated and dried. The solid was taken up in EtOAc (50 ml) and washed with saturated aqueous Na$_2$CO$_3$ solution (20 ml) and brine. The organic phase was dried over MgSO$_4$, filtrated and concentrated to give the title compound (313 mg, 95%) as orange powder.

MS: M=196.1 (M+H)$^+$

Step 3: 6-Acetyl-3-(pyrimidin-5-ylamino)-pyrazine-2-carboxylic acid methyl ester In analogy to the method described in step 2 of example A-1, the title compound was obtained as light yellow solid (38%).
MS: M=274.2 (M+H)+

Step 4: 6-Acetyl-3-(pyrimidin-5-ylamino)-pyrazine-2-carboxylic acid

In analogy to the method described in example A-2, the title compound was obtained as yellow powder (89%).
MS: M=258.0 (M−H)−

A-15: 2-Isopropyl-5-(pyrimidin-5-ylamino)-pyrimidine-4-carboxylic acid

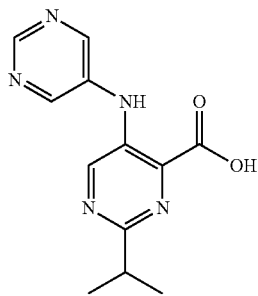 [SMILES: CC(C)c1ncc(Nc2cncnc2)c(C(=O)O)n1]

According to the method described in example A-2, the title compounds was obtained as yellow solid starting from A-4.
MS: M=258.0 (M−H)−

A-16: 3-(Pyrimidin-5-ylamino)-6-(tetrahydro-furan-3-yl)-pyrazine-2-carboxylic acid methyl ester

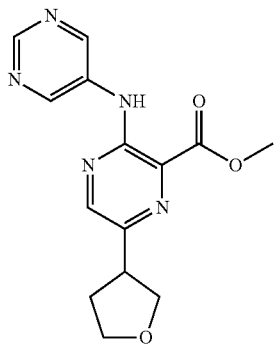 [SMILES: COC(=O)c1nc(C2CCOC2)cnc1Nc1cncnc1]

Step 1: 3-Amino-6-(furan-3-yl)-pyrazine-2-carboxylic acid methyl ester

A mixture of palladium (II) acetate (145 mg, 0.65 mmol) and 1,1'-bis(diphenylphosphino)-ferrocene (493 mg, 0.86 mmol) in DMF (70 ml) was stirred at 50° C. for 15 minutes and cooled to r.t. The mixture was evacuated and vented with argon. 3-Amino-6-bromopyrazine-2-carboxylic acid methyl ester (5.0 g, 21.5 mmol), furan-3-yl-boronic acid (2.79 g, 23.7 mmol) and triethylamine (4.51 ml, 32.3 mmol) were added and the reaction mixture was stirred at 90° C. for 16 h. The solvent was evaporated and the product was obtained after purification by silica gel chromatography using a heptane/ethyl acetate gradient as yellow solid (2.92 g, 61.8%).
MS: M=220.2 (M+H)+

Step 2: 3-Amino-6-(tetrahydro-furan-3-yl)-pyrazine-2-carboxylic acid methyl ester A solution of 3-amino-6-(furan-3-yl)-pyrazine-2-carboxylic acid methyl ester (2.9 g, 13.2 mmol) in MeOH (150 ml) was treated with palladium on carbon (10%; 0.6 g, 0.28 mmol) and hydrogenated at 1.2 atmospheres for 40 h. Another 2 equivalents of palladium on carbon were consecutively added and the hydrogenation was continued for another 72 h. The reaction mixture was filtered and the catalyst was washed with MeOH. The solution was concentrated in vacuo and the product was obtained after purification by silica gel chromatography using a heptane/ethyl acetate gradient as light yellow solid (0.3 g, 10%).
MS: M=224.1 (M+H)+

Step 3: 3-(Pyrimidin-5-ylamino)-6-(tetrahydro-furan-3-yl)-pyrazine-2-carboxylic acid methyl ester A mixture of 3-amino-6-(tetrahydrofuran-3-yl)pyrazine-2-carboxylic acid methyl ester (300 mg, 1.34 mmol), 5-bromopyrimidine (299 mg, 1.88 mmol) and potassium carbonate (334 mg, 2.42 mmol) in xylene (15 ml) and water (51 µl, 2.82 mmol) was evacuated and vented with argon. Palladium (II) acetate (12.1 mg, 54 µmol) and xantphos (23.3 mg, 40 µmol) were added and the reaction mixture was stirred at 140° C. for 16 hr. The reaction mixture was cooled to r.t., poured into 50 ml ethyl acetate and extracted with water. The organic phase was washed with brine and the aqueous layers were back-extracted with ethyl acetate. The organic layers were dried and the solvent was evaporated. The product was obtained after purification by silica gel chromatography using a heptane/ethyl acetate gradient as light solid (211 mg, 52%).
MS: M=302.1 (M+H)+

A-17: 6-Isopropyl-3-(pyrimidin-5-ylamino)-pyrazine-2-carboxylic acid

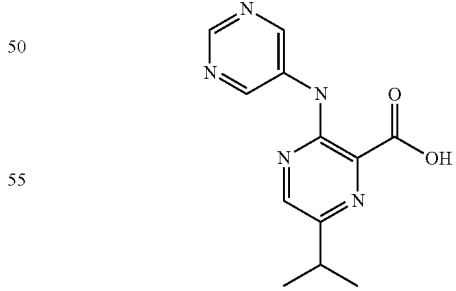

Step 1: Methyl 3-(bis(tert-butoxycarbonyl)amino)-6-(prop-1-en-2-yl)pyrazine-2-carboxylate The product was obtained starting from methyl 3-(bis(tert-butoxycarbonyl)amino)-6-bromopyrazine-2-carboxylate (1.13 g, 2.61 mmol) and 2-isopropenyl-4,4,5,5-tetramethyl- 1,3,2-dioxaborolane (672 μl, 3.4 mmol) according to the method described in example A-1, step 1 after extraction with ethyl acetate and purification by silica gel chromatography using a heptane/ethyl acetate gradient as yellow viscous oil (323 mg, 31%).

MS: M=294.2 (M-Boc+H)⁺

Step 2: Methyl 3-(bis(tert-butoxycarbonyl)amino)-6-isopropylpyrazine-2-carboxylate A solution of methyl 3-(bis(tert-butoxycarbonyl)amino)-6-(prop-1-en-2-yl)pyrazine-2-carboxylate (323 mg, 0.82 mmol) in MeOH (4 ml) was charged under an argon atmosphere at r.t. with Pd/C 10% (30 mg, 0.28 mmol). The reaction mixture was stirred at r.t. under a hydrogen atmosphere for 15 h, filtrated and the solvent was removed to yield the product as yellow viscous oil (302 mg, 92%) which was used without any purification.

MS: M=296.3 (M-Boc+H)⁺

Step 3: Methyl 3-amino-6-isopropylpyrazine-2-carboxylate

The product was obtained starting from methyl 3-(bis(tert-butoxycarbonyl)amino)-6-isopropylpyrazine-2-carboxylate (300 mg, 0.76 mmol) according to the method described in example A-12, step 3 as colorless solid (108 mg, 72%).

MS: M=196.2 (M+H)⁺

Step 4: Methyl 6-isopropyl-3-(pyrimidin-5-ylamino)pyrazine-2-carboxylate

The product was obtained starting from methyl 3-amino-6-isopropylpyrazine-2-carboxylate (54 mg, 0.28 mmol) according to the method described in example A-1, step 2 after purification by preparative HPLC using an acetonitrile/water gradient as off-white solid (38 mg, 49%).

MS: M=274.1 (M+H)⁺

Step 5: 6-Isopropyl-3-(pyrimidin-5-ylamino)-pyrazine-2-carboxylic acid

The product was obtained starting from methyl 6-isopropyl-3-(pyrimidin-5-ylamino)pyrazine-2-carboxylate (38 mg, 0.14 mmol) according to the method described in example A-11 as white solid (36 mg, 99%).

MS: M=258.1 (M-H)⁻

B. Final Products

Example 1

6-Cyclopropyl-3-(pyrimidin-5-ylamino)-pyridine-2-carboxylic acid (3-dimethylcarbamoyl-1-methyl-1H-pyrazol-4-yl)-amide

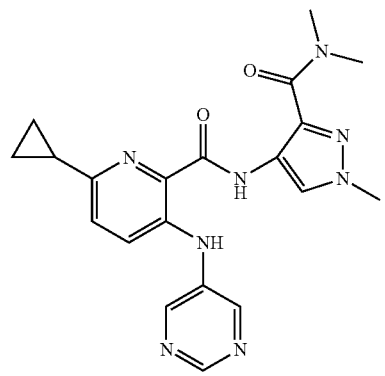 [SMILES: CN(C)C(=O)c1nn(C)cc1NC(=O)c1nc(C2CC2)ccc1Nc1cncnc1]

Step 1: 1-Methyl-4-nitro-1H-pyrazole-3-carboxylic acid dimethylamide

A solution of 1-methyl-4-nitro-1H-pyrazole-3-carboxylic acid (500 mg, 2.92 mmol) in DMF (5 ml) under inert gas atmosphere was treated with TBTU (1030 mg, 3.2 mmol), dimethylamine hydrochloride (262 mg, 3.2 mmol) and N,N-diisopropylethylamine (2.0 ml, 11.7 mmol) and stirring was continued for 4 h. All volatiles were removed and the crude product was extracted with water and ethyl acetate. The organic phase was washed with sodium bicarbonate and the aqueous phases were back-extracted with ethyl acetate and dichloromethane. The combined organic phases were dried and the solvent was evaporated. The product was obtained after purification by silica gel chromatography using a dichloromethane/methanol gradient as white solid (230 mg, 40%).

MS: M=199.3 (M+H)⁺

Step 2: 4-Amino-1-methyl-1H-pyrazole-3-carboxylic acid dimethylamide

A solution of 1-methyl-4-nitro-1H-pyrazole-3-carboxylic acid dimethylamide (100 mg, 0.5 mmol) in ethanol (4 ml) was flushed with argon and treated with Pd/C₅% (40 mg, 0.02 mmol). The reaction vessel was evacuated and flushed with hydrogen three times and the reaction was stirred at ambient temperature overnight. The reaction mixture was filtrated and the solvent was evaporated to yield an off-white solid material (83 mg, 98%) which was used without further purification.

MS: M=169.1 (M+H)⁺

Step 3: 6-Cyclopropyl-3-(pyrimidin-5-ylamino)-pyridine-2-carboxylic acid (3-dimethylcarbamoyl-1-methyl-1H-pyrazol-4-yl)-amide Intermediate A-2 (75 mg, 0.19 mmol) was dissolved in DMF (1 ml) and TBTU (68 mg, 0.21 mmol) was added under inert gas atmosphere. After 5 min. of stirring at ambient temperature N,N-diisopropylethylamine (131 μl, 0.77 mmol)

was added and stirring was continued for 10 min. 4-Amino-1-methyl-1H-pyrazole-3-carboxylic acid dimethylamide (36 mg, 0.21 mmol) was added and the reaction was stirred overnight at ambient temperature. The reaction was quenched with a small amount of water, the solvent was evaporated and the residue was extracted with water and ethyl acetate. The organic phase was dried and the solvent was evaporated. The product was obtained after purification by preparative HPLC using an acetonitrile/water gradient as yellow solid (4 mg, 5%).

MS: M=407.4 (M+H)$^+$

Example 2

6-Cyclopropyl-3-(pyrimidin-5-ylamino)-pyridine-2-carboxylic acid (1-methyl-3-methylcarbamoyl-1H-pyrazol-4-yl)-amide

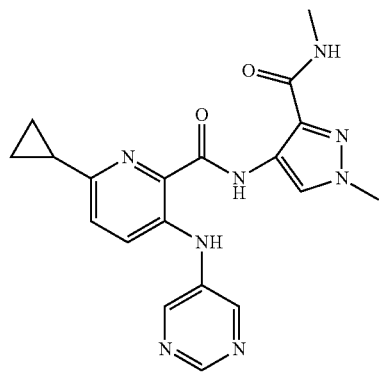 [SMILES: CNC(=O)c1nn(C)cc1NC(=O)c1nc(C2CC2)ccc1Nc1cncnc1]

Step 1: 1-Methyl-4-nitro-1H-pyrazole-3-carboxylic acid methylamide

The product was obtained according to the method described in example 1, step 1 starting from 1-methyl-4-nitro-1H-pyrazole-3-carboxylic acid and methylamine hydrochloride as light yellow solid (250 mg, 64%).

MS: M=185.1 (M+H)$^+$

Step 2: 4-Amino-1-methyl-1H-pyrazole-3-carboxylic acid methylamide

A solution of 1-methyl-4-nitro-1H-pyrazole-3-carboxylic acid methylamide (100 mg, 0.5 mmol) in ethanol (4 ml) was flushed with argon and treated with Pd/C 10% (40 mg, 0.04 mmol). The reaction vessel was evacuated and flushed with hydrogen three times and the reaction was stirred at ambient temperature overnight. The reaction mixture was filtrated and the solvent was evaporated to yield a brown viscous oil (76 mg, 91%) which was used without further purification.

MS: M=155.2 (M+H)$^+$

Step 3: 6-Cyclopropyl-3-(pyrimidin-5-ylamino)-pyridine-2-carboxylic acid (1-methyl-3-methylcarbamoyl-1H-pyrazol-4-yl)-amide Under inert gas atmosphere, 4-amino-1-methyl-1H-pyrazole-3-carboxylic acid methylamide (12 mg, 0.08 mmol) was dissolved in toluene (1.5 ml). Dimethylaluminium chloride (164 μl, 0.9M heptane solution) was added and the reaction mixture was stirred for 10 min. at ambient temperature. Intermediate A-1 (20 mg, 0.07 mmol) was added and the reaction mixture was heated to 90° C. for 5 hrs. After cooling-down to ambient temperature, a small amount of water was added and the resulting suspension was stirred vigorously for 5 min. All volatiles were removed and the product was obtained after purification by silica gel chromatography using a heptane/ethyl acetate gradient as off-white solid (7.8 mg, 28%).

MS: M=393.2 (M+H)$^+$

Example 3

6-Cyclopropyl-3-(pyrimidin-5-ylamino)-pyridine-2-carboxylic acid (3-carbamoyl-1-methyl-1H-pyrazol-4-yl)-amide

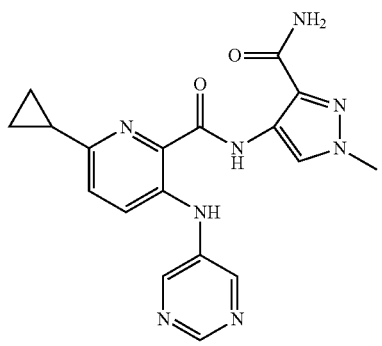 [SMILES: Cn1cc(NC(=O)c2nc(C3CC3)ccc2Nc2cncnc2)c(C(N)=O)n1]

Step 1: 1-Methyl-4-nitro-1H-pyrazole-3-carboxylic acid amide

The product was obtained according to the method described in example 1, step 1 starting from 1-methyl-4-nitro-1H-pyrazole-3-carboxylic acid and two equivalents of ammonium chloride as amine source as light yellow solid (110 mg, 37%).

MS: M=171.2 (M+H)$^+$

Step 2: 4-Amino-1-methyl-1H-pyrazole-3-carboxylic acid amide

The product was obtained according to the method described in example 2, step 2 starting from 1-methyl-4-nitro-1H-pyrazole-3-carboxylic acid amide as grey solid (45 mg, 100%).

Step 3: 6-Cyclopropyl-3-(pyrimidin-5-ylamino)-pyridine-2-carboxylic acid (1-methyl-3-methylcarbamoyl-1H-pyrazol-4-yl)-amide The product was obtained according to the method described in example 2, step 3 starting from 4-amino-1-methyl-1H-pyrazole-3-carboxylic acid amide and intermediate A-1 as off-white solid (7.5 mg, 28%)

MS: M=379.4 (M+H)$^+$.

Example 4

6-Cyclopropyl-3-(pyrimidin-5-ylamino)-pyridine-2-carboxylic acid [3-dimethylcarbamoyl-1-(2-methoxy-ethyl)-1H-pyrazol-4-yl]-amide

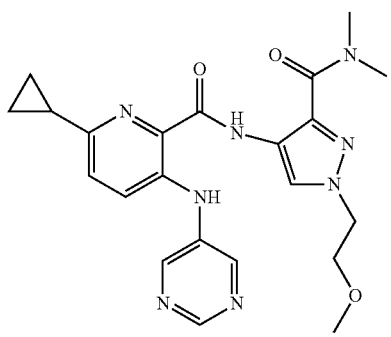 [SMILES: COCCn1cc(NC(=O)c2nc(C3CC3)ccc2Nc2cncnc2)c(C(=O)N(C)C)n1]

Step 1: 4-Nitro-1H-pyrazole-3-carboxylic acid ethyl ester

A solution of 4-nitro-1H-pyrazole-3-carboxylic acid (2.5 g, 15.9 mmol) in ethanolic HCl (38.3 mL, 1.25M) was refluxed overnight. All volatiles were removed to yield a white solid (2.9 g, 98%) which was used without any further purification.

MS: M=186.1 (M+H)$^+$

Step 2: 1-(2-Methoxyethyl)-4-nitro-1H-pyrazole-3-carboxylic acid ethyl ester To a solution of 4-nitro-1H-pyrazole-3-carboxylic acid ethyl ester (100 mg, 0.54 mmol) in DMSO (1 mL) was added potassium carbonate (164 mg, 1.19 mmol) and the reaction mixture was stirred for 5 min. 1-Bromo-2-methoxyethane (110 µl, 1.19 mml) was added and the resulting reaction mixture was stirred at ambient temperature overnight. The reaction mixture was partitioned between ethyl acetate and water and the aqueous phase was extracted with ethyl acetate. The combined organic phases were dried and the solvent was evaporated. The product was obtained as a mixture of regioisomers which were separated by silica gel chromatography using a heptane/ethyl acetate gradient to yield 72 mg (55%) of the desired regioisomer and 33 mg (25%) of 2-(2-methoxy-ethyl)-4-nitro-2H-pyrazole-3-carboxylic acid ethyl ester.

MS: M=244.3 (M+H)$^+$

Step 3: 1-(2-Methoxyethyl)-4-nitro-1H-pyrazole-3-carboxylic acid dimethylamide Under inert gas atmosphere, dimethylamine hydrochloride (73 mg, 0.89 mmol) was dissolved in toluene (1.0 ml). Dimethylaluminium chloride (990 µl, 0.9M heptane solution) was added and the reaction mixture was stirred for 10 min. at ambient temperature. 1-(2-Methoxyethyl)-4-nitro-1H-pyrazole-3-carboxylic acid ethyl ester (70 mg, 0.29 mmol) was added and the reaction mixture was heated to 90° C. overnight. After cooling-down to ambient temperature, a small amount of water was added and the resulting suspension was stirred vigorously for 5 min. All volatiles were removed and the product was obtained after purification by silica gel chromatography using a heptane/ethyl acetate gradient as light brown oil (65 mg, 93%).

MS: M=243.3 (M+H)$^+$

Step 4: 4-Amino-1-(2-methoxyethyl)-1H-pyrazole-3-carboxylic acid dimethylamide The product was obtained according to the method described in example 2, step 2 starting from 1-(2-methoxyethyl)-4-nitro-1H-pyrazole-3-carboxylic acid dimethylamide as light yellow oil (48 mg, 99%).

MS: M=213.2 (M+H)$^+$

Step 5: 6-Cyclopropyl-3-(pyrimidin-5-ylamino)-pyridine-2-carboxylic acid [3-dimethylcarbamoyl-1-(2-methoxy-ethyl)-1H-pyrazol-4-yl]-amide The product was obtained according to the method described in example 2, step 3 starting from 4-amino-1-(2-methoxyethyl)-1H-pyrazole-3-carboxylic acid dimethylamide and intermediate A-1 as yellow solid (33 mg, 52%).

MS: M=451.2 (M+H)$^+$

Example 5

6-Cyclopropyl-3-(pyrimidin-5-ylamino)-pyrazine-2-carboxylic acid (1-methyl-3-methylcarbamoyl-1H-pyrazol-4-yl)-amide

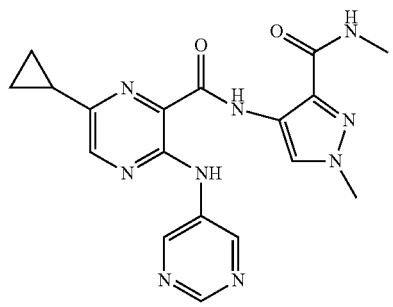 [SMILES: CNC(=O)c1nn(C)cc1NC(=O)c1nc(C2CC2)cnc1Nc1cncnc1]

The product was obtained according to the method described in example 2, step 3 starting from 4-amino-1-methyl-1H-pyrazole-3-carboxylic acid methylamide and intermediate A-10 as yellow solid (14 mg, 51%).

MS: M=394.1 (M+H)$^+$

Example 6

6-Cyclopropyl-3-(pyrimidin-5-ylamino)-pyridine-2-carboxylic acid [5-dimethylcarbamoyl-1-(2-methoxy-ethyl)-1H-pyrazol-4-yl]-amide

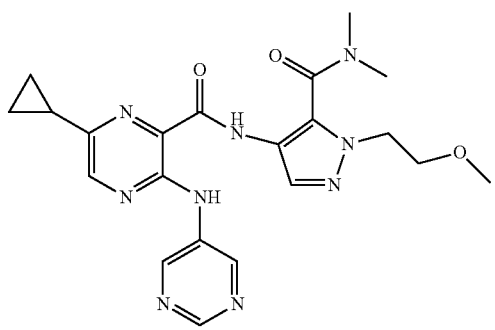 [SMILES: COCCn1ncc(NC(=O)c2nc(C3CC3)cnc2Nc2cncnc2)c1C(=O)N(C)C]

Step 1: 2-(2-Methoxyethyl)-4-nitro-2H-pyrazole-3-carboxylic acid ethyl ester The product was obtained according to the method described in example 4, step 2 as a mixture of regioisomers which were separated by silica gel chromatography using a heptane/ethyl acetate gradient to yield 33 mg (25%) of the desired regioisomer and 72 mg (55%) of 1-(2-methoxyethyl)-4-nitro-1H-pyrazole-3-carboxylic acid ethyl ester.

MS: M=244.3 (M+H)$^+$

Step 2: 2-(2-Methoxyethyl)-4-nitro-2H-pyrazole-3-carboxylic acid dimethylamide The product was obtained according to the method described in example 4, step 3 starting from 2-(2-methoxyethyl)-4-nitro-2H-pyrazole-3-carboxylic acid ethyl ester as light brown oil (20 mg, 67%).

MS: M=243.2 (M+H)$^+$

Step 3: 4-Amino-2-(2-methoxyethyl)-2H-pyrazole-3-carboxylic acid dimethylamide The product was obtained according to the method described in example 2, step 2 starting from 2-(2-methoxyethyl)-4-nitro-2H-pyrazole-3-carboxylic acid dimethylamide as grey oil (19 mg, 99%).

MS: M=213.2 (M+H)$^+$

Step 4: 6-Cyclopropyl-3-(pyrimidin-5-ylamino)-pyridine-2-carboxylic acid [5-dimethylcarbamoyl-1-(2-methoxy-ethyl)-1H-pyrazol-4-yl]-amide The product was obtained according to the method described in example 2, step 3 starting from 4-amino-2-(2-methoxyethyl)-2H-pyrazole-3-carboxylic acid dimethylamide and intermediate A-1 as yellow solid (4 mg, 12%).

MS: M=451.2 (M+H)$^+$

Example 7

6-Cyclopropyl-3-(pyrimidin-5-ylamino)-pyridine-2-carboxylic acid [3-dimethylcarbamoyl-1-(2,2,2-trifluoro-ethyl)-1H-pyrazol-4-yl]-amide

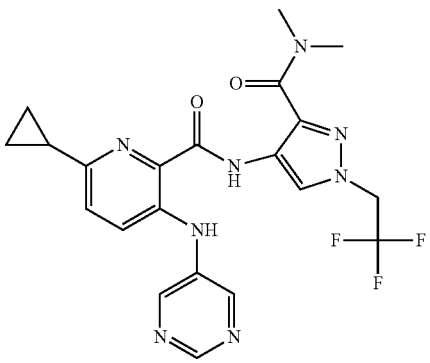 [SMILES: CN(C)C(=O)c1nn(CC(F)(F)F)cc1NC(=O)c1nc(C2CC2)ccc1Nc1cncnc1]

Step 1: 4-Nitro-1-(2,2,2-trifluoroethyl)-1H-pyrazole-3-carboxylic acid ethyl ester The product was obtained as a single regioisomer according to the method described in example 4, step 2 starting from 4-nitro-1H-pyrazole-3-carboxylic acid ethyl ester and 2,2,2-trifluoroethyl methanesulfonate after purification by silica gel chromatography using a heptane/ethyl acetate gradient as yellow oil (568 mg, 84%).

MS: M=268.1 (M+H)$^+$

Step 2: 4-Nitro-1-(2,2,2-trifluoroethyl)-1H-pyrazole-3-carboxylic acid dimethylamide The product was obtained according to the method described in example 4, step 3 starting from 4-nitro-1-(2,2,2-trifluoroethyl)-1H-pyrazole-3-carboxylic acid ethyl ester as off-white solid (38 mg, 66%).

MS: M=267.0 (M+H)$^+$

Step 3: 4-Amino-1-(2,2,2-trifluoroethyl)-1H-pyrazole-3-carboxylic acid dimethylamide The product was obtained according to the method described in example 2, step 2 starting from 4-nitro-1-(2,2,2-trifluoroethyl)-1H-pyrazole-3-carboxylic acid dimethylamide as off-white solid (32 mg, 99%).

MS: M=237.2 (M+H)$^+$

Step 4: 6-Cyclopropyl-3-(pyrimidin-5-ylamino)-pyridine-2-carboxylic acid [3-dimethylcarbamoyl-1-(2,2,2-trifluoro-ethyl)-1H-pyrazol-4-yl]-amide The product was obtained according to the method described in example 2, step 3 starting from 4-amino-1-(2,2,2-trifluoroethyl)-1H-pyrazole-3-carboxylic acid dimethylamide and intermediate A-1 as light yellow solid (11 mg, 33%).

MS: M=475.1 (M+H)$^+$

Example 8

6-Cyclopropyl-3-(pyrimidin-5-ylamino)-pyridine-2-carboxylic acid [3-methylcarbamoyl-1-(2,2,2-trifluoro-ethyl)-1H-pyrazol-4-yl]-amide

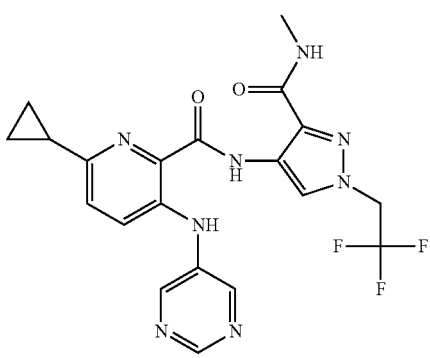 [SMILES: CNC(=O)c1nn(CC(F)(F)F)cc1NC(=O)c1nc(C2CC2)ccc1Nc1cncnc1]

Step 1: 4-Nitro-1-(2,2,2-trifluoroethyl)-1H-pyrazole-3-carboxylic acid methylamide The product was obtained according to the method described in example 4, step 3 starting from 4-nitro-1-(2,2,2-trifluoroethyl)-1H-pyrazole-3-carboxylic acid ethyl ester as light yellow oil (43 mg, 81%).

MS: M=253.2 (M+H)$^+$

Step 2: 4-Amino-1-(2,2,2-trifluoroethyl)-1H-pyrazole-3-carboxylic acid methylamide The product was obtained according to the method described in example 2, step 2 starting from 4-nitro-1-(2,2,2-trifluoroethyl)-1H-pyrazole-3-carboxylic acid methylamide as off-white solid (25 mg, 71%).

MS: M=223.2 (M+H)$^+$

Step 3: 6-Cyclopropyl-3-(pyrimidin-5-ylamino)-pyridine-2-carboxylic acid [3-methylcarbamoyl-1-(2,2,2-trifluoro-ethyl)-1H-pyrazol-4-yl]-amide The product was obtained according to the method described in example 2, step 3 starting from 4-amino-1-(2,2,2-trifluoroethyl)-1H-pyrazole-3-carboxylic acid methylamide and intermediate A-1 as light yellow solid (14 mg, 58%).

MS: M=461.3 (M+H)$^+$

Example 9

6-Cyclopropyl-3-(pyrimidin-5-ylamino)-pyridine-2-carboxylic acid [3-methylcarbamoyl-1-(3,3,3-trifluoro-propyl)-1H-pyrazol-4-yl]-amide

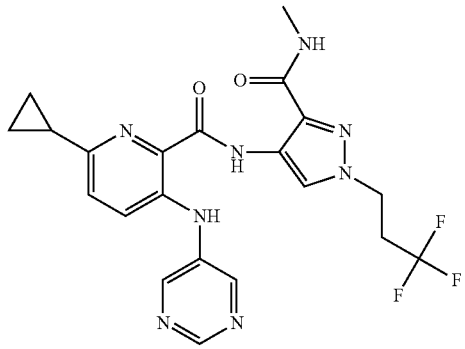 [SMILES: CNC(=O)c1nn(CCC(F)(F)F)cc1NC(=O)c1nc(C2CC2)ccc1Nc1cncnc1]

Step 1: 4-Nitro-1-(3,3,3-trifluoropropyl)-1H-pyrazole-3-carboxylic acid ethyl ester The product was obtained according to the method described in example 4, step 2 starting from 4-nitro-1H-pyrazole-3-carboxylic acid ethyl ester and 1,1,1-trifluoro-3-iodo-propane as a mixture of regioisomers which were separated by silica gel chromatography using a heptane/ethyl acetate gradient to yield 68 mg (15%) of the desired regioisomer and 141 mg (31%) of 4-nitro-2-(3,3,3-trifluoropropyl)-2H-pyrazole-3-carboxylic acid ethyl ester.

MS: M=282.0 (M+H)$^+$

Step 2: 4-Nitro-1-(3,3,3-trifluoropropyl)-1H-pyrazole-3-carboxylic acid methylamide The product was obtained according to the method described in example 4, step 3 starting from 4-nitro-1-(3,3,3-trifluoropropyl)-1H-pyrazole-3-carboxylic acid ethyl ester as light brown waxy solid (41 mg, 67%).

MS: M=267.0 (M+H)$^+$

Step 3: 4-Amino-1-(3,3,3-trifluoropropyl)-1H-pyrazole-3-carboxylic acid methylamide The product was obtained according to the method described in example 2, step 2 starting from 4-nitro-1-(3,3,3-trifluoropropyl)-1H-pyrazole-3-carboxylic acid methylamide as brown oil (36 mg, 99%).

MS: M=237.2 (M+H)$^+$

Step 4: 6-Cyclopropyl-3-(pyrimidin-5-ylamino)-pyridine-2-carboxylic acid [3-methylcarbamoyl-1-(3,3,3-trifluoro-propyl)-1H-pyrazol-4-yl]-amide The product was obtained according to the method described in example 2, step 3 starting from 4-amino-1-(3,3,3-trifluoropropyl)-1H-pyrazole-3-carboxylic acid methylamide and intermediate A-1 as light yellow solid (11 mg, 33%).

MS: M=475.5 (M+H)$^+$

Example 10

6-Cyclopropyl-3-(pyrimidin-5-ylamino)-pyridine-2-carboxylic acid [5-methylcarbamoyl-1-(3,3,3-trifluoro-propyl)-1H-pyrazol-4-yl]-amide

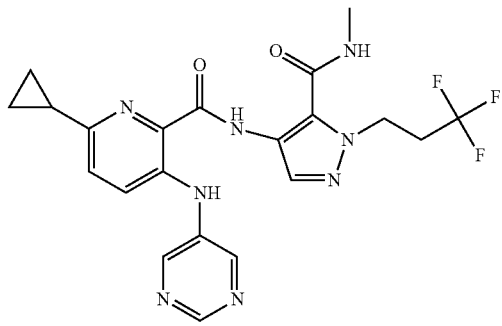 [SMILES: CNC(=O)c1c(NC(=O)c2nc(C3CC3)ccc2Nc2cncnc2)cnn1CCC(F)(F)F]

Step 1: 4-Nitro-2-(3,3,3-trifluoropropyl)-2H-pyrazole-3-carboxylic acid ethyl ester The product was obtained according to the method described in example 4, step 2 starting from 4-nitro-1H-pyrazole-3-carboxylic acid ethyl ester and 1,1,1-trifluoro-3-iodo-propane as a mixture of regioisomers which were separated by silica gel chromatography using a heptane/ethyl acetate gradient to yield 141 mg (31%) of the desired regioisomer and 68 mg (15%) of 4-nitro-1-(3,3,3-trifluoropropyl)-1H-pyrazole-3-carboxylic acid ethyl ester.
MS: M=282.0 (M+H)$^+$

Step 2: 4-Nitro-2-(3,3,3-trifluoropropyl)-2H-pyrazole-3-carboxylic acid methylamide The product was obtained according to the method described in example 4, step 3 starting from 4-nitro-2-(3,3,3-trifluoropropyl)-2H-pyrazole-3-carboxylic acid ethyl ester as colorless oil (33 mg, 50%).
MS: M=267.0 (M+H)$^+$

Step 3: 4-Amino-2-(3,3,3-trifluoropropyl)-2H-pyrazole-3-carboxylic acid methylamide The product was obtained according to the method described in example 2, step 2 starting from 4-nitro-2-(3,3,3-trifluoropropyl)-2H-pyrazole-3-carboxylic acid methylamide as brown oil (30 mg, >100%).
MS: M=237.2 (M+H)$^+$

Step 4: 6-Cyclopropyl-3-(pyrimidin-5-ylamino)-pyridine-2-carboxylic acid [5-methylcarbamoyl-1-(3,3,3-trifluoro-propyl)-1H-pyrazol-4-yl]-amide The product was obtained according to the method described in example 2, step 3 starting from 4-amino-2-(3,3,3-trifluoropropyl)-2H-pyrazole-3-carboxylic acid methylamide and intermediate A-1 as light yellow solid (12 mg, 41%).
MS: M=475.1 (M+H)$^+$

Example 11

6-Cyclopropyl-3-(pyrimidin-5-ylamino)-pyridine-2-carboxylic acid [1-(2-methoxy-ethyl)-5-methylcarbamoyl-1H-pyrazol-4-yl]-amide

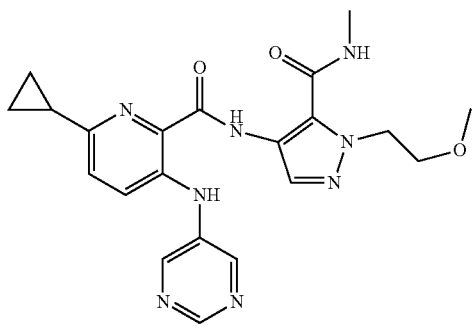 [SMILES: CNC(=O)c1c(NC(=O)c2nc(C3CC3)ccc2Nc2cncnc2)cnn1CCOC]

Step 1: 2-(2-Methoxyethyl)-4-nitro-2H-pyrazole-3-carboxylic acid methylamide The product was obtained according to the method described in example 4, step 3 starting from 2-(2-methoxyethyl)-4-nitro-2H-pyrazole-3-carboxylic acid ethyl ester (example 6, step 1; 22 mg, 40%).
MS: M=243.2 (M+H)$^+$

Step 2: 4-Amino-2-(2-methoxyethyl)-2H-pyrazole-3-carboxylic acid methylamide The product was obtained according to the method described in example 2, step 2 starting from 2-(2-methoxyethyl)-4-nitro-2H-pyrazole-3-carboxylic acid methylamide as light brown solid (16 mg, 47%).
MS: M=199.3 (M+H)$^+$

Step 3: 6-Cyclopropyl-3-(pyrimidin-5-ylamino)-pyridine-2-carboxylic acid [1-(2-methoxy-ethyl)-5-methylcarbamoyl-1H-pyrazol-4-yl]-amide The product was obtained according to the method described in example 2, step 3 starting from 4-amino-2-(2-methoxyethyl)-2H-pyrazole-3-carboxylic acid methylamide and intermediate A-1 as light yellow solid (4 mg, 26%).
MS: M=437.3 (M+H)$^+$

Example 12

6-Cyclopropyl-3-(pyrimidin-5-ylamino)-pyridine-2-carboxylic acid (1-cyclopropylmethyl-3-methylcarbamoyl-1H-pyrazol-4-yl)-amide

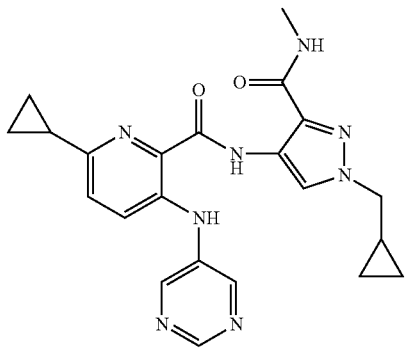 [SMILES: CNC(=O)c1nn(CC2CC2)cc1NC(=O)c1nc(C2CC2)ccc1Nc1cncnc1]

Step 1: 1-Cyclopropylmethyl-4-nitro-1H-pyrazole-3-carboxylic acid ethyl ester The product was obtained according to the method described in example 4, step 2 starting from 4-nitro-1H-pyrazole-3-carboxylic acid ethyl ester and bromomethyl-cyclopropane as a mixture of regioisomers which were separated by silica gel chromatography using a heptane/ethyl acetate gradient to yield 179 mg (46%) of the desired regioisomer and 88 mg (23%) of 2-cyclopropylmethyl-4-nitro-2H-pyrazole-3-carboxylic acid ethyl ester.
MS: M=240.1 (M+H)$^+$

Step 2: 1-Cyclopropylmethyl-4-nitro-1H-pyrazole-3-carboxylic acid methylamide The product was obtained according to the method described in example 4, step 3 starting from 1-cyclopropylmethyl-4-nitro-1H-pyrazole-3-carboxylic acid ethyl ester as light brown waxy solid (78 mg, 83%).
MS: M=225.2 (M+H)$^+$

Step 3: 4-Amino-1-cyclopropylmethyl-1H-pyrazole-3-carboxylic acid methylamide The product was obtained according to the method described in example 2, step 2 starting from 1-cyclopropylmethyl-4-nitro-1H-pyrazole-3-carboxylic acid methylamide as brown solid (58 mg, 95%).
MS: M=195.2 (M+H)$^+$

Step 4: 6-Cyclopropyl-3-(pyrimidin-5-ylamino)-pyridine-2-carboxylic acid (1-cyclopropylmethyl-3-methylcarbamoyl-1H-pyrazol-4-yl)-amide The product was obtained according to the method described in example 2, step 3 starting from 4-amino-1-cyclopropylmethyl-1H-pyrazole-3-carboxylic acid methylamide and intermediate A-1 as light yellow solid (26 mg, 49%).
MS: M=433.4 (M+H)$^+$

Example 13

6-Cyclopropyl-3-(pyrimidin-5-ylamino)-pyridine-2-carboxylic acid (1-cyclopropylmethyl-5-methylcarbamoyl-1H-pyrazol-4-yl)-amide

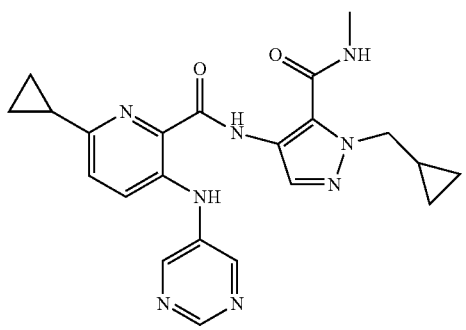 [SMILES: CNC(=O)c1c(NC(=O)c2nc(C3CC3)ccc2Nc2cncnc2)cnn1CC1CC1]

Step 1: 2-Cyclopropylmethyl-4-nitro-2H-pyrazole-3-carboxylic acid ethyl ester The product was obtained according to the method described in example 4, step 2 starting from 4-nitro-1H-pyrazole-3-carboxylic acid ethyl ester and bromomethyl-cyclopropane as a mixture of regioisomers which were separated by silica gel chromatography using a heptane/ethyl acetate gradient to yield 88 mg (23%) of the desired regioisomer and 179 mg (46%) of 1-cyclopropylmethyl-4-nitro-1H-pyrazole-3-carboxylic acid ethyl ester.
MS: M=240.1 (M+H)$^+$

Step 2: 2-Cyclopropylmethyl-4-nitro-2H-pyrazole-3-carboxylic acid methylamide The product was obtained according to the method described in example 4, step 3 starting from 2-cyclopropylmethyl-4-nitro-2H-pyrazole-3-carboxylic acid ethyl ester as white solid (40 mg, 53%).
MS: M=225.2 (M+H)$^+$

Step 3: 4-Amino-2-cyclopropylmethyl-2H-pyrazole-3-carboxylic acid methylamide The product was obtained according to the method described in example 2, step 2 starting from 2-cyclopropylmethyl-4-nitro-2H-pyrazole-3-carboxylic acid methylamide as brown solid (32 mg, 92%).
MS: M=195.3 (M+H)$^+$

Step 4: 6-Cyclopropyl-3-(pyrimidin-5-ylamino)-pyridine-2-carboxylic acid (1-cyclopropylmethyl-5-methylcarbamoyl-1H-pyrazol-4-yl)-amide The product was obtained according to the method described in example 2, step 3 starting from 4-amino-2-cyclopropylmethyl-2H-pyrazole-3-carboxylic acid methylamide and intermediate A-1 as light yellow solid (14 mg, 46%).
MS: M=433.4 (M+H)$^+$

Example 14

6-Cyclopropyl-3-(pyrimidin-5-ylamino)-pyridine-2-carboxylic acid [1-methyl-3-(morpholine-4-carbonyl)-1H-pyrazol-4-yl]-amide

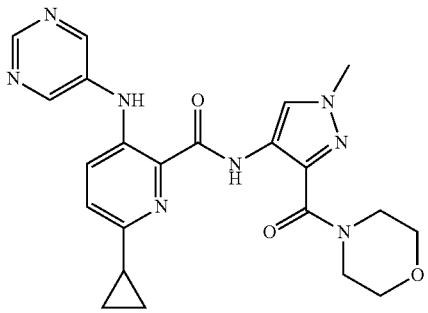 [SMILES: Cn1cc(NC(=O)c2nc(C3CC3)ccc2Nc2cncnc2)c(C(=O)N2CCOCC2)n1]

Step 1: (4-Amino-1-methyl-1H-pyrazol-3-yl)-morpholin-4-yl-methanone

According to the methods described in example 1, steps 1 and 2, the product was obtained by coupling of 1-methyl-4-nitro-1H-pyrazole-3-carboxylic acid and morpholine (90%) and subsequent hydrogenation (67%) as amorphous white solid.
MS: M=211.2 (M+H)$^+$

Step 2: 6-Cyclopropyl-3-(pyrimidin-5-ylamino)-pyridine-2-carboxylic acid [1-methyl-3-(morpholine-4-carbonyl)-1H-pyrazol-4-yl]-amide To a stirred solution of (4-amino-1-methyl-1H-pyrazol-3-yl)-morpholin-4-yl-methanone (67 mg, 0.32 mmol) at rt in dioxane (2 ml) under an argon atmosphere was added trimethylaluminium solution (0.16 ml, 2 M in toluene, 0.33 mmol). After stirring for 2 hrs at rt, A-1 (30 mg, 0.11 mmol) was added in one portion. The reaction was heated to 100° C. and stirring was continued for 16 h. The mixture was cooled to rt and H$_2$O (0.5 ml) was added. After 15 min stirring, some MgSO$_4$ was added and stirring was continued for 15 min. The mixture was filtered, washed with CH$_2$Cl$_2$ and evaporated. The product was obtained by silica gel chromatography using a CH$_2$Cl$_2$/MeOH gradient. Off-white solid (35 mg, 74%).
MS: M=449.3 (M+H)$^+$

Example 15

6-Cyclopropyl-3-(pyrimidin-5-ylamino)-pyridine-2-carboxylic acid [3-(cyclopropyl-methyl-carbamoyl)-1-methyl-1H-pyrazol-4-yl]-amide

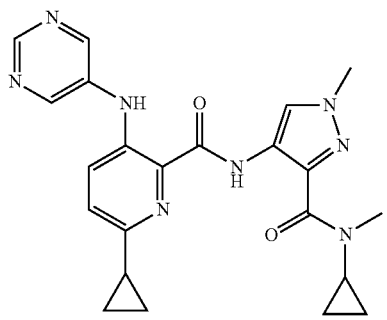 [SMILES: CN(C(=O)c1nn(C)cc1NC(=O)c1nc(C2CC2)ccc1Nc1cncnc1)C1CC1]

According to the methods described in example 14, the product was obtained by coupling of 1-methyl-4-nitro-1H-pyrazole-3-carboxylic acid and N-cyclopropylmethylamine (71%), hydrogenation (71%) and trimethylaluminium-promoted reaction with A-1 (41%). Off-white solid.
MS: M=433.4 (M+H)$^+$

Example 16

6-Cyclopropyl-3-(pyrimidin-5-ylamino)-pyridine-2-carboxylic acid [1-methyl-3-(piperidine-1-carbonyl)-1H-pyrazol-4-yl]-amide

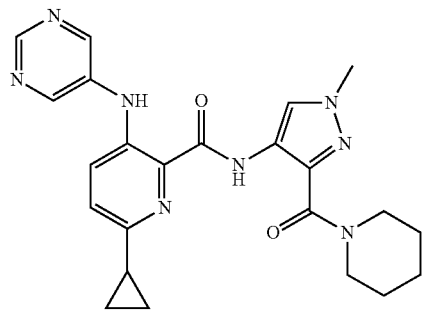 [SMILES: Cn1cc(NC(=O)c2nc(C3CC3)ccc2Nc2cncnc2)c(C(=O)N2CCCCC2)n1]

According to the methods described in example 14, the product was obtained by coupling of 1-methyl-4-nitro-1H-pyrazole-3-carboxylic acid and piperidine (quant.), hydrogenation (63%) and trimethylaluminium-promoted reaction with A-1 (89%). Off-white solid.
MS: M=447.3 (M+H)$^+$

Example 17

6-Cyclopropyl-3-(pyrimidin-5-ylamino)-pyridine-2-carboxylic acid [3-(cyclohexyl-methyl-carbamoyl)-1-methyl-1H-pyrazol-4-yl]-amide

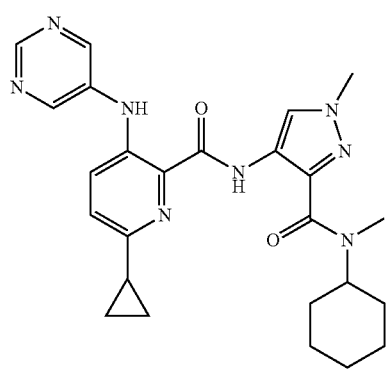 [SMILES: CN(C(=O)c1nn(C)cc1NC(=O)c1nc(C2CC2)ccc1Nc1cncnc1)C1CCCCC1]

According to the methods described in example 14, the product was obtained by coupling of 1-methyl-4-nitro-1H-pyrazole-3-carboxylic acid and N-methylcyclohexylamine (quant.), hydrogenation (80%) and trimethylaluminium-promoted reaction with A-1 (91%). Off-white solid.
MS: M=475.2 (M+H)$^+$

Example 18

6-Cyclopropyl-3-(pyrimidin-5-ylamino)-pyridine-2-carboxylic acid [1-(2-methoxy-ethyl)-3-methylcarbamoyl-1H-pyrazol-4-yl]-amide

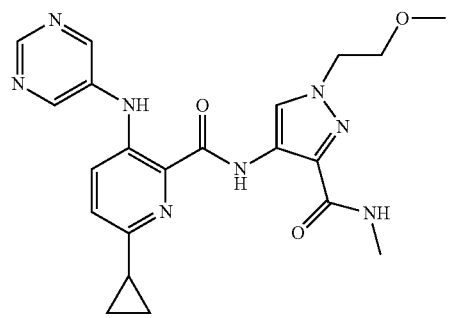 [SMILES: CNC(=O)c1nn(CCOC)cc1NC(=O)c1nc(C2CC2)ccc1Nc1cncnc1]

Step 1: 1-(2-Methoxy-ethyl)-4-nitro-1H-pyrazole-3-carboxylic acid methylamide To a solution of methylamine hydrochloride (2.0 g, 25 mmol) at rt in dioxane (60 ml) was added trimethylaluminium (2 M in toluene, 12.3 ml, 25 mmol) and stirred for 2 hrs at rt. Then 1-(2-methoxyethyl)-4-nitro-1H-pyrazole-3-carboxylic acid ethyl ester (2.0 g, 8.0 mmol; example 4, step 2) was added. The mixture was heated to 100° C. and stirring was continued overnight. The mixture was cooled to rt, then 2 ml water was added and stirring was continued for 15 min. Some MgSO$_4$ was added and stirring was continued for 15 min. The mixture was filtered, washed with CH$_2$Cl$_2$ and concentrated. The crude product was purified by silica gel chromatography using a cyclohexane/EtOAc gradient, providing the title compound (302 mg, 16%) as orange oil.

MS: M=229.2 (M+H)$^+$

Step 2: 4-Amino-1-(2-methoxy-ethyl)-1H-pyrazole-3-carboxylic acid methylamide According to the procedure described in step 2 of example 2, the title compound was obtained as oil (80%).

Step 3: 6-Cyclopropyl-3-(pyrimidin-5-ylamino)-pyridine-2-carboxylic acid [1-(2-methoxy-ethyl)-3-methylcarbamoyl-1H-pyrazol-4-yl]-amide According to the procedure described in step 2 of example 14, the title compound was obtained starting from 4-amino-1-(2-methoxy-ethyl)-1H-pyrazole-3-carboxylic acid methylamide and A-1 as yellow solid (58%).

MS: M=437.3 (M+H)$^+$

Example 19

6-Cyclopropyl-3-(pyrimidin-5-ylamino)-pyridine-2-carboxylic acid [3-(cyclopentyl-methyl-carbamoyl)-1-methyl-1H-pyrazol-4-yl]-amide

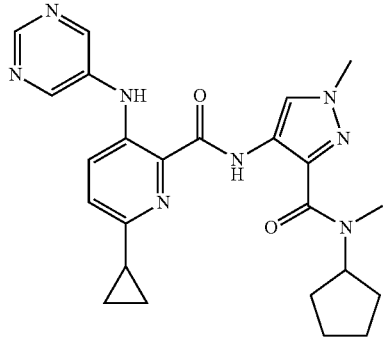 [SMILES: CN(C(=O)c1nn(C)cc1NC(=O)c1nc(C2CC2)ccc1Nc1cncnc1)C1CCCC1]

According to the methods described in example 14, the product was obtained by coupling of 1-methyl-4-nitro-1H-pyrazole-3-carboxylic acid and N-methylcyclopentylamine (quant.), hydrogenation (84%) and trimethylaluminium-promoted reaction with A-1 (55%).

MS: M=461.4 (M+H)$^+$

Example 20

6-Cyclopropyl-3-(pyrimidin-5-ylamino)-pyridine-2-carboxylic acid [3-(isopropyl-methyl-carbamoyl)-1-methyl-1H-pyrazol-4-yl]-amide

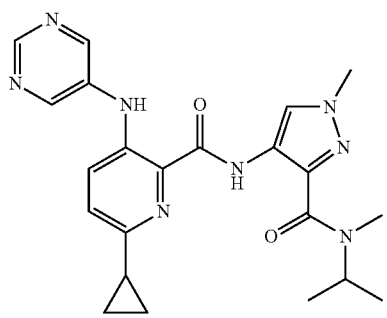 [SMILES: CC(C)N(C)C(=O)c1nn(C)cc1NC(=O)c1nc(C2CC2)ccc1Nc1cncnc1]

According to the methods described in example 14, the product was obtained by coupling of 1-methyl-4-nitro-1H-pyrazole-3-carboxylic acid and methylisopropylamine (95%), hydrogenation (60%) and trimethylaluminium-promoted reaction with A-1 (49%).

MS: M=435.4 (M+H)$^+$

Example 21

6-Cyclopropyl-3-(pyrimidin-5-ylamino)-pyridine-2-carboxylic acid [1-methyl-3-(pyrrolidine-1-carbonyl)-1H-pyrazol-4-yl]-amide

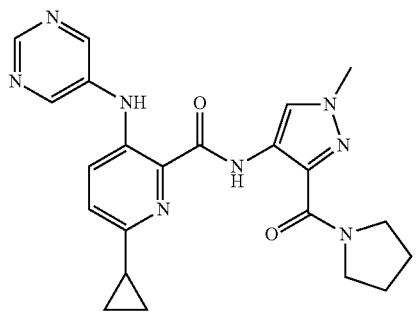 [SMILES: Cn1cc(NC(=O)c2nc(C3CC3)ccc2Nc2cncnc2)c(C(=O)N2CCCC2)n1]

According to the methods described in example 14, the product was obtained by coupling of 1-methyl-4-nitro-1H-pyrazole-3-carboxylic acid and pyrrolidine (46%), hydrogenation (89%) and trimethylaluminium-promoted reaction with A-1 (54%). Off-white solid.

MS: M=433.4 (M+H)$^+$

Example 22

6-Cyclopropyl-3-(pyrimidin-5-ylamino)-pyridine-2-carboxylic acid [4-(pyrrolidine-1-carbonyl)-pyridin-3-yl]-amide

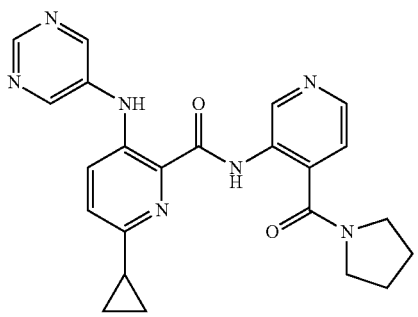 [SMILES: O=C(Nc1cnccc1C(=O)N1CCCC1)c1nc(C2CC2)ccc1Nc1cncnc1]

According to the methods described in example 14, the product was obtained by coupling of 3-nitro-4-pyridinecarboxylic acid and pyrrolidine (25%), hydrogenation (91%) and trimethylaluminium-promoted reaction with A-1 (30%). Light yellow solid.

MS: M=430.4 (M+H)$^+$

Example 23

6-Cyclopropyl-3-(pyrimidin-5-ylamino)-pyridine-2-carboxylic acid (4-dimethylcarbamoyl-pyridin-3-yl)-amide

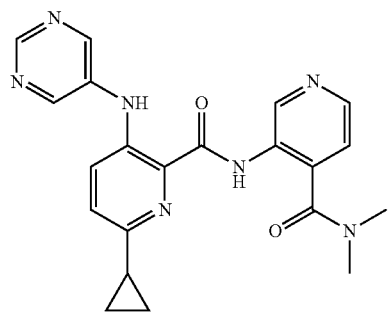 [SMILES: CN(C)C(=O)c1ccncc1NC(=O)c1nc(C2CC2)ccc1Nc1cncnc1]

According to the methods described in example 14, the product was obtained by coupling of 3-nitro-4-pyridinecarboxylic acid and dimethylamine hydrochloride (25%), hydrogenation (77%) and trimethylaluminium-promoted reaction with A-1 (26%). Light yellow solid.

MS: M=404.3 (M+H)$^+$

Example 24

6-Cyclopropyl-3-(pyrimidin-5-ylamino)-pyridine-2-carboxylic acid (4-methylcarbamoyl-pyridin-3-yl)-amide

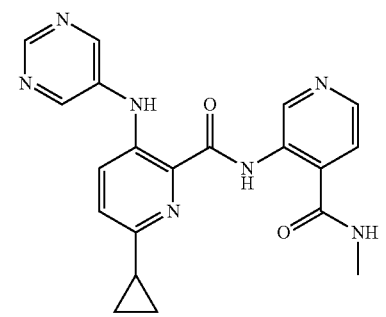 [SMILES: CNC(=O)c1ccncc1NC(=O)c1nc(C2CC2)ccc1Nc1cncnc1]

According to the methods described in example 14, the product was obtained by coupling of 3-nitro-4-pyridinecarboxylic acid and methylamine hydrochloride (38%), hydrogenation (95%) and trimethylaluminium-promoted reaction with A-1 (8%). Light yellow solid.

MS: M=390.1 (M+H)$^+$

Example 25

6-Cyclopropyl-3-(pyrimidin-5-ylamino)-pyridine-2-carboxylic acid (3-methylcarbamoyl-1-phenyl-1H-pyrazol-4-yl)-amide

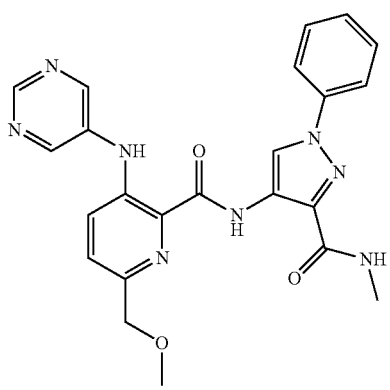 [SMILES: CNC(=O)c1nn(-c2ccccc2)cc1NC(=O)c1nc(COC)ccc1Nc1cncnc1]

Step 1: 4-Nitro-1-phenyl-1H-pyrazole-3-carboxylic acid ethyl ester

The title compound was prepared according to Z. Naturforsch. B., 2004, 59, 1132-1136. Off-white solid (27%).
MS: M=262.0 (M+H)$^+$

Step 2: 4-Nitro-1-phenyl-1H-pyrazole-3-carboxylic acid

To a stirred suspension of 4-nitro-1-phenyl-1H-pyrazole-3-carboxylic acid ethyl ester (240 mg, 0.92 mmol) at rt in ethanol (3 ml) under an argon atmosphere was added 1 N NaOH (1.8 ml). The mixture was stirred for 2 hrs. 3 N HCl was added until pH~2 was reached. Upon addition of H$_2$O (~2 ml), the product precipitated out. It was collected by filtration, washed with H$_2$O and dried. Off-white solid (184 mg, 86%).
MS: M=187.9 (M-COOH)$^-$

Step 3: 4-Amino-1 phenyl-1H-pyrazole-3-carboxylicacid methylamide

According to the methods described in step 1 of example 1 and in step 2 of example 2,4-nitro-1-phenyl-1H-pyrazole-3-carboxylic acid was coupled with methylamine hydrochloride (90%) and hydrogenated (quantitative) to give the title compound. Off-white solid.
MS: M=217.3 (M+H)$^+$

Step 4: 6-Cyclopropyl-3-(pyrimidin-5-ylamino)-pyridine-2-carboxylic acid (3-methylcarbamoyl-1-phenyl-1H-pyrazol-4-yl)-amide According to the method described in example 14, step 2,4-amino-1-phenyl-1H-pyrazole-3-carboxylic acid methylamide was reacted with A-1 to give the title compound. Off-white solid (52%).
MS: M=455.2 (M+H)$^+$

Example 26

6-Methoxymethyl-3-(pyrimidin-5-ylamino)-pyridine-2-carboxylic acid [1-(2-methoxy-ethyl)-5-methylcarbamoyl-1H-pyrazol-4-yl]-amide

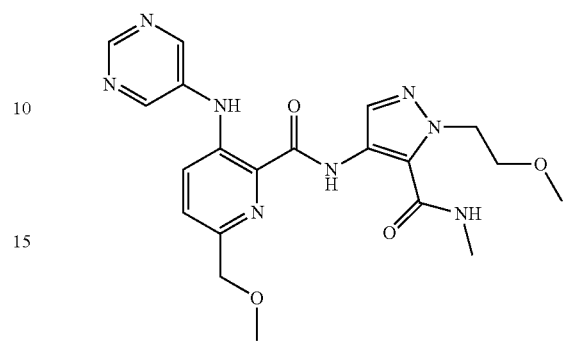

According to the methods described in example 18, the title compound was obtained by AlMe$_3$-promoted reaction of 2-(2-methoxyethyl)-4-nitro-2H-pyrazole-3-carboxylic acid ethyl ester (example 4, step 2) and methylamine hydrochloride (43%), hydrogenation (97%) and AlM$_3$-promoted reaction with A-3 (71%). Light yellow solid.
MS: M=441.3 (M+H)$^+$

Example 27

6-Cyclopropyl-3-(pyrimidin-5-ylamino)-pyridine-2-carboxylic acid [1-methyl-3-(2-methyl-pyrrolidine-1-carbonyl)-1H-pyrazol-4-yl]-amide

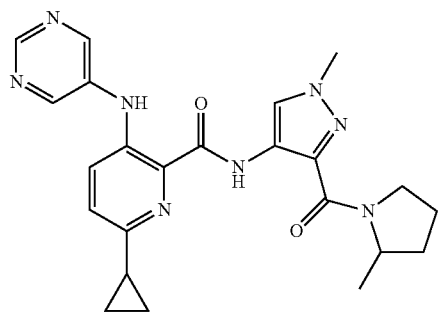 [SMILES: CC1CCCN1C(=O)c1nn(C)cc1NC(=O)c1nc(C2CC2)ccc1Nc1cncnc1]

Step 1: 4-Nitro-1H-pyrazole-3-carboxylic acid methyl ester

To a solution of 4-nitro-1H-pyrazole-3-carboxylic acid (5 g, 31.8 mmol) in dry MeOH (60 ml) was added freshly crystallized p-toluenesulphonic acid monohydrate (300 mg, 1.6 mmol). The reaction mixture was heated at 65° C. for 16 hrs. MeOH was removed in vacuo. The residue was taken up with saturated aqueous NaHCO$_3$ solution (15 ml) and extracted with EtOAc. The combined organic layers were washed with water, and then with brine, dried (Na$_2$SO$_4$), filtered, and evaporated. The crude product was purified by column chromatography over silica gel using 30% EtOAc/hexane) to provide the title compound as white solid (4.85 g, 89%).

Step 2: 1-Methyl-4-nitro-1H-pyrazole-3-carboxylic acid methyl ester

To a solution of 4-nitro-1H-pyrazole-3-carboxylic acid methyl ester (3.1 g, 18.1 mmol) in dry acetone (2 ml) was added $K_2CO_3$ (5 g, 36.2 mmol) at 25° C. The reaction mixture was cooled to 0° C., and methyl iodide (2.2 ml, 36.3 mmol) was added. The temperature was again raised to 25° C., and then heated to 70° C. for 2 hrs. The solvent was removed in vacuo The residue was diluted with EtOA and washed with water and with brine, dried ($Na_2SO_4$), filtered, and concentrated. The crude product was purified by column chromatography over silica gel. Elution with 20% EtOAc/hexane) gave the undesired isomer 2-methyl-4-nitro-2H-pyrazole-3-carboxylic acid methyl ester (1 g, 30%), subsequent elution with 40% EtOAc/hexane provided the desired isomer 1-methyl-4-nitro-1H-pyrazole-3-carboxylic acid methyl ester (1.8 g, 54%).

Step 3: 4-Amino-1-methyl-1H-pyrazole-3-carboxylic acid methyl ester

A solution of 1-methyl-4-nitro-1H-pyrazole-3-carboxylic acid methyl ester (4.8 g, 25.94 mmol) in dry MeOH (100 ml) was thoroughly purged with argon, treated with 10% Pd—C (2.7 g, 2.59 mmol), and again purged with argon. Then the reaction mixture was hydrogenated under a balloon pressure of hydrogen at rt for overnight. The reaction mixture was filtered through a bed of celite. The filtrate was concentrated and dried to give the title compound as gray-white solid (3.4 g, 84%), which was used in the next reaction step without further purification.

Step 4: 4-{[6-Cyclopropyl-3-(pyrimidin-5-ylamino)-pyridine-2-carbonyl]-amino}-1-methyl-1H-pyrazole-3-carboxylic acid methyl ester To a stirred solution of A-2 (600 mg, 2.34 mmol) in DMF (10 ml) was added EDCI (672 mg, 3.51 mmol) and HOBt (538 mg, 3.51 mmol) at 25° C. Stirring was continued for 10 min. 4-Amino-1-methyl-1H-pyrazole-3-carboxylic acid methyl ester (362 mg, 2.35 mmol) and triethylamine (0.8 ml, 5.35 mmol) were subsequently added to the above solution. The reaction mixture was stirred at 25° C. overnight, then quenched with water (8 ml), and extracted with $CH_2Cl_2$. The combined organic layers were washed with brine, dried ($Na_2SO_4$), filtered, and evaporated. The crude product thus obtained was purified by column chromatography over silica gel (2% MeOH/$CH_2Cl_2$) to provide the title compound (642 mg, 69%) as yellow sticky solid.

Step 5: General Procedure for LiHMDS-Mediated Amide Formation

To a stirred solution of the amine (1.50 mmol) in dry THF (5 ml) was added LiHMDS (1.0M in THF, 7-8 mmol) at −30° C. to −40° C. After stirring the reaction mixture at that temperature for 15 min, a solution of 4-{[6-cyclopropyl-3-(pyrimidin-5-ylamino)-pyridine-2-carbonyl]-amino}-1-methyl-1H-pyrazole-3-carboxylic acid methyl ester (1.0 mmol) in THF (3 ml) was added. The reaction mixture was stirred at rt overnight, then quenched with saturated aqueous ammonium chloride solution and extracted with EtOAc (3×5 ml). Combined organic layers were washed with brine (10 ml) and dried ($Na_2SO_4$), filtered and concentrated. The crude material was purified by prep-HPLC (column: Gemini C18 (250×21.2 mm, 5μ); elution with a gradient of 0.05% aqueous TFA solution/acetonitrile) to provide the final product.

6-Cyclopropyl-N-[1-methyl-3-(2-methyl-pyrrolidine-1-carbonyl)-1H-pyrazol-4-yl]-3-(pyrimidin-5-ylamino)-pyridine-2-carboximidic acid According to the general method described above (step 5), reaction of 2-methylpyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (19%) as sticky yellow solid.

MS: M=447.2 (M+H)$^+$

Example 28

6-Cyclopropyl-3-(pyrimidin-5-ylamino)-pyridine-2-carboxylic acid (3-cyclohexylcarbamoyl-1-methyl-1H-pyrazol-4-yl)-amide

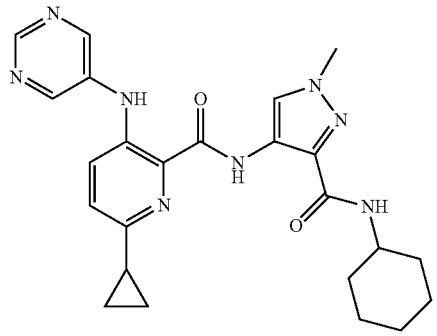 [SMILES: Cn1cc(NC(=O)c2nc(C3CC3)ccc2Nc2cncnc2)c(C(=O)NC2CCCCC2)n1]

According to the general method described in step 5 of example 27, reaction of cyclohexylamine with 4-{[6-cyclopropyl-3-(pyrimidin-5-ylamino)-pyridine-2-carbonyl]-amino}-1-methyl-1H-pyrazole-3-carboxylic acid methyl ester provided the title compound (45%) as sticky yellow solid.

MS: M=461.4 (M+H)$^+$

Example 29

6-Cyclopropyl-3-(pyrimidin-5-ylamino)-pyridine-2-carboxylic acid (2-methylcarbamoyl-phenyl)-amide

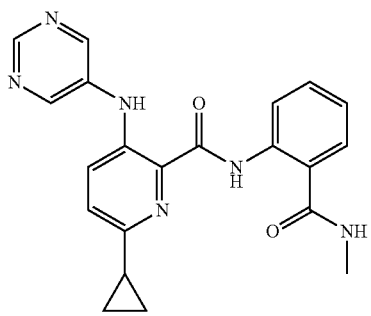 [SMILES: CNC(=O)c1ccccc1NC(=O)c1nc(C2CC2)ccc1Nc1cncnc1]

To a suspension of A-2 (50 mg, 0.19 mmol) in 3 ml AcOEt (3 ml) at rt under an argon atmosphere were added 2-amino-N-methylbenzamide (29 mg, 0.19 mmol) and N-ethyl-diisopropylamine (0.1 ml, 0.59 mmol). The yellow suspension was cooled to 0° C. and propyl-phosphonic anhydride (50% in AcOEt, 0.31 ml, 0.48 mmol) was added. The suspension was stirred at 0° for 30 min and at rt overnight. The solvent was evaporated. The crude product was purified by silica gel chromatography using a $CH_2Cl_2$/MeOH gradient to provide the title compound (46 mg, 61%) as yellow solid.

MS: M=389.2 (M+H)$^+$

Example 30

6-Cyclopropyl-3-(pyrimidin-5-ylamino)-pyridine-2-carboxylic acid [3-(azetidine-1-carbonyl)-1-methyl-1H-pyrazol-4-yl]-amide

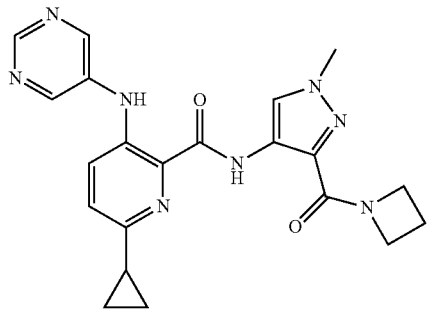 [SMILES: Cn1cc(NC(=O)c2nc(C3CC3)ccc2Nc2cncnc2)c(C(=O)N2CCC2)n1]

According to the general method described in step 5 of example 27, reaction of azetidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (14%) as amorphous yellow solid.

MS: M=419.4 (M+H)$^+$

Example 31

6-Cyclopropyl-3-(pyrimidin-5-ylamino)-pyridine-2-carboxylic acid (3-cyclopropylcarbamoyl-1-methyl-1H-pyrazol-4-yl)-amide

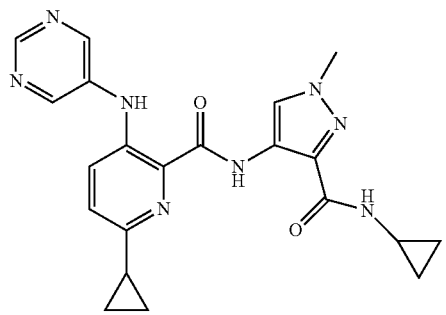 [SMILES: Cn1cc(NC(=O)c2nc(C3CC3)ccc2Nc2cncnc2)c(C(=O)NC2CC2)n1]

According to the general method described in step 5 of example 27, reaction of cyclopropylamine with 4-{[6-cyclopropyl-3-(pyrimidin-5-ylamino)-pyridine-2-carbonyl]-amino}-1-methyl-1H-pyrazole-3-carboxylic acid methyl ester provided the title compound (24%) as amorphous yellow solid.

MS: M=419.2 (M+H)$^+$

Example 32

6-Cyclopropyl-3-(pyrimidin-5-ylamino)-pyridine-2-carboxylic acid [3-(3,3-dimethyl-pyrrolidine-1-carbonyl)-1-methyl-1H-pyrazol-4-yl]-amide

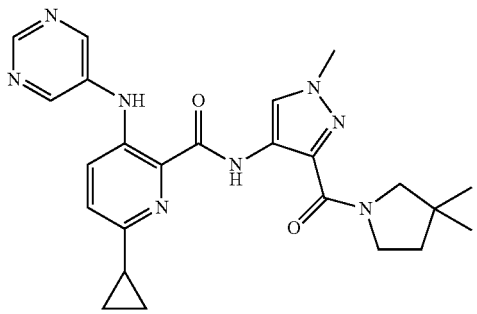 [SMILES: Cn1cc(NC(=O)c2nc(C3CC3)ccc2Nc2cncnc2)c(C(=O)N2CCC(C)(C)C2)n1]

According to the general method described in step 5 of example 27, reaction of 3,3-dimethyl-pyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (20%) as amorphous yellow solid.

MS: M=461.4 (M+H)$^+$

Example 33

6-Cyclopropyl-3-(pyrimidin-5-ylamino)-pyridine-2-carboxylic acid (3-cyclobutylcarbamoyl-1-methyl-1H-pyrazol-4-yl)-amide

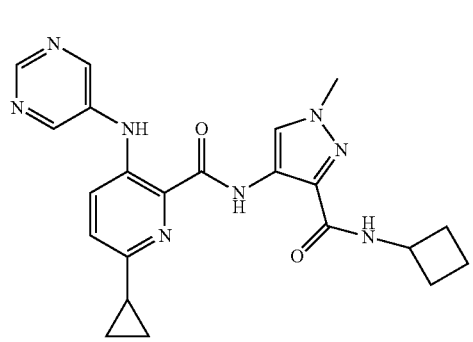 [SMILES: Cn1cc(NC(=O)c2nc(C3CC3)ccc2Nc2cncnc2)c(C(=O)NC2CCC2)n1]

According to the general method described in step 5 of example 27, reaction of cyclobutylamine with 4-{[6-cyclopropyl-3-(pyrimidin-5-ylamino)-pyridine-2-carbonyl]-amino}-1-methyl-1H-pyrazole-3-carboxylic acid methyl ester provided the title compound (24%) as yellow powder.

MS: M=433.2 (M+H)$^+$

Example 34

6-Cyclopropyl-3-(pyrimidin-5-ylamino)-pyridine-2-carboxylic acid (3-cyclopentylcarbamoyl-1-methyl-1H-pyrazol-4-yl)-amide

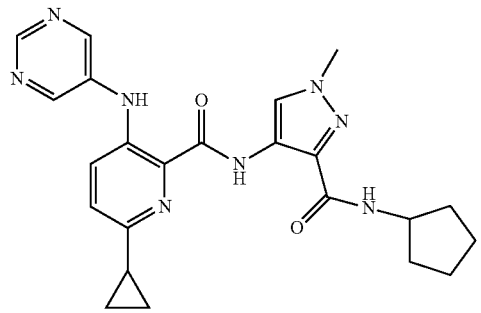 [SMILES: Cn1cc(NC(=O)c2nc(C3CC3)ccc2Nc2cncnc2)c(C(=O)NC2CCCC2)n1]

According to the general method described in step 5 of example 27, reaction of cyclopentylamine with 4-{[6-cyclopropyl-3-(pyrimidin-5-ylamino)-pyridine-2-carbonyl]-amino}-1-methyl-1H-pyrazole-3-carboxylic acid methyl ester provided the title compound (19%) as amorphous yellow solid.

MS: M=447.2 (M+H)$^+$

Example 35

6-Cyclopropyl-3-(pyrimidin-5-ylamino)-pyridine-2-carboxylic acid [3-(2,5-dimethyl-pyrrolidine-1-carbonyl)-1-methyl-1H-pyrazol-4-yl]-amide

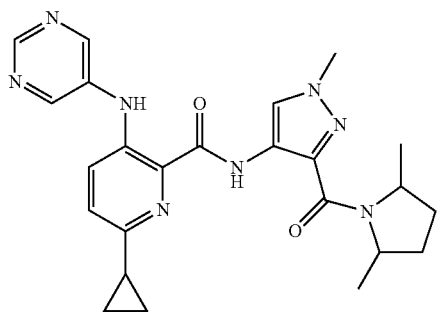 [SMILES: CC1CCC(C)N1C(=O)c1nn(C)cc1NC(=O)c1nc(C2CC2)ccc1Nc1cncnc1]

According to the general method described in step 5 of example 27, reaction of 2,5-dimethylpyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (10%) as amorphous yellow solid.

MS: M=461.4 (M+H)$^+$

Example 36

6-Cyclopropyl-3-(pyrimidin-5-ylamino)-pyridine-2-carboxylic acid [3-(3,3-difluoro-pyrrolidine-1-carbonyl)-1-methyl-1H-pyrazol-4-yl]-amide

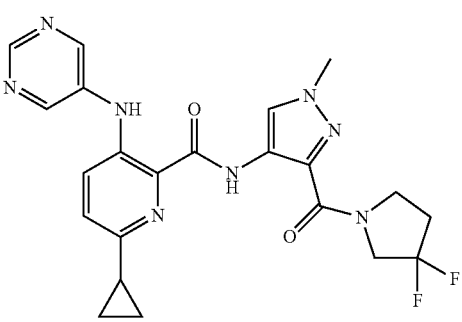 [SMILES: Cn1cc(NC(=O)c2nc(C3CC3)ccc2Nc2cncnc2)c(C(=O)N2CCC(F)(F)C2)n1]

According to the general method described in step 5 of example 27, reaction of 3,3-difluoropyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (14%) as sticky yellow solid.

MS: M=469.4 (M+H)$^+$

Example 37

6-Cyclopropyl-3-(pyrimidin-5-ylamino)-pyridine-2-carboxylic acid [3-(3-dimethylamino-pyrrolidine-1-carbonyl)-1-methyl-1H-pyrazol-4-yl]-amide

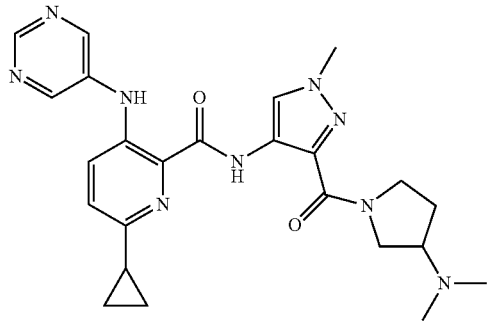 [SMILES: CN(C)C1CCN(C(=O)c2nn(C)cc2NC(=O)c2nc(C3CC3)ccc2Nc2cncnc2)C1]

According to the general method described in step 5 of example 27, reaction of 3-dimethyl-aminopyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (26%) as amorphous yellow solid.

MS: M=476.6 (M+H)$^+$

Example 38

6-Cyclopropyl-3-(pyrimidin-5-ylamino)-pyridine-2-carboxylic acid {3-[(3-hydroxy-propyl)-methyl-carbamoyl]-1-methyl-1H-pyrazol-4-yl}-amide

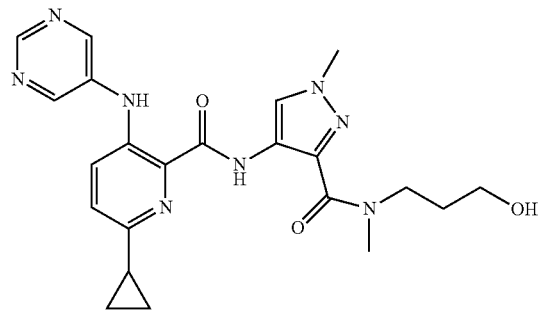 [SMILES: CN(CCCO)C(=O)c1nn(C)cc1NC(=O)c1nc(C2CC2)ccc1Nc1cncnc1]

According to the general method described in step 5 of example 27, reaction of 3-methylamino-propan-1-ol with 4-{[6-cyclopropyl-3-(pyrimidin-5-ylamino)-pyridine-2-carbonyl]-amino}-1-methyl-1H-pyrazole-3-carboxylic acid methyl ester provided the title compound (39%) as amorphous yellow solid.

MS: M=451.4 (M+H)$^+$

Example 39

6-Cyclopropyl-3-(pyrimidin-5-ylamino)-pyridine-2-carboxylic acid [3-(2-hydroxy-ethylcarbamoyl)-1-methyl-1H-pyrazol-4-yl]-amide

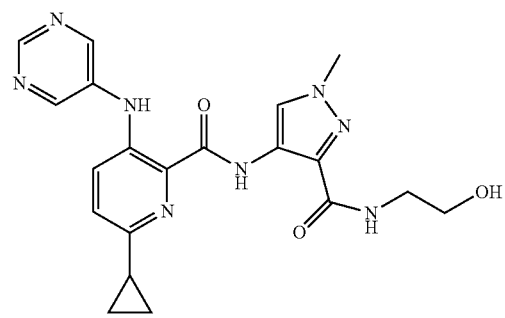

According to the general method described in step 5 of example 27, reaction of 2-amino-ethanol with 4-{[6-cyclopropyl-3-(pyrimidin-5-ylamino)-pyridine-2-carbonyl]-amino}-1-methyl-1H-pyrazole-3-carboxylic acid methyl ester provided the title compound (6%) as amorphous yellow solid.

MS: M=423.2 (M+H)$^+$

Example 40

6-Cyclopropyl-3-(pyrimidin-5-ylamino)-pyridine-2-carboxylic acid {3-[(2-hydroxy-ethyl)-methyl-carbamoyl]-1-methyl-1H-pyrazol-4-yl}-amide

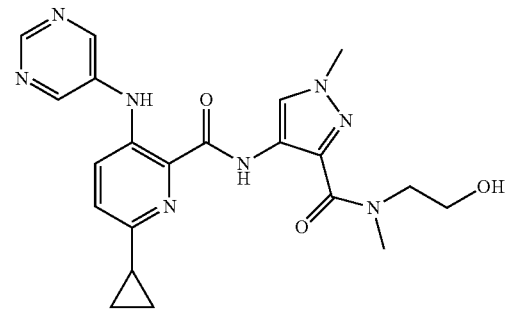 [SMILES: CN(CCO)C(=O)c1nn(C)cc1NC(=O)c1nc(C2CC2)ccc1Nc1cncnc1]

According to the general method described in step 5 of example 27, reaction of 2-methylamino-ethanol with 4-{[6-cyclopropyl-3-(pyrimidin-5-ylamino)-pyridine-2-carbonyl]-amino}-1-methyl-1H-pyrazole-3-carboxylic acid methyl ester provided the title compound (13%) as amorphous yellow solid.

MS: M=437.4 (M+H)$^+$

Example 41

6-Cyclopropyl-3-(pyrimidin-5-ylamino)-pyridine-2-carboxylic acid [3-(2-methoxy-1-methyl-ethylcarbamoyl)-1-methyl-1H-pyrazol-4-yl]-amide

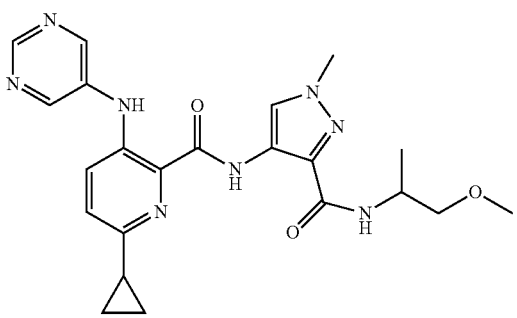 [SMILES: COCC(C)NC(=O)c1nn(C)cc1NC(=O)c1nc(C2CC2)ccc1Nc1cncnc1]

According to the general method described in step 5 of example 27, reaction of 2-methoxy-1-methyl-ethylamine with 4-{[6-cyclopropyl-3-(pyrimidin-5-ylamino)-pyridine-2-carbonyl]-amino}-1-methyl-1H-pyrazole-3-carboxylic acid methyl ester provided the title compound (16%) as amorphous yellow solid.

MS: M=451.2 (M+H)$^+$

Example 42

6-Cyclopropyl-3-(pyrimidin-5-ylamino)-pyridine-2-carboxylic acid [3-(2,3-dihydroxy-propylcarbamoyl)-1-methyl-1H-pyrazol-4-yl]-amide

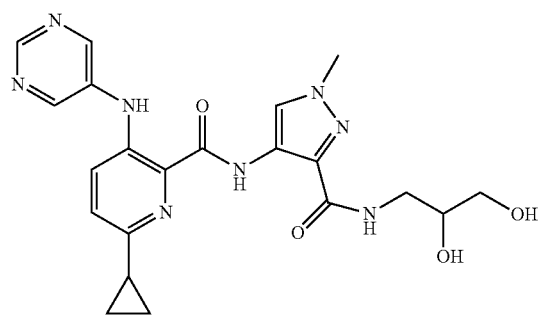 [SMILES: Cn1cc(NC(=O)c2nc(C3CC3)ccc2Nc2cncnc2)c(C(=O)NCC(O)CO)n1]

According to the general method described in step 5 of example 27, reaction of 3-amino-propane-1,2-diol with 4-{[6-cyclopropyl-3-(pyrimidin-5-ylamino)-pyridine-2-carbonyl]-amino}-1-methyl-1H-pyrazole-3-carboxylic acid methyl ester provided the title compound (15%) as sticky solid.

MS: M=453.4 (M+H)$^+$

Example 43

6-Cyclopropyl-3-(pyrimidin-5-ylamino)-pyridine-2-carboxylic acid [3-(2-hydroxy-2-methyl-propylcarbamoyl)-1-methyl-1H-pyrazol-4-yl]-amide

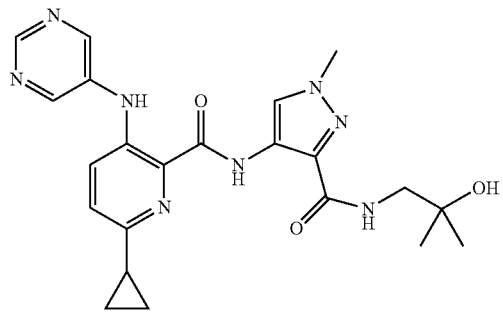 [SMILES: Cn1cc(NC(=O)c2nc(C3CC3)ccc2Nc2cncnc2)c(C(=O)NCC(C)(C)O)n1]

According to the general method described in step 5 of example 27, reaction of 1-amino-2-methyl-propan-2-ol with 4-{[6-cyclopropyl-3-(pyrimidin-5-ylamino)-pyridine-2-carbonyl]-amino}-1-methyl-1H-pyrazole-3-carboxylic acid methyl ester provided the title compound (27%) as amorphous yellow solid.

MS: M=451.2 (M+H)$^+$

Example 44

6-Cyclopropyl-3-(pyrimidin-5-ylamino)-pyridine-2-carboxylic acid [3-(3-hydroxy-pyrrolidine-1-carbonyl)-1-methyl-1H-pyrazol-4-yl]-amide

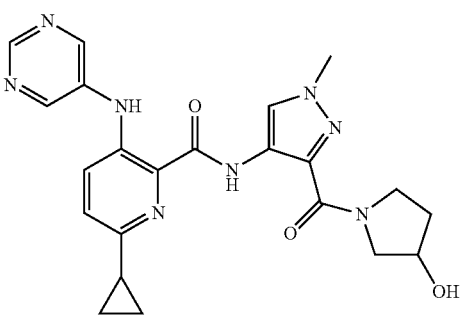 [SMILES: Cn1cc(NC(=O)c2nc(C3CC3)ccc2Nc2cncnc2)c(C(=O)N2CCC(O)C2)n1]

According to the general method described in step 5 of example 27, reaction of 3-hydroxy-pyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (15%) as sticky yellow solid.

MS: M=449.2 (M+H)$^+$

Example 45

6-Cyclopropyl-3-(pyrimidin-5-ylamino)-pyridine-2-carboxylic acid [3-(2-hydroxy-1-methyl-ethylcarbamoyl)-1-methyl-1H-pyrazol-4-yl]-amide

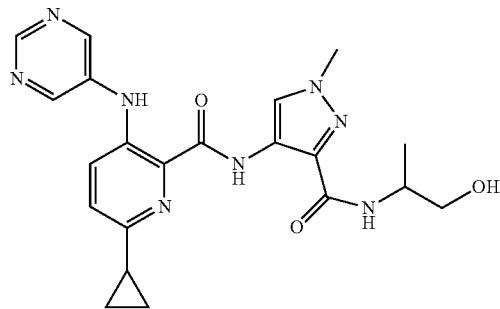 [SMILES: CC(CO)NC(=O)c1nn(C)cc1NC(=O)c1nc(C2CC2)ccc1Nc1cncnc1]

According to the general method described in step 5 of example 27, reaction of 2-amino-propan-1-ol with 4-{[6-cyclopropyl-3-(pyrimidin-5-ylamino)-pyridine-2-carbonyl]-amino}-1-methyl-1H-pyrazole-3-carboxylic acid methyl ester provided the title compound (14%) as sticky yellow solid.

MS: M=437.2 (M+H)$^+$

Example 46

6-Cyclopropyl-3-(pyrimidin-5-ylamino)-pyridine-2-carboxylic acid {3-[(2,3-dihydroxy-propyl)-methyl-carbamoyl]-1-methyl-1H-pyrazol-4-yl}-amide

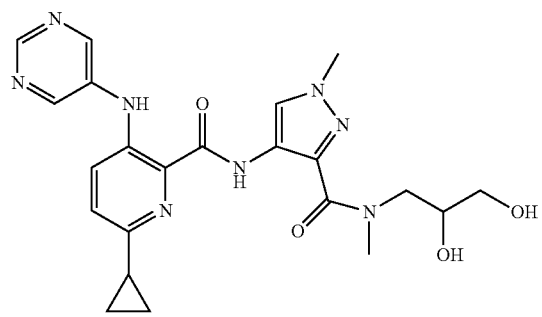 [SMILES: CN(CC(O)CO)C(=O)c1nn(C)cc1NC(=O)c1nc(C2CC2)ccc1Nc1cncnc1]

According to the general method described in step 5 of example 27, reaction of 3-methylamino-propane-1,2-diol with 4-{[6-cyclopropyl-3-(pyrimidin-5-ylamino)-pyridine-2-carbonyl]-amino}-1-methyl-1H-pyrazole-3-carboxylic acid methyl ester provided the title compound (9%) as sticky yellow solid.

MS: M=467.4 (M+H)$^+$

Example 47

6-Cyclopropyl-3-(pyrimidin-5-ylamino)-pyridine-2-carboxylic acid [1-methyl-3-(3-oxo-piperazine-1-carbonyl)-1H-pyrazol-4-yl]-amide

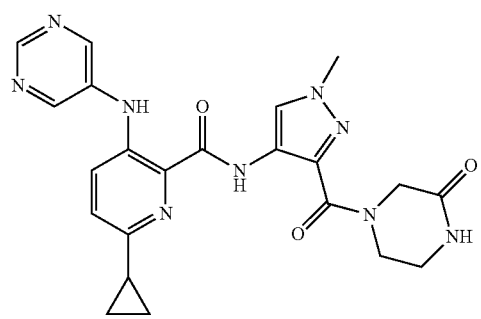 [SMILES: Cn1cc(NC(=O)c2nc(C3CC3)ccc2Nc2cncnc2)c(C(=O)N2CCNC(=O)C2)n1]

According to the general method described in step 5 of example 27, reaction of piperazine-2-one with 4-{[6-cyclopropyl-3-(pyrimidin-5-ylamino)-pyridine-2-carbonyl]-amino}-1-methyl-1H-pyrazole-3-carboxylic acid methyl ester provided the title compound (12%) as pale yellow solid.

MS: M=462.4 (M+H)$^+$

Example 48

6-Cyclopropyl-3-(pyrimidin-5-ylamino)-pyridine-2-carboxylic acid [3-(3-methoxy-pyrrolidine-1-carbonyl)-1-methyl-1H-pyrazol-4-yl]-amide

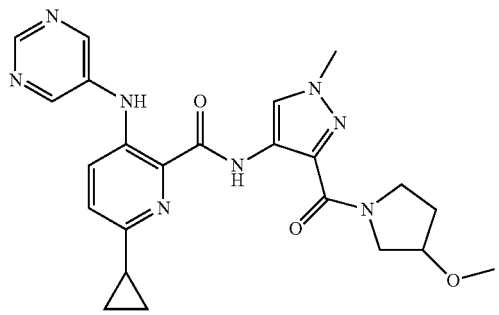 [SMILES: COC1CCN(C(=O)c2nn(C)cc2NC(=O)c2nc(C3CC3)ccc2Nc2cncnc2)C1]

According to the general method described in step 5 of example 27, reaction of 3-methoxypyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (23%) as amorphous yellow solid.

MS: M=463.2 (M+H)$^+$

Example 49

6-Cyclopropyl-3-(pyrimidin-5-ylamino)-pyridine-2-carboxylic acid [3-(2-hydroxymethyl-pyrrolidine-1-carbonyl)-1-methyl-1H-pyrazol-4-yl]-amide

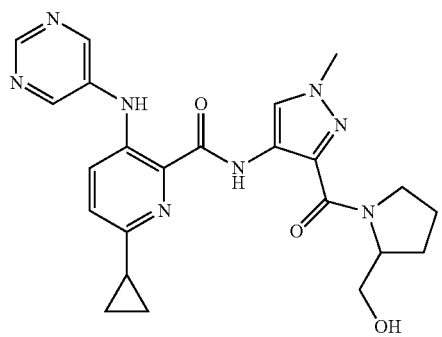 [SMILES: Cn1cc(NC(=O)c2nc(C3CC3)ccc2Nc2cncnc2)c(C(=O)N2CCCC2CO)n1]

According to the general method described in step 5 of example 27, reaction of 2-hydroxymethyl-pyrrolidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (15%) as sticky yellow solid.

MS: M=463.4 (M+H)$^+$

Example 50

6-Cyclopropyl-3-(pyrimidin-5-ylamino)-pyridine-2-carboxylic acid [3-(3-hydroxy-azetidine-1-carbonyl)-1-methyl-1H-pyrazol-4-yl]-amide

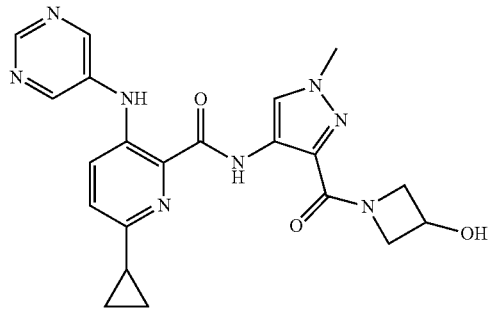 [SMILES: Cn1cc(NC(=O)c2nc(C3CC3)ccc2Nc2cncnc2)c(C(=O)N2CC(O)C2)n1]

According to the general method described in step 5 of example 27, reaction of 3-hydroxy-azetidine with 4-{[6-cyclopropyl-3-(pyrimidin-5-ylamino)-pyridine-2-carbonyl]-amino}-1-methyl-1H-pyrazole-3-carboxylic acid methyl ester provided the title compound (13%) as sticky yellow solid.

MS: M=435.1 (M+H)$^+$

Example 51

6-Cyclopropyl-3-(pyrimidin-5-ylamino)-pyridine-2-carboxylic acid [1-methyl-3-(2-oxa-6-aza-spiro[3.3]heptane-6-carbonyl)-1H-pyrazol-4-yl]-amide

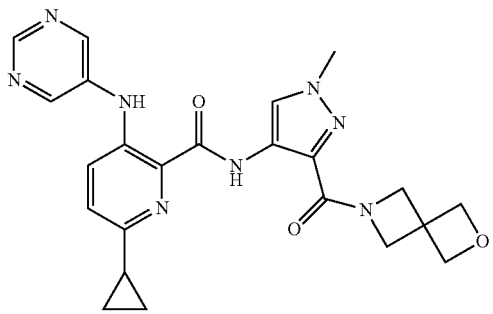 [SMILES: Cn1cc(NC(=O)c2nc(C3CC3)ccc2Nc2cncnc2)c(C(=O)N2CC3(COC3)C2)n1]

According to the general method described in step 5 of example 27, reaction of 2-oxa-6-aza-spiro[3.3]heptane with 4-{[6-cyclopropyl-3-(pyrimidin-5-ylamino)-pyridine-2-carbonyl]-amino}-1-methyl-1H-pyrazole-3-carboxylic acid methyl ester provided the title compound (5%) as sticky yellow solid.

MS: M=461.1 (M+H)$^+$

Example 52

6-Cyclopropyl-3-(pyrimidin-5-ylamino)-pyridine-2-carboxylic acid [3-(2,2-dimethyl-pyrrolidine-1-carbonyl)-1-methyl-1H-pyrazol-4-yl]-amide

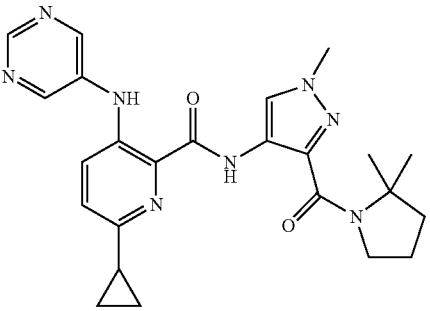 [SMILES: Cn1cc(NC(=O)c2nc(C3CC3)ccc2Nc2cncnc2)c(C(=O)N2CCCC2(C)C)n1]

Step 1: 4-{[6-Cyclopropyl-3-(pyrimidin-5-ylamino)-pyridine-2-carbonyl]-amino}-1-methyl-1H-pyrazole-3-carboxylic acid To a stirred solution of 4-{[6-cyclopropyl-3-(pyrimidin-5-ylamino)-pyridine-2-carbonyl]-amino}-1-methyl-1H-pyrazole-3-carboxylic acid methyl ester (example 27, step 4; 300 mg, 0.76 mmol) in MeOH (7 ml) was added a solution of NaOH (49 mg, 1.2 mmol) in water (2 ml) while keeping the internal bath temperature below 5° C. The reaction mixture was stirred for 12 h at rt, then concentrated. The residue was dissolved in water (10 ml), and the aqueous layer was washed with EtOAc. The aqueous phase was acidified with aqueous 1N HCl solution (pH~4-5), then saturated with sodium chloride, and extracted with EtOAc. Combined organic layers were washed with brine, dried (Na$_2$SO$_4$), and filtered. The organic layer was concentrated to give the title compound (142 mg, 45%) as yellowish sticky solid, which was directly used for next step.

Step 2: 6-Cyclopropyl-N-[3-(2,2-dimethyl-pyrrolidine-1-carbonyl)-1-methyl-1H-pyrazol-4-yl]-3-(pyrimidin-5-ylamino)-pyridine-2-carboximidic acid To stirred solution of 4-{[6-cyclopropyl-3-(pyrimidin-5-ylamino)-pyridine-2-carbonyl]-amino}-1-methyl-1H-pyrazole-3-carboxylic acid (70 mg, 0.18 mmol) in DMF were sequentially added N-methylmorpholine (0.12 ml, 0.9 mmol), HBTU (210 mg, 0.55 mmol), and 2,2-dimethylpyrrolidine (35 mg, 0.36 mmol) at rt, and the reaction mixture was allowed to stir overnight. The solvent was removed in vacuo, and the residue was dissolved in EtOAc (10 ml), and was washed with aqueous NaHCO$_3$ solution and water. The aqueous layer was back-extracted with EtOAc, and the combined organic layer was dried (Na$_2$SO$_4$), filtered, and evaporated in vacuo. The crude product was purified by prep. HPLC (column: Gemini C18 (250×21.2 mm, 5μ); elution with a gradient of 0.05% aqueous TFA solution/acetonitrile) to give the title compound (6 mg, 6%) as sticky yellow solid.

MS: M=461.1 (M+H)$^+$

Example 53

6-Cyclopropyl-3-(pyrimidin-5-ylamino)-pyridine-2-carboxylic acid [4-(3-dimethylamino-pyrrolidine-1-carbonyl)-pyridin-3-yl]-amide Step 1: 3-{[6-Cyclopropyl-3-(pyrimidin-5-ylamino)-pyridine-2-carbonyl]-amino}-isonicotinic acid methyl ester

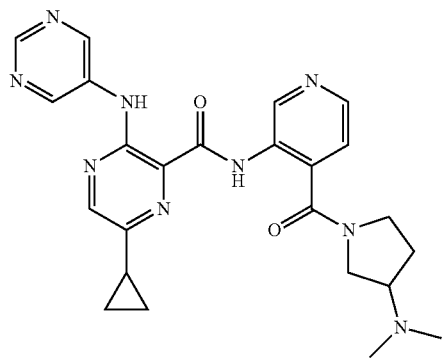 [SMILES: CN(C)C1CCN(C(=O)c2ccncc2NC(=O)c2nc(C3CC3)cnc2Nc2cncnc2)C1]

To stirred solution of A-2 (320 mg, 1.24 mmol) in dry THF (10 ml) was added HATU (942 mg, 2.48 mmol) and N-methyl morpholine (0.35 ml) at rt followed by addition of 3-amino-isonicotinic acid methyl ester (171 mg, 1.12 mmol). The reaction mixture was allowed to reflux for 10 hrs. After completion of the reaction, it was quenched with saturated NaHCO$_3$ solution (10 ml) and water (10 ml). The aqueous layer was extracted with EtOAc (5×10 ml), and then with CH$_2$Cl$_2$ (3×12 ml). The combined organic layers were washed with brine (25 ml), dried (Na$_2$SO$_4$), filtered, and was removed in vacuo. The crude residue thus obtained was purified by column chromatography over silica gel (2% MeOH/CH$_2$Cl$_2$) to give the title compound (335 mg; 69%) as yellow solid.

Step 2: 3-{[6-Cyclopropyl-3-(pyrimidin-5-ylamino)-pyridine-2-carbonyl]-amino}-isonicotinic acid To stirred suspension of 3-{[6-cyclopropyl-3-(pyrimidin-5-ylamino)-pyridine-2-carbonyl]-amino}-isonicotinic acid methyl ester (330 mg, 0.84 mmol) in MeOH (5 ml) was added a solution of NaOH (84.5 mg, 2.1 mmol) in water (2 ml) at 0-5° C. After the addition the reaction mixture was stirred at rt for 8 hrs. The solvent was removed in vacuo, the residue was dissolved in water (7 ml), and was washed with EtOAc (2×10 ml). The aqueous layer was then acidified with 1N HCl (pH~2), and concentrated to obtain the title compound (containing NaCl) as a yellowish sticky solid which was directly used as such for the next step without any further purification.
MS: M=377.4 (M+H)$^+$ Step 3: General Procedure for the Final Amide Coupling To a stirred solution of 3-{[6-cyclopropyl-3-(pyrimidin-5-ylamino)-pyridine-2-carbonyl]-amino}-isonicotinic acid (1.0 mmol) in DMF (5 ml) was added N-methyl morpholine (2.5 mmol) and then HBTU (2.0 mmol) at 25° C. Stirring was continued for 10 minutes. Amine (2.0 mmol) was added, and the reaction mixture was allowed to stir at rt overnight, then concentrated. The residue was taken up in EtOAc (10 ml), washed successively with aqueous NaHCO$_3$ solution (2×10 ml), water and then with brine, dried (Na$_2$SO$_4$), filtered, and concentrated. The crude product was purified by prep-HPLC (Column: Zorbax SB C18 (250×21.2 mm, 7μ); elution with a gradient of 0.05% aqueous TFA solution/acetonitrile).
MS: M=391.2 (M+H)$^+$ 6-Cyclopropyl-N-[4-(3-dimethylamino-pyrrolidine-1-carbonyl)-pyridin-3-yl]-3-(pyrimidin-5-ylamino)-pyridine-2-carboximidic acid According to the general method described above (step 3), reaction of 3-dimethylamino-pyrrolidine with 3-{[6-cyclopropyl-3-(pyrimidin-5-ylamino)-pyridine-2-carbonyl]-amino}-isonicotinic acid provided the title compound (13%) as sticky yellow solid
MS: M=473.4 (M+H)$^+$

Example 54

6-Cyclopropyl-3-(pyrimidin-5-ylamino)-pyridine-2-carboxylic acid (4-methylcarbamoyl-[1,2,3]thiadiazol-5-yl)-amide

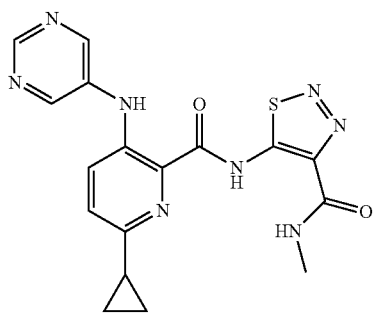 [SMILES: CNC(=O)c1nnsc1NC(=O)c1nc(C2CC2)ccc1Nc1cncnc1]

Step 1: 5-tert-Butoxycarbonylamino-[1,2,3]thiadiazole-4-carboxylic acid ethyl ester To a solution of 5-amino-[1,2,3]thiadiazole-4-carboxylic acid ethyl ester (0.5 g, 2.9 mmol) in dichloromethane (5 ml) was added consecutively a solution of di-tert-butyl-dicarbonate (0.772 g, 3.5 mmol) in dichloromethane (5 ml) and 4-dimethylaminopyridine (35 mg, 0.3 mmol). The reaction mixture was stirred at ambient temperature for 2 h. The reaction mixture was partitioned between potassium hydrogen sulfate (15 ml, 10% aqueous solution) and dichloromethane (40 ml) and extracted. The organic phase was washed with water and sodium bicarbonate, and the aqueous phases were back-extracted with dichloromethane. The combined organic phases were dried, filtrated and the solvent was evaporated to yield 0.87 g (>100%) of a light brown sticky residue that slowly became crystalline and was used for the next step without any further purification.
MS: M=274.1 (M+H)$^+$

Step 2: 5-tert-Butoxycarbonylamino-[1,2,3]thiadiazole-4-carboxylic acid

A solution of 5-tert-butoxycarbonylamino-[1,2,3]thiadiazole-4-carboxylic acid ethyl ester (0.87 g, 2.9 mmol) in a THF/ethanol mixture (18 ml; 3:1) was cooled to 0° C. and treated with lithium hydroxide (8.6 ml; 1N aqueous solution). After 15 min, the cooling bath was removed and the reaction mixture was stirred for 4 h at ambient temperature. The solvent was evaporated, and the residue was partitioned between diethylether (30 ml) and water (5 ml) and extracted. The aqueous phase was extracted with diethylether and the ether phases were washed with water. The combined aqueous phases were acidified with HCl (9 ml, 1N aqueous solution) and extracted with dichloromethane (2×40 ml). The combined organic layers were washed with water, dried and the solvent was evaporated to yield the product as colorless solid (0.66 g, 94%) which was used without any further purification.
MS: M=244.1 (M−H)⁻

Step 3: 5-tert-Butoxycarbonylamino-[1,2,3]thiadiazole-4-carboxylic acid methylamide A solution of 5-tert-butoxycarbonylamino-[1,2,3]thiadiazole-4-carboxylic acid (0.66 g, 2.7 mmol) in DMF (10 ml) was treated with TBTU (1.16 g, 3.5 mmol), N,N-diisopropyl ethyl amine (2.29 ml, 13.5 mmol) and methylamine (1.75 ml, 2M THF solution) and stirred at ambient temperature for 5 h. The reaction mixture was partitioned between potassium hydrogen sulfate (30 ml, 10% aqueous solution) and ethyl acetate (60 ml) and extracted. The organic layer was washed with water and brine, and the aqueous phases were back-extracted with ethyl acetate. The combined organic phases were dried and the solvent was evaporated. The residue was suspended in dichloromethane, sucked off, and the filtrate was evaporated. The product was obtained after purification of the crude material by silica gel chromatography using a heptane/ethyl acetate gradient as colorless solid (0.23 g, 33%).
MS: M=259.0 (M−H)⁻

Step 4: 5-Amino-[1,2,3]thiadiazole-4-carboxylic acid methylamide

A solution of 5-tert-butoxycarbonylamino-[1,2,3]thiadiazole-4-carboxylic acid methylamide (0.23 g, 0.9 mmol) in dioxane (4 ml) was treated with HCl (6 ml, 4M dioxane solution) at ambient temperature and stirred for 3 days. The solvent was evaporated, and the residue was suspended in diethylether, mixed and sucked off. The remaining solid material was dissolved in dichloromethane and extracted with NaOH (10 ml, 1M aqueous solution). The aqueous phase was extracted with dichloromethane, and the combined organic layers were dried and the solvent was evaporated to yield the product as colorless solid (0.7 g, 48%) which was used without any further purification.
MS: M=159.1 (M−H)⁻

Step 5: 6-Cyclopropyl-3-(pyrimidin-5-ylamino)-pyridine-2-carboxylic acid (4-methylcarbamoyl-[1,2,3]thiadiazol-5-yl)-amide To a solution of intermediate A-2 (40 mg, 0.16 mmol) in DMF (1.5 ml) were added TBTU (57 mg, 0.17 mmol), N,N-diisopropylethylamine (0.13 ml, 0.78 mmol) and 5-amino-[1,2,3]thiadiazole-4-carboxylic acid methylamide (27 mg, 0.17 mmol). The reaction mixture was stirred at ambient temperature overnight. The resulting suspension was sucked off and the collected solid material was thoroughly washed with THF. The final product was obtained upon drying of the precipitate as yellow solid (23 mg, 37%).
MS: M=396.2 (M)⁺

Example 55

6-Cyclopropyl-3-(pyrimidin-5-ylamino)-pyridine-2-carboxylic acid [4-(2-methyl-pyrrolidine-1-carbonyl)-pyridin-3-yl]-amide

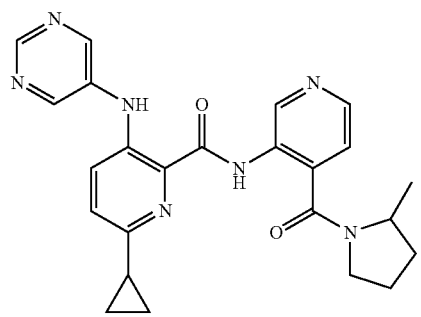 [SMILES: CC1CCCN1C(=O)c1ccncc1NC(=O)c1nc(C2CC2)ccc1Nc1cncnc1]

According to the general method described in step 3 of example 53, reaction of 2-methyl-pyrolidine with 3-{[6-cyclopropyl-3-(pyrimidin-5-ylamino)-pyridine-2-carbonyl]-amino}-isonicotinic acid provided the title compound (14%) as sticky yellow solid.
MS: M=444.4 (M+H)⁺

Example 56

6-Cyclopropyl-3-(pyrimidin-5-ylamino)-pyridine-2-carboxylic acid [4-(3,3-difluoro-pyrrolidine-1-carbonyl)-pyridin-3-yl]-amide

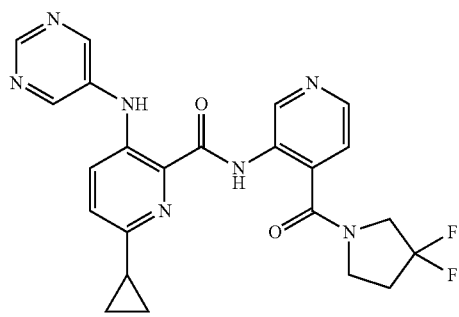 [SMILES: O=C(Nc1cnccc1C(=O)N1CCC(F)(F)C1)c1nc(C2CC2)ccc1Nc1cncnc1]

According to the general method described in step 3 of example 53, reaction of 3,3-difluoro-pyrrolidine with 3-{[6-cyclopropyl-3-(pyrimidin-5-ylamino)-pyridine-2-carbonyl]-amino}-isonicotinic acid provided the title compound (27%) as amorphous light yellow solid.
MS: M=466.0 (M+H)⁺

Example 57

6-Cyclopropyl-3-(pyrimidin-5-ylamino)-pyridine-2-carboxylic acid (4-cyclopropylcarbamoyl-pyridin-3-yl)-amide

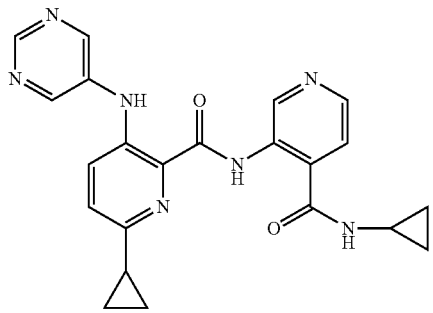 [SMILES: O=C(NC1CC1)c1ccncc1NC(=O)c1nc(C2CC2)ccc1Nc1cncnc1]

According to the general method described in step 3 of example 53, reaction of cyclopropylamine with 3-{[6-cyclopropyl-3-(pyrimidin-5-ylamino)-pyridine-2-carbonyl]-amino}-isonicotinic acid provided the title compound (28%) as yellow powder.

MS: M=416.2 (M+H)$^+$

Example 58

6-Cyclopropyl-3-(pyrimidin-5-ylamino)-pyridine-2-carboxylic acid (4-cyclobutylcarbamoyl-pyridin-3-yl)-amide

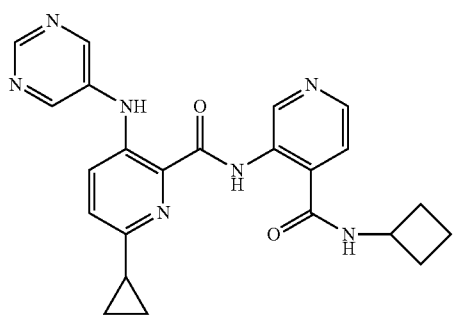 [SMILES: O=C(NC1CCC1)c1ccncc1NC(=O)c1nc(C2CC2)ccc1Nc1cncnc1]

According to the general method described in step 3 of example 53, reaction of cyclobutylamine with 3-{[6-cyclopropyl-3-(pyrimidin-5-ylamino)-pyridine-2-carbonyl]-amino}-isonicotinic acid provided the title compound (35%) as amorphous yellow solid.

MS: M=430.2 (M+H)$^+$

Example 59

6-Cyclopropyl-3-(pyrimidin-5-ylamino)-pyridine-2-carboxylic acid [4-(2,5-dimethyl-pyrrolidine-1-carbonyl)-pyridin-3-yl]-amide

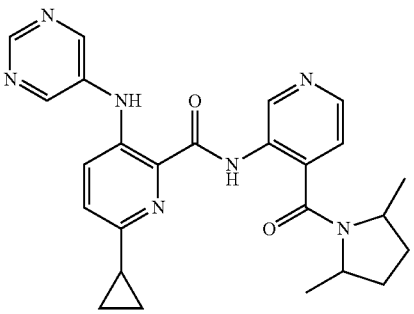 [SMILES: CC1CCC(C)N1C(=O)c1ccncc1NC(=O)c1nc(C2CC2)ccc1Nc1cncnc1]

According to the general method described in step 3 of example 53, reaction of 2,5-dimethyl-pyrrolidine with 3-{[6-cyclopropyl-3-(pyrimidin-5-ylamino)-pyridine-2-carbonyl]-amino}-isonicotinic acid provided the title compound (35%) as amorphous yellow solid.

MS: M=458.0 (M+H)$^+$

Example 60

6-Cyclopropyl-3-(pyrimidin-5-ylamino)-pyridine-2-carboxylic acid [4-(3-oxo-piperazine-1-carbonyl)-pyridin-3-yl]-amide

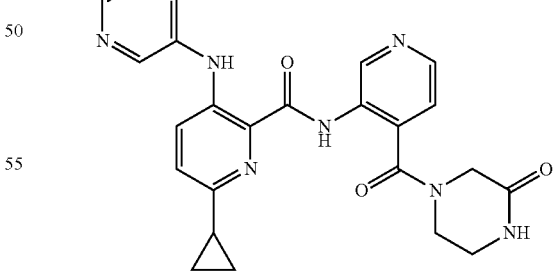

According to the general method described in step 3 of example 53, reaction of piperazine-2-one with 3-{[6-cyclopropyl-3-(pyrimidin-5-ylamino)-pyridine-2-carbonyl]-amino}-isonicotinic acid provided the title compound (14%) as amorphous light yellow solid.

MS: M=459.4 (M+H)$^+$

Example 61

6-Cyclopropyl-3-(pyrimidin-5-ylamino)-pyridine-2-carboxylic acid (4-cyclopentylcarbamoyl-pyridin-3-yl)-amide

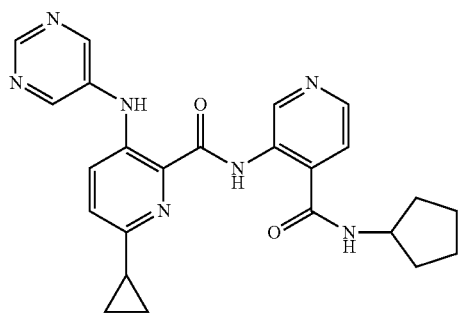 [SMILES: O=C(NC1CCCC1)c1ccncc1NC(=O)c1nc(C2CC2)ccc1Nc1cncnc1]

According to the general method described in step 3 of example 53, reaction of cyclopentylamine with 3-{[6-cyclopropyl-3-(pyrimidin-5-ylamino)-pyridine-2-carbonyl]-amino}-isonicotinic acid provided the title compound (18%) as amorphous yellow solid.

MS: M=444.4 (M+H)$^+$

Example 62

6-Cyclopropyl-3-(pyrimidin-5-ylamino)-pyridine-2-carboxylic acid [4-(3-methoxy-pyrrolidine-1-carbonyl)-pyridin-3-yl]-amide

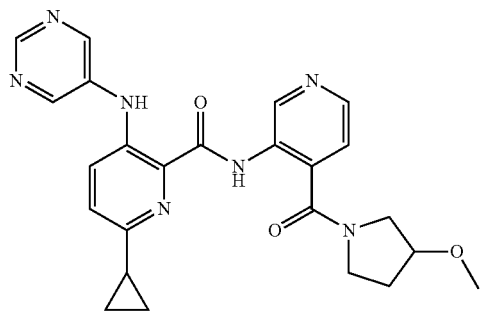 [SMILES: COC1CCN(C(=O)c2ccncc2NC(=O)c2nc(C3CC3)ccc2Nc2cncnc2)C1]

According to the general method described in step 3 of example 53, reaction of 3-methoxy-pyrrolidine with 3-{[6-cyclopropyl-3-(pyrimidin-5-ylamino)-pyridine-2-carbonyl]-amino}-isonicotinic acid provided the title compound (18%) as off-white powder.

MS: M=460.4 (M+H)$^+$

Example 63

6-Cyclopropyl-3-(pyrimidin-5-ylamino)-pyridine-2-carboxylic acid [4-(3,3-dimethyl-pyrrolidine-1-carbonyl)-pyridin-3-yl]-amide

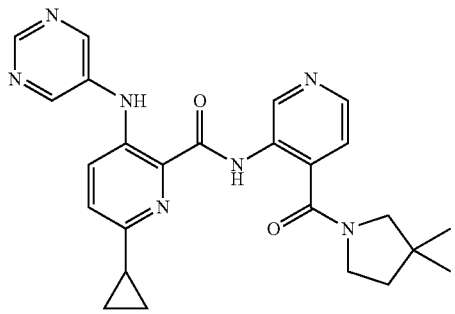 [SMILES: CC1(C)CCN(C(=O)c2ccncc2NC(=O)c2nc(C3CC3)ccc2Nc2cncnc2)C1]

According to the general method described in step 3 of example 53, reaction of 3,3-dimethyl-pyrrolidine with 3-{[6-cyclopropyl-3-(pyrimidin-5-ylamino)-pyridine-2-carbonyl]-amino}-isonicotinic acid provided the title compound (34%) as amorphous yellow solid.

MS: M=458.4 (M+H)$^+$

Example 64

6-Cyclopropyl-3-(pyrimidin-5-ylamino)-pyridine-2-carboxylic acid (4-methylcarbamoyl-2-phenyl-thiazol-5-yl)-amide

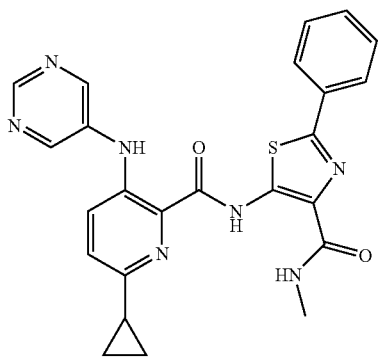 [SMILES: CNC(=O)c1nc(-c2ccccc2)sc1NC(=O)c1nc(C2CC2)ccc1Nc1cncnc1]

Step 1: 5-Amino-2-phenyl-thiazole-4-carboxylic acid ethyl ester

A solution of benzoylamino-cyano-acetic acid ethyl ester (400 mg, 1.7 mmol) in toluene (4 ml) was flushed with argon, and Lawesson's reagent (314 mg, 0.85 mmol) was added. The reaction mixture was stirred at 100° C. for 5 days. The solvent was evaporated, and the product was obtained after purification by silica gel chromatography using a heptane/ethyl acetate gradient as yellow solid (147 mg, 34%).

MS: M=249.1 (M+H)$^+$

Step 2: 5-tert-Butoxycarbonylamino-2-phenyl-thiazole-4-carboxylic acid ethyl ester To a solution of 5-amino-2-phenyl-thiazole-4-carboxylic acid ethyl ester (147 mg, 0.59 mmol) in dichloromethane (1.5 ml) was added consecutively a solution of di-tert-butyl-dicarbonate (155 mg, 0.71 mmol) in dichloromethane (1.5 ml) and 4-dimethylaminopyridine (7.3 mg, 0.06 mmol). The reaction mixture was stirred at ambient temperature for 2 h. The reaction mixture was partitioned between potassium hydrogen sulfate (5 ml, 10% aqueous solution) and dichloromethane (10 ml) and extracted. The organic phase was washed with water and sodium bicarbonate, and the aqueous phases were back-extracted with dichloromethane. The combined organic phases were dried, filtrated and the solvent was evaporated. The product was obtained after purification by silica gel chromatography using a heptane/ethyl acetate gradient as light yellow solid (152 mg, 73%).

MS: M=349.3 (M+H)$^+$

Step 3: 5-tert-Butoxycarbonylamino-2-phenyl-thiazole-4-carboxylic acid

A solution of 5-tert-butoxycarbonylamino-2-phenyl-thiazole-4-carboxylic acid ethyl ester (151 mg, 0.43 mmol) in a THF/ethanol mixture (3 ml; 2:1) was cooled to 0° C. and treated with lithium hydroxide (1.3 ml; 1N aqueous solution). After 15 min, the cooling bath was removed and the reaction mixture was stirred at 50° C. overnight. The reaction mixture was acidified with HCl (1.3 ml, 1N aqueous solution) and extracted with dichloromethane (2×10 ml). The combined organic layers were dried and the solvent was evaporated to yield the product as off-white solid (143 mg, 100%) which was used without any further purification.

MS: M=319.2 (M−H)$^−$

Step 4: 5-tert-Butoxycarbonylamino-2-phenyl-thiazole-4-carboxylic acid methylamide A solution of 5-tert-butoxycarbonylamino-2-phenyl-thiazole-4-carboxylic acid (138 mg, 0.43 mmol) in THF (2.5 ml) was treated with HATU (187 mg, 0.49 mmol), N-methylmorpholin (0.25 ml, 2.24 mmol) and methylamine (0.29 ml, 2M THF solution) and stirred at 75° C. for 6 h. The reaction mixture was partitioned between potassium hydrogen sulfate (10% aqueous solution) and ethyl acetate and extracted. The organic layer was washed with water, sodium bicarbonate and brine. The combined organic phases were dried and the solvent was evaporated. The product was obtained after purification by silica gel chromatography using a heptane/ethyl acetate gradient as light yellow solid (98 mg, 65%).

MS: M=334.3 (M+H)$^+$

Step 5: 5-Amino-2-phenyl-thiazole-4-carboxylic acid methylamide

A solution of 5-tert-butoxycarbonylamino-2-phenyl-thiazole-4-carboxylic acid methylamide (98 mg, 0.3 mmol) in dioxane (1.7 ml) was treated with HCl (1.7 ml, 4M dioxane solution) at ambient temperature and stirred for 3 days. The solvent was evaporated, and the residue was dissolved in ethyl acetate and extracted with sodium bicarbonate and brine. The organic layer was dried and the solvent was evaporated to yield the product as yellow solid (62 g, 90%) which was used without any further purification.

MS: M=234.1 (M+H)$^+$

Step 6: 6-Cyclopropyl-3-(pyrimidin-5-ylamino)-pyridine-2-carboxylic acid (4-methylcarbamoyl-2-phenyl-thiazol-5-yl)-amide To a solution of intermediate A-2 (17 mg, 0.07 mmol) and 5-amino-2-phenyl-thiazole-4-carboxylic acid methylamide (20 mg, 0.09 mmol) in THF (0.5 ml) were added HATU (28 mg, 0.07 mmol) and N-methylmorpholin (37 μl, 0.34 mmol). The reaction mixture was stirred at 75° C. overnight. The resulting suspension was sucked off and the collected solid material was thoroughly washed with THF. The final product was obtained upon drying of the precipitate as yellow solid (19 mg, 61%).

MS: M=472.2 (M+H)$^+$

Example 65

6-Cyclopropyl-3-(pyrimidin-5-ylamino)-pyridine-2-carboxylic acid (4-methylcarbamoyl-2-pyridin-2-yl-thiazol-5-yl)-amide

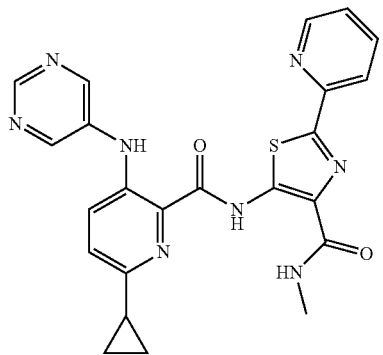 [SMILES: CNC(=O)c1nc(-c2ccccn2)sc1NC(=O)c1nc(C2CC2)ccc1Nc1cncnc1]

Step 1: Cyano-[(pyridine-2-carbonyl)-amino]-acetic acid ethyl ester

A solution of 2-picolinic acid (540 mg, 4.4 mmol) in dichloromethane (5 ml) was treated with thionyl chloride (0.4 ml, 5.5 mmol) and a drop of DMF at ambient temperature. The reaction mixture is stirred at 40° C. overnight whereupon another equivalent of thionyl chloride was added and stirring was continued at 40° C. for another 2 h. All volatiles were removed and the acid chloride was suspended in dichloromethane (5 ml) and added to a pre-cooled (0° C.) solution of amino-cyano-acetic acid ethyl ester (470 mg, 3.7 mmol) and triethylamine (2.5 ml, 18.3 mmol) in dichloromethane (5 ml). The resulting reaction mixture was slowly warmed-up to 40° C. and stirred at that temperature for 4 h. The reaction mixture was partitioned between potassium hydrogen sulfate (10% aqueous solution) and dichloromethane and extracted. The organic phase was washed with water and brine, dried and the solvent was evaporated. The product was obtained after purification by silica gel chromatography using a heptane/ethyl acetate gradient as light yellow viscous oil (334 mg, 39%).

MS: M=234.1 (M+H)$^+$

Step 2: 5-Amino-2-pyridin-2-yl-thiazole-4-carboxylic acid ethyl ester

The product was obtained starting from cyano-[(pyridine-2-carbonyl)-amino]-acetic acid ethyl ester (332 mg, 1.4 mmol) according to the method described in example 64, step 1 as off-white solid (98 mg, 27%).

MS: M=250.1 (M+H)+

Step 3: 5-tert-Butoxycarbonylamino-2-pyridin-2-yl-thiazole-4-carboxylic acid ethyl ester The product was obtained starting from 5-amino-2-pyridin-2-yl-thiazole-4-carboxylic acid ethyl ester (96 mg, 0.38 mmol) according to the method described in example 64, step 2 as off-white solid (95 mg, 70%).

MS: M=350.3 (M+H)+

Step 4: 5-tert-Butoxycarbonylamino-2-pyridin-2-yl-thiazole-4-carboxylic acid

The product was obtained starting from 5-tert-butoxycarbonylamino-2-pyridin-2-yl-thiazole-4-carboxylic acid ethyl ester (93 mg, 0.27 mmol) according to the method described in example 64, step 3 as white solid (75 mg, 87%).

MS: M=320.2 (M–H)−

Step 5: 5-tert-Butoxycarbonylamino-2-pyridin-2-yl-thiazole-4-carboxylic acid methylamide The product was obtained starting from 5-tert-butoxycarbonylamino-2-pyridin-2-yl-thiazole-4-carboxylic acid (73 mg, 0.23 mmol) according to the method described in example 64, step 4 as light yellow solid (34 mg, 45%).

MS: M=335.4 (M+H)+

Step 6: 5-Amino-2-pyridin-2-yl-thiazole-4-carboxylic acid methylamide

A solution of 5-tert-butoxycarbonylamino-2-pyridin-2-yl-thiazole-4-carboxylic acid methylamide (34 mg, 0.10 mmol) in dichloromethane (0.5 ml) was treated with trifluoroacetic acid (0.5 ml) and stirred at ambient temperature for 3 h. After solvent evaporation, the residue was dissolved in ethyl acetate and washed with NaOH (1N aqueous solution), water and brine. The organic layer was dried and the solvent was evaporated. The remaining residue was suspended in diethylether, sucked off, and the remaining material was dried to yield the product as yellow solid (10 mg, 42%).

MS: M=235.2 (M+H)+

Step 7: 6-Cyclopropyl-3-(pyrimidin-5-ylamino)-pyridine-2-carboxylic acid (4-methylcarbamoyl-2-pyridin-2-yl-thiazol-5-yl)-amide The product was obtained starting from intermediate A-2 (8 mg, 0.03 mmol) and 5-amino-2-pyridin-2-yl-thiazole-4-carboxylic acid methylamide (10 mg, 0.04 mmol) according to the method described in example 64, step 6 as yellow solid (2.5 mg, 16%).

MS: M=473.2 (M+H)+

Example 66

6-Cyclopropyl-3-(pyrimidin-5-ylamino)-pyridine-2-carboxylic acid [4-(2-hydroxy-1-methyl-ethylcarbamoyl)-pyridin-3-yl]-amide

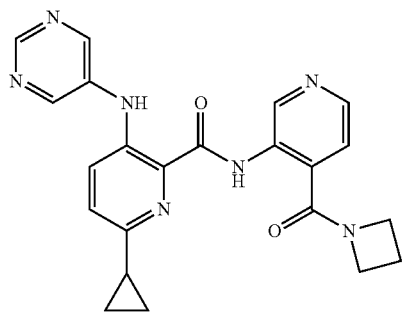 [SMILES: O=C(Nc1cnccc1C(=O)N1CCC1)c1nc(C2CC2)ccc1Nc1cncnc1]

According to the general method described in step 3 of example 53, reaction of 2-amino-propan-1-ol with 3-{[6-cyclopropyl-3-(pyrimidin-5-ylamino)-pyridine-2-carbonyl]-amino}-isonicotinic acid provided the title compound (32%) as amorphous yellow solid.

MS: M=434.0 (M+H)+

Example 67

6-Cyclopropyl-3-(pyrimidin-5-ylamino)-pyridine-2-carboxylic acid [4-(azetidine-1-carbonyl)-pyridin-3-yl]-amide

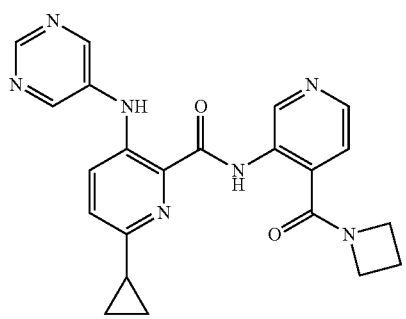 [SMILES: O=C(Nc1cnccc1C(=O)N1CCC1)c1nc(C2CC2)ccc1Nc1cncnc1]

According to the general method described in step 3 of example 53, reaction of azetidine with 3-{[6-cyclopropyl-3-(pyrimidin-5-ylamino)-pyridine-2-carbonyl]-amino}-isonicotinic acid provided the title compound (60%) as amorphous yellow solid.

MS: M=416.2 (M+H)+

Example 68

6-Cyclopropyl-3-(pyrimidin-5-ylamino)-pyridine-2-carboxylic acid [4-(2-hydroxy-ethylcarbamoyl)-pyridin-3-yl]-amide

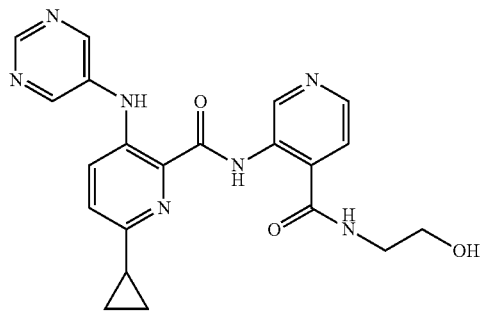 [SMILES: O=C(NCCO)c1ccncc1NC(=O)c1nc(C2CC2)ccc1Nc1cncnc1]

According to the general method described in step 3 of example 53, reaction of 2-aminoethanol with 3-{[6-cyclopropyl-3-(pyrimidin-5-ylamino)-pyridine-2-carbonyl]-amino}-isonicotinic acid provided the title compound (36%) as amorphous yellow solid.

MS: M=420.2 (M+H)$^+$

Example 69

6-Cyclopropyl-3-(pyrimidin-5-ylamino)-pyridine-2-carboxylic acid [4-(2,3-dihydroxy-propylcarbamoyl)-pyridin-3-yl]-amide

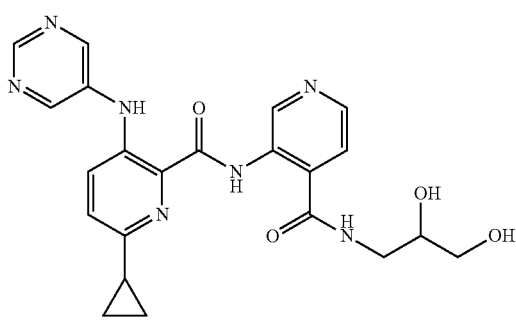 [SMILES: O=C(NCC(O)CO)c1ccncc1NC(=O)c1nc(C2CC2)ccc1Nc1cncnc1]

According to the general method described in step 3 of example 53, reaction of 3-amino-propan-1,2-diol with 3-{[6-cyclopropyl-3-(pyrimidin-5-ylamino)-pyridine-2-carbonyl]-amino}-isonicotinic acid provided the title compound (33%) as amorphous yellow solid.

MS: M=450.2 (M+H)$^+$

Example 70

6-Cyclopropyl-3-(pyrimidin-5-ylamino)-pyridine-2-carboxylic acid [4-(2-hydroxy-2-methyl-propylcarbamoyl)-pyridin-3-yl]-amide

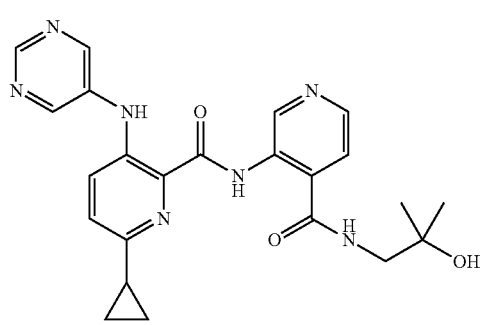 [SMILES: CC(C)(O)CNC(=O)c1ccncc1NC(=O)c1nc(C2CC2)ccc1Nc1cncnc1]

According to the general method described in step 3 of example 53, reaction of 1-amino-2-methyl-propan-2-ol with 3-{[6-cyclopropyl-3-(pyrimidin-5-ylamino)-pyridine-2-carbonyl]-amino}-isonicotinic acid provided the title compound (28%) as amorphous yellow solid.

MS: M=448.0 (M+H)$^+$

Example 71

6-Cyclopropyl-3-(pyrimidin-5-ylamino)-pyridine-2-carboxylic acid {4-[(3-hydroxy-propyl)-methyl-carbamoyl]-pyridin-3-yl}-amide

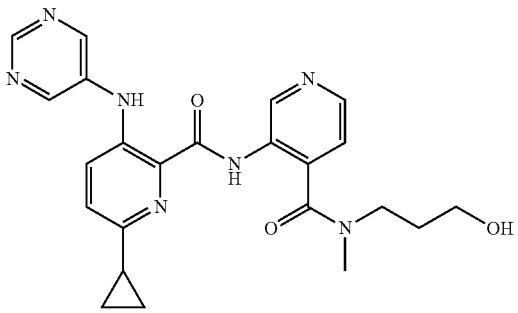 [SMILES: CN(CCCO)C(=O)c1ccncc1NC(=O)c1nc(C2CC2)ccc1Nc1cncnc1]

According to the general method described in step 3 of example 53, reaction of 3-methylamino-propan-1-ol with 3-{[6-cyclopropyl-3-(pyrimidin-5-ylamino)-pyridine-2-carbonyl]-amino}-isonicotinic acid provided the title compound (34%) as amorphous yellow solid.

MS: M=448.0 (M+H)$^+$

Example 72

6-Cyclopropyl-3-(pyrimidin-5-ylamino)-pyridine-2-carboxylic acid [4-(2-methoxy-1-methyl-ethylcarbamoyl)-pyridin-3-yl]-amide

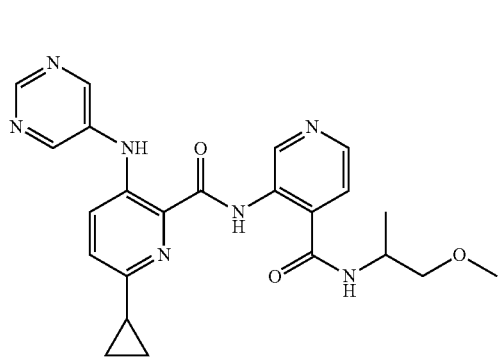 [SMILES: COCC(C)NC(=O)c1ccncc1NC(=O)c1nc(C2CC2)ccc1Nc1cncnc1]

According to the general method described in step 3 of example 53, reaction of (2-methoxy-1-methyl-ethyl)-methyl-amine with 3-{[6-cyclopropyl-3-(pyrimidin-5-ylamino)-pyridine-2-carbonyl]-amino}-isonicotinic acid provided the title compound (32%) as amorphous yellow solid.

MS: M=448.2 (M+H)$^+$

Example 73

6-Cyclopropyl-3-(pyrimidin-5-ylamino)-pyridine-2-carboxylic acid {4-[(2-hydroxy-ethyl)-methyl-carbamoyl]-pyridin-3-yl}-amide

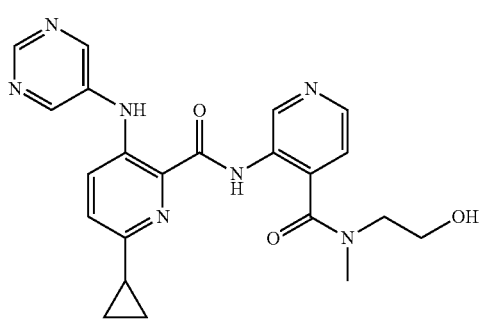 [SMILES: CN(CCO)C(=O)c1ccncc1NC(=O)c1nc(C2CC2)ccc1Nc1cncnc1]

According to the general method described in step 3 of example 53, reaction of 2-methylamino-ethanol with 3-{[6-cyclopropyl-3-(pyrimidin-5-ylamino)-pyridine-2-carbonyl]-amino}-isonicotinic acid provided the title compound (32%) as amorphous yellow solid.

MS: M=434.0 (M+H)$^+$

Example 74

6-Cyclopropyl-3-(pyrimidin-5-ylamino)-pyridine-2-carboxylic acid (3-dimethylcarbamoyl-1-pyridin-2-yl-1H-pyrazol-4-yl)-amide

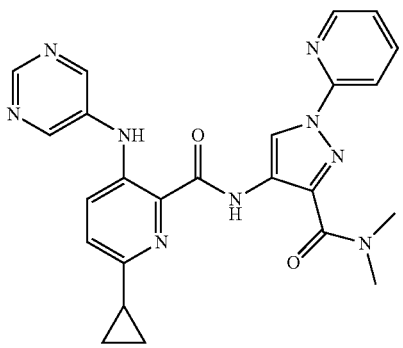 [SMILES: CN(C)C(=O)c1nn(-c2ccccn2)cc1NC(=O)c1nc(C2CC2)ccc1Nc1cncnc1]

Step 1: 4-Nitro-1H-pyrazole-3-carboxylic acid dimethylamide

A solution of 4-nitro-1H-pyrazole-3-carboxylic acid (1.0 g, 6.4 mmol) in dichloromethane (20 ml) was treated with thionyl chloride (1.4 ml, 19 mmol) and a drop of DMF at ambient temperature. The reaction mixture is stirred at 40° C. overnight whereupon another equivalent of thionyl chloride (0.46 ml, 6.4 mmol) was added and stirring was continued at 40° C. for another 24 h. All volatiles were removed and the acid chloride was suspended in dichloromethane (6 ml) and cooled to 0° C. Triethylamine (4.44 ml, 31.8 mmol) and dimethylamin (4.14 ml, 2M solution in THF) were added. The reaction mixture was allowed to warm-up to ambient temperature and stirring was continued for 3 h. The reaction mixture was partitioned between potassium hydrogen sulfate (20 ml, 10% aqueous solution) and ethyl acetate (40 ml) and extracted. The organic phase was washed with water and brine, dried and the solvent was evaporated. The crude product was triturated with diethylether, sucked off and dried to yield a light brown solid (0.35 g, 30%).

MS: M=185.1 (M+H)$^+$

Step 2: 4-Nitro-1-pyridin-2-yl-1H-pyrazole-3-carboxylic acid dimethylamide

A solution of 4-nitro-1H-pyrazole-3-carboxylic acid dimethylamide (250 mg, 1.36 mmol) in DMF (5 ml) was flushed with argon. 2-Bromopyridine (0.17 ml, 1.76 mmol), ferric acetylacetone (144 mg, 0.4 mmol), copper(I)oxide (20 mg, 0.14 mmol) and cesium carbonate (885 mg, 2.7 mmol) were added consecutively and the reaction mixture was stirred at 110° C. overnight. After cooling down, the reaction mixture was partitioned between ethyl acetate (30 ml) and water (15 ml) and extracted. The organic layer was washed with brine, dried and the solvent was evaporated. The product was obtained after purification by silica gel chromatography using a heptane/ethyl acetate gradient as light yellow solid (102 mg, 29%).

MS: M=262.1 (M+H)$^+$

Step 3: 4-Amino-1-pyridin-2-yl-1H-pyrazole-3-carboxylic acid dimethylamide

A solution of 4-nitro-1-pyridin-2-yl-1H-pyrazole-3-carboxylic acid dimethylamide (50 mg, 0.19 mmol) in THF (3 ml) was flushed with argon and treated with Pd/C 10% (11 mg, 0.01 mmol). The reaction vessel was evacuated and flushed with hydrogen three times and the reaction was stirred at ambient temperature overnight. The reaction mixture was filtrated and the solvent was evaporated to yield a solid material (44 mg, 99%) which was used without further purification.

MS: M=232.1 (M+H)$^+$

Step 4: 6-Cyclopropyl-3-(pyrimidin-5-ylamino)-pyridine-2-carboxylic acid (3-dimethyl-carbamoyl-1-pyridin-2-yl-1H-pyrazol-4-yl)-amide The product was obtained starting from intermediate A-2 (29 mg, 0.11 mmol) and 4-amino-1-pyridin-2-yl-1H-pyrazole-3-carboxylic acid dimethylamide (43 mg, 0.18 mmol) according to the method described in example 54, step 5 after purification by preparative HPLC using an acetonitrile/water gradient as light yellow solid (9.4 mg, 17%).

MS: M=470.4 (M+H)$^+$

Example 75

2-Isopropyl-5-(pyrimidin-5-ylamino)-pyrimidine-4-carboxylic acid (1-methyl-3-methylcarbamoyl-1H-pyrazol-4-yl)-amide

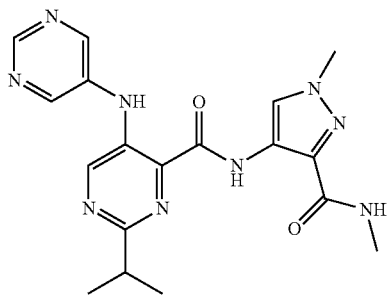 [SMILES: CNC(=O)c1nn(C)cc1NC(=O)c1nc(C(C)C)ncc1Nc1cncnc1]

According to the procedure described in step 2 of example 14, the title compound was obtained by reaction of A-4 and 4-amino-1-methyl-1H-pyrazole-3-carboxylic acid methylamide as yellow solid (69%).

MS: M=396.1 (M+H)$^+$

Example 76

2-Cyclopropyl-5-(pyrimidin-5-ylamino)-pyrimidine-4-carboxylic acid (1-methyl-3-methylcarbamoyl-1H-pyrazol-4-yl)-amide

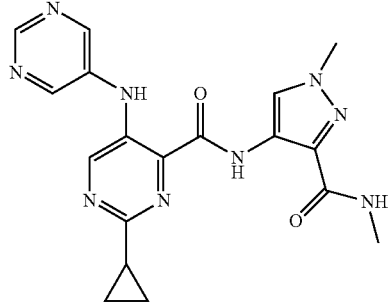 [SMILES: CNC(=O)c1nn(C)cc1NC(=O)c1nc(C2CC2)ncc1Nc1cncnc1]

According to the procedure described in step 2 of example 14, the title compound was obtained by reaction of A-5 and 4-amino-1-methyl-1H-pyrazole-3-carboxylic acid methylamide as yellow solid (78%).

MS: M=394.1 (M+H)$^+$

Example 77

2-tert-Butyl-5-(pyrimidin-5-ylamino)-pyrimidine-4-carboxylic acid (1-methyl-3-methylcarbamoyl-1H-pyrazol-4-yl)-amide

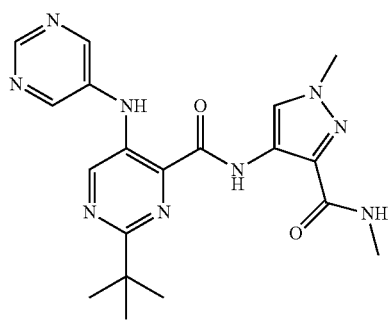 [SMILES: CNC(=O)c1nn(C)cc1NC(=O)c1nc(C(C)(C)C)ncc1Nc1cncnc1]

According to the procedure described in step 2 of example 14, the title compound was obtained by reaction of A-6 and 4-amino-1-methyl-1H-pyrazole-3-carboxylic acid methylamide as yellow solid (80%).

MS: M=410.3 (M+H)$^+$

Example 78

6-Cyclopropyl-3-(pyrimidin-5-ylamino)-pyridine-2-carboxylic acid (4-cyclohexylcarbamoyl-pyridin-3-yl)-amide

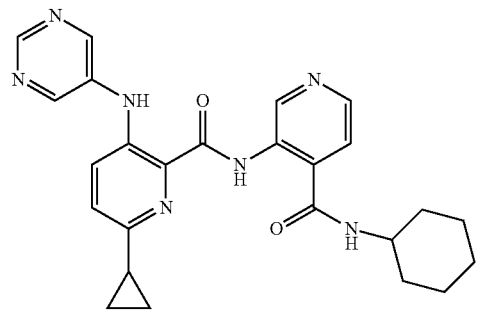 [SMILES: O=C(NC1CCCCC1)c1ccncc1NC(=O)c1nc(C2CC2)ccc1Nc1cncnc1]

According to the general method described in step 3 of example 53, reaction of cyclohexylamine with 3-{[6-cyclopropyl-3-(pyrimidin-5-ylamino)-pyridine-2-carbonyl]-amino}-isonicotinic acid provided the title compound (26%) as amorphous yellow solid.

MS: M=458.2 (M+H)$^+$

Example 79

6-Cyclopropyl-3-(pyrimidin-5-ylamino)-pyridine-2-carboxylic acid [4-(3,3-difluoro-azetidine-1-carbonyl)-pyridin-3-yl]-amide

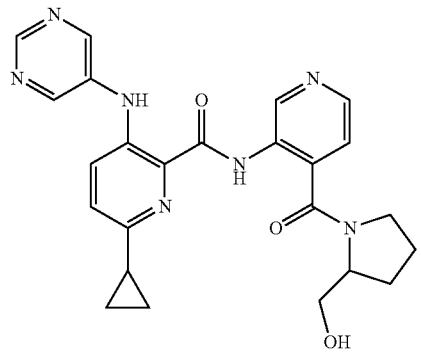 [SMILES: O=C(Nc1cnccc1C(=O)N1CCCC1CO)c1nc(C2CC2)ccc1Nc1cncnc1]

According to the general method described in step 3 of example 53, reaction of 3,3-difluoroazetidine with 3-{[6-cyclopropyl-3-(pyrimidin-5-ylamino)-pyridine-2-carbonyl]-amino}-isonicotinic acid provided the title compound as yellow powder (26%).

MS: M=452.0 (M+H)$^+$

Example 80

6-Cyclopropyl-3-(pyrimidin-5-ylamino)-pyridine-2-carboxylic acid [4-(2-hydroxymethyl-pyrrolidine-1-carbonyl)-pyridin-3-yl]-amide

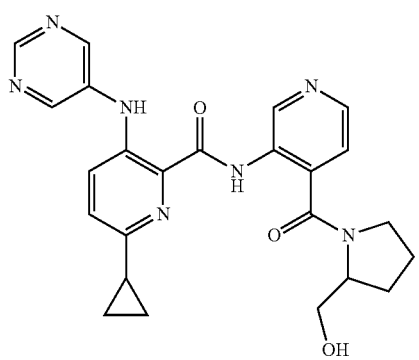 [SMILES: O=C(Nc1cnccc1C(=O)N1CCCC1CO)c1nc(C2CC2)ccc1Nc1cncnc1]

According to the general method described in step 3 of example 53, reaction of 2-hydroxymethylpyrrolidine with 3-{[6-cyclopropyl-3-(pyrimidin-5-ylamino)-pyridine-2-carbonyl]-amino}-isonicotinic acid provided the title compound as off-white solid (29%).

MS: M=460.4 (M+H)$^+$

Example 81

7-{[6-Cyclopropyl-3-(pyrimidin-5-ylamino)-pyridine-2-carbonyl]-amino}-2-phenyl-imidazo[1,2-a]pyridine-6-carboxylic acid methylamide

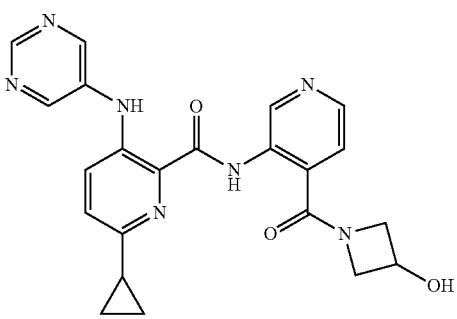 [SMILES: O=C(Nc1cnccc1C(=O)N1CC(O)C1)c1nc(C2CC2)ccc1Nc1cncnc1]

Step 1: 7-Amino-2-phenyl-imidazo[1,2-a]pyridine-6-carbonitrile hydrochloride

To a stirred suspension of 3-cyano-4,6-diaminopyridine (2.02 g, 15 mmol) at rt in ethanol (50 ml) under an argon atmosphere were added NaHCO$_3$ (2.53 g, 30 mmol) and 2-bromoacetophenone (6.0 g, 30 mmol). The mixture was heated to reflux and stirring was continued overnight. The dark brown slurry was cooled to rt and concentrated. The residual dark brown sticky solid was taken up in 3 N HCl (50 ml) and EtOAc (50 ml). The biphasic mixture was stirred at rt for 1 hr. The precipitate was collected by filtration and washed with EtOAc. Trituration of the solid in 50 ml CH$_2$Cl$_2$/MeOH 9:1 and filtration provided the title compound (2.63 g, 64%) as off-white solid.

MS: M=235.1 (M+H)$^+$

Step 2: 7-Amino-2-phenyl-imidazo[1,2-a]pyridine-6-carboxylic acid ethyl ester

To a stirred suspension of 7-amino-2-phenyl-imidazo[1,2-a]pyridine-6-carbonitrile hydrochloride (1.0 g, 3.7 mmol) at rt in EtOH (20 ml) under an argon atmosphere was added H$_2$SO$_4$ (1.5 ml, 27.7 mmol) in one portion. The mixture was heated to reflux and stirring was continued for 2 days. The mixture was cooled to rt and diluted with 10 ml H$_2$O. The solid was collected by filtration, washed with H$_2$O and dried. Then it was suspended in CH$_2$Cl$_2$/MeOH 9:1 and treated with triethylamine to give a yellow solution. The dissolved material was adsorbed on Isolute® Flash-NH$_2$ silica gel (from Separtis) and purified by chromatographie on the same silica gel as stationary phase using a CH$_2$Cl$_2$/MeOH gradient as eluent, providing the title compound as off-white solid (642 mg, 62%).

MS: M=282.1 (M+H)$^+$

Step 3: 7-Amino-2-phenyl-imidazo[1,2-a]pyridine-6-carboxylic acid methylamide

According to the procedure described in step 1 of example 18 7-amino-2-phenyl-imidazo[1,2-a]pyridine-6-carboxylic acid ethyl ester was reacted with methylamine hydrochloride to give the title compound as off-white solid (60%).

MS: M=267.1 (M+H)$^+$

Step 4: 7-{[6-Cyclopropyl-3-(pyrimidin-5-ylamino)-pyridine-2-carbonyl]-amino}-2-phenyl-imidazo[1,2-a]pyridine-6-carboxylic acid methylamide According to the procedure described in example 29, 7-amino-2-phenyl-imidazo[1,2-a]pyridine-6-carboxylic acid methylamide and A-2 were coupled to give the title compound as yellow solid (25%).

MS: M=505.1 (M+H)$^+$

Example 82

6-Cyclopropyl-3-(pyrimidin-5-ylamino)-pyridine-2-carboxylic acid [4-(3-hydroxy-azetidine-1-carbonyl)-pyridin-3-yl]-amide

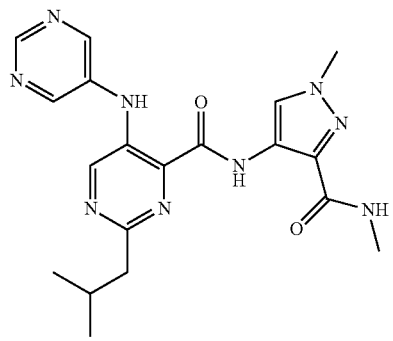 [SMILES: CNC(=O)c1nn(C)cc1NC(=O)c1nc(CC(C)C)ncc1Nc1cncnc1]

According to the general method described in step 3 of example 53, reaction of 3-hydroxy-azetidine with 3-{[6-cyclopropyl-3-(pyrimidin-5-ylamino)-pyridine-2-carbonyl]-amino}-isonicotinic acid provided the title compound (8%) as light yellow powder.

MS: M=432.0 (M+H)$^+$

Example 83

2-Isobutyl-5-(pyrimidin-5-ylamino)-pyrimidine-4-carboxylic acid (1-methyl-3-methylcarbamoyl-1H-pyrazol-4-yl)-amide

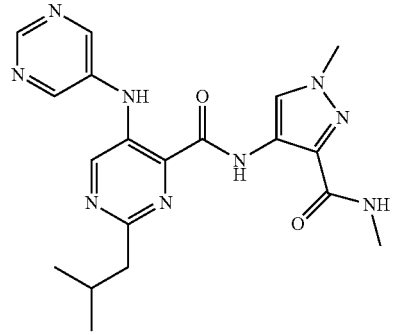 [SMILES: CNC(=O)c1nn(C)cc1NC(=O)c1nc(CC(C)C)ncc1Nc1cncnc1]

According to the procedure described in step 2 of example 14, the title compound was obtained by reaction of A-7 and 4-amino-1-methyl-1H-pyrazole-3-carboxylic acid methylamide as yellow solid (52%).

MS: M=410.3 (M+H)$^+$

Example 84

2-Cyclohexyl-5-(pyrimidin-5-ylamino)-pyrimidine-4-carboxylic acid (1-methyl-3-methylcarbamoyl-1H-pyrazol-4-yl)-amide

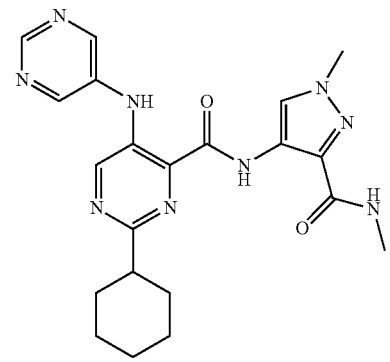 [SMILES: CNC(=O)c1nn(C)cc1NC(=O)c1nc(C2CCCCC2)ncc1Nc1cncnc1]

According to the procedure described in step 2 of example 14, the title compound was obtained by reaction of A-8 and 4-amino-1-methyl-1H-pyrazole-3-carboxylic acid methylamide as yellow solid (58%)

MS: M=436.3 (M+H)$^+$.

Example 85

6-Cyclopropyl-3-(pyrimidin-5-ylamino)-pyridine-2-carboxylic acid [4-(2,2-dimethyl-pyrrolidine-1-carbonyl)-pyridin-3-yl]-amide

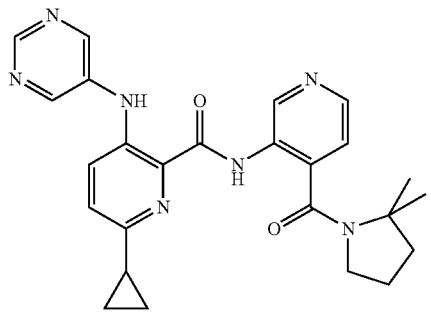 [SMILES: CC1(C)CCCN1C(=O)c1ccncc1NC(=O)c1nc(C2CC2)ccc1Nc1cncnc1]

According to the general method described in step 3 of example 53, reaction of 2,2-dimethylpyrrolidine with 3-{[6-cyclopropyl-3-(pyrimidin-5-ylamino)-pyridine-2-carbonyl]-amino}-isonicotinic acid provided the title compound (23%) as sticky yellow solid.

MS: M=458.2 (M+H)$^+$

Example 86

6-Cyclopropyl-3-(pyrimidin-5-ylamino)-pyridine-2-carboxylic acid {4-[(2,3-dihydroxy-propyl)-methyl-carbamoyl]-pyridin-3-yl}-amide

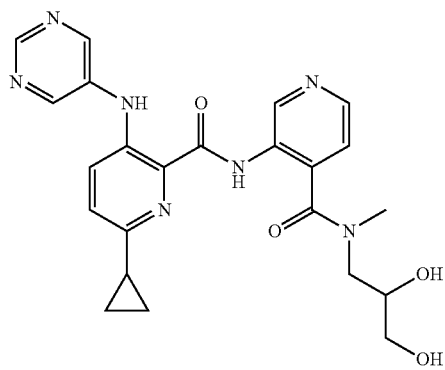 [SMILES: CN(CC(O)CO)C(=O)c1ccncc1NC(=O)c1nc(C2CC2)ccc1Nc1cncnc1]

According to the general method described in step 3 of example 53, reaction of 3-methylamino-propan-1,2-diol with 3-{[6-cyclopropyl-3-(pyrimidin-5-ylamino)-pyridine-2-carbonyl]-amino}-isonicotinic acid provided the title compound (19%) as sticky yellow solid.

MS: M=464.2 (M+H)$^+$

Example 87

6-Cyclopropyl-3-(pyrimidin-5-ylamino)-pyridine-2-carboxylic acid [4-(4-(3-hydroxy-pyrrolidine-1-carbonyl)-pyridin-3-yl]-amide

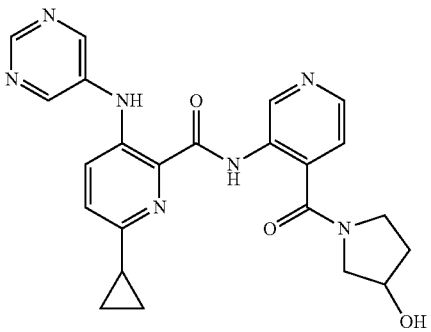 [SMILES: O=C(Nc1cnccc1C(=O)N1CCC(O)C1)c1nc(C2CC2)ccc1Nc1cncnc1]

According to the general method described in step 3 of example 53, reaction of 3-hydroxy-pyrrolidine with 3-{[6-cyclopropyl-3-(pyrimidin-5-ylamino)-pyridine-2-carbonyl]-amino}-isonicotinic acid provided the title compound (30%) as light yellow solid.

MS: M=446.0 (M+H)$^+$

Example 88

6-Cyclopropyl-3-(pyrimidin-5-ylamino)-pyridine-2-carboxylic acid [4-(2-oxa-6-aza-spiro[3.3]heptane-6-carbonyl)-pyridin-3-yl]-amide

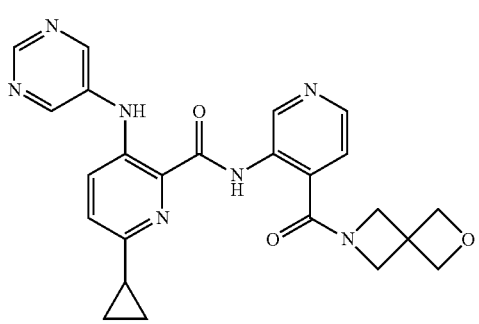 [SMILES: O=C(Nc1cnccc1C(=O)N1CC2(COC2)C1)c1nc(C2CC2)ccc1Nc1cncnc1]

According to the general method described in step 3 of example 53, reaction of 2-oxa-6-aza-spiro[3.3]heptane with 3-{[6-cyclopropyl-3-(pyrimidin-5-ylamino)-pyridine-2-carbonyl]-amino}-isonicotinic acid provided the title compound (9%) as amorphous off-white solid.

MS: M=458.2 (M+H)$^+$

Example 89

6-Cyclopropyl-3-(pyrimidin-5-ylamino)-pyridine-2-carboxylic acid (3-cyclopropylcarbamoyl-thiophen-2-yl)-amide

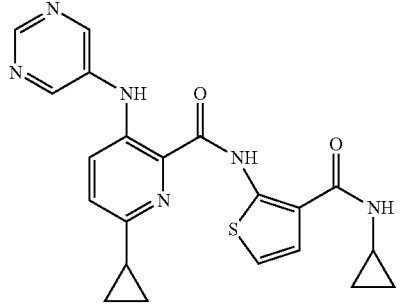 [SMILES: O=C(NC1CC1)c1ccsc1NC(=O)c1nc(C2CC2)ccc1Nc1cncnc1]

The product was obtained starting from intermediate A-2 (40 mg, 0.16 mmol) and 2-amino-N-cyclopropylthiophene-3-carboxamide (40 mg, 0.22 mmol) according to the method described in example 64, step 6 as yellow solid (35 mg, 53%).

MS: M=421.2 (M+H)$^+$

Example 90

6-Cyclopropyl-3-(pyrimidin-5-ylamino)-pyridine-2-carboxylic acid [3-(morpholine-4-carbonyl)-thiophen-2-yl]-amide

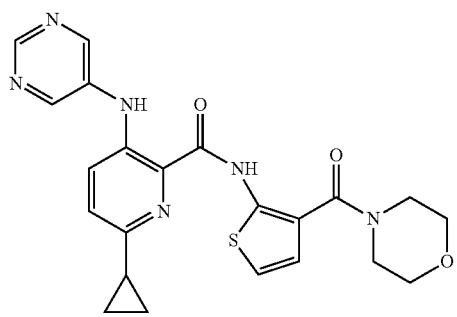 [SMILES: O=C(Nc1sccc1C(=O)N1CCOCC1)c1nc(C2CC2)ccc1Nc1cncnc1]

The product was obtained starting from intermediate A-2 (40 mg, 0.16 mmol) and 2-(morpholin-4-ylcarbonyl)thioen-2-ylamine (46 mg, 0.22 mmol) according to the method described in example 64, step 6 as light yellow solid (27 mg, 38%).

MS: M=451.2 (M+H)$^+$

Example 91

6-Cyclopropyl-3-(pyrimidin-5-ylamino)-pyridine-2-carboxylic acid [5-isopropyl-3-(morpholine-4-carbonyl)-thiophen-2-yl]-amide

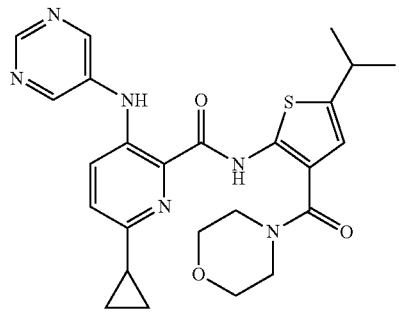 [SMILES: CC(C)c1cc(C(=O)N2CCOCC2)c(NC(=O)c2nc(C3CC3)ccc2Nc2cncnc2)s1]

The product was obtained starting from intermediate A-2 (40 mg, 0.16 mmol) and (2-amino-5-isopropylthiophene-3-yl)-morpholino-methanone (56 mg, 0.22 mmol) according to the method described in example 64, step 6 as yellow solid (49 mg, 64%).

MS: M=493.3 (M+H)$^+$

Example 92

2-Isopropyl-5-(pyrimidin-5-ylamino)-pyrimidine-4-carboxylic acid [4-(2-hydroxy-2-methyl-propylcarbamoyl)-pyridin-3-yl]-amide

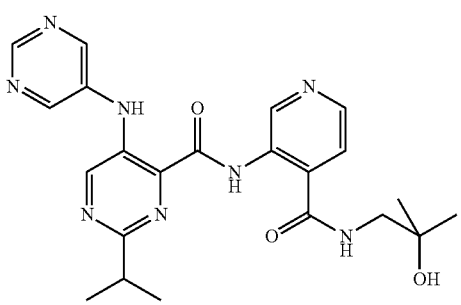 [SMILES: CC(C)c1ncc(Nc2cncnc2)c(C(=O)Nc2cnccc2C(=O)NCC(C)(C)O)n1]

Step 1: N-(2-Hydroxy-2-methyl-propyl)-3-nitro-isonicotinamide

A mixture of 3-nitroisonicotinic acid (1.75 g, 10.1 mmol), 1-amino-2-methylpropan-2-ol (968 ul, 10.1 mmol), 2-(1H-benzotriazole-1-yl)-1,1,3,3-tetramethyluronium tetrafluoroborate (4.86 g, 15.1 mmol) and triethylamine (4.9 ml, 35.3 mmol) in tetrahydrofurane (60 ml) was stirred over the weekend at rt. The reaction mixture was diluted with ethyl acetate, washed with water, with brine, dried with magnesium sulfate and concentrated. The crude product was purified by silica gel chromatography using a CH$_2$Cl$_2$/MeOH gradient as eluent, providing the title compound as off-white solid (255 mg, 11%).

MS: M=240.0 (M+H)$^+$

Step 2: 3-Amino-N-(2-hydroxy-2-methylpropyl) isonicotinamide

According to the procedure described in step 2 of example 2, the title compound was obtained as off-white solid (96%).
MS: M=210.2 (M+H)$^+$

Step 3: 2-Isopropyl-5-(pyrimidin-5-ylamino)-pyrimidine-4-carboxylic acid [4-(2-hydroxy-2-methyl-propylcarbamoyl)-pyridin-3-yl]-amide According to the procedure described in example 29, 3-amino-N-(2-hydroxy-2-methylpropyl)iso-nicotinamide was reacted with A-15 to give the title compound as yellow solid (7%).
MS: M=451.2 (M+H)$^+$

Example 93

2-tert-Butyl-5-(pyrimidin-5-ylamino)-pyrimidine-4-carboxylic acid [4-(2-hydroxy-2-methyl-propylcarbamoyl)-pyridin-3-yl]-amide

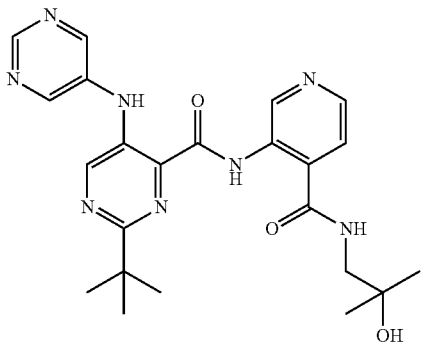 [SMILES: CC(C)(O)CNC(=O)c1ccncc1NC(=O)c1nc(C(C)(C)C)ncc1Nc1cncnc1]

According to the procedure described in example 29, 3-amino-N-(2-hydroxy-2-methylpropyl)iso-nicotinamide (step 2, example 92) was reacted with A-9 to give the title compound as yellow solid (11%).
MS: M=465.2 (M+H)$^+$

Example 94

2-{[2-tert-Butyl-5-(pyrimidin-5-ylamino)-pyrimidine-4-carbonyl]-amino}-N$^4$,N$^4$-diethyl-N$^1$-methyl-terephthalamide

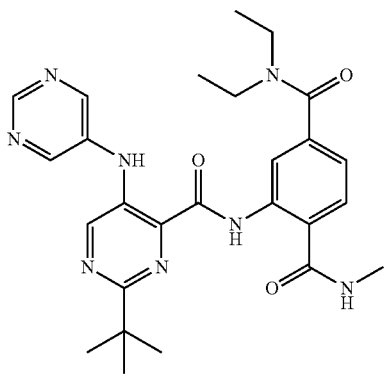 [SMILES: CCN(CC)C(=O)c1ccc(C(=O)NC)c(NC(=O)c2nc(C(C)(C)C)ncc2Nc2cncnc2)c1]

Step 1: 2-Amino-N4,N4-diethyl-N1-methylterephthalamide

In an autoclave a mixture of methyl 2-amino-4-(diethylcarbamoyl)benzoate (490 mg, 1.96 mmol) and methylamine solution (33% in ethanol; 25 ml, 200 mmol) was stirred for 24 hrs at 90° C. The reaction mixture was concentrated. The crude product was purified by silica gel chromatography using EtOAc as eluent, providing the title compound as white solid (341 mg, 70%).
MS: M=250.2 (M+H)$^+$

Step 2: 2-(2-tert-Butyl-5-(pyrimidin-5-ylamino)pyrimidine-4-carboxamido)-N4,N4-diethyl-N1-methyl-terephthalamide According to the procedure described in example 29, A-9 was reacted with 2-amino-N4,N4-diethyl-N1-methylterephthalamide to give the title compound as yellow solid (30%).
MS: M=505.2 (M+H)$^+$

Example 95

6-Cyclopropyl-3-(pyrimidin-5-ylamino)-pyrazine-2-carboxylic acid [3-(2-hydroxy-2-methyl-propylcarbamoyl)-1-methyl-1H-pyrazol-4-yl]-amide

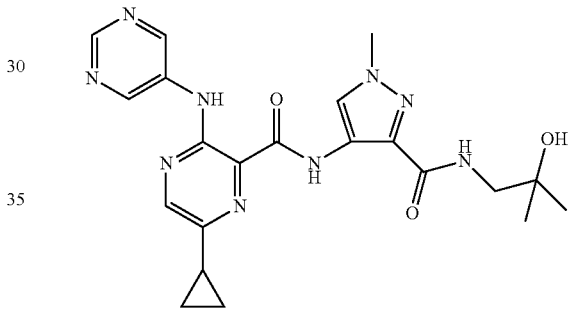

Step 1: N-(2-Hydroxy-2-methylpropyl)-1-methyl-4-nitro-1H-pyrazole-3-carboxamide To a suspension of 1-methyl-4-nitro-1H-pyrazole-3-carboxylic acid (0.9 g, 5.26 mmol) and 1-amino-2-methylpropan-2-ol (469 mg, 5.26 mmol) in THF (20 mL) cooled to 0-5° C. were added N,N-diisopropylamine (3.67 mL, 21.0 mmol) and 1-propanephosphonic acid cyclic anhydride (8.37 mL, 13.1 mmol, 50% solution in ethyl acetate). The mixture was stirred at 70° C. for 16 hours, cooled to ambient temperature, poured into ethyl acetate (50 mL) and extracted with HCl (1 M, 20 mL). The organic phase was washed with water and brine. The aqueous layers were back-extracted separately with ethyl acetate and dichloromethane. The combined organic layers were dried and concentrated in vacuo to give 1.4 g crude product. The crude material was purified by silica gel chromatography using a methanol/ethyl acetate gradient to give the title compound as colorless foam (391 mg, 31% yield).
MS: M=243.2 (M+H)$^+$

Step 2: 4-Amino-N-(2-hydroxy-2-methylpropyl)-1-methyl-1H-pyrazole-3-carboxamide To a solution of N-(2-hydroxy-2-methylpropyl)-1-methyl-4-nitro-1H-pyrazole-3-carboxamide (391 mg, 1.61 mmol) in ethanol was added under an argon atmosphere Pd/C 10% (40 mg, 0.04 mmol) at ambient temperature. The mixture was stirred at that temperature under a hydrogen atmosphere for 16 hours. The catalyst was filtered off and washed with ethanol. The filtrate was concentrated in vacuo to give the title compound as waxy solid (340 mg, 99% yield) which was used without any further purification.

MS: M=213.3 (M+H)$^+$

Step 3: 6-Cyclopropyl-3-(pyrimidin-5-ylamino)-pyrazine-2-carboxylic acid [3-(2-hydroxy-2-methyl-propylcarbamoyl)-1-methyl-1H-pyrazol-4-yl]-amide The product was obtained starting from intermediate A-11 (66 mg, 0.26 mmol) and 4-amino-N-(2-hydroxy-2-methyl-propyl)-1-methyl-1H-pyrazole-3-carboxamide (58 mg, 0.27 mmol) according to the method described in example 64, step 6 as yellow solid (82 mg, 70%).

MS: M=452.2 (M+H)$^+$

Example 96

3-(Pyrimidin-5-ylamino)-6-(tetrahydro-furan-2-yl)-pyrazine-2-carboxylic acid (1-methyl-3-methylcarbamoyl-1H-pyrazol-4-yl)-amide

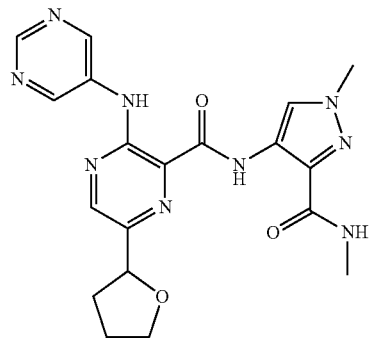

Step 1: 3-Amino-6-furan-2-yl-pyrazine-2-carboxylic acid methyl ester

A mixture of Pd(OAc)$_2$ (146 mg, 0.7 mmol) and 1,1-bis(diphenylphosphino)ferrocene (478 mg, 0.9 mmol) in DMF (65 ml) under an argon atmosphere was stirred at 50° for 15 min and cooled to rt. The reaction mixture was evacuated, then flushed with argon. 3-Amino-6-bromopyrazine-2-carboxylic acid methyl ester (5.0 g, 21.5 mmol), 2-furanboronic acid (2.65 g, 23.7 mmol) and triethylamine (4.3 ml) were added. The reaction mixture was again evacuated, then flushed with argon. The mixture was heated at 90° overnight. After cooling to rt, the black mixture was concentrated to dryness. The residue was dissolved in dichloromethane (800 ml), washed with water, dried over MgSO$_4$, filtered and evaporated. The crude product was purified by silica gel chromatography using a n-heptane/EtOAc gradient for elution, providing the title compound as yellow solid (2.84 g, 60%).

MS: M=220.3 (M+H)$^+$

Step 2: 3-Amino-6-(tetrahydrofuran-2-yl)pyrazine-2-carboxylic acid methyl ester

A solution of 3-amino-6-furan-2-yl-pyrazine-2-carboxylic acid methyl ester (1.94 g, 8.9 mmol) was dissolved in THF (80 ml) and hydrogenated over night at rt in the presence of 10% Pd/C (1.0 g). The catalyst was filtered and washed with THF. The filtrate was again hydrogenated in the presence of Pd/C 10% (1.0 g) overnight. The catalyst was filtered and washed with THF. The filtrate was concentrated. The crude product was purified by column chromatography using a CH$_2$Cl$_2$/MeOH gradient for elution, providing the title compound (611 mg, 31%) as yellow solid.

MS: M=224.1 (M+H)$^+$

Step 3: 3-Amino-N-(1-methyl-3-(methylcarbamoyl)-1H-pyrazol-4-yl)-6-(tetrahydrofuran-2-yl)pyrazine-2-carboxamide According to the procedure described in step 2 of example 14, 3-amino-6-(tetrahydrofuran-2-yl)pyrazine-2-carboxylic acid methyl ester was reacted with 4-amino-1-methyl-1H-pyrazole-3-carboxylic acid methylamide hydrochloride to obtain the title compound as yellow solid (64%).

MS: M=346.1 (M+H)$^+$

Step 4: N-(1-Methyl-3-(methylcarbamoyl)-1H-pyrazol-4-yl)-3-(pyrimidin-5-ylamino)-6-(tetrahydrofuran-2-yl)pyrazine-2-carboxamide According to the procedure described in step 2 of example A-1, the title compound was obtained as yellow solid (53%).

MS: M=424.2 (M+H)$^+$

Example 97

5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide

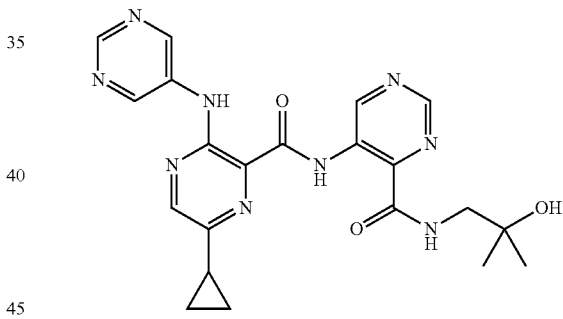

Step 1: 5-Amino-pyrimidine-4-carboxylic acid (2-hydroxy-2-methyl-propyl)-amide

To a stirred mixture of 5-aminopyrimidine-4-carboxylic acid (200 mg, 1.44 mmol) and 1-amino-2-methylpropan-2-ol (128 mg, 1.44 mmol) at rt in THF (5 ml) under an argon atmosphere were added N-ethyldiisoproplyamine (743 mg, 978 µl, 5.75 mmol) and 1-propanephosphonic acid cyclic anhydride (2.29 g, 2.16 ml, 3.59 mmol). The mixture was stirred at rt for 21 hrs, then concentrated. The crude product was purified by column chromatography with EtOAc/MeOH as eluent providing the title compound (216 mg, 72%) as off-white solid.

Step 2: 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide According to the procedure described in step 6 of example 64 the title compound (9%) was obtained from 5-aminopyrimidine-4-carboxylic acid (2-hydroxy-2-methyl-propyl)-amide and A-11 as off-white solid.
MS: M=448.1 (M−H)⁻

Example 98

6-Cyclopropyl-3-(pyrimidin-5-ylamino)-pyrazine-2-carboxylic acid [2-(2-hydroxy-2-methyl-propylcarbamoyl)-pyridin-3-yl]-amide

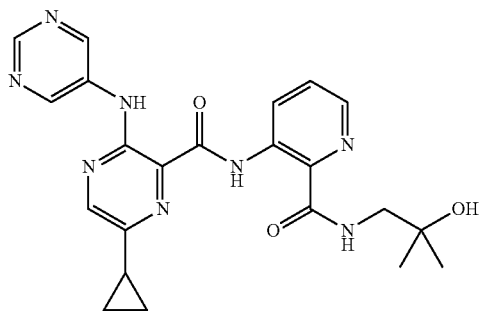 [SMILES: CC(C)(O)CNC(=O)c1ncccc1NC(=O)c1nc(C2CC2)cnc1Nc1cncnc1]

According to the procedures described in example 97, the title compound was obtained using 3-aminopicolinic acid and 1-amino-2-methylpropan-2-ol in the 1st step (24%) and A-11 in the 2nd step (69%). Yellow solid.
MS: M=449.2 (M+H)⁺

Example 99

6-Cyclopropyl-3-(pyrimidin-5-ylamino)-pyrazine-2-carboxylic acid [4-(2-isopropoxy-ethylcarbamoyl)-pyridin-3-yl]-amide

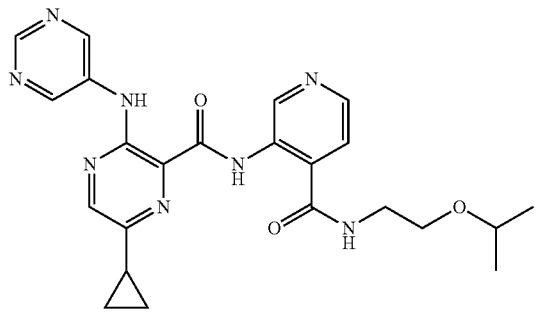 [SMILES: CC(C)OCCNC(=O)c1ccncc1NC(=O)c1nc(C2CC2)cnc1Nc1cncnc1]

Step 1: 3-{[6-Cyclopropyl-3-(pyrimidin-5-ylamino)-pyrazine-2-carbonyl]-amino}-isonicotinic acid ethyl ester According to the procedure described in step 6 of example 64 the title compound (72%) was obtained from A-11 and 3-amino-isonicotinic acid ethyl ester as yellow solid.
MS: M=404.1 (M−H)⁻

Step 2: 3-{[6-Cyclopropyl-3-(pyrimidin-5-ylamino)-pyrazine-2-carbonyl]-amino}-isonicotinic acid To a stirred suspension of 3-{[6-cyclopropyl-3-(pyrimidin-5-ylamino)-pyrazine-2-carbonyl]-amino}-isonicotinic acid ethyl ester (972 mg, 2.4 mmol) at rt in ethanol (15 ml) under an argon atmosphere was added 1 N NaOH (3 ml, 3.0 mmol). The suspension was stirred at rt for overnight. After the addition of 1 N HCl (3 ml) stirring was continued for 1 hr. The solid was collected by filtration, washed with H₂O, then EtOH and dried.
MS: M=476.0 (M−H)⁻

Step 3: 6-Cyclopropyl-3-(pyrimidin-5-ylamino)-pyrazine-2-carboxylic acid [4-(2-isopropoxy-ethylcarbamoyl)-pyridin-3-yl]-amide To a stirred mixture of 2-aminoethyl isopropyl ether (25 mg, 242 μmol) and 3-{[6-cyclopropyl-3-(pyrimidin-5-ylamino)-pyrazine-2-carbonyl]-amino}-isonicotinic acid (101 mg, 267 μmol) at rt in THF (5 ml) under an argon atmosphere were added 4-methylmorpholine (123 mg, 134 μl, 1.21 mmol) and HATU (184 mg, 485 μmol). The mixture was heated to reflux and stirring was continued for 1 day. The reaction mixture was concentrated. The crude product was purified by silica gel chromatography using an EtOAc/MeOH gradient as eluent. After trituration with MeOH, the title compound (90 mg, 80%) was obtained as yellow solid.
MS: M=463.2 (M+H)⁺

Example 100

6-Cyclopropyl-3-(pyrimidin-5-ylamino)-pyrazine-2-carboxylic acid [4-(tetrahydro-furan-3-ylcarbamoyl)-pyridin-3-yl]-amide

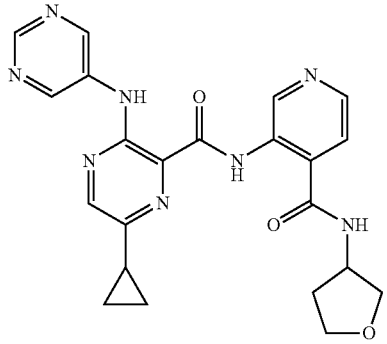 [SMILES: O=C(NC1CCOC1)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 3-aminotetrahydro-furan, providing the title compound as yellow solid (96%).
MS: M=445.4 (M−H)⁻

Example 101

6-Cyclopropyl-3-(pyrimidin-5-ylamino)-pyrazine-2-carboxylic acid {4-[(tetrahydro-furan-2-ylmethyl)-carbamoyl]-pyridin-3-yl}-amide

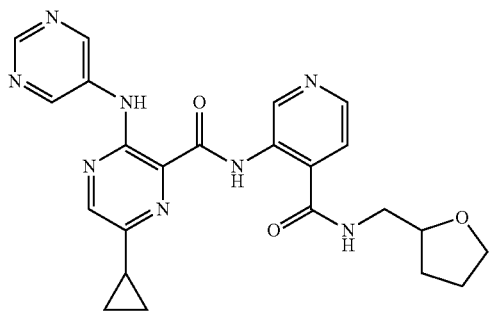 [SMILES: O=C(NCC1CCCO1)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with (tetrahydrofuran-2-yl)methanamine, providing the title compound as yellow solid (77%).

MS: M=461.3 (M+H)$^+$

Example 102

3-(Pyrimidin-5-ylamino)-6-(tetrahydro-furan-3-yl)-pyrazine-2-carboxylic acid (1-methyl-3-methylcarbamoyl-1H-pyrazol-4-yl)-amide

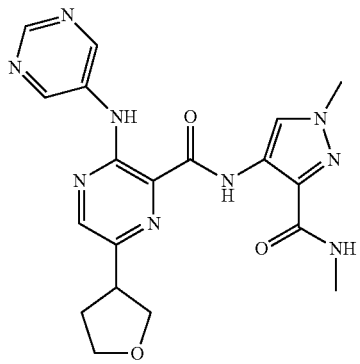 [SMILES: CNC(=O)c1nn(C)cc1NC(=O)c1nc(C2CCOC2)cnc1Nc1cncnc1]

According to the procedures described in example 96, using 3-furanboronic acid in the first step, the title compound was obtained as yellow solid.

MS: M=424.2 (M+H)$^+$

Example 103

3-(Pyrimidin-5-ylamino)-6-(tetrahydro-furan-2-yl)-pyridine-2-carboxylic acid (1-methyl-3-methylcarbamoyl-1H-pyrazol-4-yl)-amide

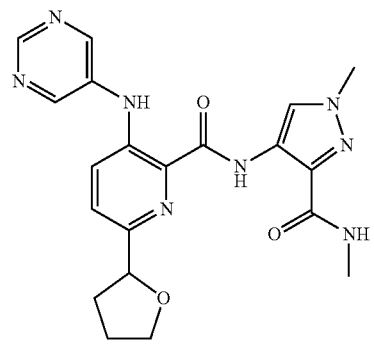 [SMILES: CNC(=O)c1nn(C)cc1NC(=O)c1nc(C2CCCO2)ccc1Nc1cncnc1]

According to the procedures described in example 96, using ethyl 3-amino-6-bromopicolinate and furan-2-ylboronic acid in the first step, the title compound was obtained as yellow solid.

MS: M=423.2 (M+H)$^+$

Example 104

6-Isobutyl-N-(1-methyl-3-(methylcarbamoyl)-1H-pyrazol-4-yl)-3-(pyrimidin-5-ylamino)pyrazine-2-carboxamide

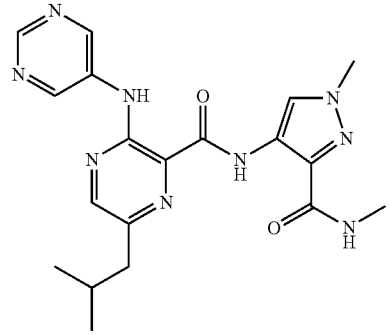 [SMILES: CNC(=O)c1nn(C)cc1NC(=O)c1nc(CC(C)C)cnc1Nc1cncnc1]

To a suspension of intermediate A-12, (30 mg, 0.1 mmol) in dioxane (1 mL) were added 4-amino-N,1-dimethyl-1H-pyrazole-3-carboxamide hydrochloride (40 mg, 0.21 mmol) and trimethylaluminium (0.1 mL, 2M toluene solution) at room temperature. The mixture was stirred at 100° C. for 16 hr. After cooling down to ambient temperature, the reaction mixture was poured into ethyl acetate (50 ml) and extracted with water and brine. The aqueous layers were back-extracted with ethyl acetate. The organic layers were dried and concentrated in vacuo. The crude material was suspended in dichloromethane and filtered. The solid material was washed with dichloromethane and dried to yield the product (17 mg, 40%) as yellow solid.

MS: M=410.3 (M+H)$^+$

Example 105

6-Cyclopropyl-3-(pyrimidin-5-ylamino)-pyrazine-2-carboxylic acid [4-(2-hydroxy-2-methyl-propylcarbamoyl)-pyridin-3-yl]-amide

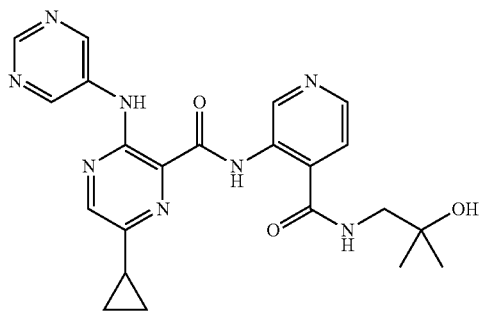 [SMILES: CC(C)(O)CNC(=O)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 1-amino-2-methylpropan-2-ol, providing the title compound as yellow solid (74%).

MS: M=447.2 (M−H)−

Example 106

6-Cyclopropyl-3-(pyrimidin-5-ylamino)-pyrazine-2-carboxylic acid [4-(oxetan-3-ylcarbamoyl)-pyridin-3-yl]-amide

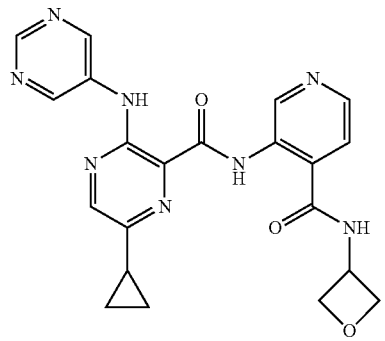 [SMILES: O=C(NC1COC1)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with oxetan-3-amine hydrochloride, providing the title compound as yellow solid (58%).

MS: M=431.1 (M−H)−

Example 107

6-Cyclopropyl-N-(1-ethyl-3-(methylcarbamoyl)-1H-pyrazol-4-yl)-3-(pyrimidin-5-ylamino)pyrazine-2-carboxamide

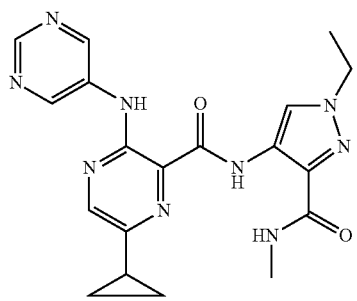 [SMILES: CCn1cc(NC(=O)c2nc(C3CC3)cnc2Nc2cncnc2)c(C(=O)NC)n1]

The product was obtained starting from intermediate A-11 (40 mg, 0.15 mmol) and 4-amino-1-ethyl-N-methyl-1H-pyrazole-3-carboxamide (34 mg, 0.2 mmol) according to the method described in example 64, step 6 as yellow solid (27 mg, 43%).

MS: M=408.3 (M+H)+

Example 108

6-Cyclopropyl-N-(1-ethyl-3-((tetrahydrofuran-2-yl)methylcarbamoyl)-1H-pyrazol-4-yl)-3-(pyrimidin-5-ylamino)pyrazine-2-carboxamide

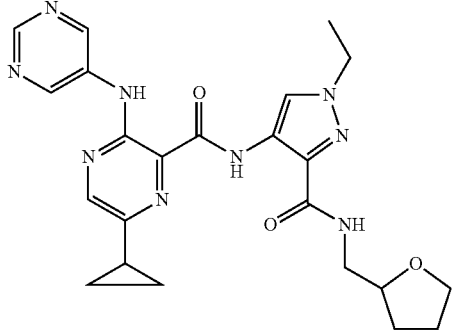 [SMILES: CCn1cc(NC(=O)c2nc(C3CC3)cnc2Nc2cncnc2)c(C(=O)NCC2CCCO2)n1]

The product was obtained starting from intermediate A-11 (40 mg, 0.15 mmol) and 4-amino-1-ethyl-N-((tetrahydrofuran-2-yl)methyl)-1H-pyrazole-3-carboxamide hydrochloride (55 mg, 0.2 mmol) according to the method described in example 64, step 6 as yellow solid (27 mg, 36%).

MS: M=478.2 (M+H)+

Example 109

6-Cyclopropyl-N-(1-methyl-3-((tetrahydrofuran-2-yl)methylcarbamoyl)-1H-pyrazol-4-yl)-3-(pyrimidin-5-ylamino)pyrazine-2-carboxamide

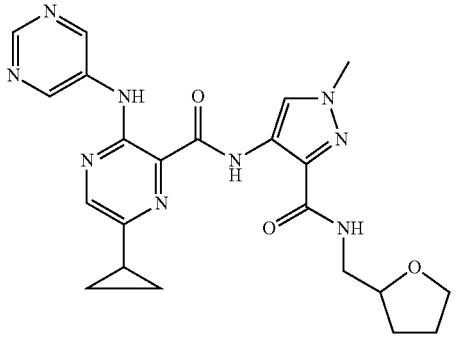 [SMILES: Cn1cc(NC(=O)c2nc(C3CC3)cnc2Nc2cncnc2)c(C(=O)NCC2CCCO2)n1]

The product was obtained starting from intermediate A-11 (40 mg, 0.15 mmol) and 4-amino-1-methyl-N-((tetrahydrofuran-2-yl)methyl)-1H-pyrazole-3-carboxamide hydrochloride (53 mg, 0.2 mmol) according to the method described in example 64, step 6 as yellow solid (30 mg, 42%).

MS: M=464.3 (M+H)⁺

Example 110

6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide

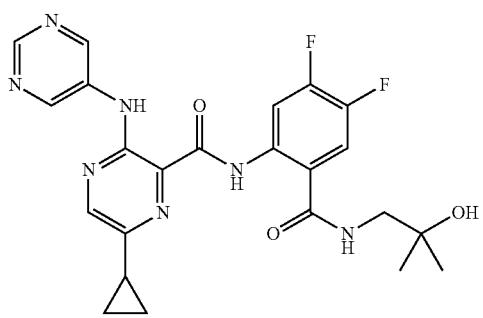 [SMILES: CC(C)(O)CNC(=O)c1cc(F)c(F)cc1NC(=O)c1nc(C2CC2)cnc1Nc1cncnc1]

According to the procedures described in example 97, the title compound was obtained using 2-amino-4,5-difluorobenzoic acid and 1-amino-2-methylpropan-2-ol in the 1st step (69%) and A-11 in the 2nd step (58%). Yellow solid.

MS: M=482.3 (M−H)⁻

Example 111

6-Cyclopropyl-N-(3-((2-hydroxy-2-methylpropyl)(methyl)carbamoyl)-1-methyl-1H-pyrazol-4-yl)-3-(pyrimidin-5-ylamino)pyrazine-2-carboxamide

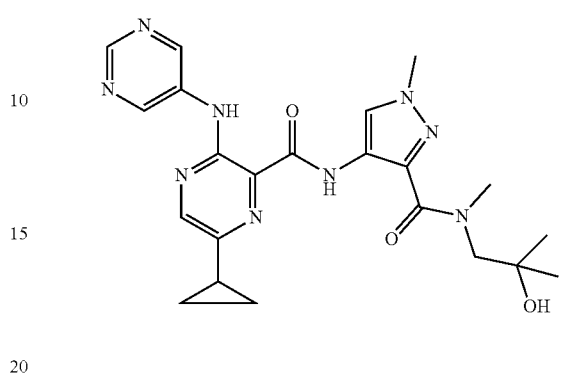

Step 1: N-(2-Hydroxy-2-methylpropyl)-N,1-dimethyl-4-nitro-1H-pyrazole-3-carboxamide To a suspension of 1-methyl-4-nitro-1H-pyrazole-3-carboxylic acid (639 mg, 3.7 mmol) and 2-methyl-1-(methylamino)propan-2-ol (500 mg, 4.85 mmol) in THF (15 mL) were added HATU (1.57 g, 4.12 mmol) and N-methylmorpholine (2.13 mL, 19.4 mmol) at ambient temperature. The mixture was heated to 70° C. and stirred for 16 h. After cooling down to ambient temperature, the reaction mixture was poured into 20 mL HCl (2N aqueous solution) and extracted with ethyl acetate (2×100 mL). The organic layers were washed with water, brine and the solvent was evaporated. The aqueous layer was back-extracted with dichloromethane, dried and concentrated in vacuo. Both residues were combined to give 2.75 g of a semi-solid yellow material. The crude material was purified by silica gel chromatography using a methanol/ethyl acetate gradient to yield the product (1.2 g, 90%) as colorless oil.

MS: M=257.3 (M+H)⁺

Step 2: 4-Amino-N-(2-hydroxy-2-methylpropyl)-N,1-dimethyl-1H-pyrazole-3-carboxamide A solution of N-(2-hydroxy-2-methylpropyl)-N,1-dimethyl-4-nitro-1H-pyrazole-3-carboxamide (1.2 g, 4.7 mmol) in ethanol (30 ml) was flushed with argon and treated with palladium on carbon 10% (120 mg, 1.13 mmol). The reaction mixture was evacuated and flushed with hydrogen and stirred at ambient temperature for 16 h. The reaction mixture was filtered, washed with ethanol and concentrated in vacuo to yield the product as dark red oil (1.0 g, 80%) which was used without any further purification.

MS: M=227.3 (M+H)⁺

Step 3: 6-Cyclopropyl-N-(3-((2-hydroxy-2-methylpropyl)(methyl)carbamoyl)-1-methyl-1H-pyrazol-4-yl)-3-(pyrimidin-5-ylamino)pyrazine-2-carboxamide The product was obtained starting from intermediate A-11 (40 mg, 0.15 mmol) and 4-amino-N-(2-hydroxy-2-methylpropyl)-N,1-dimethyl-1H-pyrazole-3-carboxamide (54 mg, 0.20 mmol) according to the method described in example 64, step 6 as yellow solid (25 mg, 34%).

MS: M=466.3 (M+H)⁺

Example 112

N-(3-(2-Hydroxy-2-methylpropylcarbamoyl)-1-methyl-1H-pyrazol-4-yl)-2-methyl-5-(pyrimidin-5-ylamino)pyrimidine-4-carboxamide

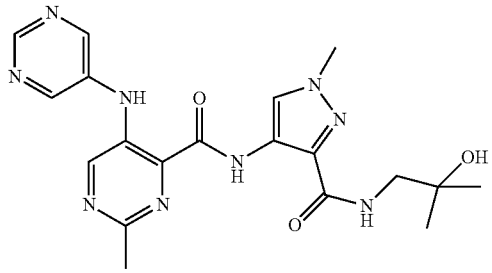 [SMILES: Cc1ncc(Nc2cncnc2)c(C(=O)Nc2cn(C)nc2C(=O)NCC(C)(C)O)n1]

The product was obtained starting from intermediate A-13 (30 mg, 0.13 mmol) and 4-amino-N-(2-hydroxy-2-methylpropyl)-1-methyl-1H-pyrazole-3-carboxamide (36 mg, 0.17 mmol) according to the method described in example 64, step 6 after purification by preparative HPLC using an acetonitrile/water gradient as yellow solid (39 mg, 71%).

MS: M=426.2 (M+H)$^+$

Example 113

6-Cyclopropyl-3-(pyrimidin-5-ylamino)-pyrazine-2-carboxylic acid [4-(2-methoxy-2-methyl-propylcarbamoyl)-pyridin-3-yl]-amide

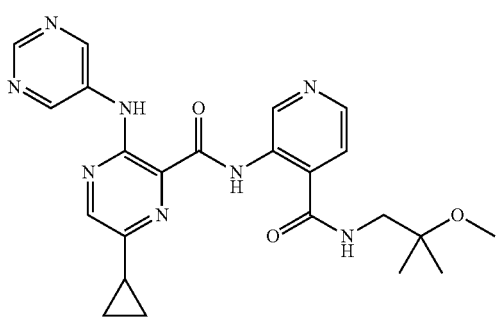 [SMILES: COC(C)(C)CNC(=O)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 2-methoxy-2-methylpropan-1-amine, providing the title compound as yellow solid (71%).

MS: M=461.2 (M–H)$^-$

Example 114

6-Cyclopropyl-3-(pyrimidin-5-ylamino)-pyrazine-2-carboxylic acid [4-(3-methoxy-2,2-dimethyl-propylcarbamoyl)-pyridin-3-yl]-amide

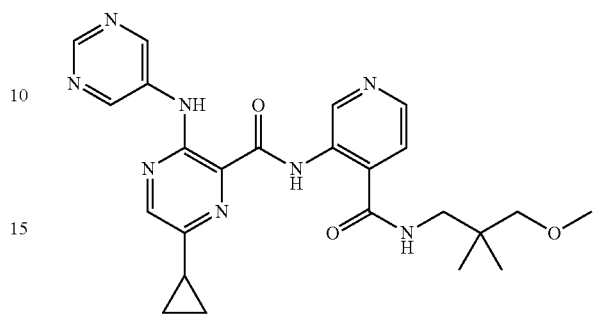

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 3-methoxy-2,2-dimethylpropan-1-amine hydrochloride, the title compound as yellow solid (54%).

MS: M=475.1 (M–H)$^-$

Example 115

6-(1-Hydroxy-ethyl)-3-(pyrimidin-5-ylamino)-pyrazine-2-carboxylic acid (1-methyl-3-methylcarbamoyl-1H-pyrazol-4-yl)-amide

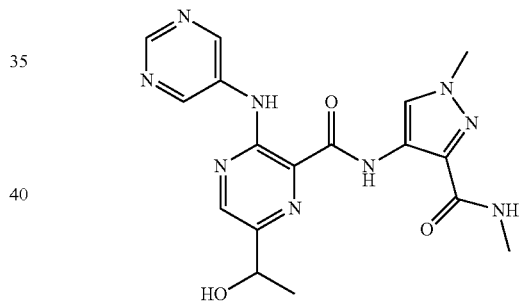

Step 1: 6-Acetyl-3-(pyrimidin-5-ylamino)-pyrazine-2-carboxylic acid (1-methyl-3-methylcarbamoyl-1H-pyrazol-4-yl)-amide According to the procedure described in step 6 of example 64, A-14 was reacted with 4-amino-1-methyl-1H-pyrazole-3-carboxylic acid methylamide hydrochloride, providing the title compound as yellow solid (10%).

MS: M=393.9 (M–H)$^-$

Step 2: 6-(1-Hydroxy-ethyl)-3-(pyrimidin-5-ylamino)-pyrazine-2-carboxylic acid (1-methyl-3-methylcarbamoyl-1H-pyrazol-4-yl)-amide To a stirred, cooled (0° C.) suspension of 6-acetyl-3-(pyrimidin-5-ylamino)-pyrazine-2-carboxylic acid (1-methyl-3-methylcarbamoyl-1H-pyrazol-4-yl)-amide (12 mg, 30.4 µmol) in ethanol (2 ml) under an argon atmosphere was added sodium borohydride (1.15 mg, 30.4 µmol) in one portion. Stirring was continued for 1 hr at rt. More sodium borohydride (3 eq.) was added in one portion. The mixture was heated to reflux and stirring as continued for 30 min. The reaction was cooled to rt and concentrated. The crude product was purified by silica gel chromatography using a $CH_2Cl_2$/MeOH gradient as eluent. The title compound (4 mg, 33%) as yellow solid.

MS: M=395.9 (M–H)⁻

Example 116

6-Cyclopropyl-3-(pyrimidin-5-ylamino)-pyrazine-2-carboxylic acid (1-methyl-5-methylcarbamoyl-1H-pyrazol-4-yl)-amide

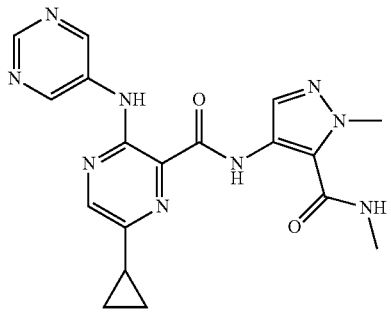 [SMILES: CNC(=O)c1c(NC(=O)c2nc(C3CC3)cnc2Nc2cncnc2)cnn1C]

According to the procedure described in step 6 of example 64, A-11 was reacted with 4-amino-2-methyl-2H-pyrazole-3-carboxylic acid methylamide (obtained from 2-methyl-4-nitro-2H-pyrazole-5-carboxylic acid amide in analogy to step 2 of example 2) to give the title compound (63%) as yellow solid.

MS: M=392.1 (M–H)⁻

Example 117

6-Cyclopropyl-3-(pyrimidin-5-ylamino)-pyrazine-2-carboxylic acid {2-[(2-methoxy-ethyl)-methyl-carbamoyl]-pyridin-3-yl}-amide

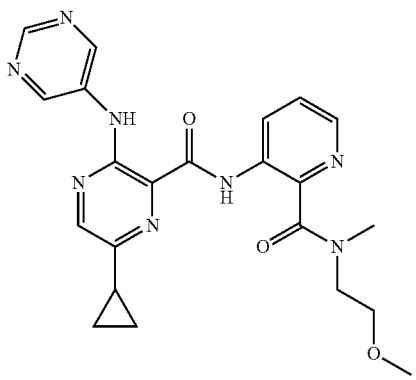 [SMILES: COCCN(C)C(=O)c1ncccc1NC(=O)c1nc(C2CC2)cnc1Nc1cncnc1]

Step 1:
3-Amino-N-(2-methoxyethyl)-N-methylpicolinamide

According to the procedure described in example 29, 3-aminopicolinic acid was reacted with 2-methoxy-N-methylethanamine to give the title compound (85%) as colourless viscous oil.

MS: M=210.1 (M+H)⁺

Step 2: 6-Cyclopropyl-N-(2-((2-methoxyethyl)(methyl)carbamoyl)pyridin-3-yl)-3-(pyrimidin-5-ylamino)pyrazine-2-carboxamide According to the procedure described in example 29, 3-amino-N-(2-methoxyethyl)-N-methylpicolinamide was reacted with A-11 to give the title compound (76%) as yellow solid.

MS: M=449.2 (M+H)⁺

Example 118

5-{[6-Cyclopropyl-3-(pyrimidin-5-ylamino)-pyrazine-2-carbonyl]-amino}-pyrimidine-4-carboxylic acid (2-methoxy-ethyl)-methyl-amide

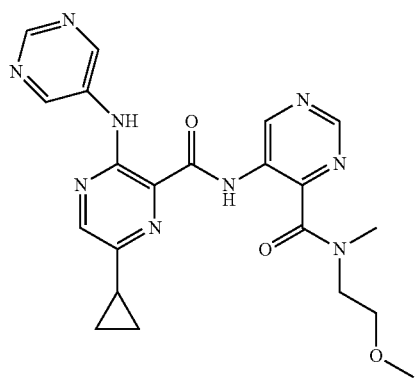 [SMILES: COCCN(C)C(=O)c1ncncc1NC(=O)c1nc(C2CC2)cnc1Nc1cncnc1]

According to the procedures described in example 117, the title compound was prepared using 5-aminopyrimidine-4-carboxylic acid in the 1ˢᵗ step. Yellow solid.

MS: M=450.1 (M+H)⁺

Example 119

6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide

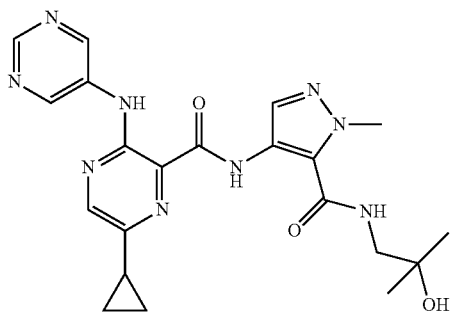 [SMILES: Cn1ncc(NC(=O)c2nc(C3CC3)cnc2Nc2cncnc2)c1C(=O)NCC(C)(C)O]

According to the procedure described in step 1 of example 111, reacting 2-methyl-4-nitro-2H-pyrazole-3-carboxylic acid and 1-amino-2-methylpropan-2-ol in the 1ˢᵗ step and coupling with A-11 in the 3ʳᵈ step, the title compound was obtained as light yellow solid.

MS: M=450.1 (M–H)⁻

Example 120

6-Cyclopropyl-3-(pyrimidin-5-ylamino)-pyrazine-2-carboxylic acid [3-(2-hydroxy-2-methyl-propylcarbamoyl)-pyridin-4-yl]-amide

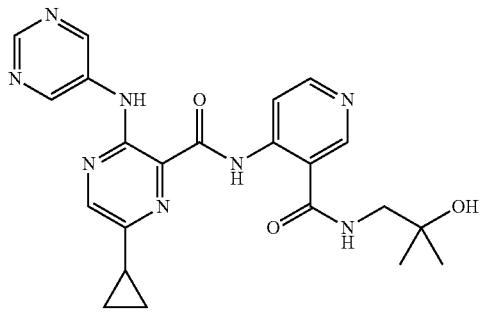 [SMILES: CC(C)(O)CNC(=O)c1cnccc1NC(=O)c1nc(C2CC2)cnc1Nc1cncnc1]

According to the procedures described in example 99, reacting 4-amino-nicotinic acid methyl ester with A-11 in the 1st step and using 1-amino-2-methylpropan-2-ol in the 3rd step, the title compound was obtained as yellow solid.

MS: M=447.2 (M−H)−

Example 121

6-Cyclopropyl-3-(pyrimidin-5-ylamino)-pyrazine-2-carboxylic acid [4-(3-methyl-oxetan-3-ylcarbamoyl)-pyridin-3-yl]-amide

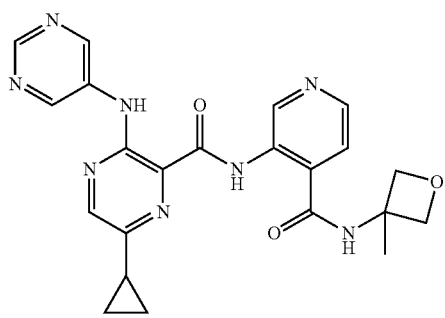 [SMILES: CC1(NC(=O)c2ccncc2NC(=O)c2nc(C3CC3)cnc2Nc2cncnc2)COC1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 3-methyloxetan-3-amine, providing the title compound was obtained as yellow solid (44%).

MS: M=445.2 (M−H)−

Example 122

5-{[6-Cyclopropyl-3-(pyrimidin-5-ylamino)-pyrazine-2-carbonyl]-amino}-pyrimidine-4-carboxylic acid (2-hydroxy-2-methyl-propyl)-methyl-amide

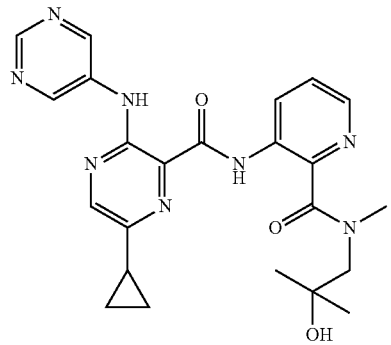 [SMILES: CN(CC(C)(C)O)C(=O)c1ncccc1NC(=O)c1nc(C2CC2)cnc1Nc1cncnc1]

According to the procedures described in example 117, the title compound was prepared using 5-aminopyrimidine-4-carboxylic acid and 2-methyl-1-(methylamino)propan-2-ol in the 1st step.

MS: M=464.2 (M+H)+

Example 123

6-Cyclopropyl-3-(pyrimidin-5-ylamino)-pyrazine-2-carboxylic acid {2-[(2-hydroxy-2-methyl-propyl)-methyl-carbamoyl]-pyridin-3-yl}-amide

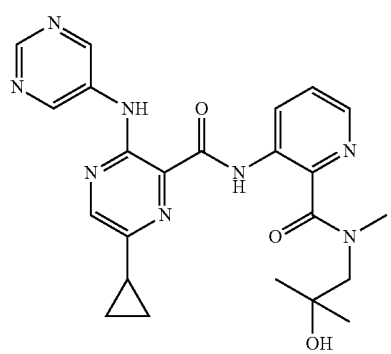 [SMILES: CN(CC(C)(C)O)C(=O)c1ncccc1NC(=O)c1nc(C2CC2)cnc1Nc1cncnc1]

According to the procedures described in example 117, the title compound was prepared, using 3-aminopicolinic acid and 2-methyl-1-(methylamino)propan-2-ol in the 1st step.

MS: M=463.2 (M+H)+

Example 124

6-Cyclopropyl-3-(pyrimidin-5-ylamino)-pyrazine-2-carboxylic acid (4-methylcarbamoyl-pyridin-3-yl)-amide

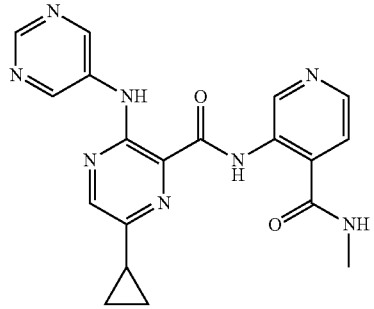 [SMILES: CNC(=O)c1ccncc1NC(=O)c1nc(C2CC2)cnc1Nc1cncnc1]

According to the procedure described in step 6 of example 64, A-11 was reacted with 3-amino-N-methylisonicotinamide to provide the title compound (73%) as yellow solid.

MS: M=391.1 (M+H)$^+$

Example 125

6-Cyclopropyl-3-(pyrimidin-5-ylamino)-pyrazine-2-carboxylic acid [4-(2-hydroxy-1,1-dimethyl-ethylcarbamoyl)-pyridin-3-yl]-amide

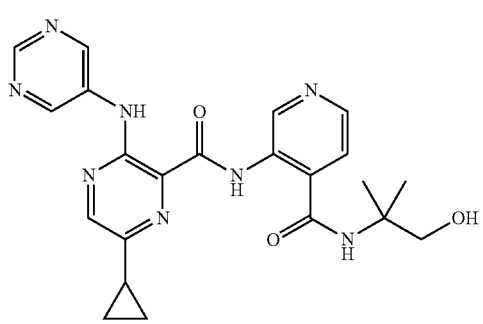 [SMILES: CC(C)(CO)NC(=O)c1ccncc1NC(=O)c1nc(C2CC2)cnc1Nc1cncnc1]

According to the procedure described in step 3 of example 99, 3-{[6-cyclopropyl-3-(pyrimidin-5-ylamino)-pyrazine-2-carbonyl]-amino}-isonicotinic acid (example 99, step 2) was reacted with 2-amino-2-methylpropan-1-ol, providing the title compound was obtained as yellow solid (33%).

MS: M=447.2 (M−H)$^-$

Example 126

2-(2-Methoxy-ethylamino)-5-(pyrimidin-5-ylamino)-pyrimidine-4-carboxylic acid (1-methyl-3-methylcarbamoyl-1H-pyrazol-4-yl)-amide

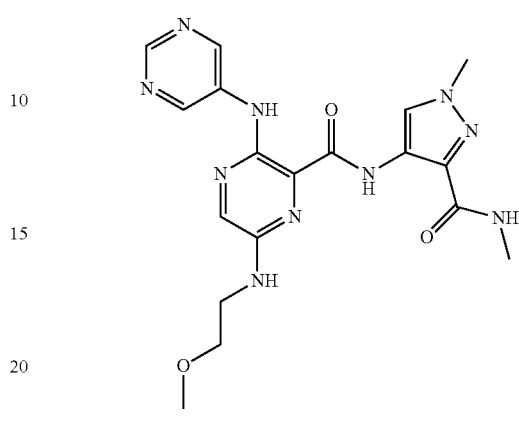

Step 1: 5-Bromo-2-methanesulfonyl-pyrimidine-4-carboxylic acid ethyl ester

A solution of 5-bromo-2-methylthio-pyrimidine-4-carboxylic acid ethyl ester (100 mg, 0.36 mmol; prepared from 5-bromo-2-methylthio-pyrimidine-4-carboxylic acid according to Coll. Czech. Chem. Commun. 1980, 45(2), 539) in dichloromethane (5 ml) was stirred at 0° C. under argon atmosphere and a solution of 3-chloroperbenzoic acid (178 mg, 0.72 mmol) in dichloromethane (5 ml) was added slowly. After continuous stirring for 30 min and warming-up to r.t., stirring was continued for another 6 h. The reaction mixture was partitioned between dichloromethane and sodium bicarbonate (saturated aqueous solution) and extracted. The organic phase was washed with water, dried and the solvent was evaporated. The product was obtained after purification by silica gel chromatography using a heptane/ethyl acetate gradient as colorless waxy solid (86 mg, 77%).

MS: M=309.0 (M+H)$^+$

Step 2: 5-Bromo-2-(2-methoxy-ethylamino)-pyrimidine-4-carboxylic acid ethyl ester A solution of 5-bromo-2-methanesulfonyl-pyrimidine-4-carboxylic acid ethyl ester (86 mg, 0.27 mmol) in dichloromethane (2 ml) was treated with 2-methoxyethylamine (124 µl, 1.44 mmol) under argon atmosphere and heated to 45° C. for 2 h. All volatiles were removed and the product was obtained after purification by silica gel chromatography using a heptane/ethyl acetate gradient as colorless oil (72 mg, 82%).

MS: M=304.2 (M+H)$^+$

Step 3: 2-(2-Methoxy-ethylamino)-5-(pyrimidin-5-ylamino)-pyrimidine-4-carboxylic acid ethyl ester A microwave reaction tube was charged with a suspension of 5-bromo-2-(2-methoxy-ethylamino)-pyrimidine-4-carboxylic acid ethyl ester (30 mg, 0.1 mmol), 5-aminopyrimidine (14 mg, 0.15 mmol) and cesium carbonate (45 mg, 0.14 mmol) in dioxane (0.6 ml) and flushed with argon. 4,5-Bis(diphenylphosphino)-9,9-dimethylxanthene (Xantphos; 19 mg, 32 µmol) and tris(dibenzylideneacetone)-dipalladium(0)

chloroform adduct (10 mg, 10 μmol) were consecutively added and the reaction tube was sealed and stirred overnight at 130° C. After cooling-down to ambient temperature, the reaction mixture was filtrated. The filtrate was concentrated in vacuo and the product was obtained after purification by preparative HPLC using an acetonitrile/water gradient as yellow solid (11 mg, 35%).

MS: M=319.2 (M+H)$^+$

Step 4: 2-(2-Methoxy-ethylamino)-5-(pyrimidin-5-ylamino)-pyrimidine-4-carboxylic acid (1-methyl-3-methylcarbamoyl-1H-pyrazol-4-yl)-amide The product was obtained starting from 2-(2-methoxy-ethylamino)-5-(pyrimidin-5-ylamino)-pyrimidine-4-carboxylic acid ethyl ester (11 mg, 35 μmol) and 4-amino-1-methyl-1H-pyrazole-3-carboxylic acid methylamide hydrochloride (20 mg, 105 μmol) according to the method described in example 104 after purification by preparative HPLC using an acetonitrile/water gradient as yellow solid (0.5 mg, 3%).

MS: M=427.2 (M+H)$^+$

Example 127

3-(Pyrimidin-5-ylamino)-6-(tetrahydro-furan-3-yl)-pyridine-2-carboxylic acid (1-methyl-3-methylcarbamoyl-1H-pyrazol-4-yl)-amide

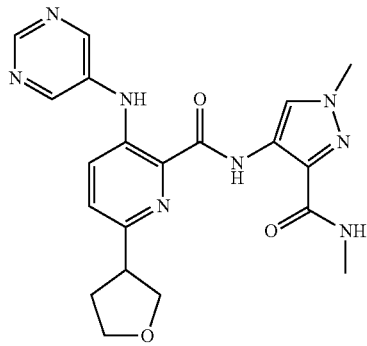 [SMILES: CNC(=O)c1nn(C)cc1NC(=O)c1nc(C2CCOC2)ccc1Nc1cncnc1]

According to the procedures described in example 96, using ethyl 3-amino-6-bromopicolinate and 3-furaneboronic acid in the first step, the title compound was obtained as yellow solid.

MS: M=423.1 (M+H)$^+$

Example 128

6-Cyclopropyl-3-(pyrimidin-5-ylamino)-pyrazine-2-carboxylic acid (2-methylcarbamoyl-pyridin-3-yl)-amide

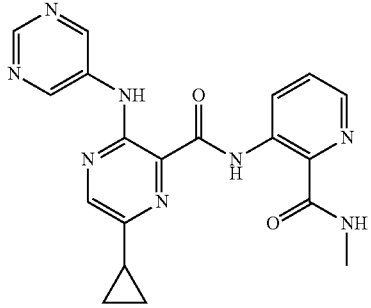 [SMILES: CNC(=O)c1ncccc1NC(=O)c1nc(C2CC2)cnc1Nc1cncnc1]

According to the procedures described in example 99, reacting ethyl 3-aminopicolinate with A-11 in the 1$^{st}$ step and methylamine hydrochloride in the 3$^{rd}$ step, the title compound was obtained as yellow solid.

MS: M=391.1 (M+H)$^+$

Example 129

6-Cyclopropyl-3-(pyrimidin-5-ylamino)-pyrazine-2-carboxylic acid (2-dimethylcarbamoyl-pyridin-3-yl)-amide

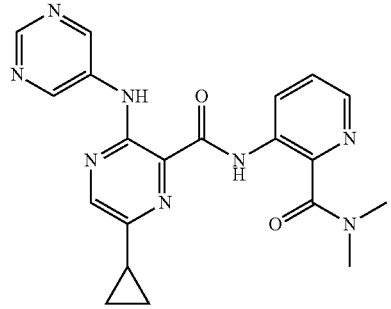

According to the procedures described in example 99, reacting ethyl 3-aminopicolinate with A-11 in the 1$^{st}$ step and dimethylamine hydrochloride in the 3$^{rd}$ step, the title compound was obtained as yellow solid.

MS: M=405.3 (M+H)$^+$

Example 130

6-Cyclopropyl-3-(pyrimidin-5-ylamino)-pyrazine-2-carboxylic acid (2-methyl-4-methylcarbamoyl-thiazol-5-yl)-amide

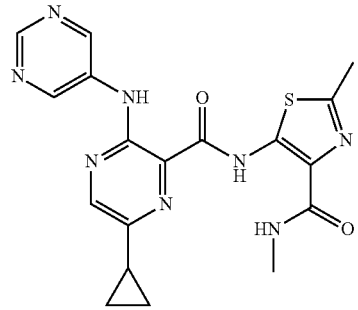 [SMILES: CNC(=O)c1nc(C)sc1NC(=O)c1nc(C2CC2)cnc1Nc1cncnc1]

Step 1: 5-{[6-Cyclopropyl-3-(pyrimidin-5-ylamino)-pyrazine-2-carbonyl]-amino}-2-methyl-thiazole-4-carboxylic acid ethyl ester The product was obtained starting from intermediate A-11 (80 mg, 0.3 mmol) and 5-amino-2-methylthiazole-4-carboxylic acid ethyl ester (75 mg, 0.4 mmol) according to the method described in example 64, step 6 after purification by silica gel chromatography using a heptane/ethyl acetate gradient yellow solid (60 mg, 45%).

MS: M=426.2 (M+H)$^+$

Step 2: 5-{[6-Cyclopropyl-3-(pyrimidin-5-ylamino)-pyrazine-2-carbonyl]-amino}-2-methyl-thiazole-4-carboxylic acid A solution of 5-{[6-cyclopropyl-3-(pyrimidin-5-ylamino)-pyrazine-2-carbonyl]-amino}-2-methyl-thiazole-4-carboxylic acid ethyl ester (70 mg, 0.16 mmol) in a THF/ethanol mixture (2.5 ml; 1.5:1) was cooled to 0° C. and treated with lithium hydroxide (0.82 ml; 1N aqueous solution). After 15 min, the cooling bath was removed and the reaction mixture was stirred at 50° C. overnight. The reaction mixture was cooled to r.t. and 0.84 ml 1M HCl was added. The suspension was filtered, the solid was washed with water and THF and dried in vacuo to yield 28 mg (43%) of a yellow solid.
MS: M=396.2 (M–H)⁻

Step 3: 6-Cyclopropyl-3-(pyrimidin-5-ylamino)-pyrazine-2-carboxylic acid (2-methyl-4-methylcarbamoyl-thiazol-5-yl)-amide The product was obtained starting from 5-{[6-cyclopropyl-3-(pyrimidin-5-ylamino)-pyrazine-2-carbonyl]-amino}-2-methyl-thiazole-4-carboxylic acid (28 mg, 0.07 mmol) and methylamine hydrochloride (6.2 mg, 0.09 mmol) according to the method described in example 64, step 6 as yellow solid (16 mg, 44%).
MS: M=411.2 (M+H)⁺

Example 131

6-Isopropyl-3-(pyrimidin-5-ylamino)-pyrazine-2-carboxylic acid (1-methyl-5-methylcarbamoyl-1H-pyrazol-4-yl)-amide

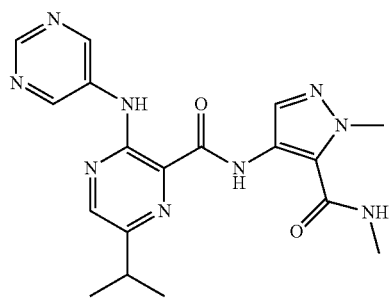 [SMILES: CNC(=O)c1c(NC(=O)c2nc(C(C)C)cnc2Nc2cncnc2)cnn1C]

The product was obtained starting from intermediate A-17 (36 mg, 0.14 mmol) and 4-amino-2-methyl-2H-pyrazole-3-carboxylic acid methylamide (23 mg, 0.15 mmol) according to the method described in example 64, step 6 as yellow solid (25 mg, 45%).
MS: M=396.2 (M+H)⁺

Example 132

6-Cyclopropyl-3-(pyrimidin-5-ylamino)-pyrazine-2-carboxylic acid [1-ethyl-5-(2-hydroxy-2-methyl-propylcarbamoyl)-1H-pyrazol-4-yl]-amide

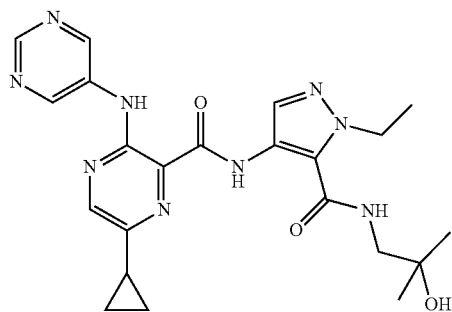 [SMILES: CCn1ncc(NC(=O)c2nc(C3CC3)cnc2Nc2cncnc2)c1C(=O)NCC(C)(C)O]

Step 1: Ethyl 1-ethyl-4-nitro-1H-pyrazole-5-carboxylate

According to the procedure described in step 2 of example 4, 4-nitro-1H-pyrazole-3-carboxylic acid ethyl ester was alkylated with iodoethane, to give the title compound (36%) as light yellow viscous oil, along with the main regioisomer ethyl 1-ethyl-4-nitro-1H-pyrazole-3-carboxylate (58%), viscous yellow oil.

Step 2: Ethyl 4-amino-1-ethyl-1H-pyrazole-5-carboxylate

According to the procedure described in step 2 of example 1, ethyl 1-ethyl-4-nitro-1H-pyrazole-5-carboxylate was converted to the title compound (94%) as light yellow viscous oil.
MS: M=184.2 (M+H)⁺

Step 3: 6-Cyclopropyl-3-(pyrimidin-5-ylamino)-pyrazine-2-carboxylic acid [1-ethyl-5-(2-hydroxy-2-methyl-propylcarbamoyl)-1H-pyrazol-4-yl]-amide According to the procedures described in example 99, ethyl 4-amino-1-ethyl-1H-pyrazole-5-carboxylate was converted to the title compound using A-11 in the 1ˢᵗ step and 1-amino-2-methylpropan-2-ol in the 3ʳᵈ step. Yellow solid.
MS: M=466.3 (M+H)⁺

Example 133

6-Cyclopropyl-3-(pyrimidin-5-ylamino)-pyrazine-2-carboxylic acid (1-ethyl-5-methylcarbamoyl-1H-pyrazol-4-yl)-amide

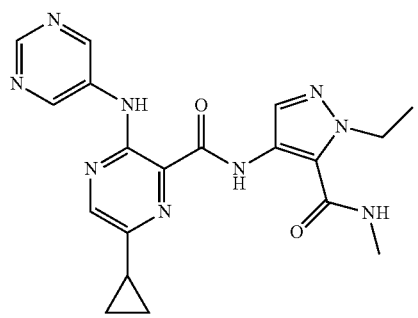 [SMILES: CCn1ncc(NC(=O)c2nc(C3CC3)cnc2Nc2cncnc2)c1C(=O)NC]

According to the procedures described in example 132, the title compound was obtained using methylamine hydrochloride in the last step.
MS: M=408.4 (M+H)⁺

Example 134

6-Cyclopropyl-3-(pyrimidin-5-ylamino)-pyrazine-2-carboxylic acid [5-(2-hydroxy-2-methyl-propylcarbamoyl)-1-isobutyl-1H-pyrazol-4-yl]-amide

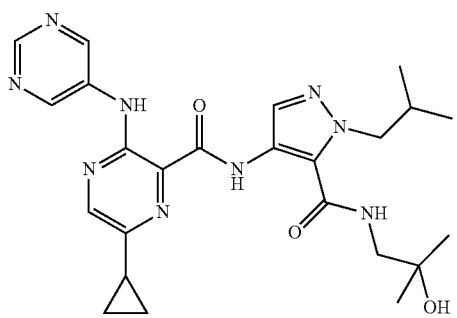 [SMILES: CC(C)Cn1ncc(NC(=O)c2nc(C3CC3)cnc2Nc2cncnc2)c1C(=O)NCC(C)(C)O]

According to the procedures described in example 132, the title compound was obtained using 1-iodo-2-methylpropane in the $1^{st}$ step and 1-amino-2-methylpropan-2-ol in the last step. Light yellow solid.

MS: M=494.2 (M+H)$^+$

Example 135

6-Cyclopropyl-3-(pyrimidin-5-ylamino)-pyrazine-2-carboxylic acid [1-methyl-5-(oxetan-3-ylcarbamoyl)-1H-pyrazol-4-yl]-amide

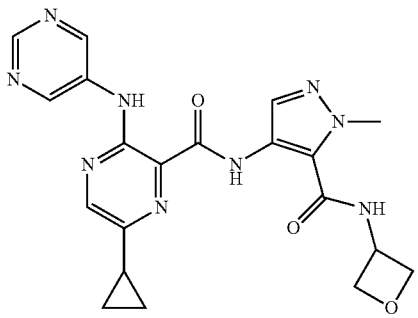 [SMILES: Cn1ncc(NC(=O)c2nc(C3CC3)cnc2Nc2cncnc2)c1C(=O)NC1COC1]

Step 1: 4-Amino-2-methyl-2H-pyrazole-3-carboxylic acid ethyl ester

According to the procedure described in step 2 of example 1, ethyl 1-methyl-4-nitro-1H-pyrazole-5-carboxylate was converted to the title compound (94%). Amorphous solid.

Step 2: 6-Cyclopropyl-3-(pyrimidin-5-ylamino)-pyrazine-2-carboxylic acid [1-methyl-5-(oxetan-3-ylcarbamoyl)-1H-pyrazol-4-yl]-amide According to the procedures described in example 99, 4-amino-2-methyl-2H-pyrazole-3-carboxylic acid ethyl ester was converted to the title compound, using intermediate A-11 in the $1^{st}$ step and oxetan-3-amine in the last step. Yellow solid.

MS: M=434.2 (M+H)$^+$

Example 136

6-Cyclopropyl-3-(pyrimidin-5-ylamino)-pyrazine-2-carboxylic acid [1-methyl-5-(3-methyl-oxetan-3-ylcarbamoyl)-1H-pyrazol-4-yl]-amide

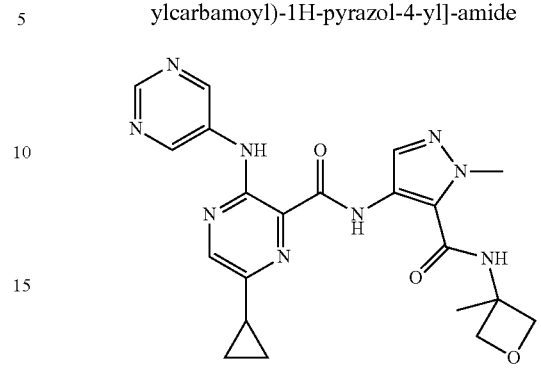

According to the procedure described in example 135, the title compound was obtained using 3-methyloxetan-3-amine in the last step. Yellow solid.

MS: M=448.1 (M−H)$^-$

Example 137

6-Cyclopropyl-3-(pyrimidin-5-ylamino)-pyrazine-2-carboxylic acid (1-isobutyl-5-methylcarbamoyl-1H-pyrazol-4-yl)-amide

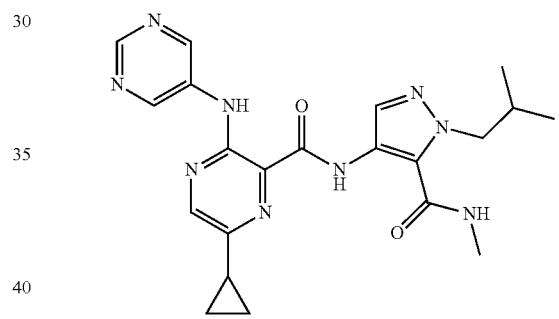

According to the procedures described in example 132, the title compound was obtained using 1-iodo-2-methylpropane in the $1^{st}$ step and methylamine hydrochloride in the last step. Yellow solid.

MS: M=434.3 (M−H)$^-$

Example 138

6-Cyclopropyl-3-(pyrimidin-5-ylamino)-pyrazine-2-carboxylic acid [5-(2-hydroxy-2-methyl-propylcarbamoyl)-1-isopropyl-1H-pyrazol-4-yl]-amide

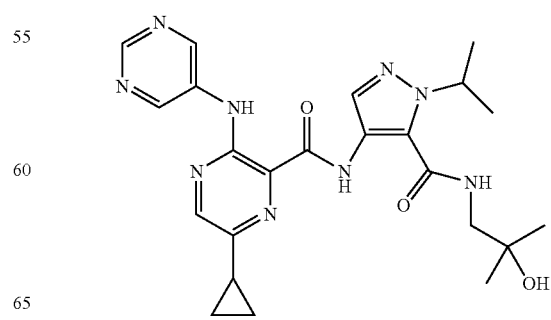

According to the procedures described in example 132, the title compound was obtained using 2-iodopropane in the 1st step and 1-amino-2-methylpropan-2-ol in the last step. Yellow solid. MS: M=480.2 (M+H)+

Example 139

6-Cyclopropyl-3-(pyrimidin-5-ylamino)-pyrazine-2-carboxylic acid (1-isopropyl-5-methylcarbamoyl-1H-pyrazol-4-yl)-amide

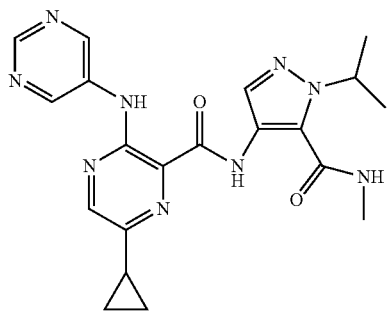 [SMILES: CNC(=O)c1c(NC(=O)c2nc(C3CC3)cnc2Nc2cncnc2)cnn1C(C)C]

According to the procedures described in example 132, the title compound was obtained using 2-iodopropane in the 1st step and methylamine hydrochloride in the last step. Yellow solid.

MS: M=422.2 (M+H)+

Example 140

6-Cyclopropyl-3-(pyrimidin-5-ylamino)-pyrazine-2-carboxylic acid [5-(3-hydroxy-3-methyl-butylcarbamoyl)-1-methyl-1H-pyrazol-4-yl]-amide

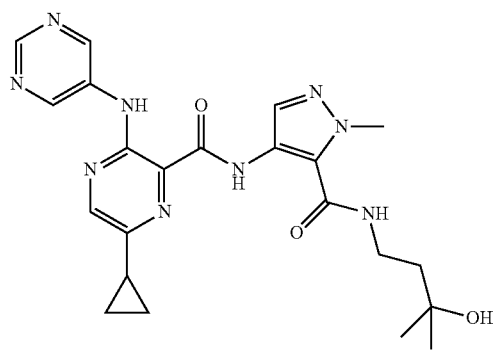 [SMILES: Cn1ncc(NC(=O)c2nc(C3CC3)cnc2Nc2cncnc2)c1C(=O)NCCC(C)(C)O]

According to the procedure described in example 135, the title compound was obtained using 4-amino-2-methylbutan-2-ol hydrochloride in the last step. Yellow solid.
MS: M=464.2 (M−H)−

Example 141

6-Cyclopropyl-3-(pyrimidin-5-ylamino)-pyrazine-2-carboxylic acid [1-methyl-5-(tetrahydro-furan-3-ylcarbamoyl)-1H-pyrazol-4-yl]-amide

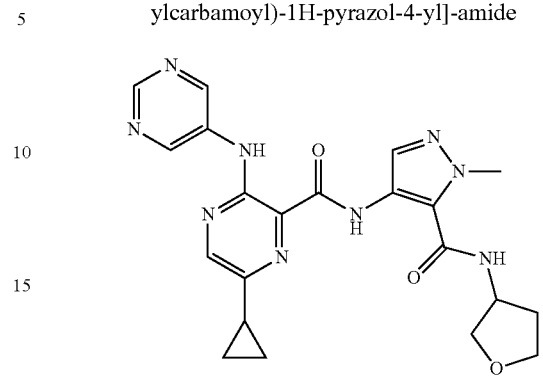

According to the procedure described in example 135, the title compound was obtained using tetrahydrofuran-3-amine hydrochloride in the last step. Yellow solid.
MS: M=448.1 (M−H)−

Example 142

6-Cyclopropyl-3-(pyrimidin-5-ylamino)-pyrazine-2-carboxylic acid [5-(3-hydroxy-2,2-dimethyl-propyl-carbamoyl)-1-methyl-1H-pyrazol-4-yl]-amide

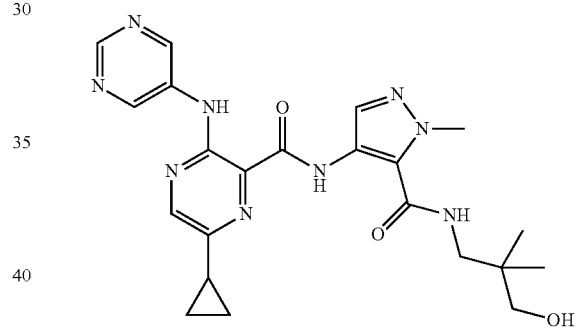

According to the procedure described in example 135, the title compound was obtained using 3-amino-2,2-dimethyl-propan-1-ol in the last step. Yellow solid.
MS: M=464.2 (M−H)−

Example 143

6-Cyclopropyl-3-(pyrimidin-5-ylamino)-pyrazine-2-carboxylic acid [5-(3,3-difluoro-azetidine-1-carbonyl)-1-methyl-1H-pyrazol-4-yl]-amide

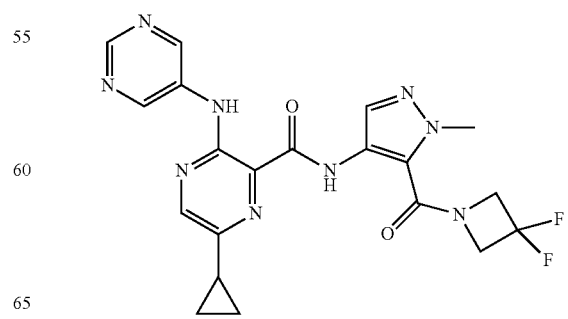

According to the procedure described in example 135, the title compound was obtained using 3,3-difluoroazetidine hydrochloride in the last step. Yellow solid.

MS: M=454.0 (M−H)⁻

Example 144

6-Cyclopropyl-3-(pyrimidin-5-ylamino)-pyrazine-2-carboxylic acid [1-methyl-5-(2,2,2-trifluoro-ethyl-carbamoyl)-1H-pyrazol-4-yl]-amide

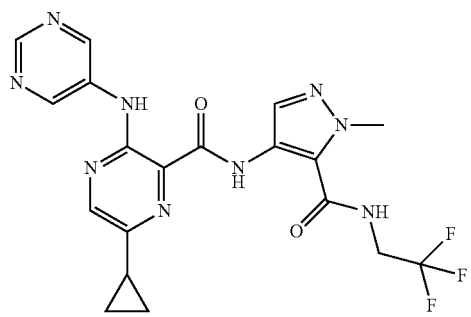 [SMILES: Cn1ncc(NC(=O)c2nc(C3CC3)cnc2Nc2cncnc2)c1C(=O)NCC(F)(F)F]

According to the procedure described in example 135, the title compound was obtained using 2,2,2-trifluoroethanamine in the last step. Yellow solid.

MS: M=460.3 (M−H)⁻

Example 145

6-Cyclopropyl-3-(pyrimidin-5-ylamino)-pyrazine-2-carboxylic acid [5-(2,2-difluoro-ethylcarbamoyl)-1-methyl-1H-pyrazol-4-yl]-amide

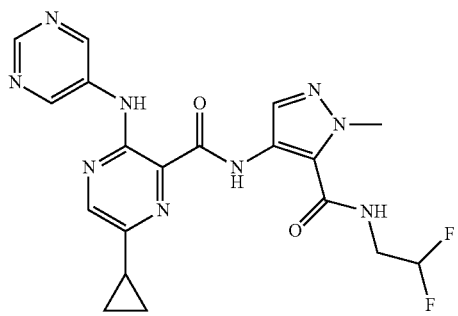 [SMILES: Cn1ncc(NC(=O)c2nc(C3CC3)cnc2Nc2cncnc2)c1C(=O)NCC(F)F]

According to the procedure described in example 135, the title compound was obtained using 2,2-difluoroethanamine in the last step. Yellow solid.

MS: M=442.1 (M−H)⁻

Example 146

6-Cyclopropyl-3-(pyrimidin-5-ylamino)-pyrazine-2-carboxylic acid [1-methyl-5-(3,3,3-trifluoro-2-hydroxy-propylcarbamoyl)-1H-pyrazol-4-yl]-amide

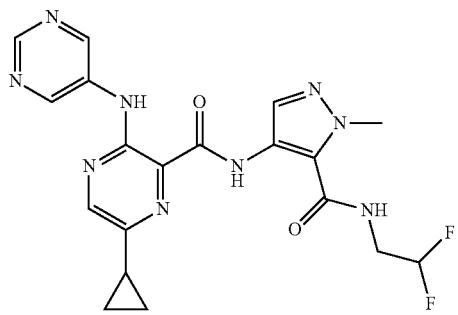 [SMILES: Cn1ncc(NC(=O)c2nc(C3CC3)cnc2Nc2cncnc2)c1C(=O)NCC(F)F]

According to the procedure described in example 135, the title compound was obtained using 3-amino-1,1,1-trifluoro-propan-2-ol in the last step. Yellow solid.

MS: M=490.2 (M−H)⁻

Example 147

6-Cyclopropyl-3-(pyrimidin-5-ylamino)-pyrazine-2-carboxylic acid [1-(2-methoxy-ethyl)-5-methylcarbamoyl-1H-pyrazol-4-yl]-amide

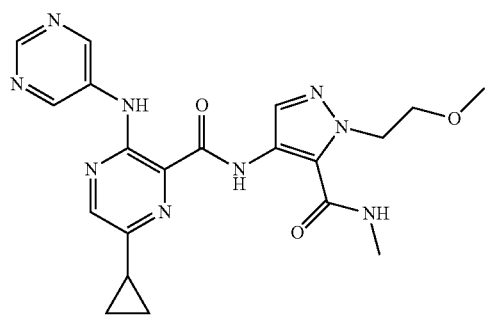 [SMILES: CNC(=O)c1c(NC(=O)c2nc(C3CC3)cnc2Nc2cncnc2)cnn1CCOC]

The product was obtained starting from intermediate A-11 (30 mg, 0.12 mmol) and 4-amino-2-(2-methoxyethyl)-2H-pyrazole-3-carboxylic acid methylamide (30 mg, 0.15 mmol; ex. 11, step 2) according to the method described in example 64, step 6 as yellow solid (38 mg, 74%).

MS: M=438.3 (M+H)⁺

Example 148

6-Cyclopropyl-3-(pyrimidin-5-ylamino)-pyridine-2-carboxylic acid (1-methyl-5-methylcarbamoyl-1H-pyrazol-4-yl)-amide

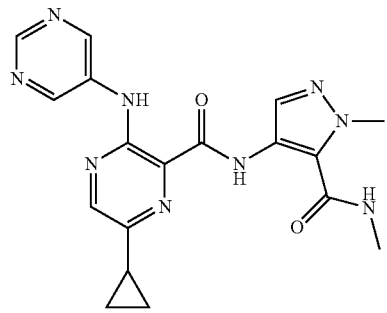 [SMILES: CNC(=O)c1c(NC(=O)c2nc(C3CC3)cnc2Nc2cncnc2)cnn1C]

The product was obtained starting from intermediate A-2 (30 mg, 0.12 mmol) and 4-amino-2-methyl-2H-pyrazole-3-carboxylic acid methylamide (24 mg, 0.15 mmol) according to the method described in example 64, step 6 as yellow solid (26 mg, 57%).

MS: M=393.2 (M+H)$^+$

Example 149

6-Cyclopropyl-3-(pyrimidin-5-ylamino)-pyrazine-2-carboxylic acid [5-(3-hydroxy-2-methyl-propylcarbamoyl)-1-methyl-1H-pyrazol-4-yl]-amide

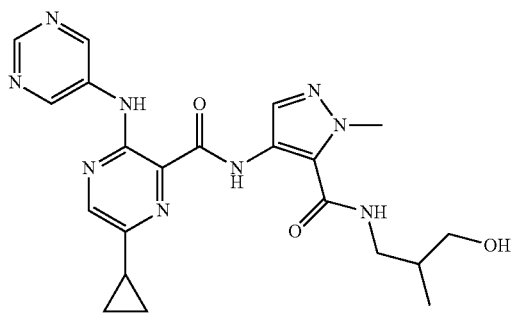 [SMILES: CC(CO)CNC(=O)c1c(NC(=O)c2nc(C3CC3)cnc2Nc2cncnc2)cnn1C]

According to the procedure described in example 135, the title compound was obtained using 3-amino-2-methylpropan-1-ol in the last step. Yellow solid.

MS: M=451.1 (M–H)$^-$

Example 150

6-Cyclopropyl-3-(pyrimidin-5-ylamino)-pyrazine-2-carboxylic acid (5-carbamoyl-1-methyl-1H-pyrazol-4-yl)-amide

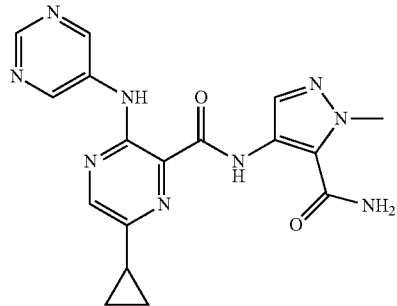 [SMILES: Cn1ncc(NC(=O)c2nc(C3CC3)cnc2Nc2cncnc2)c1C(N)=O]

According to the procedure described in example 135, the title compound was obtained as unexpected product using 2,2-difluorocyclopropanamine hydrochloride in the last step. Yellow solid.

MS: M=378.1 (M–H)$^-$

Example 151

6-Cyclopropyl-3-(pyrimidin-5-ylamino)-pyrazine-2-carboxylic acid [5-(2-methoxy-2-methyl-propylcarbamoyl)-1-methyl-1H-pyrazol-4-yl]-amide

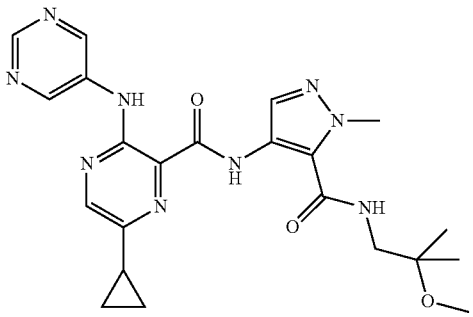 [SMILES: COC(C)(C)CNC(=O)c1c(NC(=O)c2nc(C3CC3)cnc2Nc2cncnc2)cnn1C]

According to the procedure described in example 135, the title compound was obtained using 2-methoxy-2-methylpropan-1-amine in the last step. Yellow solid.

MS: M=464.1 (M–H)$^-$

Example 152

6-Cyclopropyl-3-(pyrimidin-5-ylamino)-pyrazine-2-carboxylic acid [5-(2-hydroxy-1,1-dimethyl-ethylcarbamoyl)-1-methyl-1H-pyrazol-4-yl]-amide

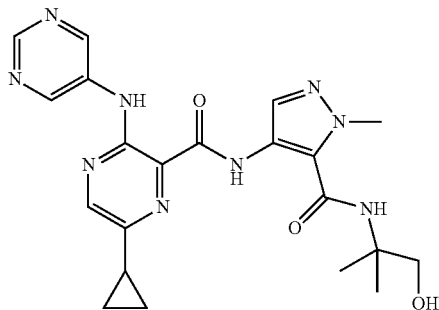 [SMILES: Cn1ncc(NC(=O)c2nc(C3CC3)cnc2Nc2cncnc2)c1C(=O)NC(C)(C)CO]

According to the procedure described in example 135, the title compound was obtained using 2-amino-2-methylpropan-1-ol in the last step. Yellow solid.

MS: M=450.1 (M–H)⁻

Example 154

2-tert-Butyl-5-(pyrimidin-5-ylamino)-pyrimidine-4-carboxylic acid (1-methyl-5-methylcarbamoyl-1H-pyrazol-4-yl)-amide

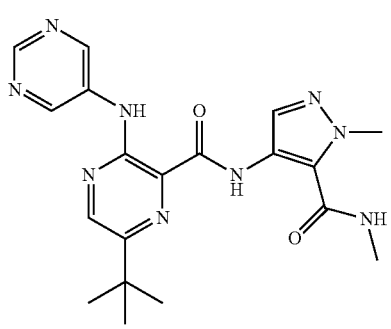

The product was obtained starting from intermediate A-6 (30 mg, 0.1 mmol) and 4-amino-2-methyl-2H-pyrazole-3-carboxylic acid methylamide (32 mg, 0.2 mmol) according to the method described in example 104 after purification by preparative HPLC using an acetonitrile/water gradient as yellow solid (33 mg, 76%).

MS: M=410.3 (M+H)⁺

Example 153

6-Cyclopropyl-3-(pyrimidin-5-ylamino)-pyrazine-2-carboxylic acid {5-[(2-hydroxy-2-methyl-propyl)-methyl-carbamoyl]-1-methyl-1H-pyrazol-4-yl}-amide

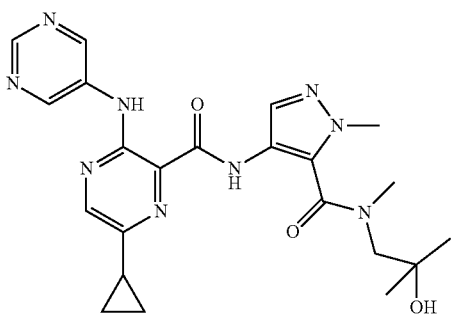 [SMILES: CN(CC(C)(C)O)C(=O)c1c(NC(=O)c2nc(C3CC3)cnc2Nc2cncnc2)cnn1C]

According to the procedure described in example 135, the title compound was obtained using 2-methyl-1-(methylamino)propan-2-ol in the last step. Yellow solid.

MS: M=464.2 (M–H)⁻

Example 155

6-Cyclopropyl-3-(pyrimidin-5-ylamino)-pyrazine-2-carboxylic acid [5-(azetidine-1-carbonyl)-1-methyl-1H-pyrazol-4-yl]-amide

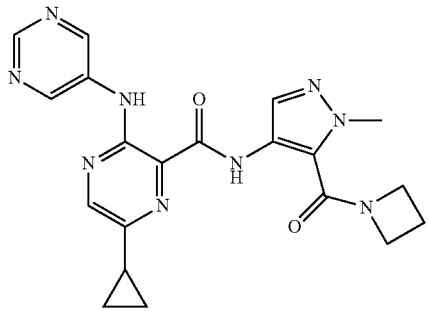 [SMILES: Cn1ncc(NC(=O)c2nc(C3CC3)cnc2Nc2cncnc2)c1C(=O)N1CCC1]

According to the procedure described in example 135, the title compound was obtained using azetidine in the last step. Yellow solid.

MS: M=418.1 (M–H)⁻

Example 156

6-Cyclopropyl-3-(pyrimidin-5-ylamino)-pyrazine-2-carboxylic acid [1-methyl-5-(pyrrolidine-1-carbonyl)-1H-pyrazol-4-yl]-amide

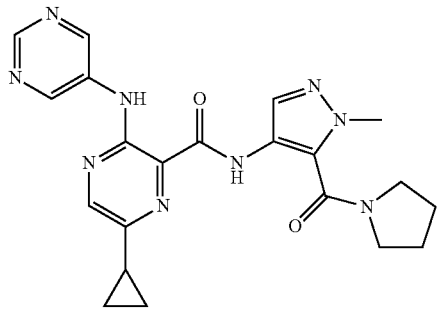

According to the procedure described in example 135, the title compound was obtained using pyrrolidine in the last step. Yellow solid.

MS: M=432.2 (M−H)−

Example 157

6-Cyclopropyl-3-(pyrimidin-5-ylamino)-pyrazine-2-carboxylic acid (5-dimethylcarbamoyl-1-methyl-1H-pyrazol-4-yl)-amide

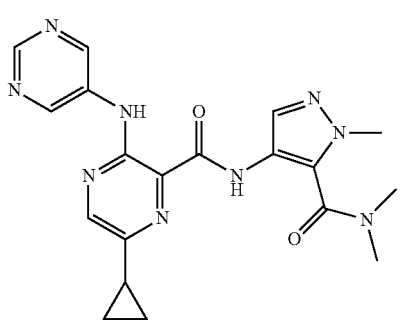 [SMILES: CN(C)C(=O)c1c(NC(=O)c2nc(C3CC3)cnc2Nc2cncnc2)cnn1C]

According to the procedure described in example 135, the title compound was obtained using dimethylamine hydrochloride in the last step. Yellow solid.

MS: M=406.3 (M+H)+

Example 158

6-Cyclopropyl-3-(pyrimidin-5-ylamino)-pyrazine-2-carboxylic acid (6-cyclopropyl-2-methylcarbamoyl-pyridin-3-yl)-amide

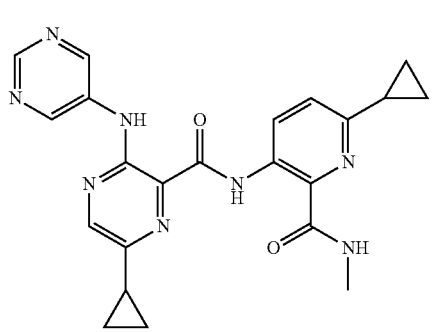 [SMILES: CNC(=O)c1nc(C2CC2)ccc1NC(=O)c1nc(C2CC2)cnc1Nc1cncnc1]

According to the procedures described in example 99, ethyl 3-amino-6-cyclopropylpicolinate (example A-1, step 1) was converted to the title compound, using methylamine hydrochloride in the last step. Yellow solid.

MS: M=431.2 (M+H)+

Example 159

6-Cyclopropyl-3-(pyrimidin-5-ylamino)-pyrazine-2-carboxylic acid [6-cyclopropyl-2-(2-hydroxy-2-methyl-propylcarbamoyl)-pyridin-3-yl]-amide

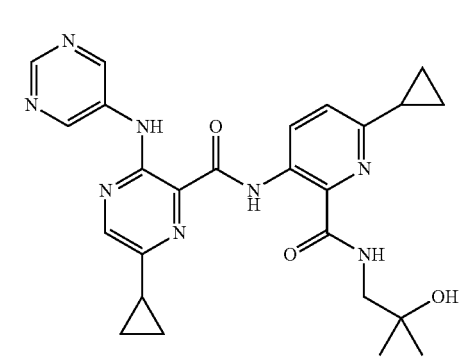 [SMILES: CC(C)(O)CNC(=O)c1nc(C2CC2)ccc1NC(=O)c1nc(C2CC2)cnc1Nc1cncnc1]

According to the procedures described in example 99, ethyl 3-amino-6-cyclopropylpicolinate (example A-1, step 1) was converted to the title compound, using 1-amino-2-methylpropan-2-ol in the last step. Yellow solid.

MS: M=489.4 (M+H)+

Example 160

3-(Pyrimidin-5-ylamino)-6-(tetrahydro-furan-3-yl)-pyrazine-2-carboxylic acid (1-methyl-5-methylcarbamoyl-1H-pyrazol-4-yl)-amide

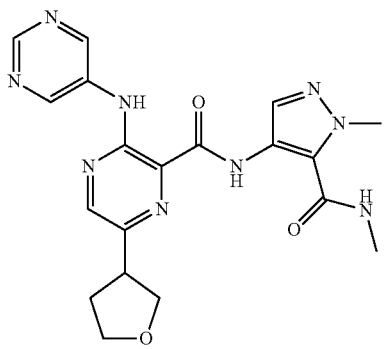 [SMILES: CNC(=O)c1c(NC(=O)c2nc(C3CCOC3)cnc2Nc2cncnc2)cnn1C]

The product was obtained starting from intermediate A-16 (30 mg, 0.1 mmol) and 4-amino-2-methyl-2H-pyrazole-3-carboxylic acid methylamide (46 mg, 0.3 mmol) according to the method described in example 104 after purification by preparative HPLC using an acetonitrile/water gradient as yellow solid (27 mg, 65%).

MS: M=424.2 (M+H)$^+$

Example 161

2-Isopropyl-5-(pyrimidin-5-ylamino)-pyrimidine-4-carboxylic acid (1-methyl-5-methylcarbamoyl-1H-pyrazol-4-yl)-amide

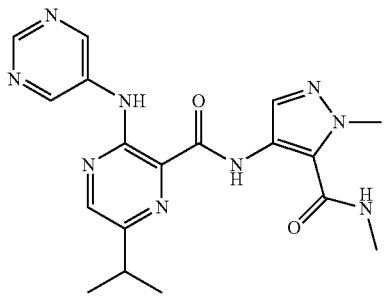 [SMILES: CNC(=O)c1c(NC(=O)c2nc(C(C)C)cnc2Nc2cncnc2)cnn1C]

The product was obtained starting from intermediate A-4 (30 mg, 0.11 mmol) and 4-amino-2-methyl-2H-pyrazole-3-carboxylic acid methylamide (51 mg, 0.33 mmol) according to the method described in example 104 after purification by preparative HPLC using an acetonitrile/water gradient as light yellow solid (21 mg, 49%).

MS: M=396.3 (M+H)$^+$

Example 162

6-Cyclopropyl-3-(pyrimidin-5-ylamino)-5-(tetrahydro-furan-2-yl)-pyrazine-2-carboxylic acid [5-(2-fluoro-ethylcarbamoyl)-1-methyl-1H-pyrazol-4-yl]-amide

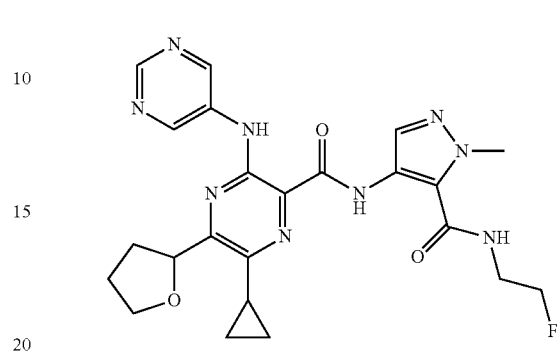

According to the procedure described in example 135, the title compound was obtained as unexpected product using 2-fluoroethanamine hydrochloride in the last step. Yellow solid.

MS: M=496.5 (M+H)$^+$

Example 163

6-Cyclopropyl-3-(pyrimidin-5-ylamino)-pyrazine-2-carboxylic acid (3-cyclopropylcarbamoyl-isoxazol-4-yl)-amide

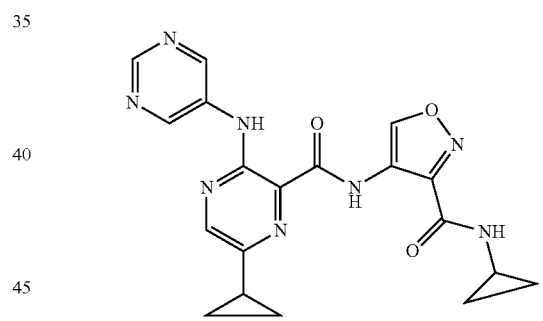

Step 1:
N-Cyclopropyl-2-chloro-2-hydroxyimino-acetamide

To a solution of cyclopropylamine (17.5 ml, 250 mmol) in water (250 ml) was added under ice-bath cooling 4-methylene-oxetan-2-one (19.1 ml, 250 mmol) at ambient temperature upon which the pH decreased from 12 to 6.9. Stirring was continued for 10 min. Sodium nitrite (19.5 g, 275 mmol) and fuming HCl (37%; 37.5 ml, 457 mmol) were added consecutively at r.t. so that the pH always remains above pH 4.5. Into the thick foamy suspension was passed chlorine (21.3 g, 300 mmol) at r.t. over 30 min to get a light brown solution. The reaction mixture was stirred for 1 h, poured into 200 ml dichloromethane and extracted. The aqueous layers were back-extracted and the organic layers were dried and evaporated. The crude product was suspended in 10 ml diethylether, filtered and dried in vacuo to give N-cyclopropyl-2-chloro-2-hydroxyimino-acetamide (14.7 g, 36%) as light yellow solid.

Step 2: 3-(Cyclopropylcarbamoyl)-isoxazole-4-carboxylic acid ethyl ester

A mixture of N-cyclopropyl-2-chloro-2-hydroxyimino-acetamide (2 g, 12.3 mmol) and (E)-3-(dimethylamino)-acrylic acid ethyl ester (1.76 ml, 12.3 mmol) in THF (25 ml) was heated at 75° C. for 2 h. The reaction was then cooled to r.t., poured into 100 mL ethyl acetate and extracted with 1 M HCl. The aqueous layers were back-extracted with ethyl acetate. The organic phase was washed with water and brine, dried and evaporated. The product was obtained after purification by silica gel chromatography using a heptane/ethyl acetate gradient as light yellow solid (1.6 g, 58%).
MS: M=225.1 (M+H)$^+$

Step 3: 3-(Cyclopropylcarbamoyl)-isoxazole-4-carboxylic acid

To a solution of 3-(cyclopropylcarbamoyl)-isoxazole-4-carboxylic acid ethyl ester (600 mg, 2.68 mmol) in THF (7 ml) and ethanol (3 ml) was added LiOH (1M; 5.35 ml, 5.35 mmol) at 0-5° C. The mixture was stirred at 20° C. for 1 h, poured into 50 ml diethyl ether and extracted. The organic phase was washed with water. The combined aqueous phases were acidified with 1M HCl (6 ml) and extracted with dichloromethane. The organic layers were dried and evaporated to yield the product as yellow oil (464 mg, 80%).
MS: M=194.9 (M–H)$^-$

Step 4: (3-Cyclopropylcarbamoyl-isoxazol-4-yl)-carbamic acid tert-butyl ester A mixture of 3-(cyclopropylcarbamoyl)-isoxazole-4-carboxylic acid (245 mg, 1.25 mmol) and thionyl chloride (182 µl, 2.5 mmol) in dichloromethane (4 ml) and DMF (5 µl, 63 µmol) was stirred at 40° C. for 4 h. The solvent was removed in vacuo. The residue was dissolved in acetone (4 ml) and a solution of sodium azide (89.3 mg, 1.37 mmol) in water (1 ml) was added dropwise at 0-5° C. over 5 min. The reaction mixture was stirred at 0-5° C. for 1 h. After removal of acetone, the residue was dissolved with ethyl acetate and extracted with water and back-extracted with ethyl acetate. The combined organic layers were washed with brine, dried and the solvent was removed to give 248 mg of a red solid. This intermediate was suspended in tert-butanol (4.8 ml, 50.0 mmol0) and heated for 16 h at 65° C. The reaction mixture was evaporated in vacuo and the product was obtained after purification by silica gel chromatography using a heptane/ethyl acetate gradient as light yellow oil (142 mg, 42.5%).
MS: M=268.2 (M+H)$^+$

Step 5: 4-Amino-isoxazole-3-carboxylic acid cyclopropylamide

A mixture of (3-Cyclopropylcarbamoylcyclopropylcarbamoyl-isoxazol-4-yl)-carbamic acid tert-butyl ester (142 mg, 531 µmol), trifluoroacetic acid (614 µl, 7.97 mmol) in dichloromethane (3 ml) was stirred for 3 h at 20° C. The volatiles were evaporated in vacuo and the resulting crude product was poured into 50 ml dichloromethane and extracted with sodium bicarbonate (saturated aqueous solution). The aqueous phase was washed with dichloromethane and the organic layers were dried and evaporated to yield the product as light yellow oil (85 mg, 91%)
MS: M=168.3 (M+H)$^+$.

Step 6: 6-Cyclopropyl-3-(pyrimidin-5-ylamino)-pyrazine-2-carboxylic acid (3-cyclopropylcarbamoyl-isoxazol-4-yl)-amide The product was obtained starting from intermediate A-11 (30 mg, 0.12 mmol) and 4-amino-isoxazole-3-carboxylic acid cyclopropylamide (27 mg, 0.15 mmol) according to the method described in example 64, step 6 as yellow solid (34 mg, 72%).
MS: M=407.3 (M+H)$^+$

Example 164

6-Cyclopropyl-3-(pyrimidin-5-ylamino)-pyrazine-2-carboxylic acid [1-methyl-5-(2,2,2-trifluoro-1-methyl-ethylcarbamoyl)-1H-pyrazol-4-yl]-amide

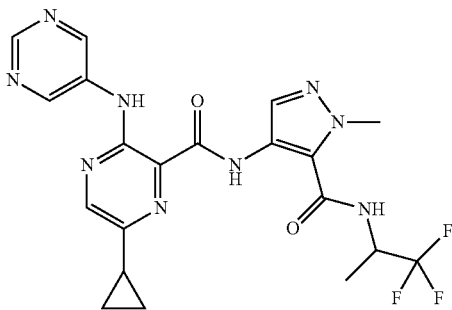 [SMILES: CC(NC(=O)c1c(NC(=O)c2nc(C3CC3)cnc2Nc2cncnc2)cnn1C)C(F)(F)F]

According to the procedure described in example 135, the title compound was obtained using 1,1,1-trifluoropropan-2-amine hydrochloride in the last step. Yellow solid.
MS: M=474.2 (M–H)$^-$

Example 165

6-Cyclopropyl-3-(pyrimidin-5-ylamino)-pyrazine-2-carboxylic acid [5-(2,2-difluoro-propylcarbamoyl)-1-methyl-1H-pyrazol-4-yl]-amide

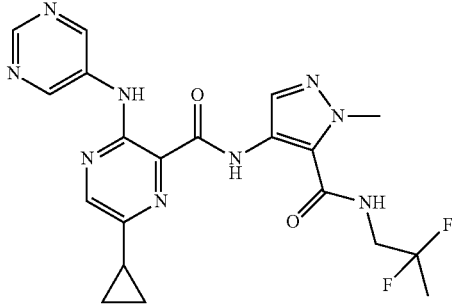 [SMILES: Cn1ncc(NC(=O)c2nc(C3CC3)cnc2Nc2cncnc2)c1C(=O)NCC(C)(F)F]

According to the procedure described in example 135, the title compound was obtained using 2,2-difluoropropan-1-amine hydrochloride in the last step. Yellow solid.
MS: M=456.1 (M–H)$^-$

Example 166

6-Chloro-3-(pyrimidin-5-ylamino)-pyridine-2-carboxylic acid (1-methyl-5-methylcarbamoyl-1H-pyrazol-4-yl)-amide

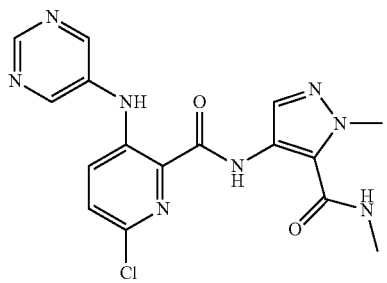 [SMILES: CNC(=O)c1c(NC(=O)c2nc(Cl)ccc2Nc2cncnc2)cnn1C]

Step 1: 3-Amino-6-chloro-pyridine-2-carboxylic acid ethyl ester

A solution of 2-bromo-6-chloro-pyridin-3-ylamine (1.0 g, 4.8 mmol) in ethanol (15 ml) and toluene (15 ml) was charged under argon atmosphere with (1,1'-bis(diphenylphosphino)-ferrocene)palladium(II) dichloride complex with dichloromethane (200 mg; 0.245 mmol) and triethylamine (1.67 ml, 12.1 mmol) in an autoclave, was flushed with carbon monoxide (3 times, 20 bar) and stirred at 80° C. under carbon monoxide atmosphere (50 bar) for 16 h. Upon cooling to ambient temperature and pressure release, the reaction mixture was filtrated and the solvents were removed. The product was obtained after purification by silica gel chromatography using a dichloromethane/methanol/ammonia gradient and recrystallisation from dichloromethane as light yellow solid (290 mg, 30%).

Step 2: 6-Chloro-3-(pyrimidin-5-ylamino)-pyridine-2-carboxylic acid ethyl ester A suspension of 3-amino-6-chloro-pyridine-2-carboxylic acid ethyl ester (200 mg, 1.0 mmol), 5-bromopyrimidine (444 mg, 2.8 mmol), potassium carbonate (496 mg, 3.6 mmol) and water (76 µl, 4.4 mmol) in o-xylene was evacuated and vented with argon. Palladium(II) acetate (27 mg, 0.12 mmol) and 4,5-bis(diphenylphosphino)-9,9-dimethylxanthene (xantphos; 87 mg, 0.15 mmol) were added under argon and the reaction mixture was stirred at 140° C. for 60 h. After cooling down to ambient temperature, the reaction mixture was diluted with dichloromethane and the product was obtained after purification by silica gel chromatography using a heptane/ethyl acetate gradient as light yellow solid (98 mg, 35%).

MS: M=279.2 (M+H)$^+$

Step 3: 6-Chloro-3-(pyrimidin-5-ylamino)-pyridine-2-carboxylic acid

A suspension of 6-chloro-3-(pyrimidin-5-ylamino)-pyridine-2-carboxylic acid ethyl ester (98 mg, 0.35 mmol) in THF (1 ml) and ethanol (0.5 ml) was cooled to 0° C. and treated with 1M LiOH (0.7 ml, 0.7 mmol). The ice bath was removed and the reaction mixture was stirred at rt. for 2 h. 1M HCl (0.7 ml, 0.7 mmol) was added and stirring was continued until a precipitate was forming. The reaction mixture was sucked off and the product was obtained upon drying of the precipitate as yellow solid (60 mg, 67%).

MS: M=249.0 (M−H)$^−$

Step 4: 6-Chloro-3-(pyrimidin-5-ylamino)-pyridine-2-carboxylic acid (1-methyl-5-methylcarbamoyl-1H-pyrazol-4-yl)-amide The product was obtained starting from 6-chloro-3-(pyrimidin-5-ylamino)-pyridine-2-carboxylic acid (30 mg, 0.12 mmol) and 4-amino-2-methyl-2H-pyrazole-3-carboxylic acid methylamide (24 mg, 0.15 mmol) according to the method described in example 64, step 6 as yellow solid (29 mg, 62%).

MS: M=387.3 (M+H)$^+$

Example 167

6-Cyclopropyl-3-(pyrimidin-5-ylamino)-pyrazine-2-carboxylic acid (5-isobutylcarbamoyl-1-methyl-1H-pyrazol-4-yl)-amide

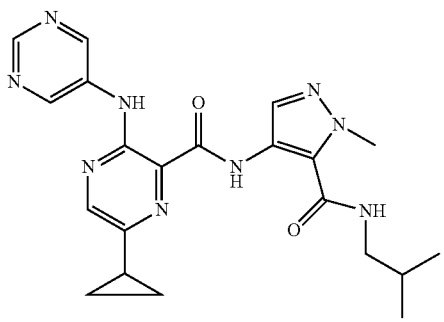 [SMILES: CC(C)CNC(=O)c1c(NC(=O)c2nc(C3CC3)cnc2Nc2cncnc2)cnn1C]

The product was obtained starting from intermediate A-11 (30 mg, 0.12 mmol) and 4-amino-N-isobutyl-1-methyl-1H-pyrazole-5-carboxamide (30 mg, 0.15 mmol) according to the method described in example 64, step 6 as yellow solid (19 mg, 37%).

MS: M=436.3 (M+H)$^+$

Example 168

6-Cyclopropyl-3-(pyrimidin-5-ylamino)-pyrazine-2-carboxylic acid [1-methyl-5-(piperidine-1-carbonyl)-1H-pyrazol-4-yl]-amide

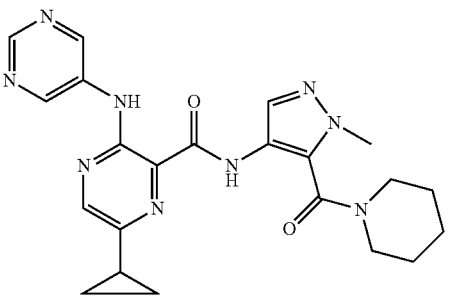 [SMILES: Cn1ncc(NC(=O)c2nc(C3CC3)cnc2Nc2cncnc2)c1C(=O)N1CCCCC1]

The product was obtained starting from intermediate A-11 (30 mg, 0.12 mmol) and (4-amino-1-methyl-1H-pyrazol-5-yl)(piperidin-1-yl)methanone (32 mg, 0.15 mmol) according to the method described in example 64, step 6 after purification by preparative HPLC using an acetonitrile/water gradient as yellow solid (22 mg, 43%).

MS: M=448.3 (M+H)+

Example 169

6-Cyclopropyl-3-(pyrimidin-5-ylamino)-pyrazine-2-carboxylic acid (5-dimethylcarbamoyl-1-ethyl-1H-pyrazol-4-yl)-amide

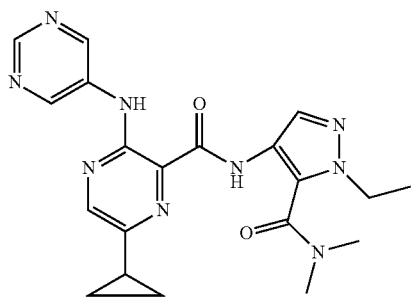 [SMILES: CCn1ncc(NC(=O)c2nc(C3CC3)cnc2Nc2cncnc2)c1C(=O)N(C)C]

The product was obtained starting from intermediate A-11 (30 mg, 0.12 mmol) and 4-amino-1-ethyl-N,N-dimethyl-1H-pyrazole-5-carboxamide (28 mg, 0.15 mmol) according to the method described in example 64, step 6 after purification by preparative HPLC using an acetonitrile/water gradient as yellow solid (36 mg, 73%).

MS: M=422.2 (M+H)+

Example 170

6-Cyclopropyl-3-(pyrimidin-5-ylamino)-pyrazine-2-carboxylic acid [1-ethyl-5-(morpholine-4-carbonyl)-1H-pyrazol-4-yl]-amide

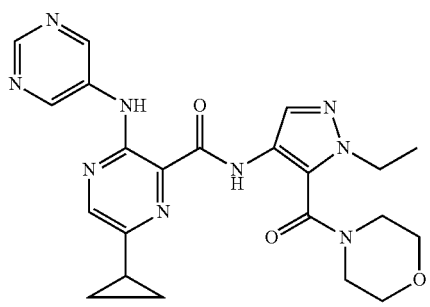 [SMILES: CCn1ncc(NC(=O)c2nc(C3CC3)cnc2Nc2cncnc2)c1C(=O)N1CCOCC1]

The product was obtained starting from intermediate A-11 (30 mg, 0.12 mmol) and (4-amino-1-ethyl-1H-pyrazol-5-yl)(morpholino)methanone (34 mg, 0.15 mmol) according to the method described in example 64, step 6 after purification by preparative HPLC using an acetonitrile/water gradient as yellow solid (39 mg, 72%).

MS: M=464.2 (M+H)+

Example 171

6-Cyclopropyl-3-(pyrimidin-5-ylamino)-pyrazine-2-carboxylic acid [5-(2-fluoro-ethylcarbamoyl)-1-methyl-1H-pyrazol-4-yl]-amide

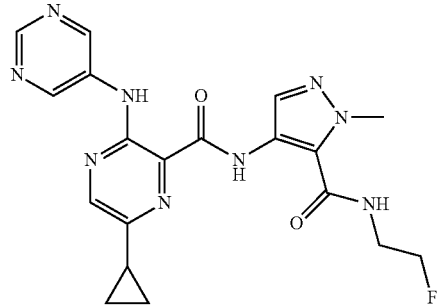 [SMILES: Cn1ncc(NC(=O)c2nc(C3CC3)cnc2Nc2cncnc2)c1C(=O)NCCF]

According to the procedure described in example 135, the title compound was obtained using 2-fluoroethanamine hydrochloride in the last step. Yellow solid.

MS: M=424.1 (M−H)−

Example 172

6-Cyclopropyl-3-(pyrimidin-5-ylamino)-pyrazine-2-carboxylic acid [5-(2-hydroxy-2-methyl-propylcarbamoyl)-1-(3,3,3-trifluoro-propyl)-1H-pyrazol-4-yl]-amide

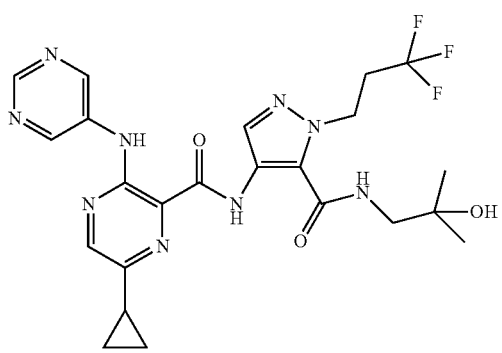 [SMILES: CC(C)(O)CNC(=O)c1c(NC(=O)c2nc(C3CC3)cnc2Nc2cncnc2)cnn1CCC(F)(F)F]

According to the procedures described in example 132, the title compound was obtained using 1,1,1-trifluoro-3-iodopropane in the 1st step and 1-amino-2-methylpropan-2-ol in the last step. Yellow solid.

MS: M=534.2 (M+H)+

Example 173

6-Cyclopropyl-3-(pyrimidin-5-ylamino)-pyrazine-2-carboxylic acid [5-methylcarbamoyl-1-(3,3,3-trifluoro-propyl)-1H-pyrazol-4-yl]-amide

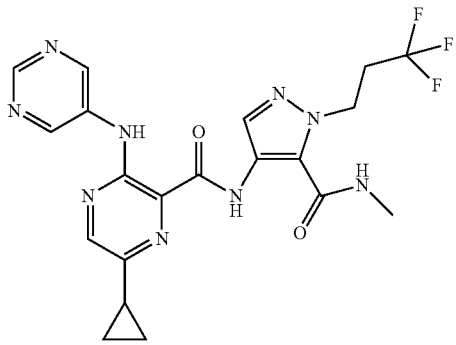 [SMILES: CNC(=O)c1c(NC(=O)c2nc(C3CC3)cnc2Nc2cncnc2)cnn1CCC(F)(F)F]

According to the procedures described in example 132, the title compound was obtained using 1,1,1-trifluoro-3-iodopropane in the 1st step and methylamine hydrochloride in the last step. Yellow solid.

MS: M=476.1 (M+H)$^+$

Example 174

6-Cyclopropyl-3-(pyrimidin-5-ylamino)-pyrazine-2-carboxylic acid [5-(3-fluoro-azetidine-1-carbonyl)-1-methyl-1H-pyrazol-4-yl]-amide

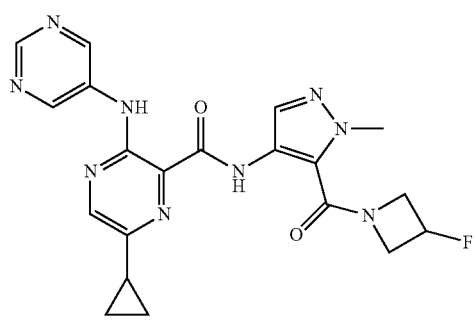 [SMILES: Cn1ncc(NC(=O)c2nc(C3CC3)cnc2Nc2cncnc2)c1C(=O)N1CC(F)C1]

According to the procedure described in example 135, the title compound was obtained using 3-fluoroazetidine hydrochloride in the last step. Yellow solid.

MS: M=436.2 (M−H)$^-$

Example 175

6-Cyclopropyl-3-(pyrimidin-5-ylamino)-pyrazine-2-carboxylic acid [5-(2-hydroxy-2-methyl-propylcarbamoyl)-1-(2,2,2-trifluoro-ethyl)-1H-pyrazol-4-yl]-amide

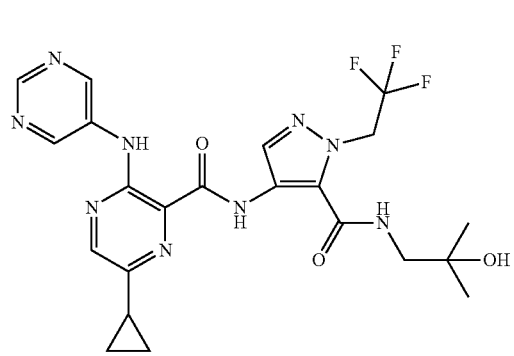 [SMILES: CC(C)(O)CNC(=O)c1c(NC(=O)c2nc(C3CC3)cnc2Nc2cncnc2)cnn1CC(F)(F)F]

According to the procedures described in example 132, the title compound was obtained using 2,2,2-trifluoroethyl trifluoromethanesulfonate in the 1st step and 1-amino-2-methylpropan-2-ol in the last step. Yellow solid.

MS: M=520.3 (M+H)$^+$

Example 176

6-Cyclopropyl-3-(pyrimidin-5-ylamino)-pyrazine-2-carboxylic acid [5-methylcarbamoyl-1-(2,2,2-trifluoro-ethyl)-1H-pyrazol-4-yl]-amide

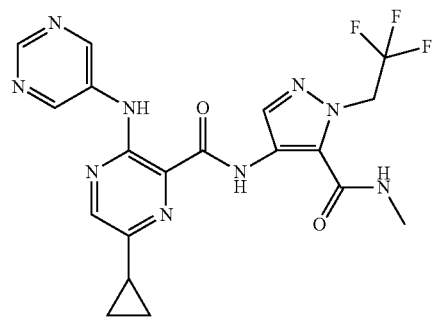 [SMILES: CNC(=O)c1c(NC(=O)c2nc(C3CC3)cnc2Nc2cncnc2)cnn1CC(F)(F)F]

According to the procedures described in example 132, the title compound was obtained using 2,2,2-trifluoroethyl trifluoromethanesulfonate in the 1st step and methylamine hydrochloride in the last step. Yellow solid.

MS: M=562.2 (M+H)$^+$

Example 177

6-Cyclopropyl-3-(pyrimidin-5-ylamino)-pyrazine-2-carboxylic acid [2-methylcarbamoyl-6-(tetrahydro-furan-2-yl)-pyridin-3-yl]-amide

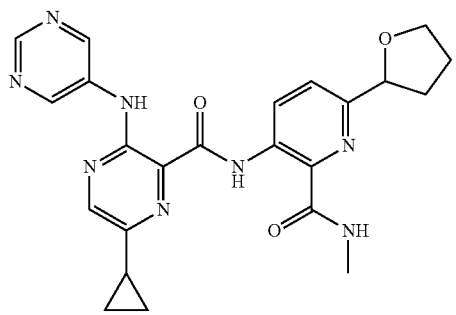 [SMILES: CNC(=O)c1nc(C2CCCO2)ccc1NC(=O)c1nc(C2CC2)cnc1Nc1cncnc1]

Step 1: Ethyl 3-amino-6-(tetrahydrofuran-3-yl)picolinate

According to step 1 and 2 of example 96, the title compound was prepared starting from ethyl 3-amino-6-bromopicolinate and furan-2-ylboronic acid. Light yellow solid.
MS: M=237.2 (M+H)$^+$

Step 2: 6-Cyclopropyl-3-(pyrimidin-5-ylamino)-pyrazine-2-carboxylic acid [2-methylcarbamoyl-6-(tetrahydro-furan-2-yl)-pyridin-3-yl]-amide According to the procedures described in example 99, ethyl 3-amino-6-(tetrahydrofuran-3-yl)picolinate was converted to the title compound, using methylamine hydrochloride in the last step. Yellow solid.
MS: M=459.3 (M−H)$^−$

Example 178

6-Cyclopropyl-3-(pyrimidin-5-ylamino)-pyrazine-2-carboxylic acid [2-(2-hydroxy-2-methyl-propylcarbamoyl)-6-(tetrahydro-furan-2-yl)-pyridin-3-yl]-amide

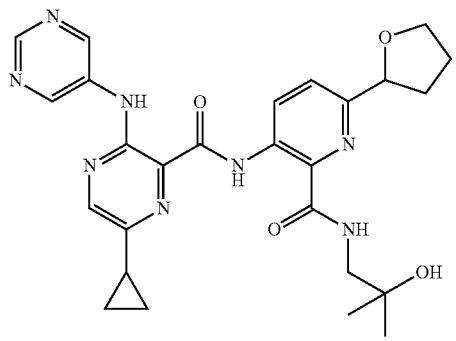 [SMILES: CC(C)(O)CNC(=O)c1nc(C2CCCO2)ccc1NC(=O)c1nc(C2CC2)cnc1Nc1cncnc1]

According to the procedures described in example 177, the title compound was prepared using 1-amino-2-methylpropan-2-ol in the last step.
MS: M=517.3 (M−H)$^−$

Example 179

6-Cyclopropyl-3-(pyrimidin-5-ylamino)-pyrazine-2-carboxylic acid [1-methyl-5-(morpholine-4-carbonyl)-1H-pyrazol-4-yl]-amide

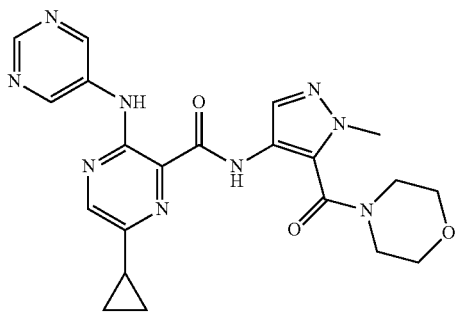 [SMILES: Cn1ncc(NC(=O)c2nc(C3CC3)cnc2Nc2cncnc2)c1C(=O)N1CCOCC1]

The product was obtained starting from intermediate A-11 (30 mg, 0.12 mmol) and (4-amino-1-methyl-1H-pyrazol-5-yl)(morpholino)methanone (32 mg, 0.15 mmol) according to the method described in example 64, step 6 after purification by preparative HPLC using an acetonitrile/water gradient as yellow solid (40 mg, 77%).
MS: M=450.3 (M+H)$^+$

Example 180

6-Cyclopropyl-3-(pyrimidin-5-ylamino)-pyrazine-2-carboxylic acid (6-ethyl-2-methylcarbamoyl-pyridin-3-yl)-amide

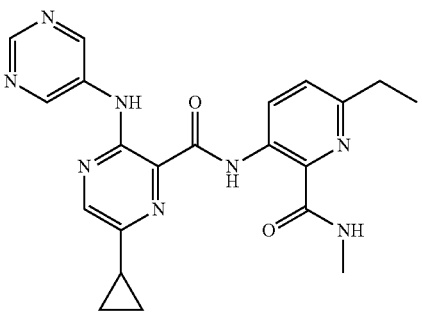 [SMILES: CCc1ccc(NC(=O)c2nc(C3CC3)cnc2Nc2cncnc2)c(C(=O)NC)n1]

According to the procedures described in example 99, the title compound was obtained using 3-amino-6-ethyl-pyridine-2-carboxylic acid ethyl ester (CAS 908833-49-8) in the 1$^{st}$ step and methylamine hydrochloride in the last step. Yellow solid.
MS: M=417.1 (M−H)$^−$

Example 181

6-Cyclopropyl-3-(pyrimidin-5-ylamino)-pyrazine-2-carboxylic acid [6-ethyl-2-(2-hydroxy-2-methyl-propylcarbamoyl)-pyridin-3-yl]-amide

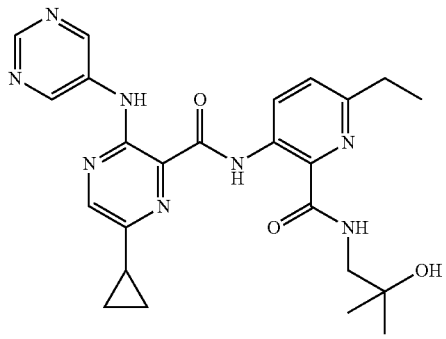 [SMILES: CCc1ccc(NC(=O)c2nc(C3CC3)cnc2Nc2cncnc2)c(C(=O)NCC(C)(C)O)n1]

According to the procedures described in example 99, the title compound was obtained using 3-amino-6-ethyl-pyridine-2-carboxylic acid ethyl ester (CAS 908833-49-8) in the 1$^{st}$ step and 1-amino-2-methylpropan-2-ol in the last step. Yellow solid.

MS: M=475.2 (M–H)$^-$

Example 182

6-Cyclopropyl-3-(pyrimidin-5-ylamino)-pyrazine-2-carboxylic acid (6-methyl-2-methylcarbamoyl-pyridin-3-yl)-amide

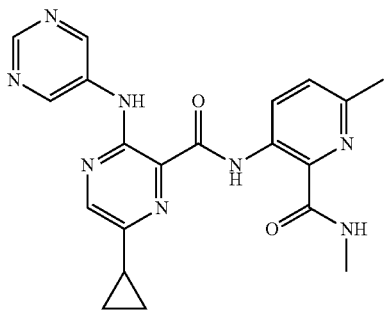 [SMILES: CNC(=O)c1nc(C)ccc1NC(=O)c1nc(C2CC2)cnc1Nc1cncnc1]

According to the procedures described in example 99, the title compound was obtained using 3-amino-6-methyl-pyridine-2-carboxylic acid ethyl ester (CAS 908832-89-3) in the 1$^{st}$ step and methylamine hydrochloride in the last step. Yellow solid.

MS: M=405.4 (M+H)$^+$

Example 183

6-Cyclopropyl-3-(pyrimidin-5-ylamino)-pyrazine-2-carboxylic acid [2-(2-hydroxy-2-methyl-propylcarbamoyl)-6-methyl-pyridin-3-yl]-amide

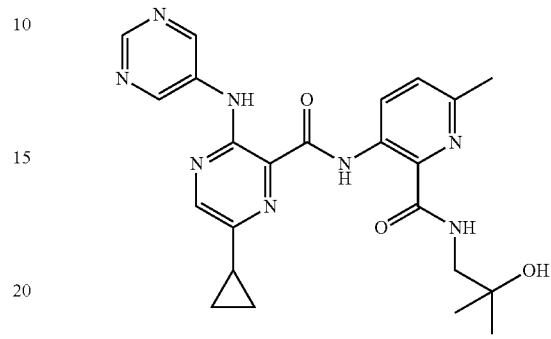

According to the procedures described in example 99, the title compound was obtained using 3-amino-6-methyl-pyridine-2-carboxylic acid ethyl ester (CAS 908832-89-3) in the 1$^{st}$ step and 1-amino-2-methylpropan-2-ol in the last step. Yellow solid.

MS: M=461.3 (M–H)$^-$

Example 184

6-Acetyl-3-(pyrimidin-5-ylamino)-pyrazine-2-carboxylic acid (1-methyl-5-methylcarbamoyl-1H-pyrazol-4-yl)-amide

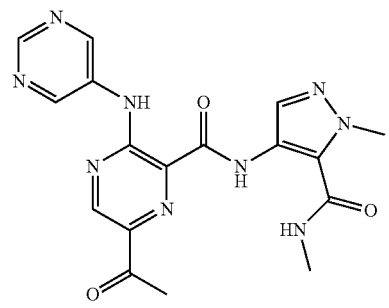 [SMILES: CNC(=O)c1c(NC(=O)c2nc(C(C)=O)cnc2Nc2cncnc2)cnn1C]

The product was obtained starting from intermediate A-14 (40 mg, 0.15 mmol) and 4-amino-2-methyl-2H-pyrazole-3-carboxylic acid methylamide (31 mg, 0.2 mmol) according to the method described in example 64, step 6 as yellow solid (36 mg, 59%).

MS: M=396.3 (M+H)$^+$

Example 185

6-Cyclopropyl-3-(pyrimidin-5-ylamino)-pyrazine-2-carboxylic acid (3-ethylcarbamoyl-4,5,6,7-tetrahydro-benzo[b]thiophen-2-yl)-amide

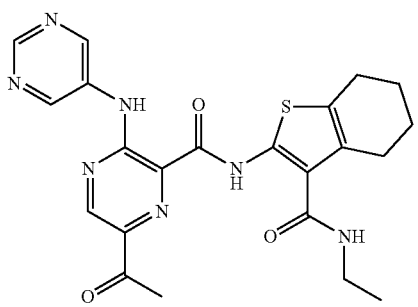 [SMILES: CCNC(=O)c1c(NC(=O)c2nc(C(C)=O)cnc2Nc2cncnc2)sc2c1CCCC2]

According to the procedure described in step 6 of example 64, the title compound was obtained from intermediate A-11 and 2-amino-N-ethyl-4,5,6,7-tetrahydrobenzo[b]thiophene-3-carbox-amide.
MS: M=464.2 (M+H)$^+$

Example 186

2-Isopropyl-5-(pyridin-3-ylamino)-pyrimidine-4-carboxylic acid (1-methyl-5-methylcarbamoyl-1H-pyrazol-4-yl)-amide

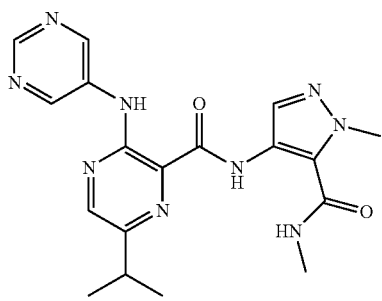 [SMILES: CNC(=O)c1c(NC(=O)c2nc(C(C)C)cnc2Nc2cncnc2)cnn1C]

Step 1: 5-Bromo-2-isopropyl-pyrimidine-4-carboxylic acid (1-methyl-5-methylcarbamoyl-1H-pyrazol-4-yl)-amide The product was obtained starting from 5-bromo-2-isopropyl-pyrimidine-4-carboxylic acid (intermediate A-4, step 1; 300 mg, 1.22 mmol) and 4-amino-2-methyl-2H-pyrazole-3-carboxylic acid methylamide (245 mg, 1.59 mmol) according to the method described in example 64, step 6 after extraction with ethyl acetate and purification by silica gel chromatography using ethyl acetate as light brown solid (472 mg, 96%).
MS: M=381.3 (M+H)$^+$ Step 2: 2-Isopropyl-5-(pyridin-3-ylamino)-pyrimidine-4-carboxylic acid (1-methyl-5-methylcarbamoyl-1H-pyrazol-4-yl)-amide A mixture of 5-bromo-2-isopropyl-pyrimidine-4-carboxylic acid (1-methyl-5-methylcarbamoyl-1H-pyrazol-4-yl)-amide (40 mg, 105 µmol), 3-aminopyridine (15 mg, 157 µmol) and potassium phosphate tribasic (31 mg, 147 µmol) in toluene (1 ml) was treated with tris(dibenzylideneacetone)dipalladium(0)-chloroform adduct (10.9 mg, 10.5 µmol) and xantphos (20 mg, 34.6 µmol) were added and the reaction mixture was stirred at 120° C. for 16 h. The reaction was cooled to r.t., filtrated and the product was obtained after purification by preparative HPLC using an acetonitrile/water gradient as yellow solid (10 mg, 25%).
MS: M=395.2 (M+H)$^+$

Example 187

6-(1-Hydroxy-ethyl)-3-(pyrimidin-5-ylamino)-pyrazine-2-carboxylic acid (1-methyl-5-methylcarbamoyl-1H-pyrazol-4-yl)-amide

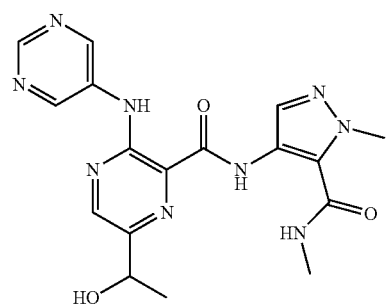 [SMILES: CNC(=O)c1c(NC(=O)c2nc(C(C)O)cnc2Nc2cncnc2)cnn1C]

The product was obtained starting from 6-acetyl-3-(pyrimidin-5-ylamino)-pyrazine-2-carboxylic acid (1-methyl-5-methylcarbamoyl-1H-pyrazol-4-yl)-amide (example 184) according to the method described in example 115, step 2 after purification by preparative HPLC using an acetonitrile/water gradient as light yellow solid (41%).
MS: M=398.3 (M+H)$^+$

Example 188

5-(3-Fluoro-phenylamino)-2-isopropyl-pyrimidine-4-carboxylic acid (1-methyl-5-methylcarbamoyl-1H-pyrazol-4-yl)-amide

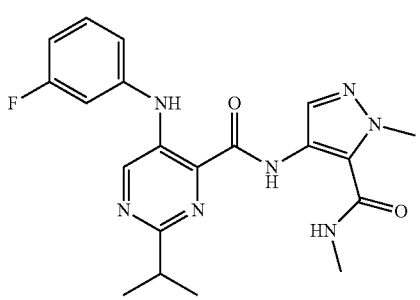 [SMILES: CNC(=O)c1c(NC(=O)c2nc(C(C)C)ncc2Nc2cccc(F)c2)cnn1C]

The product was obtained according to the procedure described in example 186, step 2 using 3-fluoroaniline instead of 3-aminopyridine as yellow solid (25%)
MS: M=412.4 (M+H)$^+$

Example 189

6-Methoxymethyl-3-(pyrimidin-5-ylamino)-pyridine-2-carboxylic acid (1-methyl-5-methylcarbamoyl-1H-pyrazol-4-yl)-amide

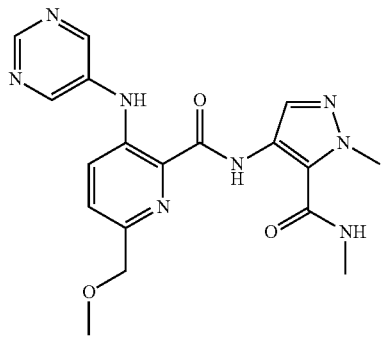 [SMILES: CNC(=O)c1c(NC(=O)c2nc(COC)ccc2Nc2cncnc2)cnn1C]

Step 1: 6-Methoxymethyl-3-(pyrimidin-5-ylamino)-pyridine-2-carboxylic acid

The product was obtained from intermediate A-3 according to the method described in example 163, step 3 as yellow solid (100%)
MS: M=259.1 (M–H)⁻

Step 2: 6-Methoxymethyl-3-(pyrimidin-5-ylamino)-pyridine-2-carboxylic acid (1-methyl-5-methylcarbamoyl-1H-pyrazol-4-yl)-amide The product was obtained starting from 6-methoxymethyl-3-(pyrimidin-5-ylamino)-pyridine-2-carboxylic acid (30 mg, 0.12 mmol) and 4-amino-2-methyl-2H-pyrazole-3-carboxylic acid methylamide (23 mg, 0.15 mmol) according to the method described in example 64, step 6 after purification by preparative HPLC using an acetonitrile/water gradient as off-white solid (28 mg, 61%).
MS: M=397.3 (M+H)⁺

Example 190

5-(5-Fluoro-pyridin-3-ylamino)-2-isopropyl-pyrimidine-4-carboxylic acid (1-methyl-5-methylcarbamoyl-1H-pyrazol-4-yl)-amide

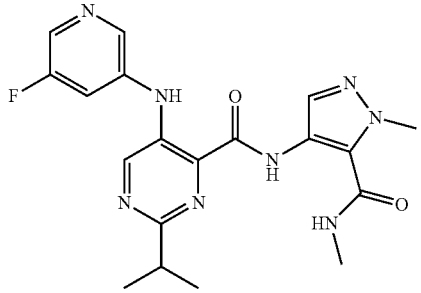 [SMILES: CNC(=O)c1c(NC(=O)c2nc(C(C)C)ncc2Nc2cncc(F)c2)cnn1C]

The product was obtained according to the procedure described in example 186, step 2 using 5-fluoro-3-aminopyridine instead of 3-aminopyridine and after an additional purification by silica gel chromatography using ethyl acetate as light yellow solid (10%)
MS: M=413.3 (M+H)⁺

Example 191

5-(4-Fluoro-phenylamino)-2-isopropyl-pyrimidine-4-carboxylic acid (1-methyl-5-methylcarbamoyl-1H-pyrazol-4-yl)-amide

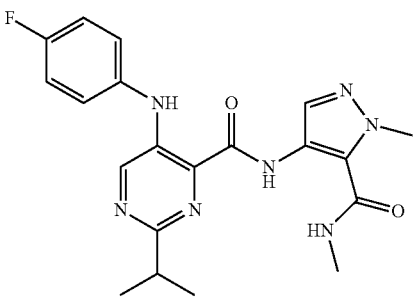 [SMILES: CNC(=O)c1c(NC(=O)c2nc(C(C)C)ncc2Nc2ccc(F)cc2)cnn1C]

The product was obtained according to the procedure described in example 186, step 2 using 4-fluoroaniline instead of 3-aminopyridine as yellow solid (51%)
MS: M=412.3 (M+H)⁺

Example 192

6-Cyclopropyl-3-(pyrimidin-5-ylamino)-pyrazine-2-carboxylic acid (3-methoxy-2-methylcarbamoyl-phenyl)-amide

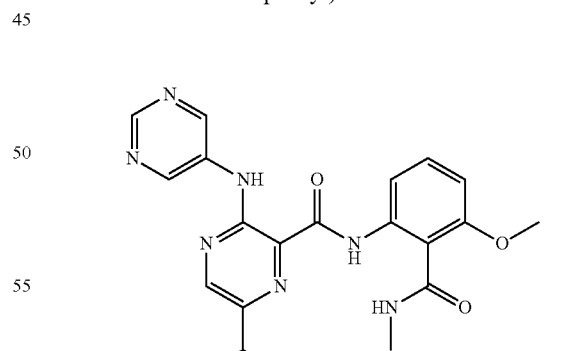

The product was obtained starting from intermediate A-11 (30 mg, 0.12 mmol) and 2-amino-6-methoxy-N-methyl-benzamide (27 mg, 0.15 mmol; prepared from 2-amino-6-methoxybenzoic acid according to Bioorg. Med. Chem. Lett. 2008, 18, 6041) according to the method described in example 64, step 6 as yellow solid (45 mg, 92%).
MS: M=420.2 (M+H)⁺

Example 193

2-Cyclobutyl-5-(pyrimidin-5-ylamino)-pyrimidine-4-carboxylic acid (1-methyl-5-methylcarbamoyl-1H-pyrazol-4-yl)-amide

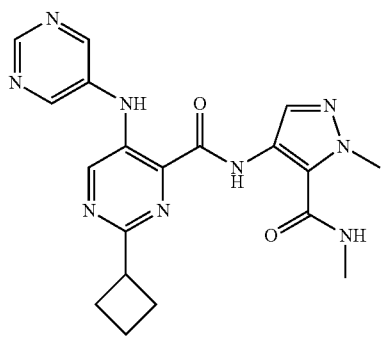 [SMILES: CNC(=O)c1c(NC(=O)c2nc(C3CCC3)ncc2Nc2cncnc2)cnn1C]

Step 1: 5-Bromo-2-cyclobutyl-pyrimidine-4-carboxylic acid

The product was obtained starting from cyclobutanecarboxamidine (200 mg, 1.5 mmol) and mucobromic acid (180 mg, 0.7 mmol) according to the method described in intermediate A-4, step 1 as light brown solid (38 mg, 21%).

MS: M=257.1 (M+H)$^+$

Step 2: 5-Bromo-2-cyclobutyl-pyrimidine-4-carboxylic acid (1-methyl-5-methylcarbamoyl-1H-pyrazol-4-yl)-amide The product was obtained starting from 5-bromo-2-cyclobutyl-pyrimidine-4-carboxylic acid (37 mg, 0.14 mmol) and 4-amino-2-methyl-2H-pyrazole-3-carboxylic acid methylamide (29 mg, 0.19 mmol) according to the method described in example 64, step 6 after purification by preparative HPLC using an acetonitrile/water gradient as off-white solid (24 mg, 42%).

MS: M=393.2 (M+H)$^+$

Step 3: 2-Cyclobutyl-5-(pyrimidin-5-ylamino)-pyrimidine-4-carboxylic acid (1-methyl-5-methylcarbamoyl-1H-pyrazol-4-yl)-amide The product was obtained starting from 5-bromo-2-cyclobutyl-pyrimidine-4-carboxylic acid (1-methyl-5-methylcarbamoyl-1H-pyrazol-4-yl)-amide (23 mg, 58 µmol) and 5-aminopyrimidine (8 mg, 82 µmol) according to the method described in example A-1, step 2 after purification by preparative HPLC using an acetonitrile/water gradient as yellow solid (1 mg, 5%).

MS: M=408.4 (M+H)$^+$

Example 194

6-Cyclopropyl-3-(pyrimidin-5-ylamino)-pyrazine-2-carboxylic acid [2-(azetidine-1-carbonyl)-pyridin-3-yl]-amide

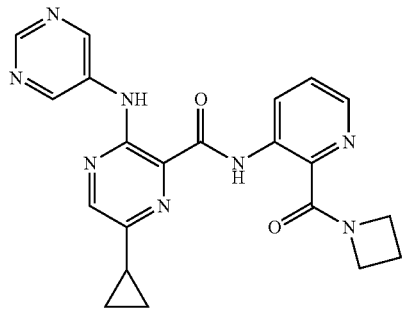 [SMILES: O=C(Nc1cccnc1C(=O)N1CCC1)c1nc(C2CC2)cnc1Nc1cncnc1]

According to the procedures described in example 97, the title compound was obtained using 3-aminopicolinic acid and azetidine in the 1$^{st}$ step. Yellow solid.

MS: M=417.2 (M+H)$^+$

Example 195

6-Cyclopropyl-3-(pyrimidin-5-ylamino)-pyrazine-2-carboxylic acid [2-(piperidine-1-carbonyl)-pyridin-3-yl]-amide

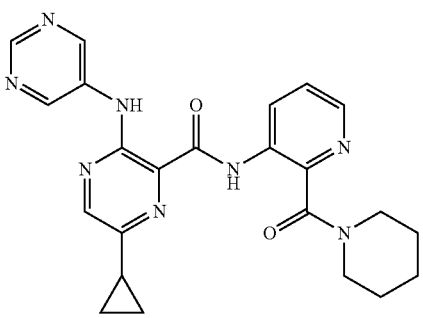 [SMILES: O=C(Nc1cccnc1C(=O)N1CCCCC1)c1nc(C2CC2)cnc1Nc1cncnc1]

According to the procedures described in example 97, the title compound was obtained using 3-aminopicolinic acid and piperidine in the 1$^{st}$ step. Yellow solid.

MS: M=445.4 (M+H)$^+$

Example 196

6-Cyclopropyl-3-(pyrimidin-5-ylamino)-pyrazine-2-carboxylic acid (3-chloro-2-methylcarbamoyl-phenyl)-amide

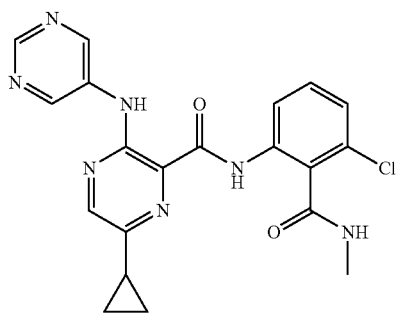 [SMILES: CNC(=O)c1c(Cl)cccc1NC(=O)c1nc(C2CC2)cnc1Nc1cncnc1]

According to the procedures described in example 99, the title compound was prepared using methyl 2-amino-6-chlorobenzoate in the 1$^{st}$ step and methylamine hydrochloride in the last step. Yellow solid.

MS: M=424.2 (M+H)$^+$

Example 197

6-Cyclopropyl-3-(pyrimidin-5-ylamino)-pyrazine-2-carboxylic acid (5-ethylcarbamoyl-1-methyl-1H-pyrazol-4-yl)-amide

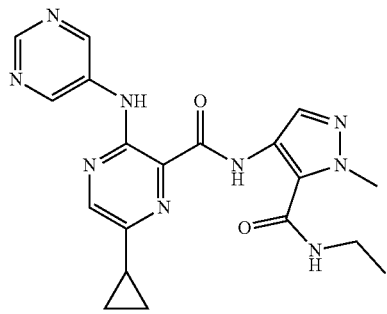 [SMILES: CCNC(=O)c1c(NC(=O)c2nc(C3CC3)cnc2Nc2cncnc2)cnn1C]

The product was obtained starting from intermediate A-11 (30 mg, 0.12 mmol) and 4-amino-N-ethyl-1-methyl-1H-pyrazole-5-carboxamide (25 mg, 0.15 mmol) according to the method described in example 64, step 6 as yellow solid (17 mg, 35%).

MS: M=408.3 (M+H)$^+$

Example 198

6-Cyclopropyl-3-(pyrimidin-5-ylamino)-pyrazine-2-carboxylic acid [2-(pyrrolidine-1-carbonyl)-pyridin-3-yl]-amide

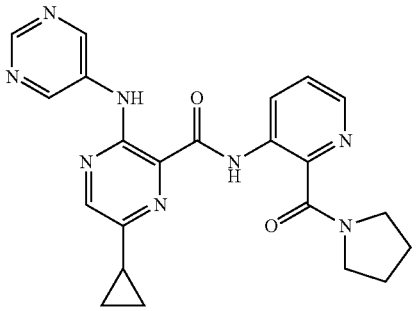 [SMILES: O=C(Nc1cccnc1C(=O)N1CCCC1)c1nc(C2CC2)cnc1Nc1cncnc1]

According to the procedures described in example 97, the title compound was obtained using 3-aminopicolinic acid and pyrrolidine in the 1$^{st}$ step. Yellow solid.

MS: M=431.3 (M+H)$^+$

Example 199

6-Cyclopropyl-3-(pyrimidin-5-ylamino)-pyrazine-2-carboxylic acid [2-(ethyl-methyl-carbamoyl)-pyridin-3-yl]-amide

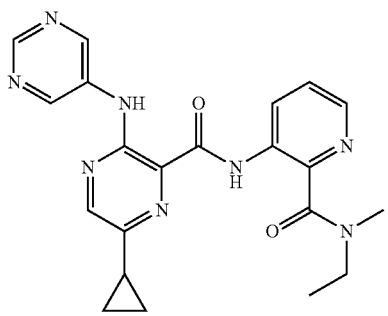 [SMILES: CCN(C)C(=O)c1ncccc1NC(=O)c1nc(C2CC2)cnc1Nc1cncnc1]

According to the procedures described in example 97, the title compound was obtained using 3-aminopicolinic acid and methylethylamine in the 1$^{st}$ step. Yellow solid.

MS: M=419.3 (M+H)$^+$

Example 200

6-Cyclopropyl-3-(pyrazin-2-ylamino)-pyrazine-2-carboxylic acid (1-methyl-5-methylcarbamoyl-1H-pyrazol-4-yl)-amide

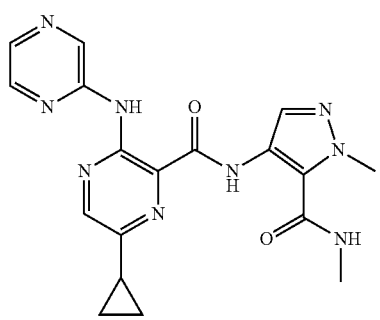 [SMILES: CNC(=O)c1c(NC(=O)c2nc(C3CC3)cnc2Nc2cnccn2)cnn1C]

Step 1: Methyl 3-bromo-6-cyclopropylpyrazine-2-carboxylate

To a solution of methyl 3-amino-6-cyclopropylpyrazine-2-carboxylate (1 g, 5.18 mmol, intermediate A-10, step 2) in dibromethane (16.0 ml, 229 mmol) at 0° under an argon atmosphere was added isoamyl nitrite (1.49 ml, 11.1 mmol) and trimethylbromosilane (2.03 ml, 15.7 mmol). The mixture was stirred at 0° for 10 min and at r.t overnight. The reaction mixture was poured onto ice, neutralized with solid NaHCO$_3$, extracted with dichloromethane, dried over MgSO$_4$, filtered and evaporated. The title compound was obtained after silica gel chromatography using a heptane/ethylacetate gradient as viscous oil (450 mg, 34%).

MS: M=257.1 (M+H)$^+$

Step 2: Methyl 6-cyclopropyl-3-(pyrazin-2-ylamino)pyrazine-2-carboxylate

The title compound was obtained according to the procedure described for step 2 of intermediate A-2 using pyrazine-2-amine. Yellow solid.

MS: M=272.2 (M+H)$^+$

Step 3: 6-Cyclopropyl-N-(1-methyl-5-(methylcarbamoyl)-1H-pyrazol-4-yl)-3-(pyrazin-2-ylamino)pyrazine-2-carboxamide According to the procedure described in step 2 of example 14, methyl 6-cyclopropyl-3-(pyrazin-2-ylamino)pyrazine-2-carboxylate was reacted with 4-amino-N,1-dimethyl-1H-pyrazole-5-carboxamide to give the title compound. Yellow solid.

MS: M=394 (M+H)$^+$

Example 201

6-Cyclopropyl-3-(pyrimidin-5-ylamino)-pyrazine-2-carboxylic acid (1-ethyl-5-ethylcarbamoyl-1H-pyrazol-4-yl)-amide

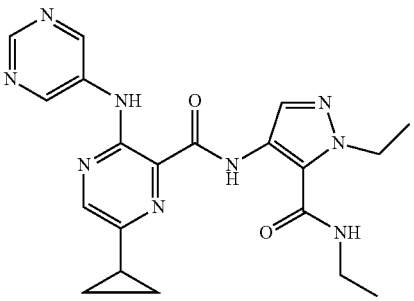 [SMILES: CCNC(=O)c1c(NC(=O)c2nc(C3CC3)cnc2Nc2cncnc2)cnn1CC]

The product was obtained starting from intermediate A-11 (30 mg, 0.12 mmol) and 4-amino-N,1-diethyl-1H-pyrazole-5-carboxamide (27 mg, 0.15 mmol) according to the method described in example 64, step 6 as yellow solid (40 mg, 82%).

MS: M=422.2 (M+H)$^+$

Example 202

6-Cyclopropyl-3-(pyrimidin-5-ylamino)-pyrazine-2-carboxylic acid (1-ethyl-5-isobutylcarbamoyl-1H-pyrazol-4-yl)-amide

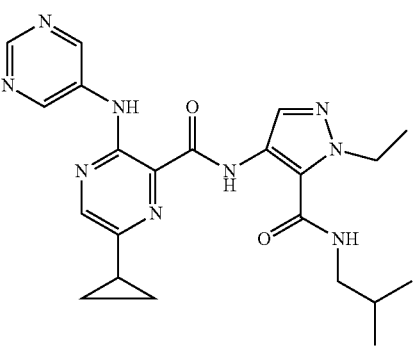 [SMILES: CCn1ncc(NC(=O)c2nc(C3CC3)cnc2Nc2cncnc2)c1C(=O)NCC(C)C]

The product was obtained starting from intermediate A-11 (30 mg, 0.12 mmol) and 4-amino-1-ethyl-N-isobutyl-1H-pyrazole-5-carboxamide (32 mg, 0.15 mmol) according to the method described in example 64, step 6 as yellow solid (43 mg, 82%).

MS: M=450.2 (M+H)$^+$

Example 203

6-Cyclopropyl-3-(pyrimidin-5-ylamino)-pyrazine-2-carboxylic acid [5-(ethyl-methyl-carbamoyl)-1-methyl-1H-pyrazol-4-yl]-amide

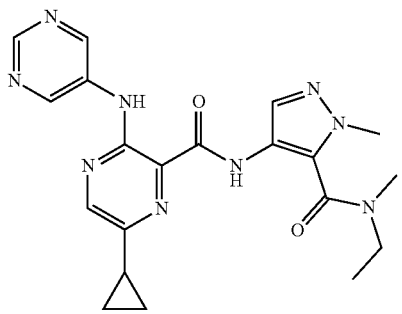 [SMILES: CCN(C)C(=O)c1c(NC(=O)c2nc(C3CC3)cnc2Nc2cncnc2)cnn1C]

According to the procedure described in example 135, the title compound was obtained using N-methylethanamine in the last step. Yellow solid.

MS: M=422.2 (M+H)+

Example 204

5-{[6-Cyclopropyl-3-(pyrimidin-5-ylamino)-pyrazine-2-carbonyl]-amino}-pyrimidine-4-carboxylic acid ethyl-methyl-amide

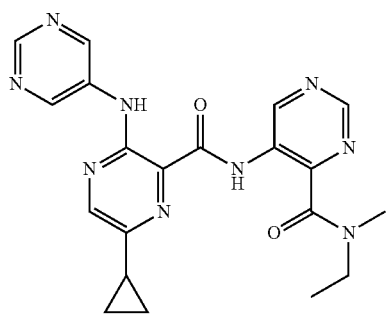 [SMILES: CCN(C)C(=O)c1ncncc1NC(=O)c1nc(C2CC2)cnc1Nc1cncnc1]

According to the procedures described in example 99, the title compound was obtained using 5-amino-pyrimidine-4-carboxylic acid methyl ester in the 1st step and N-methylethanamine in the last step. Yellow solid.

MS: M=420.3 (M+H)+

Example 205

5-{[6-Cyclopropyl-3-(pyrimidin-5-ylamino)-pyrazine-2-carbonyl]-amino}-pyrimidine-4-carboxylic acid dimethylamide

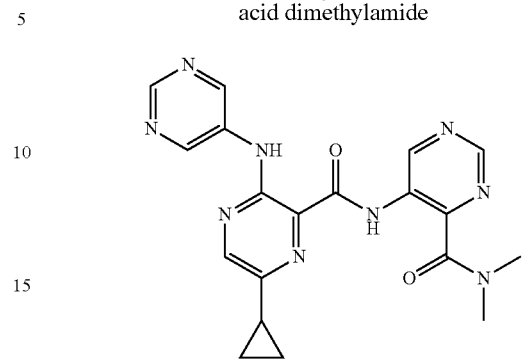

According to the procedures described in example 99, the title compound was obtained using 5-amino-pyrimidine-4-carboxylic acid methyl ester in the 1st step and dimethylamine hydrochloride in the last step. Yellow solid.

MS: M=404.2 (M−H)−

Example 206

6-Cyclopropyl-3-(pyrimidin-5-ylamino)-pyrazine-2-carboxylic acid (2-dimethylcarbamoyl-3-methoxy-phenyl)-amide

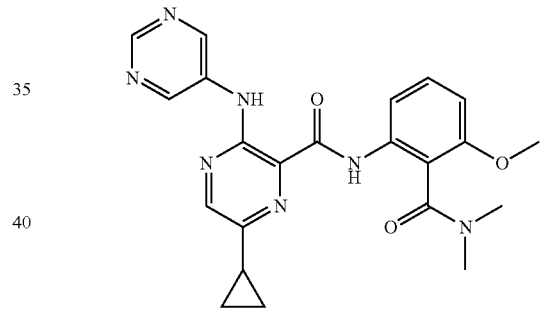

Step 1:
2-Amino-6-methoxy-N,N-dimethyl-benzamide

The product was obtained starting from 2-amino-6-methoxybenzoic acid (100 mg, 0.6 mmol) and dimethylamine (2M in THF, 420 μl, 0.84 mmol) according to the method described in example 64, step 6 after extraction with ethyl acetate and purification by silica gel chromatography using an amine phase and a heptane/ethyl acetate gradient as colorless oil (26 mg, 22%).

Step 2: 6-Cyclopropyl-3-(pyrimidin-5-ylamino)-pyrazine-2-carboxylic acid (2-dimethylcarbamoyl-3-methoxy-phenyl)-amide The product was obtained starting from intermediate A-11 (34 mg, 0.13 mmol) and 2-amino-6-methoxy-N,N-dimethyl-benzamide (26 mg, 0.13 mmol) according to the method described in example 64, step 6 after purification by preparative HPLC using an acetonitrile/water gradient as yellow solid (40 mg, 68%).

MS: M=434.4 (M+H)+

Example 207

6-Cyclopropyl-3-(pyrimidin-5-ylamino)-pyrazine-2-carboxylic acid [2-(2-hydroxy-2-methyl-propylcarbamoyl)-4-isopropyl-phenyl]-amide

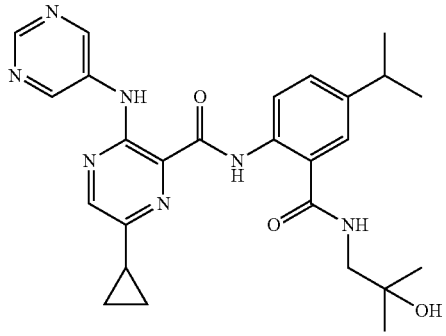 [SMILES: CC(C)c1ccc(NC(=O)c2nc(C3CC3)cnc2Nc2cncnc2)c(C(=O)NCC(C)(C)O)c1]

According to the procedures described in example 99, the title compound was obtained using methyl 2-amino-5-isopropylbenzoate (CAS 1029420-48-1) in the 1$^{st}$ step and 1-amino-2-methyl-propan-2-ol in the last step. Yellow solid.

MS: M=490.4 (M+H)$^+$

Example 208

6-Cyclopropyl-3-(pyrimidin-5-ylamino)-pyrazine-2-carboxylic acid (4-isopropyl-2-methylcarbamoyl-phenyl)-amide

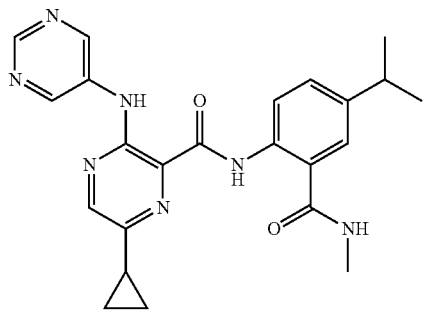 [SMILES: CNC(=O)c1cc(C(C)C)ccc1NC(=O)c1nc(C2CC2)cnc1Nc1cncnc1]

According to the procedures described in example 99, the title compound was obtained using methyl 2-amino-5-isopropylbenzoate (CAS 1029420-48-1) in the 1$^{st}$ step and methylamine hydrochloride in the last step. Yellow solid.

MS: M=432.4 (M+H)$^+$

Example 209

6-Cyclopropyl-3-(pyrimidin-5-ylamino)-pyrazine-2-carboxylic acid (6-methoxymethyl-2-methylcarbamoyl-pyridin-3-yl)-amide

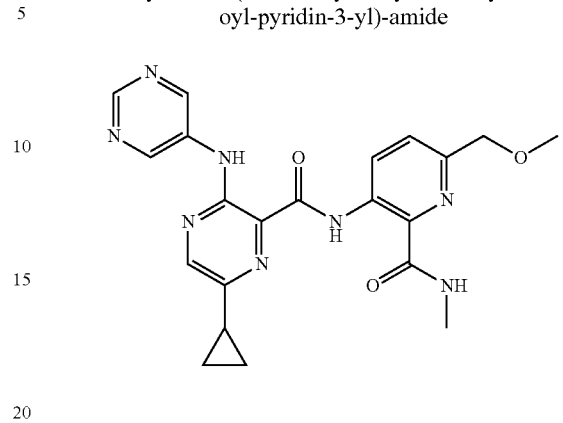

Step 1: Methyl 3-(tert-butoxycarbonylamino)-6-(methoxymethyl)picolinate

To a stirred solution of 3-bromo-6-methoxymethyl-pyridine-2-carboxylic acid methyl ester (933 mg, 3.59 mmol; intermediate A-3, step 6) and tert-butyl carbamate (504 mg, 4.3 mmol) at r.t. in dioxane (15 ml) under an argon atmosphere were added cesium carbonate (1.64 g, 5.02 mmol), Pd$_2$(dba)$_3$ (65.7 mg, 71.7 µmol) and Xantphos (62.3 mg, 108 µmol; CAS 161265-03-8). The mixture was degassed under vacuum and flushed with argon, then heated to 100° C. overnight. The mixture was cooled to r.t., diluted with CH$_2$Cl$_2$, and the solids were filtered off and washed with some CH$_2$Cl$_2$. The filtrate was concentrated. The crude product was purified by silica gel chromatography using a cyclohexane/EtOAc gradient to give the title compound (598 mg, 56%) as viscous light yellow oil.

MS: M=297.3 (M+H)$^+$

Step 2: 3-Amino-6-methoxymethyl-pyridine-2-carboxylic acid methyl ester

To a stirred solution of methyl 3-(tert-butoxycarbonylamino)-6-(methoxymethyl)picolinate (695 mg, 2.35 mmol) at r.t. in dichloromethane (10 ml) under an argon atmosphere was added 2,2,2-trifluoroacetic acid (903 µl, 11.7 mmol) in one portion. The mixture was stirred at 50° C. overnight, then cooled to r.t. and treated carefully with 10% aq. Na$_2$CO$_3$ (10 ml). The aqueous solution was extracted with CH$_2$Cl$_2$ (10 ml). The combined organics were washed with brine (10 ml), dried over MgSO$_4$, filtered and concentrated to leave the product as a light brown solid (424 mg, 92%) which was used for the next step without further purification.

MS: M=197.1 (M+H)$^+$

Step 3: 6-cyclopropyl-N-(2-(2-hydroxy-2-methylpropylcarbamoyl)-6-(methoxymethyl)pyridin-3-yl)-3-(pyrimidin-5-ylamino)pyrazine-2-carboxamide According to the procedures described in example 99, the title compound was prepared using intermediate A-11 and 3-amino-6-methoxymethyl-pyridine-2-carboxylic acid methyl ester in the 1$^{st}$ step and methylamine hydrochloride in the last step. Yellow solid.

MS: M=433.3 (M+H)$^+$

Example 210

6-Cyclopropyl-3-(pyrimidin-5-ylamino)-pyrazine-2-carboxylic acid [2-(2-hydroxy-2-methyl-propylcarbamoyl)-6-methoxymethyl-pyridin-3-yl]-amide

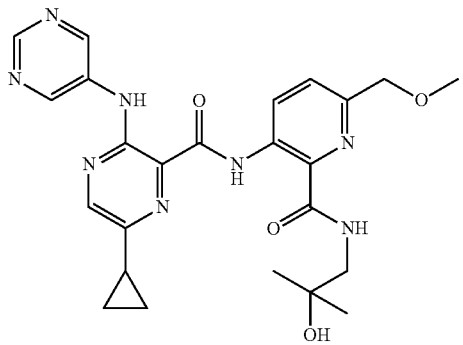 [SMILES: COCc1ccc(NC(=O)c2nc(C3CC3)cnc2Nc2cncnc2)c(C(=O)NCC(C)(C)O)n1]

According to the procedures described in example 209, the title compound was obtained using 1-amino-2-methyl-propan-2-ol in the last step. Yellow solid.

MS: M=491.3 (M+H)$^+$

Example 211

6-Cyclopropyl-3-(pyrimidin-5-ylamino)-pyrazine-2-carboxylic acid [4-(azetidine-1-carbonyl)-pyrimidin-5-yl]-amide

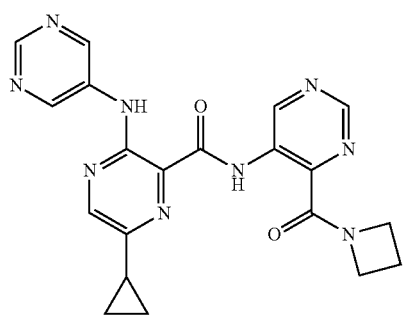 [SMILES: O=C(Nc1cncnc1C(=O)N1CCC1)c1nc(C2CC2)cnc1Nc1cncnc1]

According to the procedures described in example 97, the title compound was obtained using 5-amino-pyrimidine-4-carboxylic acid and azetidine in the 1$^{st}$ step. Yellow solid.

MS: M=416.1 (M–H)$^-$

Example 212

6-Cyclopropyl-3-(pyrimidin-5-ylamino)-pyrazine-2-carboxylic acid [4-(piperidine-1-carbonyl)-pyrimidin-5-yl]-amide

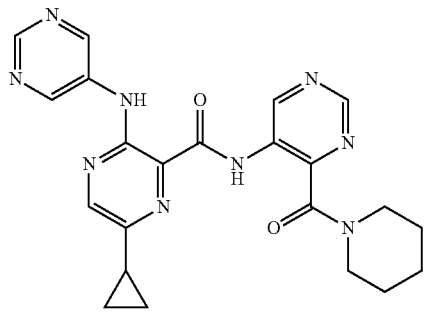 [SMILES: O=C(Nc1cncnc1C(=O)N1CCCCC1)c1nc(C2CC2)cnc1Nc1cncnc1]

According to the procedures described in example 99, the title compound was obtained using 5-amino-pyrimidine-4-carboxylic acid methyl ester in the 1$^{st}$ step and piperidine in the last step. Yellow solid.

MS: M=444.2 (M–H)$^-$

Example 213

6-Cyclopropyl-3-(pyrimidin-5-ylamino)-pyrazine-2-carboxylic acid [2-(2-hydroxy-2-methyl-propylcarbamoyl)-4-(2-methoxy-ethoxy)-phenyl]-amide

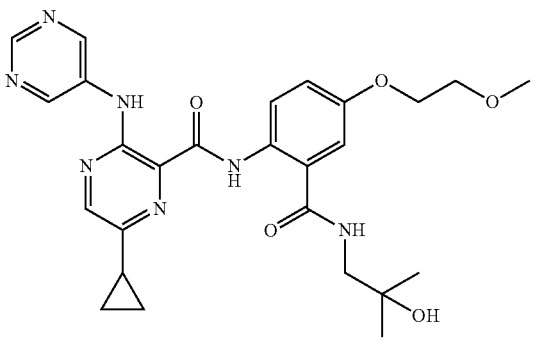 [SMILES: COCCOc1ccc(NC(=O)c2nc(C3CC3)cnc2Nc2cncnc2)c(C(=O)NCC(C)(C)O)c1]

According to the procedures described in example 99, the title compound was obtained using methyl 2-amino-5-(2-methoxyethoxy)benzoate (CAS 773071-76-4) in the 1$^{st}$ step and 1-amino-2-methyl-propan-2-ol in the last step. Yellow solid.

MS: M=552.3 (M+H)$^+$

Example 214

6-Cyclopropyl-3-(pyrimidin-5-ylamino)-pyrazine-2-carboxylic acid [4-(2-methoxy-ethoxy)-2-methylcarbamoyl-phenyl]-amide

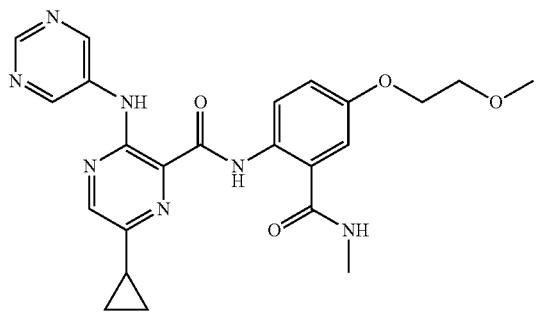 [SMILES: CNC(=O)c1cc(OCCOC)ccc1NC(=O)c1nc(C2CC2)cnc1Nc1cncnc1]

According to the procedures described in example 99, the title compound was obtained using methyl 2-amino-5-(2-methoxyethoxy)benzoate (CAS 773071-76-4) in the 1$^{st}$ step and methylamine hydrochloride in the last step. Yellow solid.
MS: M=464.3 (M+H)$^+$

Example 215

6-Cyclopropyl-3-(pyrimidin-5-ylamino)-pyrazine-2-carboxylic acid [4-(2-hydroxy-ethoxy)-2-(2-hydroxy-2-methyl-propylcarbamoyl)-phenyl]-amide

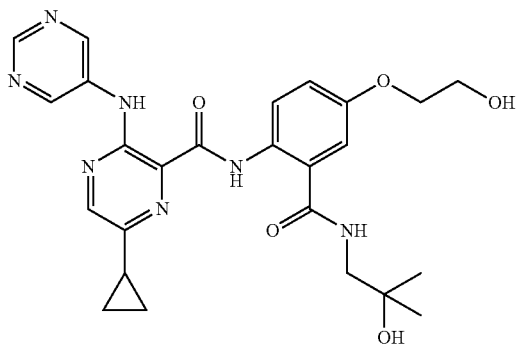 [SMILES: CC(C)(O)CNC(=O)c1cc(OCCO)ccc1NC(=O)c1nc(C2CC2)cnc1Nc1cncnc1]

Step 1: Methyl 2-amino-5-(2-hydroxyethoxy)benzoate

2-Amino-5-(2-hydroxyethoxy)benzoic acid hydrochloride (0.209 g, 895 µmol; CAS 78299-60-2) was suspended in dichloromethane (10 ml) at r.t under an argon atmosphere. The reaction mixture was diluted with MeOH (3 ml). Then trimethylsilyldiazomethane solution (1.45 ml, 2.9 mmol; 2M in hexane) was added dropwise. The reaction mixture was stirred at r.t for 1 hr. The solvents were evaporated. The crude product was purified by silica gel chromatography using a n-heptane/EtOAc gradient to give the title compound (154 mg, 82%) as light yellow, waxy solid.
MS: M=212.1 (M+H)$^+$

Step 2: 6-Cyclopropyl-3-(pyrimidin-5-ylamino)-pyrazine-2-carboxylic acid [4-(2-hydroxy-ethoxy)-2-(2-hydroxy-2-methyl-propylcarbamoyl)-phenyl]-amide According to the procedures described in example 99, the title compound was obtained using methyl 2-amino-5-(2-hydroxyethoxy)benzoate and intermediate A-11 in the first step and 1-amino-2-methyl-propan-2-ol in the last step. Yellow solid.
MS: M=508.3 (M+H)$^+$

Example 216

6-Cyclopropyl-3-(pyrimidin-5-ylamino)-pyrazine-2-carboxylic acid [4-(2-hydroxy-ethoxy)-2-methylcarbamoyl-phenyl]-amide

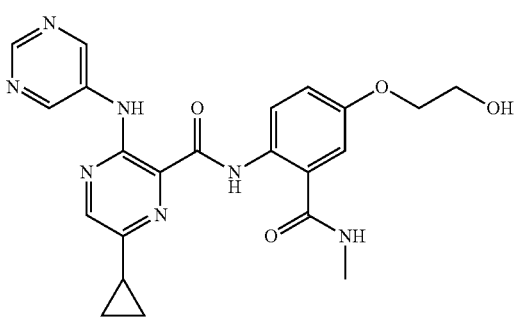 [SMILES: CNC(=O)c1cc(OCCO)ccc1NC(=O)c1nc(C2CC2)cnc1Nc1cncnc1]

According to the procedure described in example 215, the title compound was obtained using methylamine hydrochloride in the last step. Yellow solid.
MS: M=450.3 (M+H)$^+$

Example 217

6-Cyclopropyl-3-(pyridin-3-ylamino)-pyrazine-2-carboxylic acid (1-methyl-5-methylcarbamoyl-1H-pyrazol-4-yl)-amide

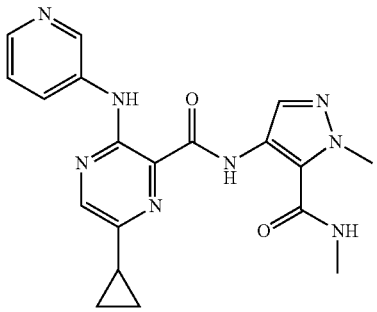 [SMILES: CNC(=O)c1c(NC(=O)c2nc(C3CC3)cnc2Nc2cccnc2)cnn1C]

Step 1: 6-Cyclopropyl-3-(pyridin-3-ylamino)pyrazine-2-carboxylic acid methyl ester The product was obtained starting from 3-amino-6-cyclopropylpyrazine-2-carboxylic acid methyl ester (200 mg, 1.04 mmol; intermediate A-10, step 2) and 3-bromopyridine (142 µl, 1.45 mmol) according to the method described in example A-1, step 2 as yellow solid (192 mg, 68%).
MS: M=271.4 (M+H)$^+$

Step 2: 6-Cyclopropyl-3-(pyridin-3-ylamino)pyrazine-2-carboxylic acid

The product was obtained starting from 6-cyclopropyl-3-(pyridin-3-ylamino)pyrazine-2-carboxylic acid methyl ester (192 mg, 0.71 mmol) according to the method described in example A-11 as off-white solid (162 mg, 89%).
MS: M=255.2 (M–H)$^-$ Step 3: 6-Cyclopropyl-3-(pyridin-3-ylamino)-pyrazine-2-carboxylic acid (1-methyl-5-methylcarbamoyl-1H-pyrazol-4-yl)-amide The product was obtained starting from 6-cyclopropyl-3-(pyridin-3-ylamino)pyrazine-2-carboxylic acid (30 mg, 0.12 mmol) and 4-amino-2-methyl-2H-pyrazole-3-carboxylic acid methylamide (23 mg, 0.15 mmol) according to the method described in example 64, step 6 as yellow solid (30 mg, 64%).

MS: M=393.2 (M+H)+

Example 218

5-{[6-Cyclopropyl-3-(pyrimidin-5-ylamino)-pyrazine-2-carbonyl]-amino}-pyrimidine-4-carboxylic acid methylamide

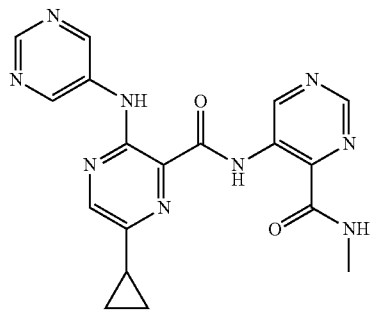 [SMILES: CNC(=O)c1ncncc1NC(=O)c1nc(C2CC2)cnc1Nc1cncnc1]

According to the procedures described in example 99, the product was obtained using 5-amino-pyrimidine-4-carboxylic acid methyl ester in the 1st step and methylamine hydrochloride in the last step. Yellow solid.

MS: M=390.0 (M−H)−

Example 219

6-Cyclopropyl-3-(pyrimidin-5-ylamino)-pyrazine-2-carboxylic acid [4-(pyrrolidine-1-carbonyl)-pyrimidin-5-yl]-amide

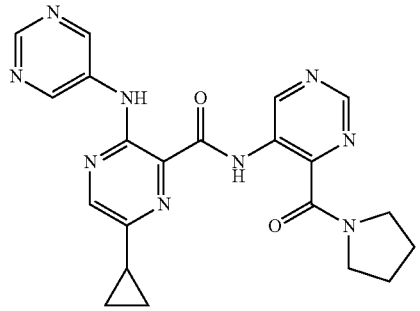 [SMILES: O=C(Nc1cncnc1C(=O)N1CCCC1)c1nc(C2CC2)cnc1Nc1cncnc1]

According to the procedures described in example 99, the product was obtained using 5-amino-pyrimidine-4-carboxylic acid methyl ester in the 1st step and pyrrolidine in the last step. Yellow solid.

MS: M=430.2 (M−H)−

Example 220

6-Cyclopropyl-3-(pyrimidin-5-ylamino)-pyrazine-2-carboxylic acid (2-ethylcarbamoyl-pyridin-3-yl)-amide

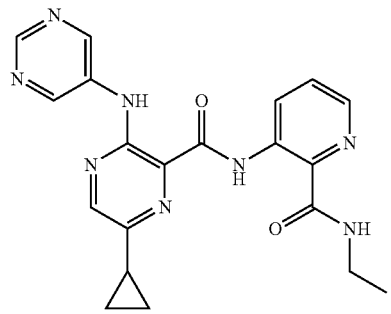 [SMILES: CCNC(=O)c1ncccc1NC(=O)c1nc(C2CC2)cnc1Nc1cncnc1]

According to the procedures described in example 97, the product was obtained using 3-aminopicolinic acid and ethylamine hydrochloride in the 1st step. Yellow solid.

MS: M=405.4 (M+H)+

Example 221

6-Cyclopropyl-3-(pyrimidin-5-ylamino)-pyrazine-2-carboxylic acid (2-isopropylcarbamoyl-pyridin-3-yl)-amide

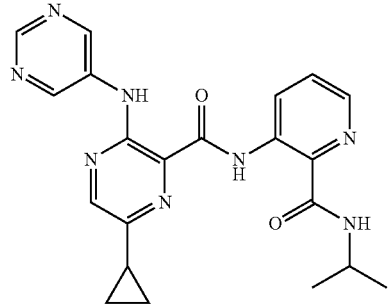 [SMILES: CC(C)NC(=O)c1ncccc1NC(=O)c1nc(C2CC2)cnc1Nc1cncnc1]

According to the procedures described in example 97, the product was obtained using 3-aminopicolinic acid and propane-2-amine in the 1st step. Yellow solid.

MS: M=419.4 (M+H)+

Example 222

6-Cyclopropyl-3-(pyrimidin-5-ylamino)-pyrazine-2-carboxylic acid (5-dipropylcarbamoyl-1-methyl-1H-pyrazol-4-yl)-amide

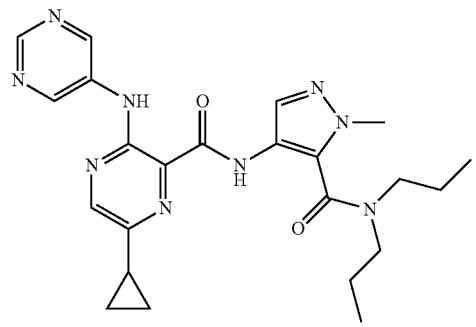 [SMILES: CCCN(CCC)C(=O)c1c(NC(=O)c2nc(C3CC3)cnc2Nc2cncnc2)cnn1C]

According to the procedures described in example 135, the title compound was obtained using dipropylamine in the last step. Yellow solid.

MS: M=464.4 (M+H)$^+$

Example 223

6-Cyclopropyl-3-(pyrimidin-5-ylamino)-pyrazine-2-carboxylic acid [5-(butyl-methyl-carbamoyl)-1-methyl-1H-pyrazol-4-yl]-amide

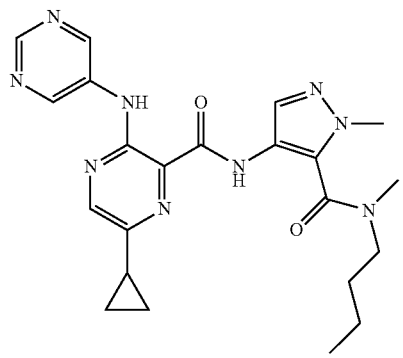 [SMILES: CCCCN(C)C(=O)c1c(NC(=O)c2nc(C3CC3)cnc2Nc2cncnc2)cnn1C]

According to the procedures described in example 135, the title compound was obtained using N-methylbutane-1-amine in the last step. Yellow solid.

MS: M=448.2 (M–H)$^-$

Example 224

6-Cyclopropyl-3-(pyrimidin-5-ylamino)-pyrazine-2-carboxylic acid (3-methyl-2-methylcarbamoyl-phenyl)-amide

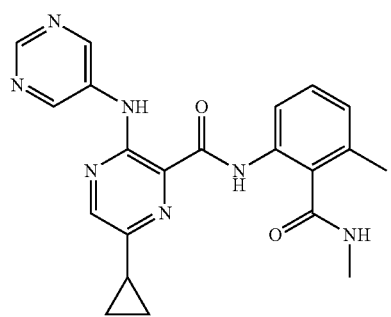 [SMILES: CNC(=O)c1c(C)cccc1NC(=O)c1nc(C2CC2)cnc1Nc1cncnc1]

According to the procedure described in step 6 of example 64, the title compound was obtained from intermediate A-11 and 2-amino-N,6-dimethylbenzamide. Yellow solid.

MS: M=404.3 (M+H)$^+$

Example 225

6-Cyclopropyl-3-(pyrimidin-5-ylamino)-pyrazine-2-carboxylic acid (4-methoxy-2-methylcarbamoyl-phenyl)-amide

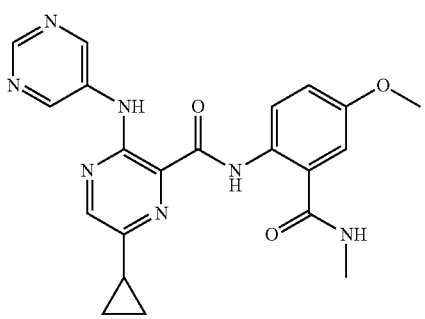 [SMILES: CNC(=O)c1cc(OC)ccc1NC(=O)c1nc(C2CC2)cnc1Nc1cncnc1]

According to the procedure described in step 6 of example 64, the title compound was obtained from intermediate A-11 and 2-amino-5-methoxy-N-methylbenzamide. Yellow solid.

MS: M=420.2 (M+H)$^+$

Example 226

6-Cyclopropyl-3-(pyrimidin-5-ylamino)-pyrazine-2-carboxylic acid [5-[(2-hydroxy-ethyl)-methyl-carbamoyl]-1-methyl-1H-pyrazol-4-yl]-amide

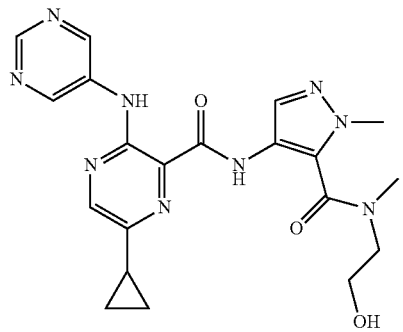 [SMILES: CN(CCO)C(=O)c1c(NC(=O)c2nc(C3CC3)cnc2Nc2cncnc2)cnn1C]

According to the procedures described in example 135, the title compound was obtained using 2-(methylamino)ethanol in the last step. Yellow solid.

MS: M=436.2 (M−H)⁻

Example 227

6-Cyclopropyl-3-(pyrimidin-5-ylamino)-pyrazine-2-carboxylic acid [5-(isopropyl-methyl-carbamoyl)-1-methyl-1H-pyrazol-4-yl]-amide

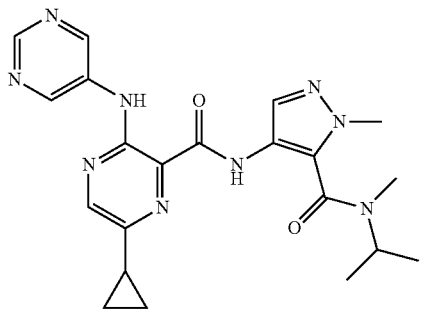 [SMILES: CC(C)N(C)C(=O)c1c(NC(=O)c2nc(C3CC3)cnc2Nc2cncnc2)cnn1C]

According to the procedures described in example 135, the title compound was obtained using N-methylpropan-2-amine in the last step. Yellow solid.

MS: M=434.3 (M−H)⁻

Example 228

6-Cyclopropyl-3-(pyrimidin-5-ylamino)-pyrazine-2-carboxylic acid (5-diethylcarbamoyl-1-methyl-1H-pyrazol-4-yl)-amide

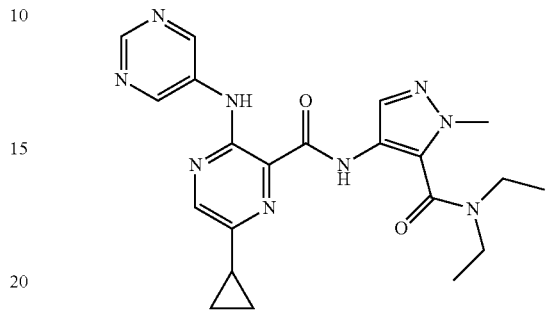

According to the procedures described in example 135, the title compound was obtained using diethylamine in the last step. Yellow solid.

MS: M=434.3 (M−H)⁻

Example 229

6-Cyclopropyl-3-(pyrimidin-5-ylamino)-pyrazine-2-carboxylic acid [1-methyl-5-(methyl-propyl-carbamoyl)-1H-pyrazol-4-yl]-amide

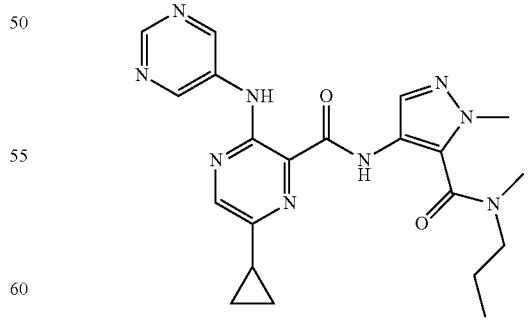

According to the procedures described in example 135, the title compound was obtained using N-methylpropan-1-amine in the last step. Yellow solid.

MS: M=434.3 (M−H)⁻

Example 230

6-Cyclopropyl-3-(pyrimidin-5-ylamino)-pyrazine-2-carboxylic acid {5-[ethyl-(2-hydroxy-ethyl)-carbamoyl]-1-methyl-1H-pyrazol-4-yl}-amide

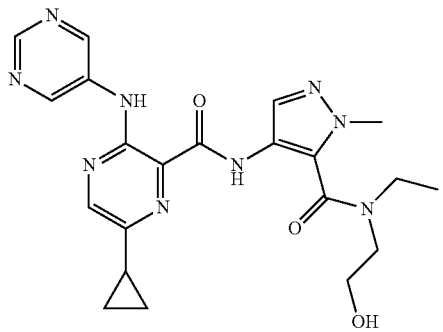 [SMILES: CCN(CCO)C(=O)c1c(NC(=O)c2nc(C3CC3)cnc2Nc2cncnc2)cnn1C]

According to the procedures described in example 135, the title compound was obtained using 2-(ethylamino)ethanol in the last step. Yellow solid.

MS: M=450.2 (M–H)⁻

Example 231

6-Cyclopropyl-3-(pyrimidin-5-ylamino)-pyrazine-2-carboxylic acid {1-methyl-5-[methyl-(tetrahydro-pyran-4-yl)-carbamoyl]-1H-pyrazol-4-yl}-amide

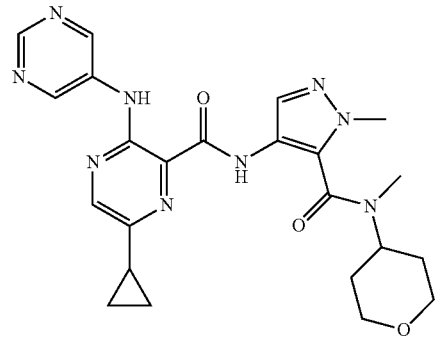 [SMILES: CN(C(=O)c1c(NC(=O)c2nc(C3CC3)cnc2Nc2cncnc2)cnn1C)C1CCOCC1]

According to the procedures described in example 135, the title compound was obtained using N-methyltetrahydro-2H-pyran-4-amine hydrochloride in the last step. Yellow solid.

MS: M=476.1 (M–H)⁻

Example 232

6-Cyclopropyl-3-(pyrimidin-5-ylamino)-pyrazine-2-carboxylic acid {1-methyl-5-[(tetrahydro-furan-2-ylmethyl)-carbamoyl]-1H-pyrazol-4-yl}-amide

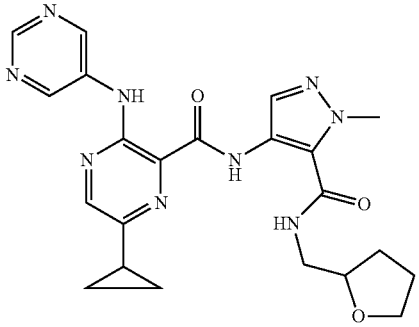 [SMILES: Cn1ncc(NC(=O)c2nc(C3CC3)cnc2Nc2cncnc2)c1C(=O)NCC1CCCO1]

The product was obtained starting from intermediate A-11 (30 mg, 0.12 mmol) and 4-amino-1-methyl-N-((tetrahydro-furan-2-yl)methyl)-1H-pyrazole-5-carboxamide (34 mg, 0.15 mmol) according to the method described in example 64, step 6 as yellow solid (24 mg, 44%).

MS: M=464.4 (M+H)⁺

Example 233

6-Cyclopropyl-3-(pyrimidin-5-ylamino)-pyrazine-2-carboxylic acid {1-ethyl-5-[(tetrahydro-furan-2-ylmethyl)-carbamoyl]-1H-pyrazol-4-yl}-amide

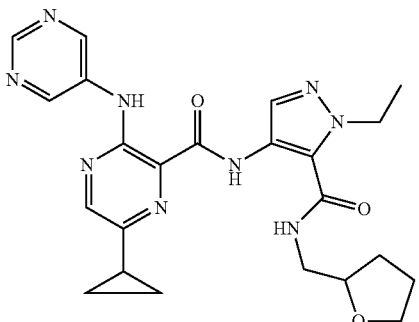

The product was obtained starting from intermediate A-11 (30 mg, 0.12 mmol) and 4-amino-1-ethyl-N-((tetrahydrofuran-2-yl)methyl)-1H-pyrazole-5-carboxamide (36 mg, 0.15 mmol) according to the method described in example 64, step 6 as yellow solid (37 mg, 66%).

MS: M=478.3 (M+H)⁺

Example 234

6-Cyclopropyl-3-(pyridin-3-ylamino)-pyrazine-2-carboxylic acid [5-(azetidine-1-carbonyl)-1-methyl-1H-pyrazol-4-yl]-amide

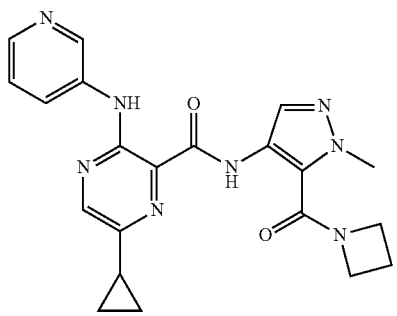 [SMILES: Cn1ncc(NC(=O)c2nc(C3CC3)cnc2Nc2cccnc2)c1C(=O)N1CCC1]

Step 1: Azetidin-1-yl(2-methyl-4-nitro-2H-pyrazol-3-yl)methanone

To a suspension of 2-methyl-4-nitro-2H-pyrazole-3-carboxylic acid (300 mg, 1.75 mmol), azetidine (354 µl, 5.25 mmol) and diisopropylethylamine (920 µl, 5.26 mmol) in ethyl acetate (7.5 ml) was added 1-propanephosphonic acid cyclic anhydride (3.68 ml, 6.13 mmol; 50% in ethyl acetate) at 0° C. The ice bath was removed and stirring at r.t. was continued for 40 h. The reaction mixture was poured into ethyl acetate (100 ml) and extracted with sodium bicarbonate (saturated aqueous solution) water and brine. The aqueous layer was back-extracted with ethyl acetate, the combined organic phases were dried, evaporated, and the product was purified by silica gel chromatography using an amine phase and a heptane/ethyl acetate gradient to yield a white solid (269 mg, 73%).

MS: M=211.1 (M+H)$^+$

Step 2: (4-Amino-2-methyl-2H-pyrazol-3-yl)-azetidin-1-yl-methanone

To a solution of azetidin-1-yl-(2-methyl-4-nitro-2H-pyrazol-3-yl)methanone (268 mg, 1.28 mmol) in ethanol (4.5 ml) was added Pd/C 10% (72 mg, 67.7 µmol) and the reaction mixture was stirred at r.t. under a hydrogen atmosphere for 6 h. The reaction mixture was filtered and concentrated in vacuo and the off-white solid was used without further purification in the next step.

MS: M=181.1 (M+H)$^+$

Step 3: 6-Cyclopropyl-3-(pyridin-3-ylamino)-pyrazine-2-carboxylic acid [5-(azetidine-1-carbonyl)-1-methyl-1H-pyrazol-4-yl]-amide The product was obtained starting from 6-cyclopropyl-3-(pyridin-3-ylamino)pyrazine-2-carboxylic acid (30 mg, 0.12 mmol; example 217, step 2) and (4-amino-2-methyl-2H-pyrazol-3-yl)-azetidin-1-yl-methanone (27 mg, 0.15 mmol) according to the method described in example 64, step 6 after purification by preparative HPLC using an acetonitrile/water gradient as light yellow solid (37 mg, 75%).

MS: M=419.3 (M+H)$^+$

Example 235

6-Cyclopropyl-3-(pyrimidin-5-ylamino)-pyrazine-2-carboxylic acid [1-methyl-5-(2-methyl-piperidine-1-carbonyl)-1H-pyrazol-4-yl]-amide

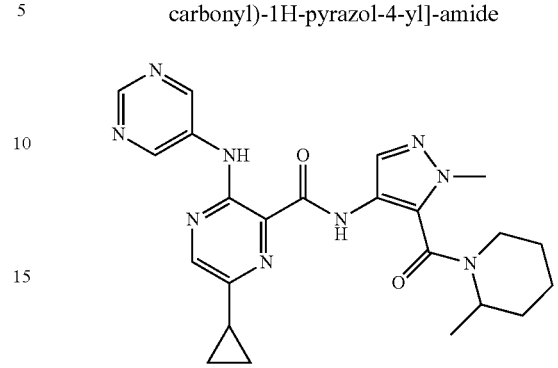

According to the procedures described in example 135, the title compound was obtained using 2-methylpiperidine in the last step. Yellow solid.

MS: M=460.4 (M−H)$^−$

Example 236

3-[(4-{[6-Cyclopropyl-3-(pyrimidin-5-ylamino)-pyrazine-2-carbonyl]-amino}-2-methyl-2H-pyrazole-3-carbonyl)-amino]-pyrrolidine-1-carboxylic acid tert-butyl ester

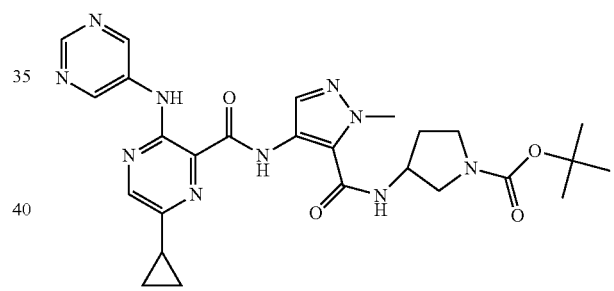

Step 1: 4-Amino-2-methyl-2H-pyrazole-3-carboxylic acid ethyl ester

To a solution of 2-methyl-4-nitro-2H-pyrazole-3-carboxylic acid ethyl ester (1.97 g, 9.89 mmol; prepared from 2-methyl-4-nitro-2H-pyrazole-3-carboxylic acid according to WO 2009/026241) in EtOH (20 ml) under argon atmosphere was added 10% Pd/C (200 mg). The black suspension was stirred at r.t. under a hydrogen atmosphere for 20 h. The catalyst was filtered off and washed with EtOH. The product was obtained upon evaporation as light brown oil (1.63 g, 97%) and used without further purification.

MS: M=170.2 (M+H)$^+$

Step 2: 4-{[6-Cyclopropyl-3-(pyrimidin-5-ylamino)-pyrazine-2-carbonyl]-amino}-2-methyl-2H-pyrazole-3-carboxylic acid ethyl ester The product was obtained starting from intermediate A-11 (950 mg, 3.69 mmol) and 4-amino-2-methyl-2H-pyrazole-3-carboxylic acid ethyl ester (625 mg, 3.69 mmol) according to the method described in example 64, step 6 after purification by silica gel chromatography using a dichloromethane/methanol gradient as yellow solid (1.24 g, 82%)

MS: M=407.2 (M−H)⁻

Step 3: 4-{[6-Cyclopropyl-3-(pyrimidin-5-ylamino)-pyrazine-2-carbonyl]-amino}-2-methyl-2H-pyrazole-3-carboxylic acid To a suspension of 4-{[6-cyclopropyl-3-(pyrimidin-5-ylamino)-pyrazine-2-carbonyl]-amino}-2-methyl-2H-pyrazole-3-carboxylic acid ethyl ester (1.13 g, 2.77 mmol) in ethanol (15 ml) and water (12 ml) was added 1N NaOH (3.32 ml) at r.t. under argon atmosphere. The yellow suspension was stirred at 85° C. for 1 h. After cooling down to r.t., the mixture was treated with 1M HCl (3.3 ml) and stirred for 30 min. The product was collected by filtration, washed with water and EtOH, and dried to yield a light yellow solid (1.0 g, 95%).

MS: M=381.4 (M+H)⁺

Step 4: 3-[(4-{[6-Cyclopropyl-3-(pyrimidin-5-ylamino)-pyrazine-2-carbonyl]-amino}-2-methyl-2H-pyrazole-3-carbonyl)-amino]-pyrrolidine-1-carboxylic acid tert-butyl ester The product was obtained starting from 4-{[6-cyclopropyl-3-(pyrimidin-5-ylamino)-pyrazine-2-carbonyl]-amino}-2-methyl-2H-pyrazole-3-carboxylic acid (30 mg, 79 µmol) and tert-butyl-3-aminopyrrolidine-1-carboxylate hydrochloride (23 mg, 103 µmol) according to the method described in example 64, step 6 after purification by preparative HPLC using an acetonitrile/water gradient as yellow solid (28 mg, 65%).

MS: M=549.5 (M+H)⁺

Example 237

6-Cyclopropyl-3-(pyrimidin-5-ylamino)-pyrazine-2-carboxylic acid {1-methyl-5-[methyl-(2,2,2-trifluoro-ethyl)-carbamoyl]-1H-pyrazol-4-yl}-amide

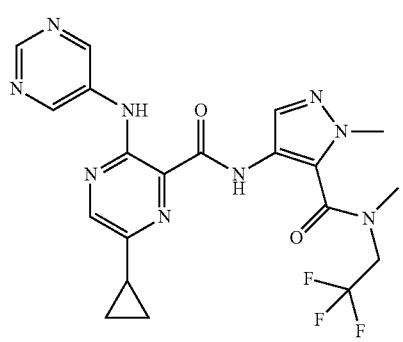 [SMILES: CN(CC(F)(F)F)C(=O)c1c(NC(=O)c2nc(C3CC3)cnc2Nc2cncnc2)cnn1C]

According to the procedures described in example 135, the title compound was obtained using 2,2,2-trifluoro-N-methyl-ethanamine hydrochloride in the last step. Yellow solid.

MS: M=474.2 (M−H)⁻

Example 238

6-Cyclopropyl-3-(pyrimidin-5-ylamino)-pyrazine-2-carboxylic acid [5-(cyclopropyl-methyl-carbamoyl)-1-methyl-1H-pyrazol-4-yl]-amide

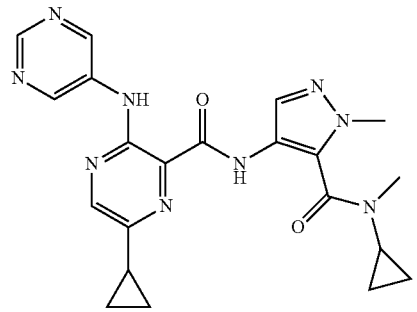 [SMILES: CN(C(=O)c1c(NC(=O)c2nc(C3CC3)cnc2Nc2cncnc2)cnn1C)C1CC1]

According to the procedures described in example 135, the title compound was obtained using N-methylcyclopropanamine oxalate in the last step. Yellow solid.

MS: M=432.2 (M−H)⁻

Example 239

6-Cyclopropyl-3-(pyrimidin-5-ylamino)-pyrazine-2-carboxylic acid [1-methyl-5-(2-methyl-pyrrolidine-1-carbonyl)-1H-pyrazol-4-yl]-amide

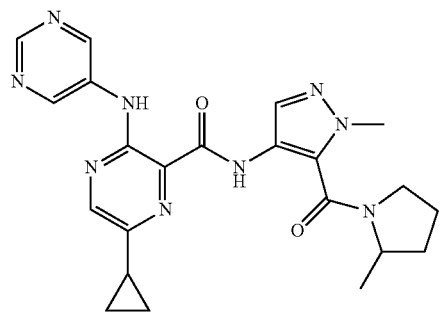 [SMILES: CC1CCCN1C(=O)c1c(NC(=O)c2nc(C3CC3)cnc2Nc2cncnc2)cnn1C]

According to the procedures described in example 135, the title compound was obtained using 2-methylpyrrolidine in the last step. Yellow solid.

MS: M=446.2 (M−H)⁻

Example 240

6-Cyclopropyl-3-(pyrimidin-5-ylamino)-pyrazine-2-carboxylic acid [1-methyl-5-(methyl-oxetan-3-yl-carbamoyl)-1H-pyrazol-4-yl]-amide

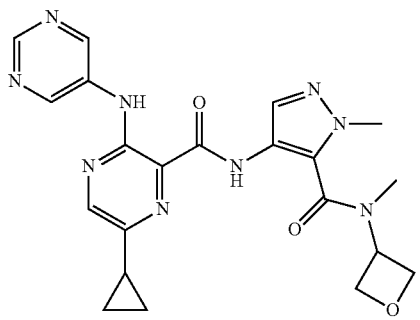 [SMILES: CN(C(=O)c1c(NC(=O)c2nc(C3CC3)cnc2Nc2cncnc2)cnn1C)C1COC1]

According to the procedures described in example 135, the title compound was obtained using N-methyl-3-oxetanamine phosphate in the last step. Yellow solid.

MS: M=448.3 (M−H)⁻

Example 241

6-Cyclopropyl-3-(pyrimidin-5-ylamino)-pyrazine-2-carboxylic acid [1-methyl-5-(1-methyl-piperidin-3-ylcarbamoyl)-1H-pyrazol-4-yl]-amide

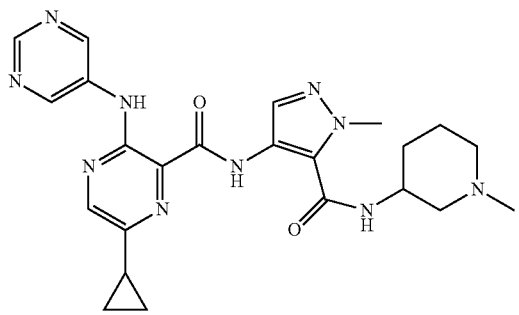 [SMILES: CN1CCCC(NC(=O)c2c(NC(=O)c3nc(C4CC4)cnc3Nc3cncnc3)cnn2C)C1]

The product was obtained starting from 4-{[6-cyclopropyl-3-(pyrimidin-5-ylamino)-pyrazine-2-carbonyl]-amino}-2-methyl-2H-pyrazole-3-carboxylic acid (25 mg, 66 µmol; example 236, step 3) and 1-methyl-piperidin-3-ylamine dihydrochloride (12 mg, 66 µmol) according to the method described in example 64, step 6 after purification by preparative HPLC using an acetonitrile/water gradient as yellow solid (11 mg, 33%).

MS: M=477.3 (M+H)⁺

Example 242

6-Cyclopropyl-3-(pyrimidin-5-ylamino)-pyrazine-2-carboxylic acid [1-methyl-5-(1-methyl-piperidin-4-ylcarbamoyl)-1H-pyrazol-4-yl]-amide

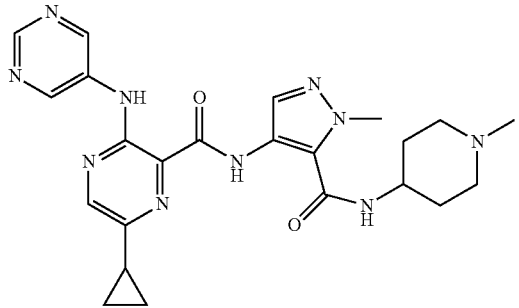 [SMILES: CN1CCC(NC(=O)c2c(NC(=O)c3nc(C4CC4)cnc3Nc3cncnc3)cnn2C)CC1]

The product was obtained starting from 4-{[6-cyclopropyl-3-(pyrimidin-5-ylamino)-pyrazine-2-carbonyl]-amino}-2-methyl-2H-pyrazole-3-carboxylic acid (25 mg, 66 µmol; example 236, step 3) and 1-methyl-piperidin-4-ylamine (10 mg, 85 pimp according to the method described in example 64, step 6 after purification by preparative HPLC using an acetonitrile/water gradient as yellow solid (17 mg, 50%).

MS: M=477.2 (M+H)⁺

Example 243

6-Cyclopropyl-3-(pyrimidin-5-ylamino)-pyrazine-2-carboxylic acid [5-methylcarbamoyl-1-(tetrahydro-furan-2-ylmethyl)-1H-pyrazol-4-yl]-amide

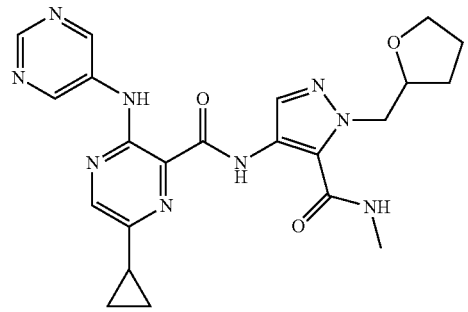

According to the procedures described in example 132, the title compound was obtained using 2-iodomethyl-tetrahydrofuran in the 1$^{st}$ step and methylamine hydrochloride in the last step. Yellow solid.

MS: M=462.3 (M−H)⁻

Example 244

6-Cyclopropyl-3-(pyrimidin-5-ylamino)-pyrazine-2-carboxylic acid [5-(2-hydroxy-2-methyl-propylcarbamoyl)-1-(tetrahydro-furan-2-ylmethyl)-1H-pyrazol-4-yl]-amide

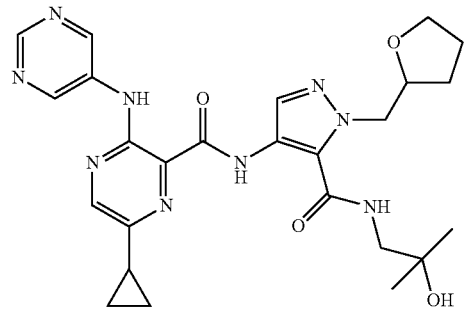 [SMILES: CC(C)(O)CNC(=O)c1c(NC(=O)c2nc(C3CC3)cnc2Nc2cncnc2)cnn1CC1CCCO1]

According to the procedures described in example 132, the title compound was obtained using 2-iodomethyl-tetrahydrofuran in the 1$^{st}$ step and 1-amino-2-methylpropan-2-ol in the last step. Yellow solid.

MS: M=520.3 (M−H)⁻

Example 245

6-Cyclopropyl-3-(pyrimidin-5-ylamino)-pyrazine-2-carboxylic acid {5-[(2-fluoro-ethyl)-methyl-carbamoyl]-1-methyl-1H-pyrazol-4-yl}-amide

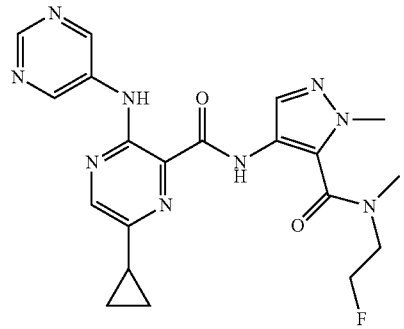 [SMILES: CN(CCF)C(=O)c1c(NC(=O)c2nc(C3CC3)cnc2Nc2cncnc2)cnn1C]

According to the procedures described in example 135, the title compound was obtained using 2-fluoro-N-methylethanamine hydrochloride in the last step. Yellow solid.

MS: M=438.2 (M–H)⁻

Example 246

6-Cyclopropyl-3-(pyrimidin-5-ylamino)-pyrazine-2-carboxylic acid {2-[methyl-(tetrahydro-pyran-4-yl)-carbamoyl]-pyridin-3-yl}-amide

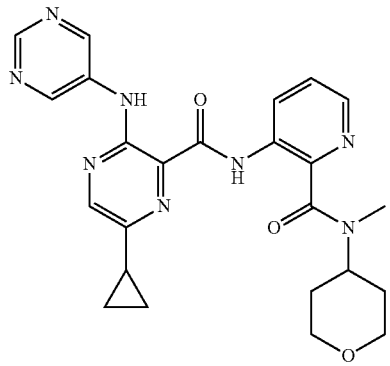 [SMILES: CN(C(=O)c1ncccc1NC(=O)c1nc(C2CC2)cnc1Nc1cncnc1)C1CCOCC1]

According to the procedures described in example 97, the title compounds was obtained using 3-aminopicolinic acid and N-methyltetrahydro-2H-pyran-4-amine hydrochloride in the first step. Yellow solid.

MS: M=236.2 (M+H)⁺

Example 247

6-Cyclopropyl-3-(pyrimidin-5-ylamino)-pyrazine-2-carboxylic acid {1-methyl-5-[methyl-(1-methyl-pyrrolidin-3-yl)-carbamoyl]-1H-pyrazol-4-yl}-amide

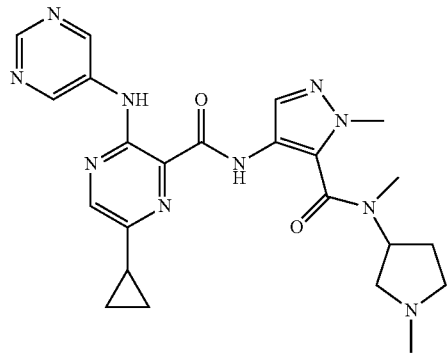 [SMILES: CN1CCC(N(C)C(=O)c2c(NC(=O)c3nc(C4CC4)cnc3Nc3cncnc3)cnn2C)C1]

The product was obtained starting from 4-{[6-cyclopropyl-3-(pyrimidin-5-ylamino)-pyrazine-2-carbonyl]-amino}-2-methyl-2H-pyrazole-3-carboxylic acid (25 mg, 66 µmol; example 236, step 3) and N,1-dimethyl-pyrrolidin-3-ylamine (10 mg, 85 µmol) according to the method described in example 64, step 6 after purification by preparative HPLC using an acetonitrile/water gradient as yellow solid (12 mg, 35%).

MS: M=477.3 (M+H)⁺

Example 248

6-Cyclopropyl-3-(pyrimidin-5-ylamino)-pyrazine-2-carboxylic acid {2-[methyl-(2,2,2-trifluoro-ethyl)-carbamoyl]-pyridin-3-yl}-amide

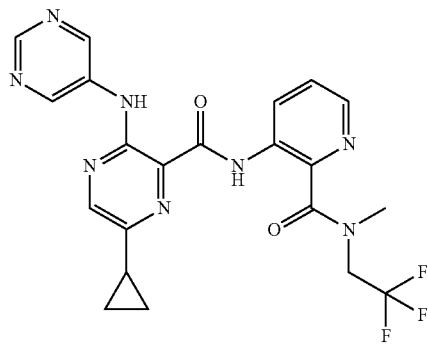 [SMILES: CN(CC(F)(F)F)C(=O)c1ncccc1NC(=O)c1nc(C2CC2)cnc1Nc1cncnc1]

According to the procedures described in example 97, the title compounds was obtained using 3-aminopicolinic acid and 2,2,2-trifluoro-N-methylethanamine hydrochloride in the first step. Yellow solid.

MS: M=234.1 (M+H)⁺

Example 249

6-Cyclopropyl-3-(pyrimidin-5-ylamino)-pyrazine-2-carboxylic acid [2-(cyclopropyl-methyl-carbamoyl)-pyridin-3-yl]-amide

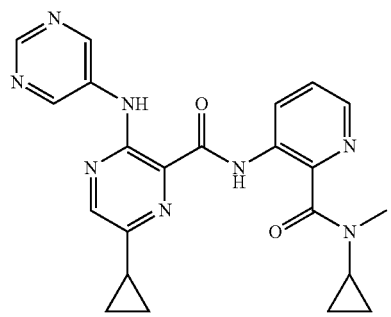 [SMILES: CN(C(=O)c1ncccc1NC(=O)c1nc(C2CC2)cnc1Nc1cncnc1)C1CC1]

According to the procedures described in example 97, the title compounds was obtained using 3-aminopicolinic acid and N-methylcyclopropanamine oxalate in the first step. Yellow solid.

MS: M=234.1 (M+H)⁺

Example 250

6-Cyclopropyl-3-(pyrimidin-5-ylamino)-pyrazine-2-carboxylic acid [5-methylcarbamoyl-1-(tetrahydrofuran-3-yl)-1H-pyrazol-4-yl]-amide

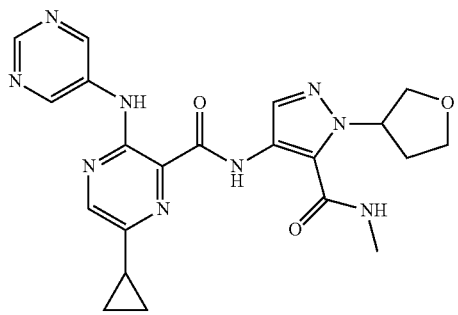 [SMILES: CNC(=O)c1c(NC(=O)c2nc(C3CC3)cnc2Nc2cncnc2)cnn1C1CCOC1]

According to the procedures described in example 132, the title compound was obtained using tetrahydrofuran-3-yl trifluoromethanesulfonate in the 1$^{st}$ step and methylamine hydrochloride in the last step. Yellow solid.
MS: M=448.2 (M–H)$^-$

Example 251

6-Cyclopropyl-3-(pyrimidin-5-ylamino)-pyrazine-2-carboxylic acid [1-methyl-5-(pyrrolidin-3-ylcarbamoyl)-1H-pyrazol-4-yl]-amide

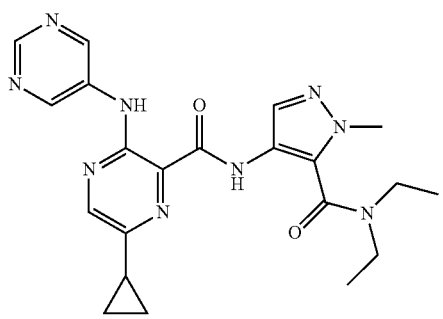 [SMILES: CCN(CC)C(=O)c1c(NC(=O)c2nc(C3CC3)cnc2Nc2cncnc2)cnn1C]

A solution of 3-[(4-{[6-cyclopropyl-3-(pyrimidin-5-ylamino)-pyrazine-2-carbonyl]-amino}-2-methyl-2H-pyrazole-3-carbonyl)-amino]-pyrrolidine-1-carboxylic acid tert-butyl ester (38 mg, 69 µmol; example 236) in 1,4-dioxane (0.38 ml) was treated with HCl in dioxane (4M; 380 µl, 1.5 mmol) and the reaction mixture was stirred at r.t. for 4 h. The precipitate was filtered off and dried to yield the product as yellow solid (25 mg, 75%).
MS: M=449.3 (M+H)$^+$

Example 252

6-Cyclopropyl-3-(pyrimidin-5-ylamino)-pyrazine-2-carboxylic acid [2-(2-methyl-pyrrolidine-1-carbonyl)-pyridin-3-yl]-amide

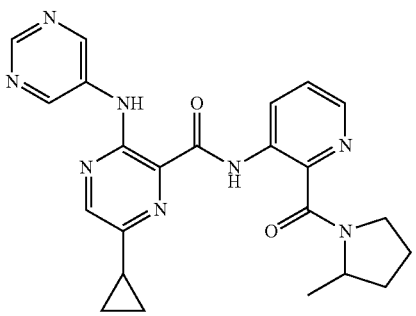 [SMILES: CC1CCCN1C(=O)c1ncccc1NC(=O)c1nc(C2CC2)cnc1Nc1cncnc1]

According to the procedures described in example 97, the title compounds was obtained using 3-aminopicolinic acid and 2-methylpyrrolidine in the first step. Yellow solid.
MS: M=445.4 (M+H)$^+$

Example 253

6-Cyclopropyl-3-(pyrimidin-5-ylamino)-pyrazine-2-carboxylic acid [2-(2-methyl-piperidine-1-carbonyl)-pyridin-3-yl]-amide

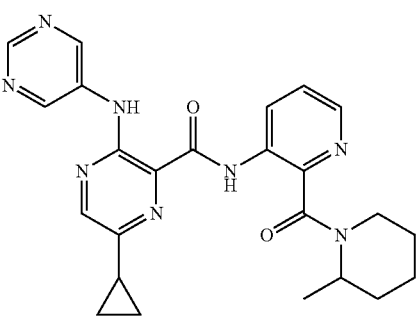 [SMILES: CC1CCCCN1C(=O)c1ncccc1NC(=O)c1nc(C2CC2)cnc1Nc1cncnc1]

According to the procedures described in example 97, the title compounds was obtained using 3-aminopicolinic acid and 2-methylpiperidine in the first step. Yellow solid.
MS: M=449.4 (M+H)+

Example 254

6-Cyclopropyl-3-(pyrimidin-5-ylamino)-pyrazine-2-carboxylic acid [2-(3-methyl-morpholine-4-carbonyl)-pyridin-3-yl]-amide

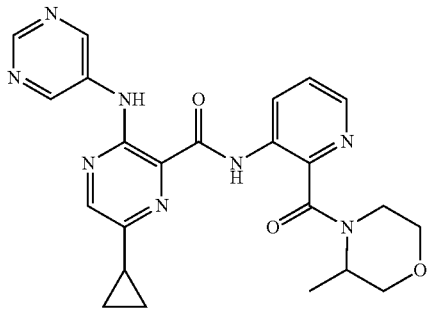 [SMILES: CC1COCCN1C(=O)c1ncccc1NC(=O)c1nc(C2CC2)cnc1Nc1cncnc1]

According to the procedures described in example 97, the title compounds was obtained using 3-aminopicolinic acid and 3-methylmorpholine in the first step. Yellow solid.

MS: M=461.4 (M+H)$^+$

Example 255

6-Cyclopropyl-3-(pyrimidin-5-ylamino)-pyrazine-2-carboxylic acid (1-methyl-5-{[(S)-1-(tetrahydrofuran-2-yl)methyl]-carbamoyl}-1H-pyrazol-4-yl)-amide

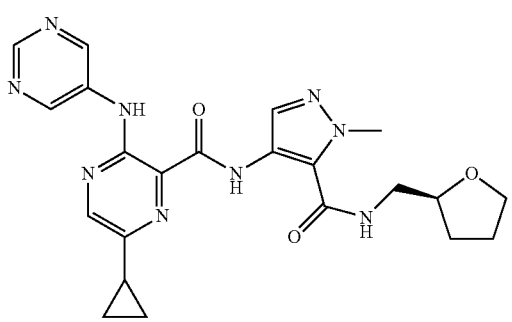 [SMILES: Cn1ncc(NC(=O)c2nc(C3CC3)cnc2Nc2cncnc2)c1C(=O)NC[C@@H]1CCCO1]

The product was obtained starting from 4-{[6-cyclopropyl-3-(pyrimidin-5-ylamino)-pyrazine-2-carbonyl]-amino}-2-methyl-2H-pyrazole-3-carboxylic acid (30 mg, 79 µmol; example 236, step 3) and (S)-(tetrahydrofuran-2-yl)methanamine (15 µl, 142 µmol) according to the method described in example 64, step 6 after purification by preparative HPLC using an acetonitrile/water gradient as yellow solid (31 mg, 84%).

MS: M=464.3 (M+H)$^+$

Example 256

6-Cyclopropyl-3-(pyrimidin-5-ylamino)-pyrazine-2-carboxylic acid (1-methyl-5-{[(R)-1-(tetrahydrofuran-2-yl)methyl]-carbamoyl}-1H-pyrazol-4-yl)-amide

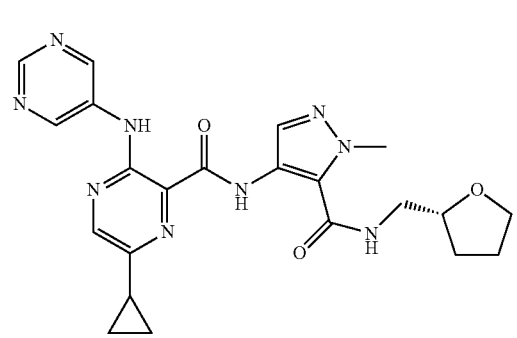 [SMILES: Cn1ncc(NC(=O)c2nc(C3CC3)cnc2Nc2cncnc2)c1C(=O)NC[C@H]1CCCO1]

The product was obtained starting from 4-{[6-cyclopropyl-3-(pyrimidin-5-ylamino)-pyrazine-2-carbonyl]-amino}-2-methyl-2H-pyrazole-3-carboxylic acid (30 mg, 79 µmol; example 236, step 3) and (R)-(tetrahydrofuran-2-yl)methanamine (15 µl, 142 µmol) according to the method described in example 64, step 6 after purification by preparative HPLC using an acetonitrile/water gradient as yellow solid (35 mg, 96%).

MS: M=464.3 (M+H)$^+$

Example 257

6-Cyclopropyl-3-(pyrimidin-5-ylamino)-pyrazine-2-carboxylic acid {1-methyl-5-[methyl-(tetrahydrofuran-2-ylmethyl)-carbamoyl]-1H-pyrazol-4-yl}-amide

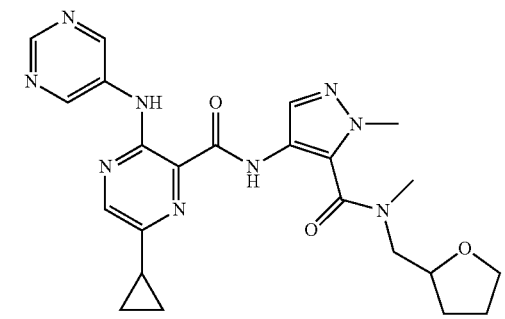 [SMILES: CN(CC1CCCO1)C(=O)c1c(NC(=O)c2nc(C3CC3)cnc2Nc2cncnc2)cnn1C]

According to the procedures described in example 135, the title compound was obtained using N-methyl-1-(tetrahydrofuran-2-yl)methanamine in the last step. Yellow solid.

MS: M=476.2 (M–H)$^-$

Example 258

6-Methoxy-3-(pyrimidin-5-ylamino)-pyrazine-2-carboxylic acid (1-methyl-5-methylcarbamoyl-1H-pyrazol-4-yl)-amide

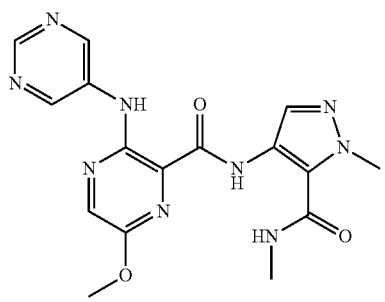 [SMILES: CNC(=O)c1c(NC(=O)c2nc(OC)cnc2Nc2cncnc2)cnn1C]

Step 1: Methyl 3-(bis(tert-butoxycarbonyl)amino)-6-methoxypyrazine-2-carboxylate To a solution of methyl 3-(bis(tert-butoxycarbonyl)amino)-6-bromopyrazine-2-carboxylate (500 mg, 1.16 mmol; example A-10, step 1) in MeOH (10 ml) was added sodium methoxide (30%; 280 µl, 1.5 mmol) at room temperature and stirring was continued at r.t. for 2 h. The reaction mixture was poured into ethyl acetate (75 ml) and extracted with potassium hydrogen sulfate (10%). The organic phase was washed with water and brine and the aqueous layers were back-extracted with ethyl acetate. The organic layers were dried and evaporated and the product was obtained after purification by silica gel chromatography using a heptane/ethyl acetate gradient as colorless solid (320 mg, 71%).

MS: M=284.1 (M-Boc+H)$^+$

Step 2: 3-Amino-6-methoxypyrazine-2-carboxylic acid methyl ester

The product was obtained starting from methyl 3-(bis(tert-butoxycarbonyl)amino)-6-methoxypyrazine-2-carboxylate (140 mg, 0.36 mmol) according to the method described in example A-12, step 3 without chromatographic purification as yellow solid (65 mg, 97%).

MS: M=184.1 (M+H)$^+$

Step 3: 6-Methoxy-3-(pyrimidin-5-ylamino)-pyrazine-2-carboxylic acid methyl ester A mixture of 3-amino-6-methoxypyrazine-2-carboxylic acid methyl ester (65 mg, 355 mmol), 5-bromopyrimidine (84.6 mg, 532 µmol) and cesium carbonate (162 mg, 497 µmol) in dioxane (1.5 ml) was treated with tris(dibenzylideneacetone)dipalladium(0)-chloroform adduct (36.7 mg, 35.5 µmol) and xantphos (67.8 mg, 117 µmol) under argon atmosphere and the reaction mixture was stirred at 110° C. for 16 h. After cooling down to ambient temperature, the reaction mixture was diluted with acetonitrile/water. The precipitated solid was sucked off, washed with acetonitrile/water, THF and MeOH and dried to yield the product as yellow solid (57 mg, 55.3%).

MS: M=262.2 (M+H)$^+$

Step 4: 6-Methoxy-3-(pyrimidin-5-ylamino)-pyrazine-2-carboxylic acid

The product was obtained starting from 6-methoxy-3-(pyrimidin-5-ylamino)-pyrazine-2-carboxylic acid methyl ester (55 mg, 0.19 mmol) according to the method described in example A-11 as yellow solid (52 mg, 99%).

MS: M=246.3 (M–H)$^-$

Step 5: 6-Methoxy-3-(pyrimidin-5-ylamino)-pyrazine-2-carboxylic acid (1-methyl-5-methylcarbamoyl-1H-pyrazol-4-yl)-amide The product was obtained starting from 6-methoxy-3-(pyrimidin-5-ylamino)-pyrazine-2-carboxylic acid (50 mg, 0.18 mmol) and 4-amino-2-methyl-2H-pyrazole-3-carboxylic acid methylamide (36 mg, 0.23 mmol) according to the method described in example 64, step 6 after purification by preparative HPLC using an acetonitrile/water gradient as yellow solid (16 mg, 22%).

MS: M=384.2 (M+H)$^+$

Example 259

6-Cyclopropyl-3-(pyrimidin-5-ylamino)-pyrazine-2-carboxylic acid (6-chloro-4-methylcarbamoyl-pyridin-3-yl)-amide

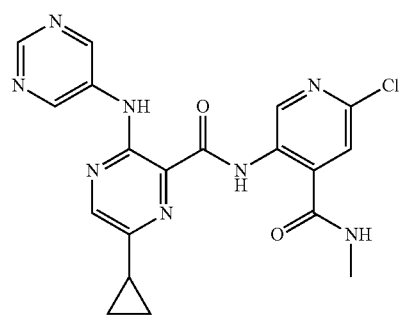 [SMILES: CNC(=O)c1cc(Cl)ncc1NC(=O)c1nc(C2CC2)cnc1Nc1cncnc1]

According to the procedures described in example 97, the title compound was obtained using 5-amino-2-chloroisonicotinic acid and methylamine hydrochloride in the 1$^{st}$ step. Yellow solid.

MS: M=423.0 (M–H)$^-$

Example 260

6-Cyclopropyl-3-(pyrimidin-5-ylamino)-pyrazine-2-carboxylic acid [6-chloro-4-(2-hydroxy-2-methyl-propylcarbamoyl)-pyridin-3-yl]-amide

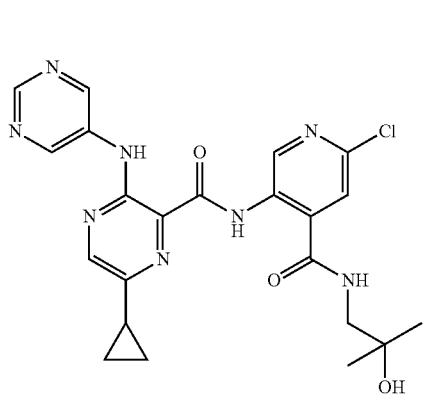 [SMILES: CC(C)(O)CNC(=O)c1cc(Cl)ncc1NC(=O)c1nc(C2CC2)cnc1Nc1cncnc1]

According to the procedures described in example 97, the title compound was obtained using 5-amino-2-chloroisonicotinic acid and 1-amino-2-methyl-propan-2-ol in the $1^{st}$ step. Yellow solid.

MS: M=481.1 (M–H)⁻

Example 261

6-Cyclopropyl-3-(pyrimidin-5-ylamino)-pyrazine-2-carboxylic acid (4-cyano-2-methylcarbamoyl-phenyl)-amide

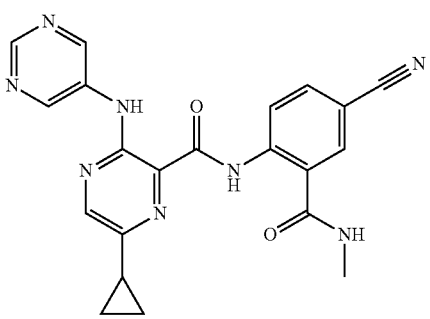 [SMILES: CNC(=O)c1cc(C#N)ccc1NC(=O)c1nc(C2CC2)cnc1Nc1cncnc1]

According to the procedures described in example 97, the title compound was obtained using 2-amino-5-cyano-benzoic acid and methylamine hydrochloride in the $1^{st}$ step. Yellow solid.

MS: M=413.1 (M–H)⁻

Example 262

6-Cyclopropyl-3-(pyrimidin-5-ylamino)-pyrazine-2-carboxylic acid [4-cyano-2-(2-hydroxy-2-methyl-propylcarbamoyl)-phenyl]-amide

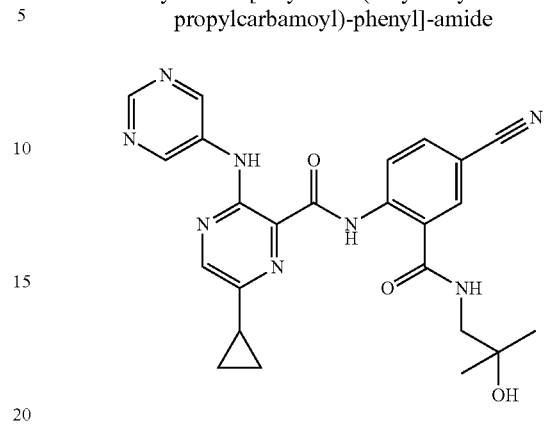

According to the procedures described in example 97, the title compound was obtained using 2-amino-5-cyano-benzoic acid and 1-amino-2-methyl-propan-2-ol in the $1^{st}$ step. Yellow solid.

MS: M=481.1 (M–H)⁻

Example 263

6-Cyclopropyl-3-(pyrimidin-5-ylamino)-pyrazine-2-carboxylic acid (3,4-dimethyl-2-methylcarbamoyl-phenyl)-amide

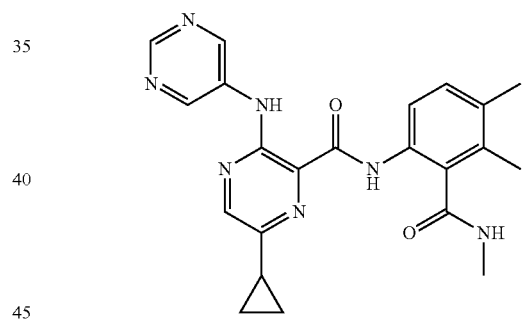

Step 1: Methyl 6-(6-cyclopropyl-3-(pyrimidin-5-ylamino)pyrazine-2-carboxamido)-2,3-dimethylbenzoate According to the procedure described in step 6 of example 64, the title compound was obtained from A-11 and methyl 6-amino-2,3-dimethylbenzoate. Yellow solid.

MS: M=419.3 (M+H)⁺⁻

Step 2: 6-{[6-Cyclopropyl-3-(pyrimidin-5-ylamino)-pyrazine-2-carbonyl]-amino}-2,3-dimethyl-benzoic acid To a solution of methyl 6-(6-cyclopropyl-3-(pyrimidin-5-ylamino)pyrazine-2-carboxamido)-2,3-dimethylbenzoate (0.05 g, 119 μmol) in pyridine (1 ml) at r.t under an argon atmosphere was added lithium iodide (125 mg, 932 μmol). The mixture was heated at 100° for 16 hr. The solvent was evaporated. The crude product was used directly in the next step.

Step 3: 6-Cyclopropyl-N-(3,4-dimethyl-2-(methylcarbamoyl)phenyl)-3-(pyrimidin-5-ylamino)-pyrazine-2-carboxamide According to the method described in step 3 of example 99, the title compound was obtained by reacting the crude 6-{[6-cyclopropyl-3-(pyrimidin-5-ylamino)-pyrazine-2-carbonyl]-amino}-2,3-dimethyl-benzoic acid with methylamine hydrochloride. Yellow solid.

MS: M=418.3 (M+H)$^{+-}$

Example 264

6-Cyclopropyl-3-(pyrimidin-5-ylamino)-pyrazine-2-carboxylic acid [1-(2-hydroxy-ethyl)-5-methylcarbamoyl-1H-pyrazol-4-yl]-amide

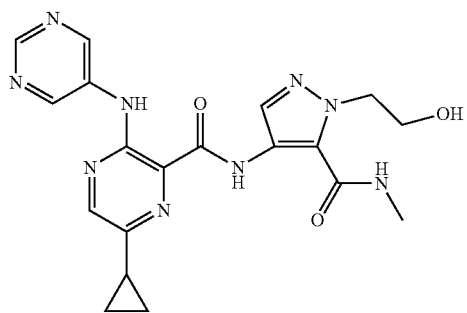 [SMILES: CNC(=O)c1c(NC(=O)c2nc(C3CC3)cnc2Nc2cncnc2)cnn1CCO]

Step 1: 6-Cyclopropyl-N-(5-(methylcarbamoyl)-1-(2-(tetrahydro-2H-pyran-2-yloxy)ethyl)-1H-pyrazol-4-yl)-3-(pyrimidin-5-ylamino)pyrazine-2-carboxamide According to the procedures described in example 132, the title compound was obtained using 2-(2-bromoethoxy)tetrahydro-2H-pyran in the 1$^{st}$ step and methylamine hydrochloride in the last step. Yellow solid.

MS: M=508.3 (M+H)$^+$

Step 2: 6-Cyclopropyl-3-(pyrimidin-5-ylamino)-pyrazine-2-carboxylic acid [1-(2-hydroxy-ethyl)-5-methylcarbamoyl-1H-pyrazol-4-yl]-amide To a suspension of 6-cyclopropyl-N-(5-(methylcarbamoyl)-1-(2-(tetrahydro-2H-pyran-2-yloxy)ethyl)-1H-pyrazol-4-yl)-3-(pyrimidin-5-ylamino)pyrazine-2-carboxamide (0.07 g, 138 µmol, Eq: 1.00) at r.t under Ar in MeOH (2.7 ml) was added a amount catalytic amount of para-toluene sulfonic acid. The mixture was stirred at 70° for 1 hr. The solvent was evaporated. The residue was dissolved in dichloromethane, then washed with water. The organic was dried over MgSO$_4$, filtered and evaporated. The crude product was purified by silica gel chromatography using a dichloromethane/MeOH gradient to obtain the tile compound (53 mg, 91%) as yellow solid.

MS: M=424.1 (M+H)$^+$

Example 265

6-Cyclopropyl-3-(pyrimidin-5-ylamino)-pyrazine-2-carboxylic acid (6-cyclopropyl-2-dimethylcarbamoyl-pyridin-3-yl)-amide

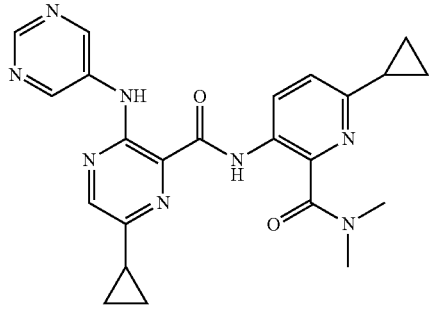 [SMILES: CN(C)C(=O)c1nc(C2CC2)ccc1NC(=O)c1nc(C2CC2)cnc1Nc1cncnc1]

According to the procedures described in example 99, ethyl 3-amino-6-cyclopropylpicolinate (example A-1, step 1) was converted to the title compound, using dimethylamine hydrochloride in the last step. Yellow solid.

MS: M=443.2 (M–H)$^-$

Example 266

3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide

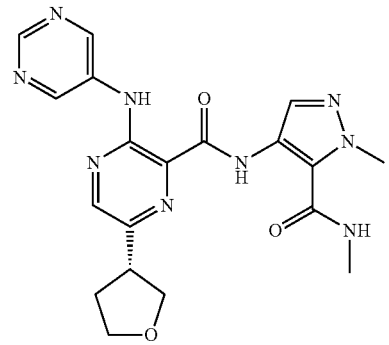 [SMILES: CNC(=O)c1c(NC(=O)c2nc([C@H]3CCOC3)cnc2Nc2cncnc2)cnn1C]

Step 1: 3-Amino-6-(R)-(tetrahydro-furan-3-yl)-pyrazine-2-carboxylic acid methyl ester The product was obtained together with its enantiomer starting from 3-amino-6-(furan-3-yl)-pyrazine-2-carboxylic acid methyl ester (1.7 g, 7.76 mmol) according to the method described in example A-16, step 2 after purification by chiral preparative HPLC using a Chiralpak AD column and an EtOH/heptane gradient as light yellow solid (118 mg, 6.75%).

MS: M=224.1 (M+H)$^+$

Step 2: 3-(Pyrimidin-5-ylamino)-6-(R)-(tetrahydro-furan-3-yl)-pyrazine-2-carboxylic acid methyl ester The product was obtained starting from 3-amino-6-(R)-(tetrahydro-furan-3-yl)-pyrazine-2-carboxylic acid methyl ester (110 mg, 0.49 mmol) according to the method described in example A-16, step 3 after purification by preparative HPLC using an acetonitrile/water gradient as light yellow solid (23 mg, 15%)

MS: M=302.1 (M+H)+

Step 3: 3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide The product was obtained starting from 3-(pyrimidin-5-ylamino)-6-(R)-tetrahydro-furan-3-yl-pyrazine-2-carboxylic acid methyl ester (23 mg, 76 μmol) and 4-amino-2-methyl-2H-pyrazole-3-carboxylic acid methylamide (35 mg, 228 μmol) according to the method described in example 104 after purification by preparative HPLC using an acetonitrile/water gradient as yellow solid (23 mg, 70%).

MS: M=424.2 (M+H)+

Example 267

3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide

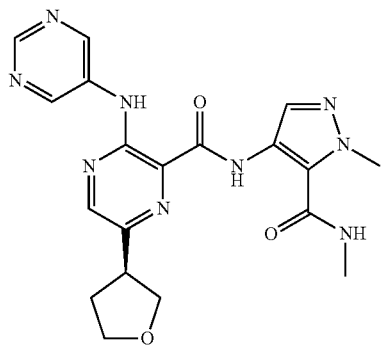 [SMILES: CNC(=O)c1c(NC(=O)c2nc([C@@H]3CCOC3)cnc2Nc2cncnc2)cnn1C]

Step 1: 3-Amino-6-(S)-(tetrahydro-furan-3-yl)-pyrazine-2-carboxylic acid methyl ester The product was obtained together with its enantiomer starting from 3-amino-6-(furan-3-yl)-pyrazine-2-carboxylic acid methyl ester (1.7 g, 7.76 mmol) according to the method described in example A-16, step 2 after purification by prep chiral preparative HPLC using a Chiralpak AD column and an EtOH/heptane gradient as light yellow solid (116 mg, 6.6%).

MS: M=224.1 (M+H)+

Step 2: 3-(Pyrimidin-5-ylamino)-6-(5)-(tetrahydro-furan-3-yl)-pyrazine-2-carboxylic acid methyl ester The product was obtained starting from 3-amino-6-(S)-(tetrahydro-furan-3-yl)-pyrazine-2-carboxylic acid methyl ester (110 mg, 0.49 mmol) according to the method described in example A-16, step 3 after purification by preparative HPLC using an acetonitrile/water gradient as light yellow solid (54 mg, 36%)

MS: M=302.1 (M+H)+

Step 3: 3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide The product was obtained starting from 3-(pyrimidin-5-ylamino)-6-(S)-tetrahydro-furan-3-yl-pyrazine-2-carboxylic acid methyl ester (30 mg, 0.1 mmol) and 4-amino-2-methyl-2H-pyrazole-3-carboxylic acid methylamide (46 mg, 0.3 mmol) according to the method described in example 104 after purification by preparative HPLC using an acetonitrile/water gradient as yellow solid (28 mg, 66%).

MS: M=424.2 (M+H)+

Example 268

6-Cyclopropyl-3-(pyrimidin-5-ylamino)-pyrazine-2-carboxylic acid (2-dimethylcarbamoyl-6-methyl-pyridin-3-yl)-amide

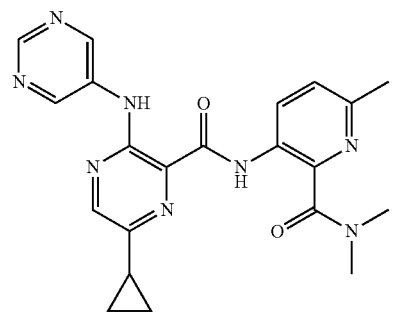 [SMILES: Cc1ccc(NC(=O)c2nc(C3CC3)cnc2Nc2cncnc2)c(C(=O)N(C)C)n1]

According to the procedures described in example 99, the title compound was obtained using 3-amino-6-methyl-pyridine-2-carboxylic acid ethyl ester (CAS 908832-89-3) in the 1$^{st}$ step and dimethylamine hydrochloride in the last step. Yellow solid.

MS: M=417.3 (M−H)−

Example 269

6-Cyclopropyl-3-(pyrimidin-5-ylamino)-pyrazine-2-carboxylic acid {2-[(2-hydroxy-ethyl)-methyl-carbamoyl]-pyridin-3-yl}-amide

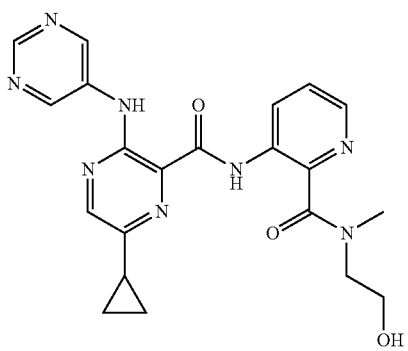 [SMILES: CN(CCO)C(=O)c1ncccc1NC(=O)c1nc(C2CC2)cnc1Nc1cncnc1]

According to the procedures described in example 97, the title compound was obtained using 3-aminopicolinic acid and 2-(methylamino)ethanol in the 1$^{st}$ step.

MS: M=435.3 (M+H)+

Example 270

6-Cyclopropyl-3-(pyrimidin-5-ylamino)-pyrazine-2-carboxylic acid {2-[ethyl-(2-hydroxy-ethyl)-carbamoyl]-pyridin-3-yl}-amide

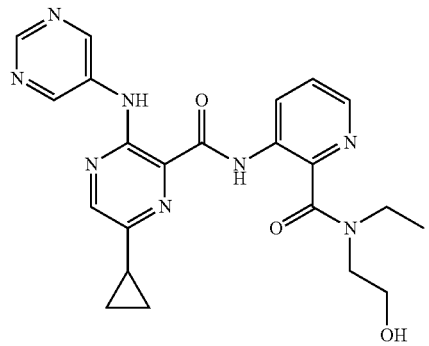 [SMILES: CCN(CCO)C(=O)c1ncccc1NC(=O)c1nc(C2CC2)cnc1Nc1cncnc1]

According to the procedures described in example 97, the title compound was obtained using 3-aminopicolinic acid and 2-(ethylamino)ethanol in the 1st step.
MS: M=449.3 (M+H)+

Example 272

6-Cyclopropyl-3-(pyrimidin-5-ylamino)-pyrazine-2-carboxylic acid [2-(azetidine-1-carbonyl)-6-cyclopropyl-pyridin-3-yl]-amide

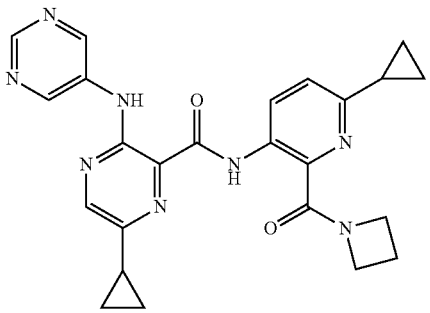

According to the procedures described in example 99, ethyl 3-amino-6-cyclopropylpicolinate (example A-1, step 1) was converted to the title compound, using azetidine in the last step. Yellow solid.
MS: M=457.3 (M+H)+

Example 271

6-Cyclopropyl-3-(pyrimidin-5-ylamino)-pyrazine-2-carboxylic acid [2-(2-hydroxy-ethylcarbamoyl)-pyridin-3-yl]-amide

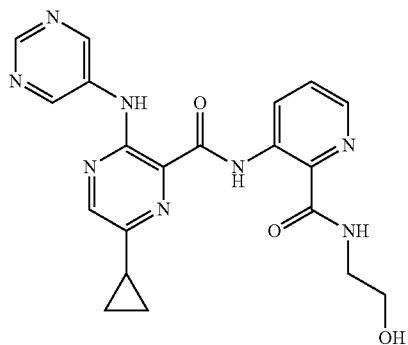 [SMILES: O=C(NCCO)c1ncccc1NC(=O)c1nc(C2CC2)cnc1Nc1cncnc1]

According to the procedures described in example 97, the title compound was obtained using 3-aminopicolinic acid and 2-aminoethanol in the 1st step.
MS: M=421.1 (M+H)+

Example 273

6-Cyclopropyl-3-(pyrimidin-5-ylamino)-pyrazine-2-carboxylic acid [2-(2-hydroxy-1,1-dimethyl-ethylcarbamoyl)-pyridin-3-yl]-amide

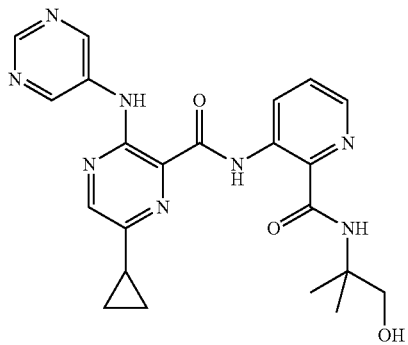 [SMILES: CC(C)(CO)NC(=O)c1ncccc1NC(=O)c1nc(C2CC2)cnc1Nc1cncnc1]

According to the procedures described in example 97, the title compound was obtained using 3-aminopicolinic acid and 2-amino-2-methylpropan-1-ol in the 1st step.
MS: M=449.2 (M+H)+

Example 274

6-Cyclopropyl-3-(pyrimidin-5-ylamino)-pyrazine-2-carboxylic acid (4-acetylamino-2-methylcarbamoyl-phenyl)-amide

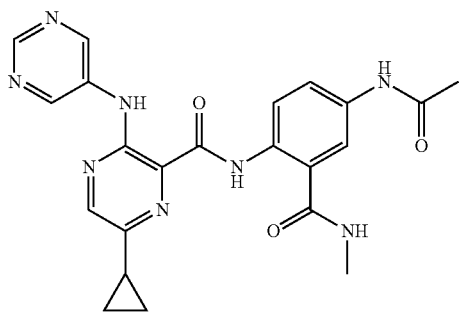 [SMILES: CNC(=O)c1cc(NC(C)=O)ccc1NC(=O)c1nc(C2CC2)cnc1Nc1cncnc1]

According to the procedures described in example 99, the title compound was obtained reacting intermediate A-11 and methyl 5-acetamido-2-aminobenzoate (CAS 54002-34-5) in the 1$^{st}$ step and using methylamine hydrochloride in the last step. Yellow solid.

MS: M=448.2 (M+H)$^+$

Example 275

6-Cyclopropyl-3-(pyrimidin-5-ylamino)-pyrazine-2-carboxylic acid [2-(3-methyl-oxetan-3-ylcarbamoyl)-pyridin-3-yl]-amide

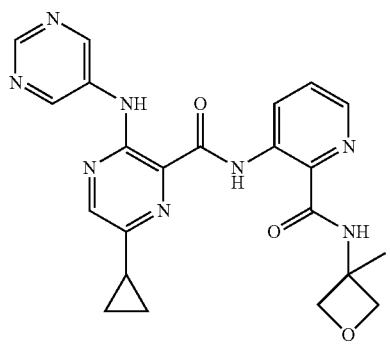 [SMILES: CC1(NC(=O)c2ncccc2NC(=O)c2nc(C3CC3)cnc2Nc2cncnc2)COC1]

According to the procedures described in example 97, the title compound was obtained using 3-aminopicolinic acid and 3-methyloxetan-3-amine in the 1$^{st}$ step.

MS: M=447.3 (M+H)$^+$

Example 276

6-Cyclopropyl-3-(pyrimidin-5-ylamino)-pyrazine-2-carboxylic acid {2-[methyl-(tetrahydro-furan-2-ylm-ethyl)-carbamoyl]-pyridin-3-yl}-amide

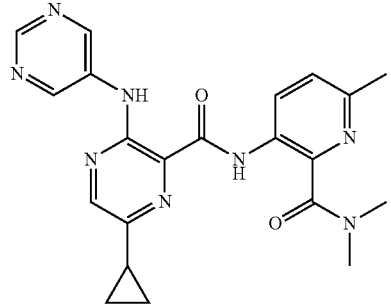 [SMILES: Cc1ccc(NC(=O)c2nc(C3CC3)cnc2Nc2cncnc2)c(C(=O)N(C)C)n1]

According to the procedures described in example 99, the title compound was obtained using ethyl 3-aminopicolinate in the 1$^{st}$ step and ethyl 3-aminopicolinate in the last step.

MS: M=406.4 (M+H)$^+$

Example 277

6-Cyclopropyl-3-(pyrimidin-5-ylamino)-pyrazine-2-carboxylic acid [2-(oxetan-3-ylcarbamoyl)-pyridin-3-yl]-amide

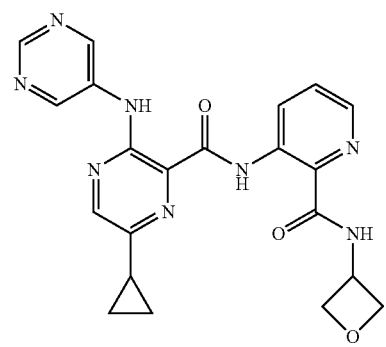 [SMILES: O=C(NC1COC1)c1ncccc1NC(=O)c1nc(C2CC2)cnc1Nc1cncnc1]

According to the procedures described in example 97, the title compound was obtained using 3-aminopicolinic acid and oxetan-3-amine hydrochloride in the 1$^{st}$ step.

MS: M=433.3 (M+H)$^+$

Example 278

6-Cyclopropyl-3-(pyrimidin-5-ylamino)-pyrazine-2-carboxylic acid [2-(azetidine-1-carbonyl)-6-methyl-pyridin-3-yl]-amide

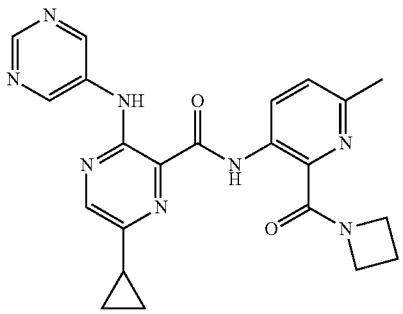 [SMILES: Cc1ccc(NC(=O)c2nc(C3CC3)cnc2Nc2cncnc2)c(C(=O)N2CCC2)n1]

Step 1: (3-Amino-6-methyl-pyridin-2-yl)-azetidin-1-yl-methanone

To a stirred mixture of 3-amino-6-methylpicolinic acid (525 mg, 2.17 mmol) and azetidine (124 mg, 146 μl, 2.17 mmol) at r.t. in THF (15 ml) under an argon atmosphere were added HATU (1.65 g, 4.35 mmol) and 4-methylmorpholine (719 μl, 6.52 mmol). The mixture was heated to 70° C. overnight, then cooled to r.t. and concentrated. The crude product was purified by silica gel chromatography using a n-heptane/EtOAc gradient to give the title compound (272 mg, 65%) as off-white solid.
MS: M=192.2 (M+H)$^+$

Step 2: 6-Cyclopropyl-3-(pyrimidin-5-ylamino)-pyrazine-2-carboxylic acid [2-(azetidine-1-carbonyl)-6-methyl-pyridin-3-yl]-amide In analogy to the procedure described in step 6 of example 64, the title compound was obtained reacting intermediate A-11 and (3-amino-6-methyl-pyridin-2-yl)-azetidin-1-yl-methanone. Yellow solid.
MS: M=431.3 (M−H)$^-$

Example 279

6-Cyclopropyl-3-(pyrimidin-5-ylamino)-pyrazine-2-carboxylic acid {1-methyl-5-[(S)-(tetrahydro-furan-3-yl)carbamoyl]-1H-pyrazol-4-yl}-amide

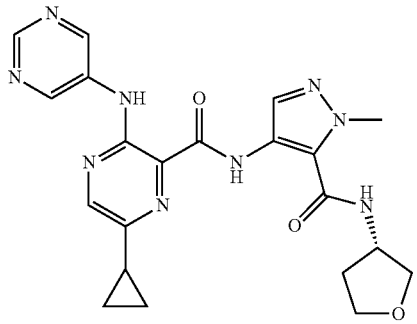 [SMILES: Cn1ncc(NC(=O)c2nc(C3CC3)cnc2Nc2cncnc2)c1C(=O)N[C@H]1CCOC1]

According to the procedure described in example 135, the title compound was obtained using (S)-tetrahydrofuran-3-amine hydrochloride in the last step. Yellow solid.
MS: M=450.2 (M+H)$^+$

Example 280

6-Cyclopropyl-3-(pyrimidin-5-ylamino)-pyrazine-2-carboxylic acid {1-methyl-5-[(R)-(tetrahydro-furan-3-yl)carbamoyl]-1H-pyrazol-4-yl}-amide

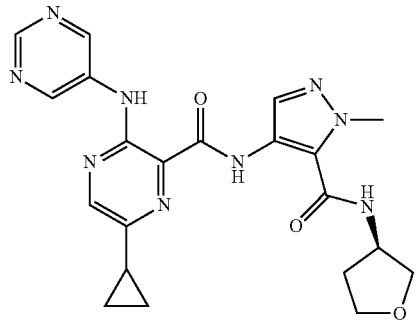 [SMILES: Cn1ncc(NC(=O)c2nc(C3CC3)cnc2Nc2cncnc2)c1C(=O)N[C@@H]1CCOC1]

According to the procedure described in example 135, the title compound was obtained using (R)-tetrahydrofuran-3-amine methanesulfonate in the last step. Yellow solid.
MS: M=450.2 (M+H)$^+$

Example 281

5-{[6-Cyclopropyl-3-(pyrimidin-5-ylamino)-pyrazine-2-carbonyl]-amino}-2-methyl-pyrimidine-4-carboxylic acid (2-hydroxy-2-methyl-propyl)-amide

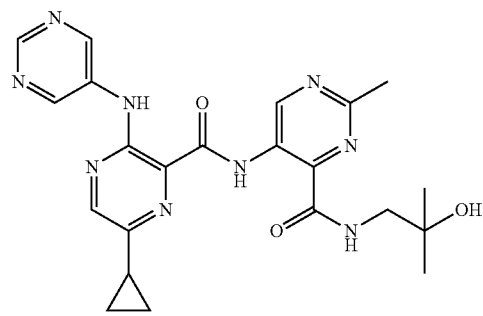 [SMILES: Cc1ncc(NC(=O)c2nc(C3CC3)cnc2Nc2cncnc2)c(C(=O)NCC(C)(C)O)n1]

Step 1: 5-Bromo-N-(2-hydroxy-2-methylpropyl)-2-methylpyrimidine-4-carboxamide The title compound was obtained using the procedure described in step 3 of example 99, the title compound was obtained by reacting 5-bromo-2-methylpyrimidine-4-carboxylic acid and 1-amino-2-methylpropan-2-ol. Oil.
MS: M=285.7 (M+H)$^+$

Step 2: 5-Amino-N-(2-hydroxy-2-methylpropyl)-2-methylpyrimidine-4-carboxamide According to the procedures described in steps 1 and 2 of example 209, the title compound was obtained by reacting 5-bromo-N-(2-hydroxy-2-methylpropyl)-2-methylpyrimidine-4-carbox-amide with tert-butyl carbamate and subsequent cleavage of the Boc group. Yellow gum.
MS: M=225.2 (M+H)$^+$

247

Step 3: 5-{[6-Cyclopropyl-3-(pyrimidin-5-ylamino)-pyrazine-2-carbonyl]-amino}-2-methyl-pyrimidine-4-carboxylic acid (2-hydroxy-2-methyl-propyl)-amide The title compound was prepared according to the procedure described in step 6 of example 64. Yellow solid.

MS: M=464.3 (M+H)$^+$

Example 282

6-Cyclopropyl-3-(pyrimidin-5-ylamino)-pyrazine-2-carboxylic acid (5-methylcarbamoyl-1-oxetan-2-ylmethyl-1H-pyrazol-4-yl)-amide

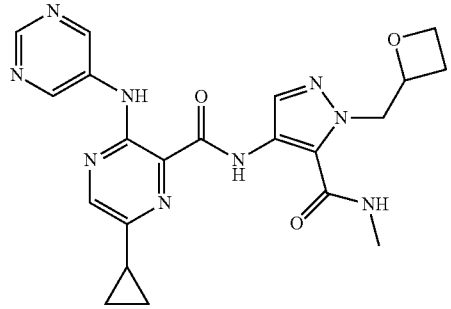 [SMILES: CNC(=O)c1c(NC(=O)c2nc(C3CC3)cnc2Nc2cncnc2)cnn1CC1CCO1]

According to the procedures described in example 132, the title compound was obtained using 2-(iodomethyl)oxetane in the 1$^{st}$ step and methylamine hydrochloride in the last step. Yellow solid.

MS: M=450.3 (M+H)$^+$

Example 283

6-Cyclopropyl-3-(pyrimidin-5-ylamino)-pyrazine-2-carboxylic acid [5-(2-hydroxy-2-methyl-propylcarbamoyl)-1-oxetan-2-ylmethyl-1H-pyrazol-4-yl]-amide

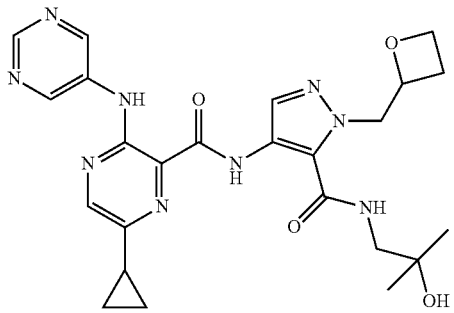 [SMILES: CC(C)(O)CNC(=O)c1c(NC(=O)c2nc(C3CC3)cnc2Nc2cncnc2)cnn1CC1CCO1]

According to the procedures described in example 132, the title compound was obtained using 2-(iodomethyl)oxetane in the 1$^{st}$ step and 1-amino-2-methylpropan-2-ol in the last step. Yellow solid.

MS: M=508.3 (M+H)$^+$

248

Example 284

6-Cyclopropyl-3-(pyrimidin-5-ylamino)-pyrazine-2-carboxylic acid (2-dimethylcarbamoyl-4,5-difluoro-phenyl)-amide

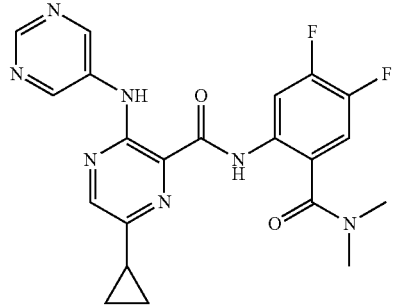 [SMILES: CN(C)C(=O)c1cc(F)c(F)cc1NC(=O)c1nc(C2CC2)cnc1Nc1cncnc1]

According to the procedures described in example 99, the title compound was obtained reacting intermediate A-11 and methyl 2-amino-4,5-difluorobenzoate in the 1$^{st}$ step and using dimethylamino hydrochloride in the last step. Yellow solid.

MS: M=440.1 (M+H)$^+$

Example 285

5-{[6-Cyclopropyl-3-(pyrimidin-5-ylamino)-pyrazine-2-carbonyl]-amino}-2-methyl-pyrimidine-4-carboxylic acid methylamide

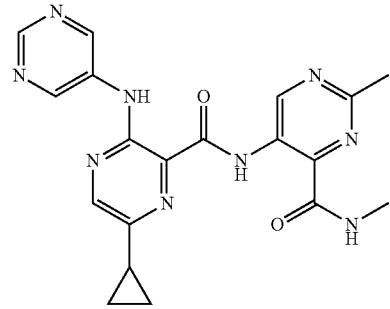 [SMILES: CNC(=O)c1nc(C)ncc1NC(=O)c1nc(C2CC2)cnc1Nc1cncnc1]

According to the procedures described in example 281, the title compound was obtained using methylamine hydrochloride in the 1st step. Yellow solid.

MS: M=440.1 (M+H)$^+$

Example 286

6-Cyclopropyl-3-(pyrimidin-5-ylamino)-pyrazine-2-carboxylic acid [5-methylcarbamoyl-1-(tetrahydro-furan-3-ylmethyl)-1H-pyrazol-4-yl]-amide

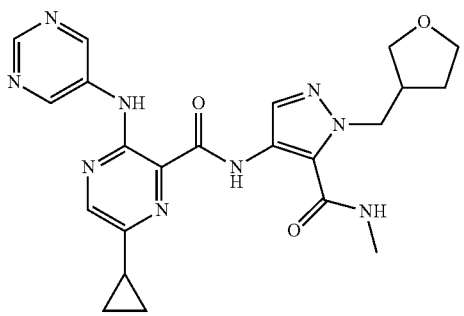 [SMILES: CNC(=O)c1c(NC(=O)c2nc(C3CC3)cnc2Nc2cncnc2)cnn1CC1CCOC1]

According to the procedures described in example 132, the title compound was obtained using 3-(iodomethyl)tetrahydrofuran in the 1$^{st}$ step and methylamine hydrochloride in the last step. Yellow solid.

MS: M=464.3 (M+H)$^+$

Example 287

6-Cyclopropyl-3-(pyrimidin-5-ylamino)-pyrazine-2-carboxylic acid [5-(2-hydroxy-2-methyl-propylcarbamoyl)-1-(tetrahydro-furan-3-ylmethyl)-1H-pyrazol-4-yl]-amide

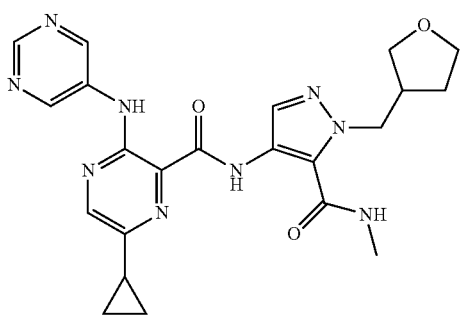 [SMILES: CNC(=O)c1c(NC(=O)c2nc(C3CC3)cnc2Nc2cncnc2)cnn1CC1CCOC1]

According to the procedures described in example 132, the title compound was obtained using 3-(iodomethyl)tetrahydrofuran in the 1$^{st}$ step and 1-amino-2-methylpropan-2-ol in the last step. Yellow solid.

MS: M=522.4 (M+H)$^+$

Example 288

6-Cyclopropyl-3-(pyrimidin-5-ylamino)-pyrazine-2-carboxylic acid (4,5-difluoro-2-methylcarbamoyl-phenyl)-amide

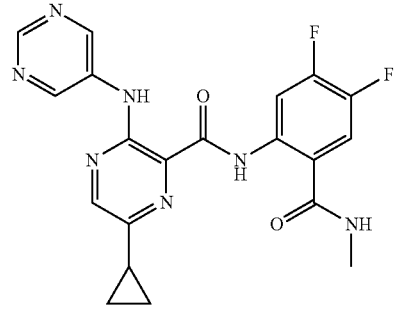 [SMILES: CNC(=O)c1cc(F)c(F)cc1NC(=O)c1nc(C2CC2)cnc1Nc1cncnc1]

According to the procedures described in example 99, the title compound was obtained reacting intermediate A-11 and methyl 2-amino-4,5-difluorobenzoate in the 1$^{st}$ step and using methyl-amino hydrochloride in the last step. Yellow solid.

MS: M=426.1 (M+H)$^+$

Example 289

3-(Pyrimidin-5-ylamino)-6-pyrrolidin-1-yl-pyrazine-2-carboxylic acid (1-methyl-5-methylcarbamoyl-1H-pyrazol-4-yl)-amide

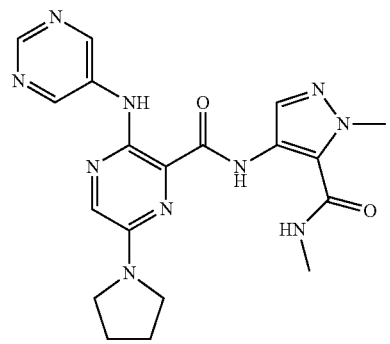 [SMILES: CNC(=O)c1c(NC(=O)c2nc(N3CCCC3)cnc2Nc2cncnc2)cnn1C]

Step 1: Methyl 3-(bis(tert-butoxycarbonyl)amino)-6-pyrrolidin-1-yl-pyrazine-2-carboxylate A pre-dried flask was charged with copper(I) bromide (0.35 mg, 2.89 μmol), (R)-(+)-1,1'-bi-2-naphthol (1.66 mg, 5.78 μmol) and cesium carbonate (113 mg, 347 μmol) under argon atmosphere. DMF (0.5 ml), methyl 3-(bis(tert-butoxycarbonyl)amino)-6-bromopyrazine-2-carboxylate (50 mg, 116 μmol) and pyrrolidine (14.3 μl, 174 μmol) were added and the reaction mixture was stirred at r.t. for 1.5 h. The reaction mixture was poured into water (10 ml) and extracted with ethyl acetate. The combined organic layer was washed with brine, dried, evaporated and purified by silica gel chromatography using a heptane/ethyl acetate gradient to yield the product as yellow solid (37 mg, 68%).

MS: M=423.3 (M+H)$^+$

Step 2: 3-Amino-6-pyrrolidin-1-yl-pyrazine-2-carboxylatic acid methyl ester

The product was obtained starting from methyl 3-(bis(tert-butoxycarbonyl)amino)-6-pyrrolidin-1-yl-pyrazine-2-carboxylate (167 mg, 0.39 mmol) according to the method described in example A-12, step 3 without chromatographic purification as orange solid (87 mg, 99%).

MS: M=223.2 (M+H)⁺

Step 3: 3-(Pyrimidin-5-ylamino)-6-pyrrolidin-1-yl-pyrazine-2-carboxylic acid methyl ester The product was obtained starting from 3-amino-6-pyrrolidin-1-yl-pyrazine-2-carboxylatic acid methyl ester (85 mg, 0.38 mmol) according to the method described in example 258, step 3 after purification by preparative HPLC using an acetonitrile/water gradient as orange solid (90 mg, 70%).

MS: M=301.3 (M+H)⁺

Step 4: 3-(Pyrimidin-5-ylamino)-6-pyrrolidin-1-yl-pyrazine-2-carboxylic acid

The product was obtained starting from 3-(pyrimidin-5-ylamino)-6-pyrrolidin-1-yl-pyrazine-2-carboxylic acid methyl ester (87 mg, 0.29 mmol) according to the method described in example A-11 as yellow solid (80 mg, 87%).

Step 5: 3-(Pyrimidin-5-ylamino)-6-pyrrolidin-1-yl-pyrazine-2-carboxylic acid (1-methyl-5-methylcarbamoyl-1H-pyrazol-4-yl)-amide The product was obtained starting from 3-(pyrimidin-5-ylamino)-6-pyrrolidin-1-yl-pyrazine-2-carboxylic acid (30 mg, 94 µmol) and 4-amino-2-methyl-2H-pyrazole-3-carboxylic acid methylamide (19 mg, 123 µmol) according to the method described in example 64, step 6 after purification by preparative HPLC using an acetonitrile/water gradient as yellow solid (10 mg, 26%).

MS: M=423.3 (M+H)⁺

Example 290

6-Cyclopropyl-3-(pyrimidin-5-ylamino)-pyrazine-2-carboxylic acid (2-fluoro-6-methylcarbamoyl-phenyl)-amide

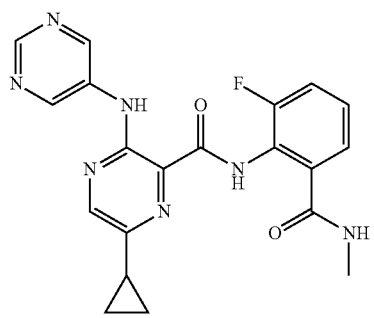 [SMILES: CNC(=O)c1cccc(F)c1NC(=O)c1nc(C2CC2)cnc1Nc1cncnc1]

According to the procedures described in example 278, the title compound was obtained using 2-amino-3-fluorobenzoic acid and methylamine hydrochloride in the 1ˢᵗ step. Yellow solid.

MS: M=408.4 (M+H)⁺

Example 291

6-Cyclopropyl-3-(pyrimidin-5-ylamino)-pyrazine-2-carboxylic acid [2-(azetidine-1-carbonyl)-4,5-difluoro-phenyl]-amide

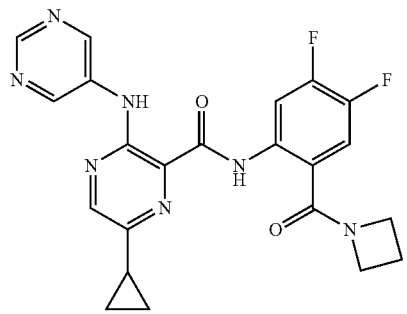 [SMILES: O=C(Nc1cc(F)c(F)cc1C(=O)N1CCC1)c1nc(C2CC2)cnc1Nc1cncnc1]

According to the procedures described in example 278, the title compound was obtained reacting methyl 2-amino-4,5-difluorobenzoate and azetidine in the 1ˢᵗ step. Yellow solid.

MS: M=452.2 (M+H)⁺

Example 292

6-Cyclopropyl-3-(pyrimidin-5-ylamino)-pyrazine-2-carboxylic acid (5-fluoro-2-methylcarbamoyl-phenyl)-amide

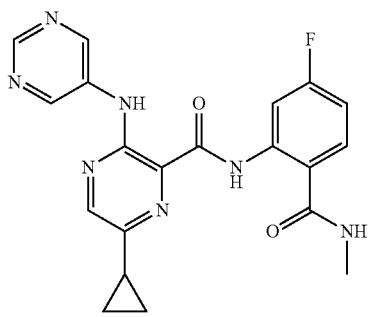 [SMILES: CNC(=O)c1ccc(F)cc1NC(=O)c1nc(C2CC2)cnc1Nc1cncnc1]

According to the procedures described in example 278, the title compound was obtained reacting 2-amino-4-fluorobenzoic acid and methylamine hydrochloride in the 1ˢᵗ step. Yellow solid.

MS: M=408.4 (M+H)⁺

Example 293

6-Cyclopropyl-3-(pyrimidin-5-ylamino)-pyrazine-2-carboxylic acid [2-fluoro-6-(2-hydroxy-2-methyl-propylcarbamoyl)-phenyl]-amide

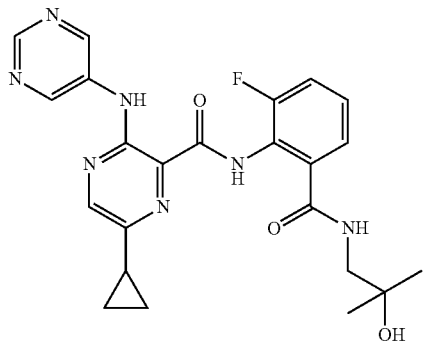 [SMILES: CC(C)(O)CNC(=O)c1cccc(F)c1NC(=O)c1nc(C2CC2)cnc1Nc1cncnc1]

According to the procedures described in example 278, the title compound was obtained using 2-amino-3-fluorobenzoic acid and 1-amino-2-methylpropan-2-ol in the 1st step. Yellow solid.

MS: M=466.3 (M+H)+

Example 294

6-Cyclopropyl-3-(pyrimidin-5-ylamino)-pyrazine-2-carboxylic acid (2-dimethylcarbamoyl-5-fluoro-phenyl)-amide

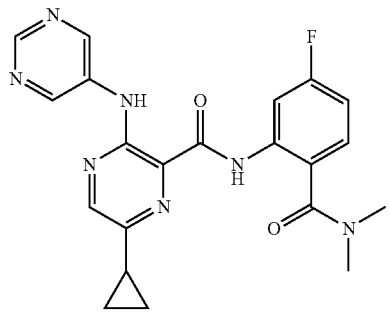 [SMILES: CN(C)C(=O)c1ccc(F)cc1NC(=O)c1nc(C2CC2)cnc1Nc1cncnc1]

According to the procedures described in example 278, the title compound was obtained reacting 2-amino-4-fluorobenzoic acid and dimethylamine hydrochloride in the 1st step. Yellow solid.

MS: M=422.2 (M+H)+

Example 295

6-Cyclopropyl-3-(pyrimidin-5-ylamino)-pyrazine-2-carboxylic acid [2-(2-hydroxy-2-methyl-propylcarbamoyl)-4-trifluoromethyl-phenyl]-amide

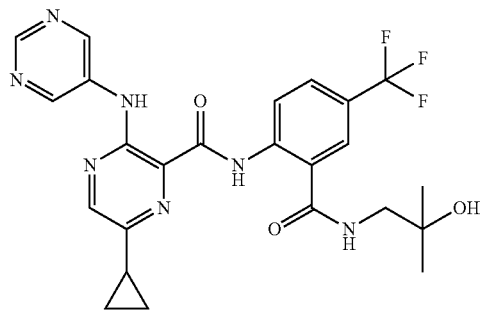 [SMILES: CC(C)(O)CNC(=O)c1cc(C(F)(F)F)ccc1NC(=O)c1nc(C2CC2)cnc1Nc1cncnc1]

According to the procedures described in example 278, the title compound was obtained reacting 2-amino-5-(trifluoromethyl)benzoic acid and 1-amino-2-methylpropan-2-ol in the 1st step. Yellow solid.

MS: M=516.4 (M+H)+

Example 296

6-Cyclopropyl-3-(pyrimidin-5-ylamino)-pyrazine-2-carboxylic acid (2-methylcarbamoyl-4-trifluoromethyl-phenyl)-amide

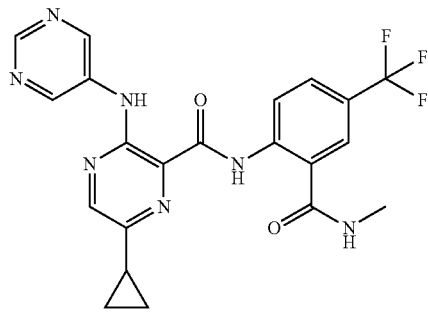 [SMILES: CNC(=O)c1cc(C(F)(F)F)ccc1NC(=O)c1nc(C2CC2)cnc1Nc1cncnc1]

According to the procedures described in example 278, the title compound was obtained reacting 2-amino-5-(trifluoromethyl)benzoic acid and methylamine hydrochloride in the 1st step. Yellow solid.

MS: M=458.3 (M+H)+

Example 297

6-Morpholin-4-yl-3-(pyrimidin-5-ylamino)-pyrazine-2-carboxylic acid (1-methyl-5-methylcarbamoyl-1H-pyrazol-4-yl)-amide

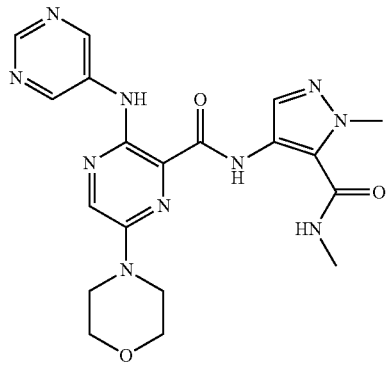 [SMILES: CNC(=O)c1c(NC(=O)c2nc(N3CCOCC3)cnc2Nc2cncnc2)cnn1C]

According to the procedures described in example 289, the product was prepared as yellow solid by using morpholine in the 1$^{st}$ step.

MS: M=439.4 (M+H)$^+$

Example 298

6-Cyclopropyl-3-(pyrimidin-5-ylamino)-pyrazine-2-carboxylic acid (2-dimethylcarbamoyl-4-fluoro-phenyl)-amide

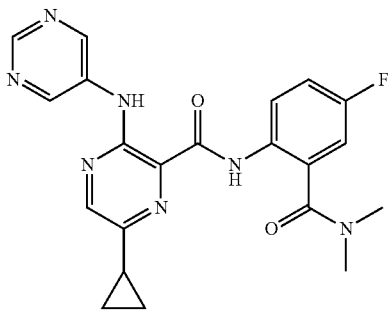 [SMILES: CN(C)C(=O)c1cc(F)ccc1NC(=O)c1nc(C2CC2)cnc1Nc1cncnc1]

According to the procedures described in example 278, the title compound was obtained reacting 2-amino-5-fluorobenzoic acid and dimethylamine hydrochloride in the 1$^{st}$ step. Yellow solid.

MS: M=422.2 (M+H)$^+$

Example 299

6-Cyclopropyl-3-(pyrimidin-5-ylamino)-pyrazine-2-carboxylic acid (3,5-difluoro-2-methylcarbamoyl-phenyl)-amide

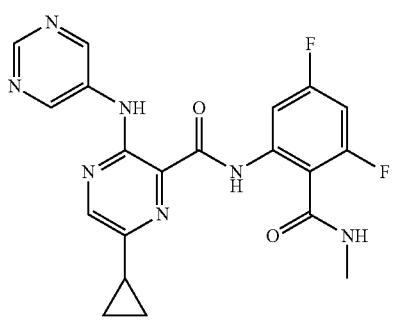 [SMILES: CNC(=O)c1c(F)cc(F)cc1NC(=O)c1nc(C2CC2)cnc1Nc1cncnc1]

According to the procedures described in example 278, the title compound was obtained reacting 2-amino-4,6-difluorobenzoic acid and methylamine hydrochloride in the 1$^{st}$ step. Yellow solid.

MS: M=426.2 (M+H)$^+$

Example 300

6-Cyclopropyl-3-(pyrimidin-5-ylamino)-pyrazine-2-carboxylic acid (2-dimethylcarbamoyl-3,5-difluoro-phenyl)-amide

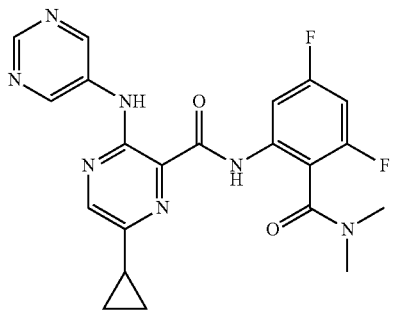 [SMILES: CN(C)C(=O)c1c(F)cc(F)cc1NC(=O)c1nc(C2CC2)cnc1Nc1cncnc1]

According to the procedures described in example 278, the title compound was obtained reacting 2-amino-4,6-difluorobenzoic acid and dimethylamine hydrochloride in the 1$^{st}$ step. Yellow solid.

MS: M=440.3 (M+H)$^+$

Example 301

6-Cyclopropyl-3-(pyrimidin-5-ylamino)-pyrazine-2-carboxylic acid [5-fluoro-2-(2-hydroxy-2-methyl-propylcarbamoyl)-phenyl]-amide

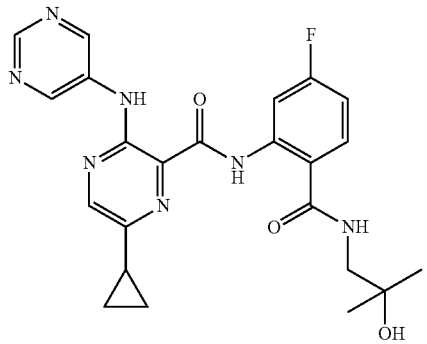 [SMILES: CC(C)(O)CNC(=O)c1ccc(F)cc1NC(=O)c1nc(C2CC2)cnc1Nc1cncnc1]

According to the procedures described in example 278, the title compound was obtained reacting 2-amino-4-fluoro-benzoic acid and 1-amino-2-methyl-propan-2-ol in the 1$^{st}$ step. Yellow solid.

MS: M=466.2 (M+H)$^+$

Example 302

6-Cyclopropyl-3-(pyrimidin-5-ylamino)-pyrazine-2-carboxylic acid [2-(azetidine-1-carbonyl)-5-fluoro-phenyl]-amide

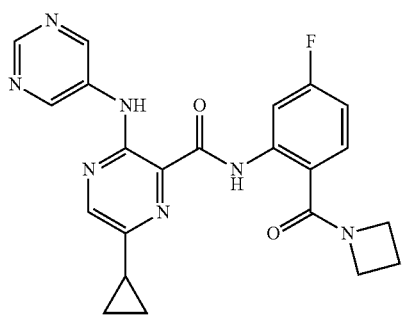 [SMILES: O=C(Nc1cc(F)ccc1C(=O)N1CCC1)c1nc(C2CC2)cnc1Nc1cncnc1]

According to the procedures described in example 278, the title compound was obtained reacting 2-amino-4-fluoro-benzoic acid and azetidine in the 1$^{st}$ step. Yellow solid.

MS: M=434.3 (M+H)$^+$

Example 303

6-Cyclopropyl-3-(pyrimidin-5-ylamino)-pyrazine-2-carboxylic acid (2-dimethylcarbamoyl-6-fluoro-phenyl)-amide

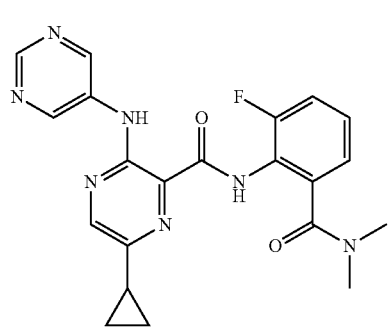 [SMILES: CN(C)C(=O)c1cccc(F)c1NC(=O)c1nc(C2CC2)cnc1Nc1cncnc1]

According to the procedures described in example 278, the title compound was obtained reacting 2-amino-3-fluoro-benzoic acid and dimethylamino hydrochloride in the 1$^{st}$ step. Yellow solid.

MS: M=422.3 (M+H)$^+$

Example 304

6-Azetidin-1-yl-3-(pyrimidin-5-ylamino)-pyrazine-2-carboxylic acid (1-methyl-5-methylcarbamoyl-1H-pyrazol-4-yl)-amide

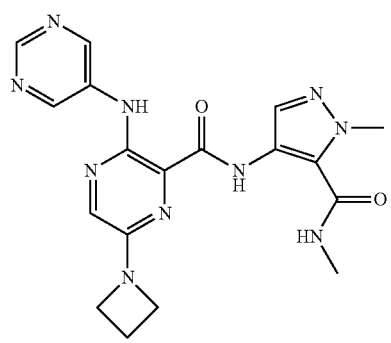 [SMILES: CNC(=O)c1c(NC(=O)c2nc(N3CCC3)cnc2Nc2cncnc2)cnn1C]

According to the procedures described in example 289, the product was prepared as light yellow solid by using azetidine in the 1$^{st}$ step.

MS: M=409.3 (M+H)$^+$

Example 305

6-Cyclopropyl-3-(pyrimidin-5-ylamino)-pyrazine-2-carboxylic acid [2-(azetidine-1-carbonyl)-4-fluoro-phenyl]-amide

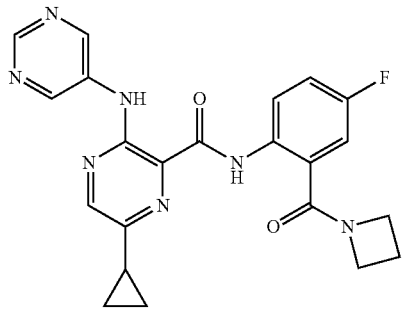 [SMILES: O=C(Nc1ccc(F)cc1C(=O)N1CCC1)c1nc(C2CC2)cnc1Nc1cncnc1]

According to the procedures described in example 278, the title compound was obtained reacting 2-amino-5-fluoro-benzoic acid and azetidine in the 1$^{st}$ step. Yellow solid.

MS: M=434.4 (M+H)$^+$

Example 306

6-Cyclopropyl-3-(pyrimidin-5-ylamino)-pyrazine-2-carboxylic acid [4-fluoro-2-(2-hydroxy-2-methyl-propylcarbamoyl)-phenyl]-amide

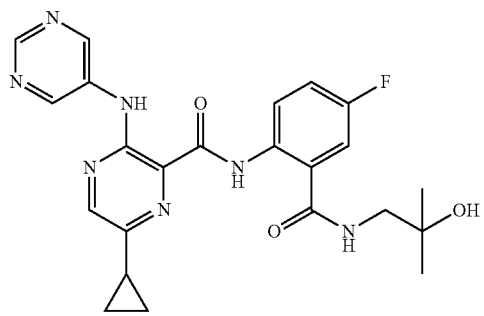 [SMILES: CC(C)(O)CNC(=O)c1cc(F)ccc1NC(=O)c1nc(C2CC2)cnc1Nc1cncnc1]

According to the procedures described in example 278, the title compound was obtained reacting 2-amino-5-fluoro-benzoic acid and 1-amino-2-methylpropan-2-ol in the 1$^{st}$ step. Yellow powder.

MS: M=466.2 (M+H)$^+$

Example 307

6-Cyclopropyl-3-(pyrimidin-5-ylamino)-pyrazine-2-carboxylic acid (3-fluoro-2-methylcarbamoyl-phenyl)-amide

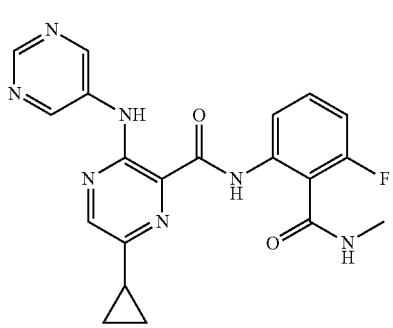 [SMILES: CNC(=O)c1c(F)cccc1NC(=O)c1nc(C2CC2)cnc1Nc1cncnc1]

According to the procedures described in example 278, the title compound was obtained reacting 2-amino-6-fluoro-benzoic acid and methylamine hydrochloride in the 1$^{st}$ step. Yellow powder.

MS: M=408.3 (M+H)$^+$

Example 308

6-Cyclopropyl-3-(pyrimidin-5-ylamino)-pyrazine-2-carboxylic acid (2-dimethylcarbamoyl-3-fluoro-phenyl)-amide

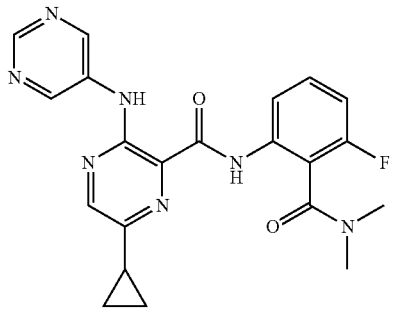 [SMILES: CN(C)C(=O)c1c(F)cccc1NC(=O)c1nc(C2CC2)cnc1Nc1cncnc1]

According to the procedures described in example 278, the title compound was obtained reacting 2-amino-6-fluoro-benzoic acid and dimethylamine hydrochloride in the 1$^{st}$ step. Yellow powder.

MS: M=422.1 (M+H)$^+$

Example 309

6-Cyclopropyl-3-(pyrimidin-5-ylamino)-pyrazine-2-carboxylic acid [2-(azetidine-1-carbonyl)-3-fluoro-phenyl]-amide

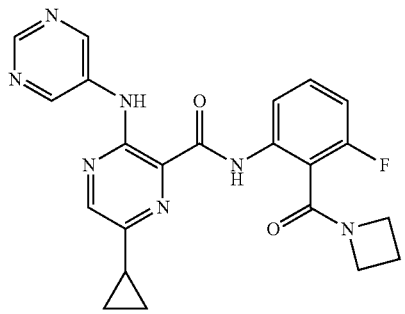 [SMILES: O=C(Nc1cccc(F)c1C(=O)N1CCC1)c1nc(C2CC2)cnc1Nc1cncnc1]

According to the procedures described in example 278, the title compound was obtained reacting 2-amino-6-fluoro-benzoic acid and azetidine in the 1$^{st}$ step. Yellow powder.

MS: M=434.3 (M+H)$^+$

Example 310

6-Cyclopropyl-3-(pyrimidin-5-ylamino)-pyrazine-2-carboxylic acid [3-fluoro-2-(2-hydroxy-2-methyl-propylcarbamoyl)-phenyl]-amide

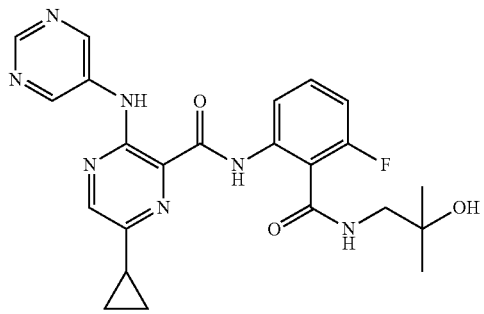 [SMILES: CC(C)(O)CNC(=O)c1c(F)cccc1NC(=O)c1nc(C2CC2)cnc1Nc1cncnc1]

According to the procedures described in example 278, the title compound was obtained reacting 2-amino-6-fluoro-benzoic acid and 1-amino-2-methylpropan-2-ol in the 1$^{st}$ step. Yellow powder.

MS: M=466.2 (M+H)$^+$

Example 311

6-(Ethyl-methyl-amino)-3-(pyrimidin-5-ylamino)-pyrazine-2-carboxylic acid (1-methyl-5-methylcarbamoyl-1H-pyrazol-4-yl)-amide

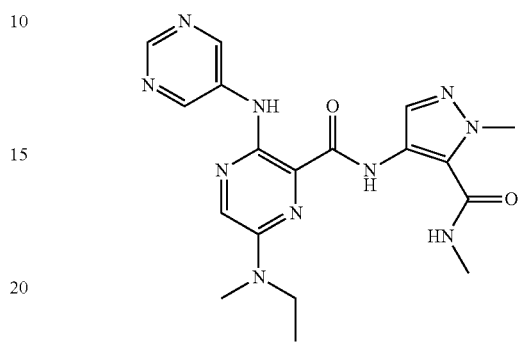

According to the procedures described in example 289, the product was prepared as light yellow solid by using N-methyl-ethylamine in the 1$^{st}$ step.

MS: M=411.3 (M+H)$^+$

Example 312

6-Cyclopropyl-3-(pyrimidin-5-ylamino)-pyrazine-2-carboxylic acid (4-fluoro-2-methylcarbamoyl-phenyl)-amide

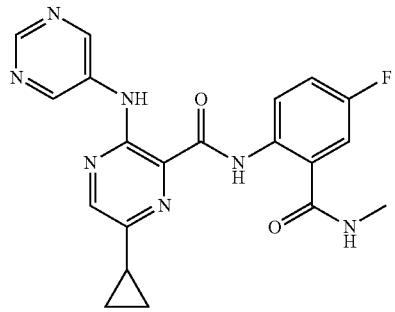 [SMILES: CNC(=O)c1cc(F)ccc1NC(=O)c1nc(C2CC2)cnc1Nc1cncnc1]

According to the procedures described in example 278, the title compound was obtained reacting 2-amino-5-fluoro-benzoic acid and methylamine hydrochloride in the 1$^{st}$ step. Yellow powder.

MS: M=408.3 (M+H)$^+$

Example 313

6-Cyclopropyl-3-(pyrimidin-5-ylamino)-pyrazine-2-carboxylic acid [5-(2-dimethylamino-ethylcarbamoyl)-1-methyl-1H-pyrazol-4-yl]-amide

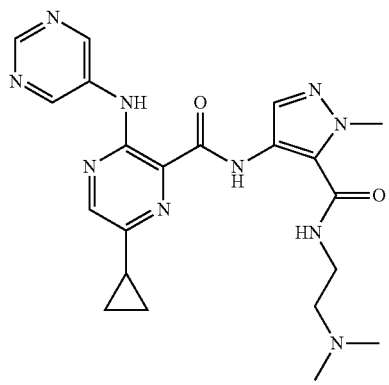 [SMILES: CN(C)CCNC(=O)c1c(NC(=O)c2nc(C3CC3)cnc2Nc2cncnc2)cnn1C]

The product was obtained starting from 4-{[6-cyclopropyl-3-(pyrimidin-5-ylamino)-pyrazine-2-carbonyl]-amino}-2-methyl-2H-pyrazole-3-carboxylic acid (30 mg, 79 µmol; example 236, step 3) and N,N-dimethylethylene-1,2-diamine (11 µl, 100 µmol) according to the method described in example 64, step 6 as yellow solid (10 mg, 28%).

MS: M=451.2 (M+H)+

Example 314

2-Cyclopropyl-5-(pyrimidin-5-ylamino)-pyrimidine-4-carboxylic acid (1-methyl-5-methylcarbamoyl-1H-pyrazol-4-yl)-amide

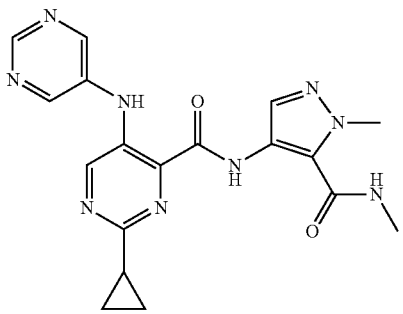 [SMILES: CNC(=O)c1c(NC(=O)c2nc(C3CC3)ncc2Nc2cncnc2)cnn1C]

Step 1: 2-Cyclopropyl-5-(pyrimidin-5-ylamino)-pyrimidine-4-carboxylic acid

A suspension of intermediate A-5 (75 mg, 0.28 mmol) in ethanol (2 ml) was treated with NaOH (1M, 0.55 ml, 551 µmol) under an Argon atmosphere, and the mixture was stirred at r.t for 17 h. HCl (1N, 0.55 ml) was added and the reaction mixture was poured into dichloromethane (5 ml) and separated. The organic layer was dried and evaporated to yield the product as yellow solid (35 mg, 49%).

MS: M=256.1 (M–H)−

Step 2: 2-Cyclopropyl-5-(pyrimidin-5-ylamino)-pyrimidine-4-carboxylic acid (1-methyl-5-methylcarbamoyl-1H-pyrazol-4-yl)-amide The product was obtained starting from 2-cyclopropyl-5-(pyrimidin-5-ylamino)-pyrimidine-4-carboxylic acid (35 mg, 135 µmol) and 4-amino-2-methyl-2H-pyrazole-3-carboxylic acid methylamide (25 mg, 163 µmol) according to the method described in example 64, step 6 as light yellow solid (22 mg, 41%).

MS: M=394.2 (M+H)+

Example 315

6-Cyclopropyl-3-(pyrimidin-5-ylamino)-pyrazine-2-carboxylic acid [1-methyl-5-(1-methyl-azetidin-3-ylcarbamoyl)-1H-pyrazol-4-yl]-amide

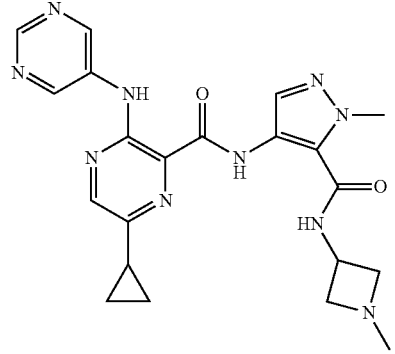 [SMILES: CN1CC(NC(=O)c2c(NC(=O)c3nc(C4CC4)cnc3Nc3cncnc3)cnn2C)C1]

The product was obtained starting from 4-{[6-cyclopropyl-3-(pyrimidin-5-ylamino)-pyrazine-2-carbonyl]-amino}-2-methyl-2H-pyrazole-3-carboxylic acid (30 mg, 79 µmol; example 236, step 3) and 1-methylazetidin-3-amine dihydrochloride (16 mg, 100 µmol) according to the method described in example 64, step 6 after purification by preparative HPLC using an acetonitrile/water gradient as yellow solid (11 mg, 31%).

MS: M=449.3 (M+H)+

Example 316

6-Cyclopropyl-3-(pyrimidin-5-ylamino)-pyrazine-2-carboxylic acid (2-dimethylcarbamoyl-3,4-difluoro-phenyl)-amide

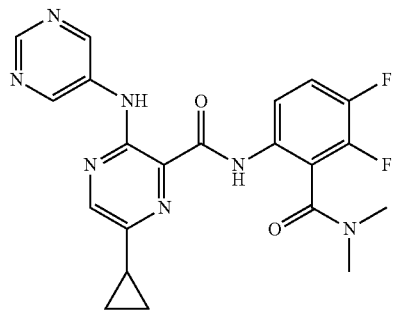 [SMILES: CN(C)C(=O)c1c(NC(=O)c2nc(C3CC3)cnc2Nc2cncnc2)ccc(F)c1F]

According to the procedures described in example 278, the title compound was obtained reacting 2-amino-5,6-difluorobenzoic acid and dimethylamine hydrochloride in the 1st step. Yellow powder.

MS: M=440.2 (M+H)+

Example 317

6-Cyclopropyl-3-(pyrimidin-5-ylamino)-pyrazine-2-carboxylic acid (3,4-difluoro-2-methylcarbamoyl-phenyl)-amide

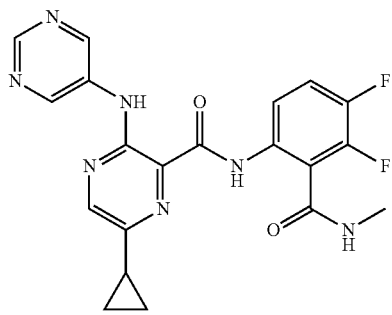 [SMILES: CNC(=O)c1c(NC(=O)c2nc(C3CC3)cnc2Nc2cncnc2)ccc(F)c1F]

According to the procedures described in example 278, the title compound was obtained reacting 2-amino-5,6-difluorobenzoic acid and methylamine hydrochloride in the 1$^{st}$ step. Yellow powder.

MS: M=426.1 (M+H)$^+$

Example 318

6-Cyclopropyl-3-(pyrimidin-5-ylamino)-pyrazine-2-carboxylic acid [3,4-difluoro-2-(2-hydroxy-2-methyl-propylcarbamoyl)-phenyl]-amide

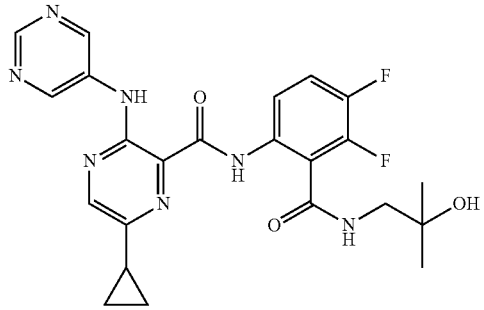 [SMILES: CC(C)(O)CNC(=O)c1c(NC(=O)c2nc(C3CC3)cnc2Nc2cncnc2)ccc(F)c1F]

According to the procedures described in example 278, the title compound was obtained reacting 2-amino-5,6-difluorobenzoic acid and 1-amino-2-methylpropan-2-ol in the 1$^{st}$ step. Yellow powder.

MS: M=484.3 (M+H)$^+$

Example 319

6-Cyclopropyl-3-(pyrimidin-5-ylamino)-pyrazine-2-carboxylic acid [2-(azetidine-1-carbonyl)-3,4-difluoro-phenyl]-amide

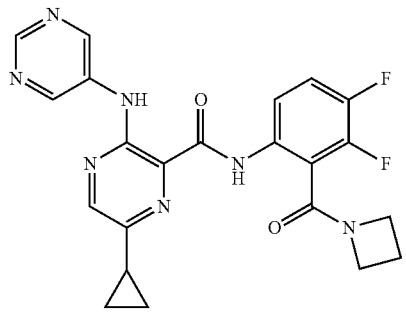 [SMILES: O=C(Nc1ccc(F)c(F)c1C(=O)N1CCC1)c1nc(C2CC2)cnc1Nc1cncnc1]

According to the procedures described in example 278, the title compound was obtained reacting 2-amino-5,6-difluorobenzoic acid and azetidine in the 1$^{st}$ step. Yellow powder.

MS: M=452.2 (M+H)$^+$

Example 320

6-Cyclopropyl-3-(pyrimidin-5-ylamino)-pyrazine-2-carboxylic acid [6-(azetidine-1-carbonyl)-2,3-difluoro-phenyl]-amide

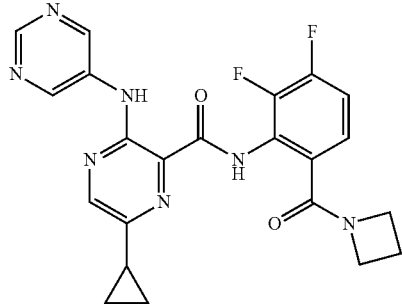 [SMILES: O=C(Nc1c(C(=O)N2CCC2)ccc(F)c1F)c1nc(C2CC2)cnc1Nc1cncnc1]

According to the procedures described in example 278, the title compound was obtained reacting 2-amino-3,4-difluorobenzoic acid and azetidine in the 1$^{st}$ step. Yellow powder.

MS: M=452.2 (M+H)$^+$

Example 321

3-(4-{[6-Cyclopropyl-3-(pyrimidin-5-ylamino)-pyrazine-2-carbonyl]-amino}-3-methylcarbamoyl-phenyl)-propionic acid ethyl ester

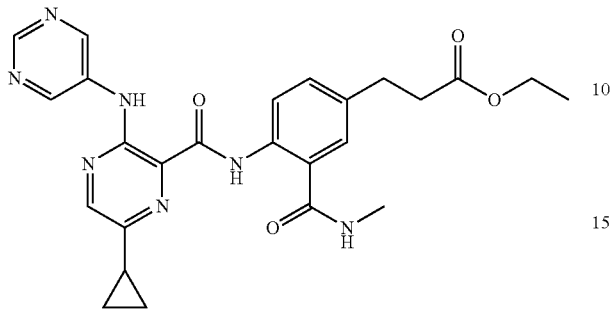

Step 1: 5-Bromo-N-methyl-2-nitrobenzamide

According to the procedure described in step 1 of example 111, the title compound was obtained by coupling 5-bromo-2-nitrobenzoic acid and methylamine hydrochloride. Off-white solid.

Step 2: (E)-Ethyl 3-(3-(methylcarbamoyl)-4-nitrophenyl)acrylate

A mixture of 5-bromo-N-methyl-2-nitrobenzamide (1.366 g, 5.27 mmol) and sodium acetate (1.08 g, 13.2 mmol) in DMF (6 ml) was degassed and flushed with argon. To this mixture was added a solution of degassed palladium (II) acetate (35.5 mg, 158 µmol) and tri-o-tolylphosphine (96.3 mg, 316 µmol). The resulting solution was then degassed and flushed with argon to give a brown solution which was heated at 130° C. overnight. The reaction mixture at r.t. into water (10 ml) The aqueous solution was extracted with methylene chloride. The organic layers were dried over MgSO$_4$. The crude product was purified by silica gel chromatography using a heptane/EtOAc gradient to obtain the title compound (1.09 g, 75%) as light yellow solid.
MS: M=279.0 (M+H)$^+$

Step 3: Ethyl 3-(4-amino-3-(methylcarbamoyl)phenyl)propanoate

To a stirred solution of (E)-ethyl 3-(3-(methylcarbamoyl)-4-nitrophenyl)acrylate (345 mg, 1.24 mmol) in ethanol (10 ml) at r.t. under an argon atmosphere was added 10% Pd/C (52.8 mg, 496 µmol). The black suspension was hydrogenated at normal pressure and r.t. overnight. The catalyst was removed by filtration. The filtrate was concentrated. The crude product was purified by silica gel chromatography using a methylenchloride/MeOH gradient to give the title compound (175 mg, 57%) as white solid.
MS: M=251.2 (M+H)$^+$

Step 4: Ethyl 3-(4-(6-cyclopropyl-3-(pyrimidin-5-ylamino)pyrazine-2-carboxamido)-3-(methyl-carbamoyl)phenyl)propanoate According to the procedure described in step 6 of example 64, the title compound was obtained by reaction intermediate A-11 with ethyl 3-(4-amino-3-(methylcarbamoyl)phenyl) propanoate. Yellow solid.
MS: M=490.4 (M+H)$^+$

Example 322

6-Cyclopropyl-3-(pyrimidin-5-ylamino)-pyrazine-2-carboxylic acid (2-methylcarbamoyl-4-methylcarbamoylmethoxy-phenyl)-amide

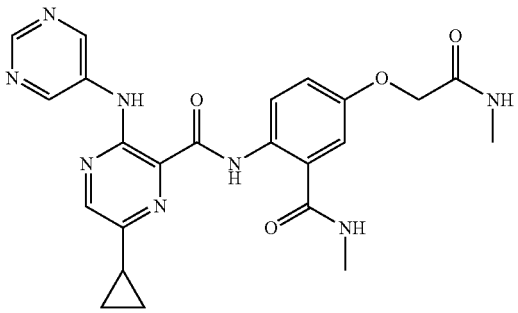 [SMILES: CNC(=O)COc1ccc(NC(=O)c2nc(C3CC3)cnc2Nc2cncnc2)c(C(=O)NC)c1]

Step 1: Methyl 2-amino-5-(2-amino-2-oxoethoxy)benzoate

To a suspension of NaH (299 mg, 7.48 mmol) in DMF (20 ml) at 0° under argon atmosphere was added methyl 2-amino-5-hydroxybenzoate (1.25 g, 7.48 mmol) and 2-iodoacetamide (1.38 g, 7.48 mmol). The mixture was stirred at 0° for 1 hr and at r.t overnight. At 0° water was given to the reaction mixture. The product was extracted with EtOAc. The organic layers were dried over MgSO$_4$, filtered and concentrated. The crude product was purified by silica gel chromatography using a methylenchloride gradient to obtain the title compound (1.03 g, 64%) as off-white solid.
MS: M=225.0 (M+H)$^+$

Step 2: 6-Cyclopropyl-3-(pyrimidin-5-ylamino)-pyrazine-2-carboxylic acid (2-methylcarbamoyl-4-methylcarbamoylmethoxy-phenyl)-amide According to the procedures described in example 99, the title compound was obtained as unexpected product using intermediate A-11 and methyl 2-amino-5-(2-amino-2-oxoethoxy)benzoate in the 1$^{st}$ step and methylamine hydrochloride in the 3$^{rd}$ step. Yellow solid.
MS: M=477.2 (M+H)$^+$

Example 323

6-Cyclopropyl-3-(pyrimidin-5-ylamino)-pyrazine-2-carboxylic acid [2-(azetidine-1-carbonyl)-3,5-difluoro-phenyl]-amide

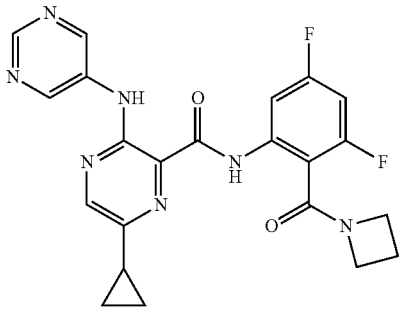 [SMILES: O=C(Nc1cc(F)cc(F)c1C(=O)N1CCC1)c1nc(C2CC2)cnc1Nc1cncnc1]

According to the procedures described in example 278, the title compound was obtained reacting 2-amino-4,6-difluoro-benzoic acid and azetidine in the 1st step. Yellow powder.

MS: M=450.1 (M−H)⁻

Example 324

6-Cyclopropyl-3-(pyrimidin-5-ylamino)-pyrazine-2-carboxylic acid [3,5-difluoro-2-(2-hydroxy-2-methyl-propylcarbamoyl)-phenyl]-amide

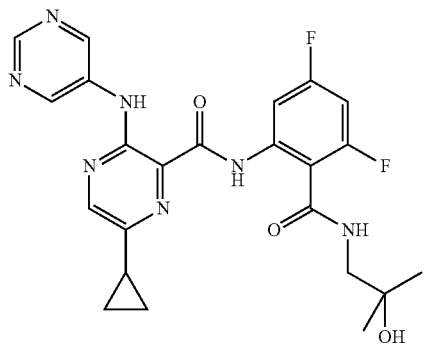 [SMILES: CC(C)(O)CNC(=O)c1c(F)cc(F)cc1NC(=O)c1nc(C2CC2)cnc1Nc1cncnc1]

According to the procedures described in example 278, the title compound was obtained reacting 2-amino-4,6-difluoro-benzoic acid and 1-amino-2-methylpropan-2-ol in the 1st step. Yellow powder.

MS: M=482.2 (M−H)⁻

Example 325

6-Cyclopropyl-3-(pyrimidin-5-ylamino)-pyrazine-2-carboxylic acid (6-dimethylcarbamoyl-2,3-difluoro-phenyl)-amide

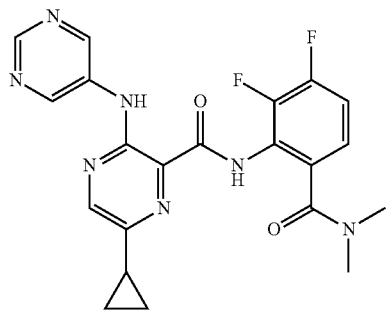 [SMILES: CN(C)C(=O)c1ccc(F)c(F)c1NC(=O)c1nc(C2CC2)cnc1Nc1cncnc1]

According to the procedures described in example 278, the title compound was obtained reacting 2-amino-3,4-difluoro-benzoic acid and dimethyl hydrochloride in the 1st step. Yellow powder.

MS: M=440.1 (M+H)⁺

Example 326

6-Cyclopropyl-3-(pyrimidin-5-ylamino)-pyrazine-2-carboxylic acid [2,3-difluoro-6-(2-hydroxy-2-methyl-propylcarbamoyl)-phenyl]-amide

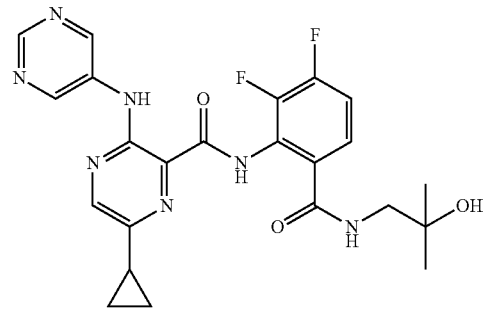 [SMILES: CC(C)(O)CNC(=O)c1ccc(F)c(F)c1NC(=O)c1nc(C2CC2)cnc1Nc1cncnc1]

According to the procedures described in example 278, the title compound was obtained reacting 2-amino-3,4-difluoro-benzoic acid and 1-amino-2-methylpropan-2-ol in the 1st step. Yellow powder.

MS: M=484.4 (M+H)⁺

Example 327

6-Cyclopropyl-3-(pyrimidin-5-ylamino)-pyrazine-2-carboxylic acid (2,3-difluoro-6-methylcarbamoyl-phenyl)-amide

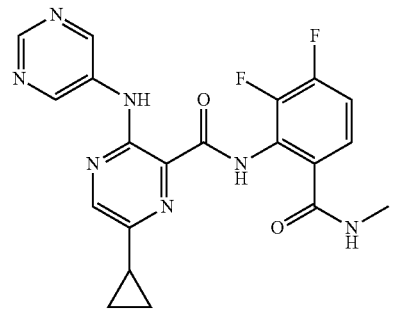 [SMILES: CNC(=O)c1ccc(F)c(F)c1NC(=O)c1nc(C2CC2)cnc1Nc1cncnc1]

According to the procedures described in example 278, the title compound was obtained reacting 2-amino-3,4-difluoro-benzoic acid and methylamine hydrochloride in the 1st step. Yellow powder.

MS: M=424.1 (M+H)⁺

Example 328

3-(4-{[6-Cyclopropyl-3-(pyrimidin-5-ylamino)-pyrazine-2-carbonyl]-amino}-3-methylcarbamoyl-phenyl)-propionic acid

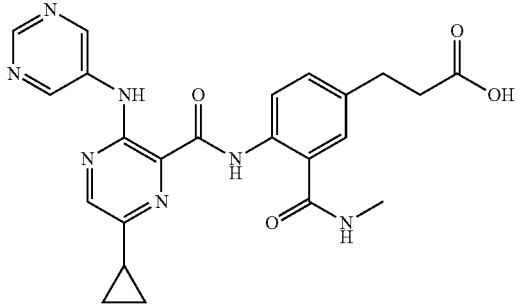 [SMILES: CNC(=O)c1cc(CCC(=O)O)ccc1NC(=O)c1nc(C2CC2)cnc1Nc1cncnc1]

In analogy to the procedure described in step 2 of example 99, 6-amino-2,3-difluoro-N-(2-hydroxy-2-methylpropyl)benzamide (example 321) was converted to the title compound.

MS: M=460.4 (M–H)+

Example 329

2-Isopropyl-5-(pyrimidin-5-ylamino)-pyrimidine-4-carboxylic acid [2-(2-hydroxy-2-methyl-propylcarbamoyl)-pyridin-3-yl]-amide

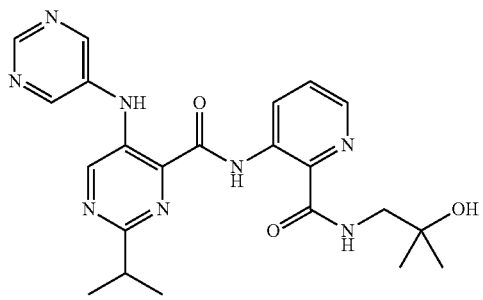 [SMILES: CC(C)c1ncc(Nc2cncnc2)c(C(=O)Nc2cccnc2C(=O)NCC(C)(C)O)n1]

The product was obtained as yellow solid (74 mg, 53%) after purification by preparative HPLC using an acetonitrile/water gradient and silica gel chromatography using a heptane/ethyl acetate gradient according to the procedures described in example 98 using intermediate A-15 in the $2^{nd}$ step.

MS: M=451.3 (M+H)+

Example 330

2-tert-Butyl-5-(pyrimidin-5-ylamino)-pyrimidine-4-carboxylic acid [2-(2-hydroxy-2-methyl-propylcarbamoyl)-pyridin-3-yl]-amide

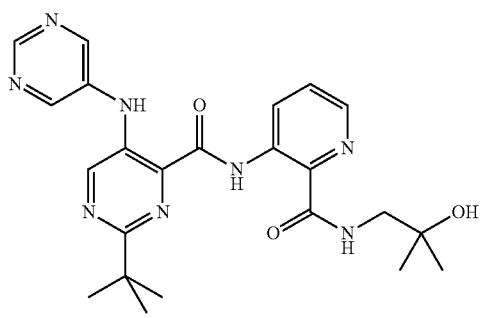 [SMILES: CC(C)(O)CNC(=O)c1ncccc1NC(=O)c1nc(C(C)(C)C)ncc1Nc1cncnc1]

The product was obtained as yellow solid (65 mg, 48%) after purification by preparative HPLC using an acetonitrile/water gradient according to the procedures described in example 98 using intermediate A-9 in the $2^{nd}$ step.

MS: M=465.3 (M+H)+

Example 331

2-Isobutyl-5-(pyrimidin-5-ylamino)-pyrimidine-4-carboxylic acid [2-(2-hydroxy-2-methyl-propylcarbamoyl)-pyridin-3-yl]-amide

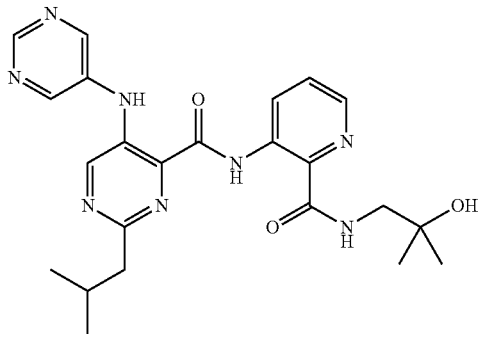 [SMILES: CC(C)Cc1ncc(Nc2cncnc2)c(C(=O)Nc2cccnc2C(=O)NCC(C)(C)O)n1]

Step 1: 2-Isobutyl-5-(pyrimidin-5-ylamino)-pyrimidine-4-carboxylic acid

The product was obtained as yellow solid (188 mg, 98%) according to the method described in example 314, step 1 starting from intermediate A-7.

MS: M=272.2 (M–H)−

Step 2: 2-Isobutyl-5-(pyrimidin-5-ylamino)-pyrimidine-4-carboxylic acid [2-(2-hydroxy-2-methyl-propylcarbamoyl)-pyridin-3-yl]-amide The product was obtained as yellow solid (63 mg, 62%) after purification by preparative HPLC using an acetonitrile/water gradient according to the procedures described in example 98 using 2-isobutyl-5-(pyrimidin-5-ylamino)-pyrimidine-4-carboxylic acid in the $2^{nd}$ step.

MS: M=465.3 (M+H)+

Example 332

2-Isobutyl-5-(pyrimidin-5-ylamino)-pyrimidine-4-carboxylic acid (1-methyl-5-methylcarbamoyl-1H-pyrazol-4-yl)-amide

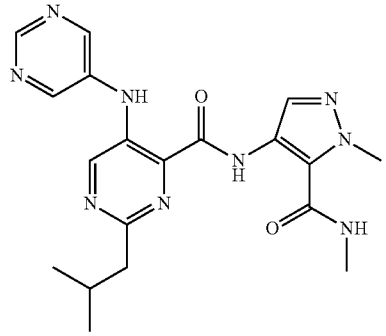 [SMILES: CNC(=O)c1c(NC(=O)c2nc(CC(C)C)ncc2Nc2cncnc2)cnn1C]

The product was obtained starting from 2-isobutyl-5-(pyrimidin-5-ylamino)-pyrimidine-4-carboxylic acid (60 mg, 0.22 mmol; example 331, step 1) and 4-amino-2-methyl-2H-pyrazole-3-carboxylic acid methylamide (44 mg, 0.28 mmol) according to the method described in example 64, step 6 after

Example 333

4-Methyl-5'-(pyrimidin-5-ylamino)-3,4,5,6-tetrahydro-2H-[1,2]bipyrazinyl-6'-carboxylic acid (1-methyl-5-methylcarbamoyl-1H-pyrazol-4-yl)-amide

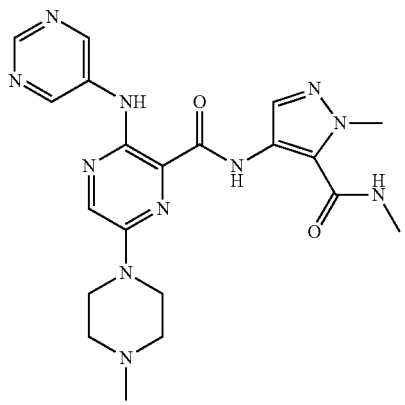 [SMILES: CNC(=O)c1c(NC(=O)c2nc(N3CCN(C)CC3)cnc2Nc2cncnc2)cnn1C]

According to the procedures described in example 289, the product was prepared as yellow solid by using N-methylpiperazine in the 1$^{st}$ step.

MS: M=452.2 (M+H)$^+$

Example 334

6-Cyclopropyl-3-(pyrimidin-5-ylamino)-pyrazine-2-carboxylic acid [5-(methoxy-methyl-carbamoyl)-1-methyl-1H-pyrazol-4-yl]-amide

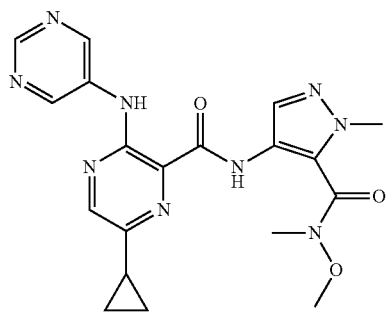 [SMILES: CON(C)C(=O)c1c(NC(=O)c2nc(C3CC3)cnc2Nc2cncnc2)cnn1C]

The product was obtained starting from 4-{[6-cyclopropyl-3-(pyrimidin-5-ylamino)-pyrazine-2-carbonyl]-amino}-2-methyl-2H-pyrazole-3-carboxylic acid (50 mg, 131 µmol; example 236, step 3) and N,O-dimethylhydroxylamine hydrochloride (14 mg, 145 µmol) according to the method described in example 64, step 6 after purification by preparative HPLC using an acetonitrile/water gradient as yellow foam (47 mg, 84%).

MS: M=424.3 (M+H)$^+$

Example 335

6-Cyclopropyl-3-(pyrimidin-5-ylamino)-pyrazine-2-carboxylic acid [5-(isoxazolidine-2-carbonyl)-1-methyl-1H-pyrazol-4-yl]-amide

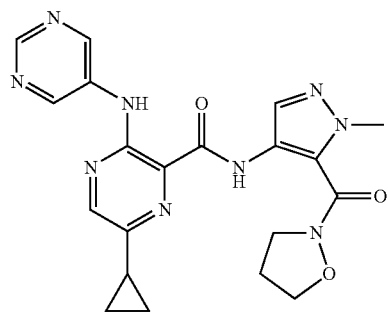 [SMILES: Cn1ncc(NC(=O)c2nc(C3CC3)cnc2Nc2cncnc2)c1C(=O)N1CCCO1]

The product was obtained starting from 4-{[6-cyclopropyl-3-(pyrimidin-5-ylamino)-pyrazine-2-carbonyl]-amino}-2-methyl-2H-pyrazole-3-carboxylic acid (50 mg, 131 µmol; example 236, step 3) and isoxazolidine hydrochloride (17 mg, 145 µmol) according to the method described in example 64, step 6 after purification by preparative HPLC using an acetonitrile/water gradient as yellow solid (9 mg, 16%).

MS: M=436.2 (M+H)$^+$

Example 336

6-Cyclopropyl-3-(pyrimidin-5-ylamino)-pyrazine-2-carboxylic acid [5-(2-hydroxy-cyclopentylcarbamoyl)-1-methyl-1H-pyrazol-4-yl]-amide

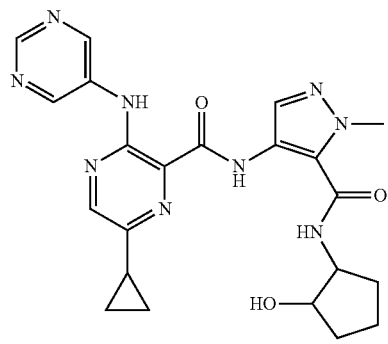 [SMILES: Cn1ncc(NC(=O)c2nc(C3CC3)cnc2Nc2cncnc2)c1C(=O)NC1CCCC1O]

The product was obtained starting from 4-{[6-cyclopropyl-3-(pyrimidin-5-ylamino)-pyrazine-2-carbonyl]-amino}-2-methyl-2H-pyrazole-3-carboxylic acid (50 mg, 131 µmol; example 236, step 3) and 2-aminocyclopentanol (15 mg, 140 µmol) according to the method described in example 64, step 6 after purification by preparative HPLC using an acetonitrile/water gradient as yellow solid (24 mg, 40%).

MS: M=464.3 (M+H)$^+$

Example 337

5-(Pyrimidin-5-ylamino)-2-(2,2,2-trifluoro-ethoxy)-pyrimidine-4-carboxylic acid (1-methyl-5-methyl-carbamoyl-1H-pyrazol-4-yl)-amide

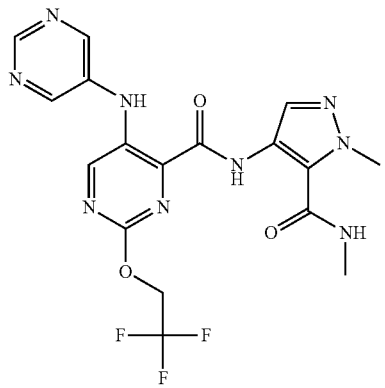 [SMILES: CNC(=O)c1c(NC(=O)c2nc(OCC(F)(F)F)ncc2Nc2cncnc2)cnn1C]

Step 1: 5-Bromo-2-(2,2,2-trifluoro-ethoxy)-pyrimidine-4-carboxylic acid ethyl ester To a solution of sodium trifluoroethoxide, prepared from trifluoroethanol (2 ml) and sodium hydride (37 mg, 0.84 mmol) at 0-5° C., was added dropwise a solution of ethyl 5-bromo-2-(methylsulfonyl)pyrimidine-4-carboxylic acid ethyl ester (200 mg, 0.65 mmol; example 126, step 1) dissolved in trifluoroethanol (2 ml) at the same temperature. The ice bath was removed after 15 min and the mixture was stirred at r.t. for 4 h. The reaction mixture was poured into ethyl acetate (20 ml) and extracted with potassium hydrogen sulfate (10%, 10 ml). The organic phase was washed with water and brine and the aqueous layers were back-extracted with ethyl acetate. The combined organic layers were dried and evaporated and the product was obtained after purification by silica gel chromatography using a heptane/ethyl acetate gradient as colorless oil (186 mg, 87%).

MS: M=329.0 (M+H)$^+$

Step 2: 5-(Pyrimidin-5-ylamino)-2-(2,2,2-trifluoro-ethoxy)-pyrimidine-4-carboxylic acid ethyl ester The product was obtained starting from 5-bromo-2-(2,2,2-trifluoro-ethoxy)-pyrimidine-4-carboxylic acid ethyl ester (225 mg, 0.68 mmol) according to the method described in example A-13 as yellow solid (160 mg, 83%).

MS: M=344.2 (M+H)$^+$

Step 3: 5-(Pyrimidin-5-ylamino)-2-(2,2,2-trifluoro-ethoxy)-pyrimidine-4-carboxylic acid The product was obtained starting from 5-(pyrimidin-5-ylamino)-2-(2,2,2-trifluoro-ethoxy)-pyrimidine-4-carboxylic acid ethyl ester (160 mg, 0.46 mmol) according to the method described in example 314, step 1 as yellow solid (145 mg, 99%).

MS: M=314.0 (M-H)$^-$

Step 4: 5-(Pyrimidin-5-ylamino)-2-(2,2,2-trifluoro-ethoxy)-pyrimidine-4-carboxylic acid (1-methyl-5-methylcarbamoyl-1H-pyrazol-4-yl)-amide The product was obtained starting from 5-(pyrimidin-5-ylamino)-2-(2,2,2-trifluoro-ethoxy)-pyrimidine-4-carboxy-lic acid (50 mg, 0.16 mmol) and 4-amino-2-methyl-2H-pyrazole-3-carboxylic acid methylamide (32 mg, 0.21 mmol) according to the method described in example 64, step 6 as yellow solid (50 mg, 69%).

MS: M=452.1 (M+H)$^+$

Example 338

6-Cyclopropyl-3-(pyrimidin-5-ylamino)-pyrazine-2-carboxylic acid [4-(2-hydroxy-2-methyl-propoxy)-2-methylcarbamoyl-phenyl]-amide

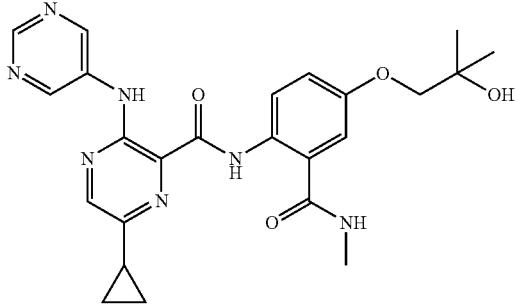 [SMILES: CNC(=O)c1cc(OCC(C)(C)O)ccc1NC(=O)c1nc(C2CC2)cnc1Nc1cncnc1]

Step 1: Methyl 5-(2-hydroxy-2-methylpropoxy)-2-nitrobenzoate

A mixture of methyl 5-hydroxy-2-nitrobenzoate (0.5 g, 2.54 mmol), 2,2-dimethyloxirane (6.86 ml, 7.61 mmol), potassium carbonate (351 mg, 2.54 mmol) and sodium dihydrogen phosphate monohydrate (350 mg, 2.54 mmol) in acetonitrile (4 ml) and water (0.6 ml) was stirred at 140° (5 bar) in a steel bomb for 6 hr. After cooling to r.t, the mixture was diluted with water, extracted with AcOEt, dried over MgSO$_4$, filtered and evaporated. The crude product was purified by silica gel chromatography using a methylenechloride/MeOH gradient to obtain the title compound (200 mg, 29%) as light yellow viscous oil.

MS: M=270.4 (M+H)$^+$

As a second product, 2-hydroxy-2-methylpropyl 5-(2-hydroxy-2-methylpropoxy)-2-nitro-benzoate was obtained (248 mg, 30%) as a off-white solid.

MS: M=345.5 (M+NH$_4$)$^+$

Step 2: 5-(2Hydroxy-2-methylpropoxy)-2-nitrobenzoic acid

To a solution of 2-hydroxy-2-methylpropyl 5-(2-hydroxy-2-methylpropoxy)-2-nitrobenzoate (0.24 g, 733 μmol) in MeOH (10 ml) at r.t was added NaOH 1 N (2.2 ml, 2.2 mmol). The solution was stirred at r.t overnight. 2.2 ml 1 N HCl were added. The solvents were evaporated. The residue was dissolved in methylenechloride/MeOH 9:1 (100 ml), washed with 10 ml H$_2$O, dried over MgSO$_4$, filtered and evaporated to give the title compound (149 mg, 80%) as off-white solid.

MS: M=245.2 (M-H)$^-$

Step 3: 2-Amino-5-(2-hydroxy-2-methylpropoxy)benzoic acid

A solution of 5-(2-hydroxy-2-methylpropoxy)-2-nitrobenzoic acid (0.145 g, 568 μmol) in ethanol (5 ml) was hydrogenated at normal pressure in the presence of 20 mg Pd/C 10% at r.t overnight. The catalyst was filtered and washed with EtOH. The filtrate was concentrated to give the title compound (127 mg, 99%) as grayish foam.
MS: M=226.2 (M+H)⁺

Step 4: 6-Cyclopropyl-N-(4-(2-hydroxy-2-methyl-propoxy)-2-(methylcarbamoyl)phenyl)-3-(pyrimidin-5-ylamino)pyrazine-2-carboxamide According to the procedures described in example 278, the title compound was obtained reacting methylamine hydrochloride in the 1$^{st}$ step. Yellow powder.
MS: M=478.0 (M+H)⁺

Example 339

3-(Pyrimidin-5-ylamino)-6-(2,2,2-trifluoro-ethoxy)-pyrazine-2-carboxylic acid (1-methyl-5-methylcarbamoyl-1H-pyrazol-4-yl)-amide

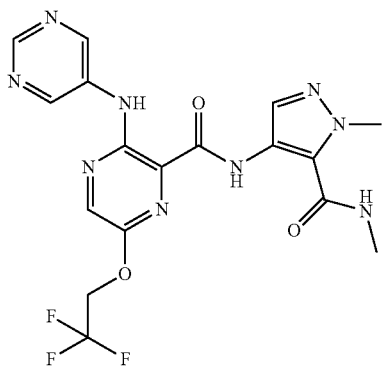 [SMILES: CNC(=O)c1c(NC(=O)c2nc(OCC(F)(F)F)cnc2Nc2cncnc2)cnn1C]

Step 1: 3-(Bis(tert-butoxycarbonyl)amino)-6-(2,2,2-trifluoro-ethoxy)-pyrazine-2-carboxylic acid methyl ester A suspension of methyl 3-(bis(tert-butoxycarbonyl)amino)-6-bromopyrazine-2-carboxylate (500 mg, 1.16 mmol), 2,2,2-trifluoroethanol (84 µl, 1.16 mmol), cesium carbonate (415 mg, 1.27 mmol) and dry DMSO (5 ml) was stirred at r.t. for 3 h. The reaction mixture was poured into ethyl acetate (100 ml) and extracted with saturated sodium bicarbonate (aqueous solution). The organic layer was washed with water and brine and the aqueous layers were back-extracted with ethyl acetate. The combined organic layers were dried, evaporated and the product was obtained after purification by silica gel chromatography using a heptane/ethyl acetate gradient as white solid (456 mg, 87%).
MS=474.1 (M+Na)⁺

Step 2: 3-Amino-6-(2,2,2-trifluoro-ethoxy)-pyrazine-2-carboxylic acid methyl ester The product was obtained starting from 3-(bis(tert-butoxycarbonyl)amino)-6-(2,2,2-trifluoro-ethoxy)-pyrazine-2-carboxylic acid methyl ester (456 mg, 1.0 mmol) according to the method described in example A-12, step 3 after purification by silica gel chromatography using a heptane/ethyl acetate gradient as off-white solid (136 mg, 54%).

Step 3: 3-(Pyrimidin-5-ylamino)-6-(2,2,2-trifluoro-ethoxy)-pyrazine-2-carboxylic acid methyl ester The product was obtained starting from 3-amino-6-(2,2,2-trifluoro-ethoxy)-pyrazine-2-carboxylic acid methyl ester (182 mg, 0.72 mmol) according to the method described in example A-1, step 2 as light-yellow solid (126 mg, 53%).
MS: M=330.2 (M+H)⁺

Step 4: 3-(Pyrimidin-5-ylamino)-6-(2,2,2-trifluoro-ethoxy)-pyrazine-2-carboxylic acid The product was obtained starting from 3-(pyrimidin-5-ylamino)-6-(2,2,2-trifluoro-ethoxy)-pyrazine-2-carboxylic acid methyl ester (122 mg, 0.37 mmol) according to the method described in example 314, step 1 as yellow solid (115 mg, 98%).
MS: M=314.0 (M–H)⁻

Step 5: 3-(Pyrimidin-5-ylamino)-6-(2,2,2-trifluoro-ethoxy)-pyrazine-2-carboxylic acid (1-methyl-5-methylcarbamoyl-1H-pyrazol-4-yl)-amide The product was obtained starting from 3-(pyrimidin-5-ylamino)-6-(2,2,2-trifluoro-ethoxy)-pyrazine-2-carboxylic acid (114 mg, 0.36 mmol) and 4-amino-2-methyl-2H-pyrazole-3-carboxylic acid methylamide (67 mg, 0.43 mmol) according to the method described in example 64, step 6 as yellow solid (92 mg, 56%).
MS: M=452.1 (M+H)⁺

Example 340

2-(1-Hydroxy-1-methyl-ethyl)-5-(pyrimidin-5-ylamino)-pyrimidine-4-carboxylic acid (1-methyl-5-methylcarbamoyl-1H-pyrazol-4-yl)-amide

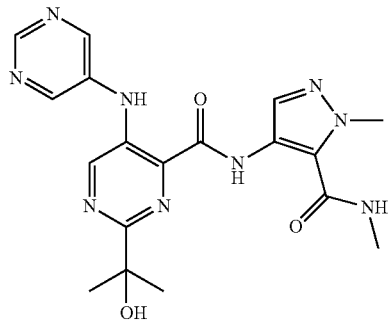 [SMILES: CNC(=O)c1c(NC(=O)c2nc(C(C)(C)O)ncc2Nc2cncnc2)cnn1C]

Step 1: 5-Bromo-2-(1-hydroxy-1-methyl-ethyl)-pyrimidine-4-carboxylic acid

The product was obtained starting from 2-hydroxy-2-methylpropylamidine hydrochloride (4.34 g, 31.3 mmol) according to the method described in example A-4, step 1 as brown viscous oil (2.82 g, 70%)
MS: M=279.1 (M+NH₃+H)⁺

Step 2: 5-Bromo-2-(1-hydroxy-1-methyl-ethyl)-pyrimidine-4-carboxylic acid (1-methyl-5-methylcarbamoyl-1H-pyrazol-4-yl)-amide The product was obtained starting from 5-bromo-2-(2-hydroxypropan-2-yl)pyrimidine-4-carboxylic acid (150 mg, 0.575 mmol) and 4-amino-2-methyl-2H-pyrazole-3-carboxylic acid methylamide (106 mg, 0.69 mmol) according to the method described in example 64, step 6 after purification by silica gel chromatography using a heptane/ethyl acetate gradient as light brown waxy solid (31 mg, 13%).
MS: M=399.0 (M+H)⁺

Step 3: 2-(1-Hydroxy-1-methyl-ethyl)-5-(pyrimidin-5-ylamino)-pyrimidine-4-carboxylic acid (1-methyl-5-methylcarbamoyl-1H-pyrazol-4-yl)-amide The product was obtained starting from 5-bromo-2-(1-hydroxy-1-methyl-ethyl)-pyrimidine-4-carboxylic acid (1-methyl-5-methylcarbamoyl-1H-pyrazol-4-yl)-amide (26 mg, 66 μmol) according to the method described in example A-13 after purification by preparative HPLC using an acetonitrile/water gradient as light yellow solid (3 mg, 11%).
MS: M=412.3 (M+H)+

Example 341

6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide

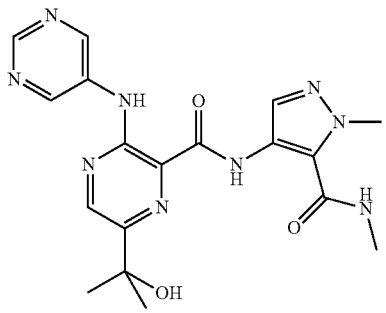 [SMILES: CNC(=O)c1c(NC(=O)c2nc(C(C)(C)O)cnc2Nc2cncnc2)cnn1C]

Step 1: 3-(Bis(tert-butoxycarbonyl)amino)-6-(2-hydroxypropan-2-yl)pyrazine-2-carboxylic acid ethyl ester A solution of methyl 3-(bis(tert-butoxycarbonyl)amino)-6-(prop-1-en-2-yl)pyrazine-2-carboxylate (761 mg, 1.93 mmol; example A-17, step 1), tetrabutylammonium borohydride (995 mg, 3.87 mmol), 5,10,15,20-tetraphenyl-21H,23H-porphine manganese(III) chloride (136 mg, 0.19 mmol) in toluene (20 ml) and ethanol (20 ml) was stirred at r.t. for 40 h with compressed air bubbling through the reaction mixture. Water (40 ml) was added and the reaction mixture was extracted with ethyl acetate (120 ml). The organic phase was washed with water and brine and the aqueous layers were back-extracted with ethyl acetate. The combined organic layers were dried, evaporated and the crude product was obtained after purification by preparative HPLC using a methanol/water gradient. The methanol was evaporated and the resulting aqueous suspension was subsequently extracted with dichloromethane, dried and the solvent was evaporated to yield the product as green oil (164 mg, 20%).
MS: M=448.2 (M+Na)+

Step 2: 3-Amino-6-(2-hydroxypropan-2-yl)pyrazine-2-carboxylic acid ethyl ester

The product was obtained starting from 3-(bis(tert-butoxycarbonyl)amino)-6-(2-hydroxypropan-2-yl)pyrazine-2-carboxylic acid ethyl ester (160 mg, 0.38 mmol) according to the method described in example A-12, step 3 and was used without any purification for the next step.
MS: M=226.2 (M+H)+

Step 3: 6-(2-Hydroxypropan-2-yl)-3-(pyrimidin-5-ylamino)pyrazine-2-carboxylic acid ethyl ester The product was obtained starting from 3-amino-6-(2-hydroxypropan-2-yl)pyrazine-2-carboxylic acid ethyl ester according to the method described in example A-1, step 2 after purification by preparative HPLC using an acetonitrile/water gradient as yellow solid (9 mg, 8%).
MS: M=304.1 (M+H)+

Step 4: 6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide The product was obtained from 6-(2-hydroxypropan-2-yl)-3-(pyrimidin-5-ylamino)pyrazine-2-carboxylic acid ethyl ester (8 mg, 26 μmol) and 4-amino-2-methyl-2H-pyrazole-3-carboxylic acid methylamide (10 mg, 65 μmol) according to the method described in example 104 after purification by preparative HPLC using an acetonitrile/water gradient as yellow solid (1.6 mg, 15%).
MS: M=412.2 (M+H)+

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:
1. A compound of formula (I)

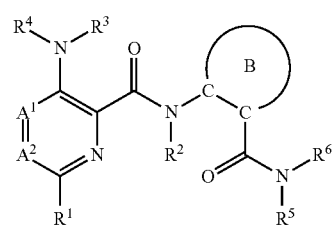

wherein
A$^1$ is selected from the group consisting of CH and N;
A$^2$ is selected from the group consisting of CR$^{19}$ and N, provided that A$^1$ and A$^2$ are not N simultaneously;

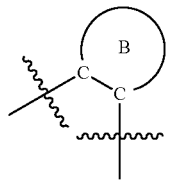

is aryl or heteroaryl, wherein said aryl and said heteroaryl are optionally substituted by 1 to 3 substituents independently selected from the group consisting of lower alkyl, lower alkoxy, lower hydroxyalkyl, lower haloalkyl, lower-alkoxy-lower-alkyl, lower alkyl-C(O)—, —C(O)—N(R$^8$)$_2$, —N(R$^8$)—C(O)-lower alkyl, cyano, halogen, R$^9$ and amino, and wherein said lower alkyl is optionally substituted by oxo, —C(O)OH, lower alkoxy-C(O)— or R$^7$, and wherein said lower alkoxy is optionally substituted by hydroxyl, lower alkoxy or —C(O)—N(R$^8$)$_2$, and wherein said amino is optionally substituted by 1 or 2 substituents independently selected from the group consisting of lower alkyl, lower hydroxyalkyl, lower-alkoxy-lower-alkyl and lower alkyl-C(O)—;

R$^1$ is lower alkyl, lower alkoxy, lower hydroxyalkyl, lower haloalkyl, lower-alkoxy-lower-alkyl, lower alkyl-C(O)—, —O-lower haloalkyl, cyano, halogen, R$^7$ or amino, wherein said lower alkyl is optionally substituted by R$^7$, and wherein said amino is optionally substituted by 1 or 2 substituents independently selected from the group consisting of lower alkyl and lower-alkoxy-lower-alkyl;

R$^2$ and R$^3$ are independently hydrogen or lower alkyl;

R$^4$ is aryl or heteroaryl, wherein said aryl and said heteroaryl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino, and wherein said amino is optionally substituted by 1 or 2 substituents independently selected from the group consisting of lower alkyl and lower-alkoxy-lower-alkyl;

R$^5$ and R$^6$ are independently hydrogen, lower alkyl, lower alkoxy, lower haloalkyl, lower cyanoalkyl, lower hydroxyalkyl, lower-alkoxy-lower-alkyl, cycloalkyl or heterocyclyl, wherein said lower alkyl is optionally substituted by oxo, R$^7$ or —N(R$^8$)$_2$, and wherein said lower haloalkyl is optionally substituted by hydroxyl, and wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano, —C(O)-lower alkoxy and —N($R^8$)$_2$, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino, and wherein said amino is optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl;

$R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl; and $R^{19}$ is hydrogen or tetrahydrofuran-2-yl;

or a pharmaceutically acceptable salt thereof.

2. A compound of formula (I)

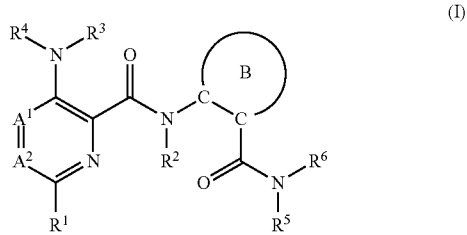

(I)

wherein $A^1$ and $A^2$ are independently selected from the group consisting of CH and N, provided that $A^1$ and $A^2$ are not N simultaneously;

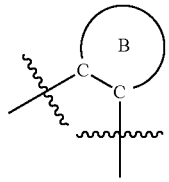

is aryl or heteroaryl, wherein said aryl and said heteroaryl are optionally substituted by 1 or 2 substituents independently selected from the group consisting of lower alkyl optionally substituted by oxo or $R^7$, lower alkoxy, lower hydroxyalkyl, lower haloalkyl, lower-alkoxy-lower-alkyl, lower alkyl-C(O)—, —C(O)—N($R^8$)$_2$, —N($R^8$)—C(O)-lower alkyl, cyano, halogen, $R^9$ and amino optionally substituted by 1 or 2 substituents independently selected from the group consisting of lower alkyl, lower hydroxyalkyl and lower-alkoxy-lower-alkyl;

$R^1$ is lower alkyl optionally substituted by $R^7$, lower alkoxy, lower hydroxyalkyl, lower haloalkyl, lower-alkoxy-lower-alkyl, lower alkyl-C(O)—, cyano, halogen, $R^7$ or amino optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is heteroaryl optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino optionally substituted by 1 or 2 substituents independently selected from the group consisting of lower alkyl and lower-alkoxy-lower-alkyl;

$R^5$ and $R^6$ are independently hydrogen, lower alkyl optionally substituted by oxo or $R^7$, lower haloalkyl, lower cyanoalkyl, lower hydroxyalkyl, lower-alkoxy-lower-alkyl, cycloalkyl or heterocyclyl, wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano and amino optionally substituted by 1 or 2 substituents independently selected from the group consisting of lower alkyl and lower-alkoxy-lower-alkyl, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl; and $R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl;

or a pharmaceutically acceptable salt thereof.

3. The compound or a pharmaceutically acceptable salt thereof of claim 1, wherein $R^2$ and $R^3$ are hydrogen.

4. The compound or a pharmaceutically acceptable salt thereof of claim 1, wherein $R^4$ is 3-fluoro-phenyl, 4-fluoro-phenyl, pyridin-3-yl, 5-fluoro-pyridin-3-yl, pyrimidin-5-yl or pyrazin-2-yl.

5. The compound or a pharmaceutically acceptable salt thereof of claim 1, wherein

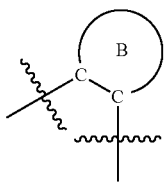

is selected from the group consisting of:

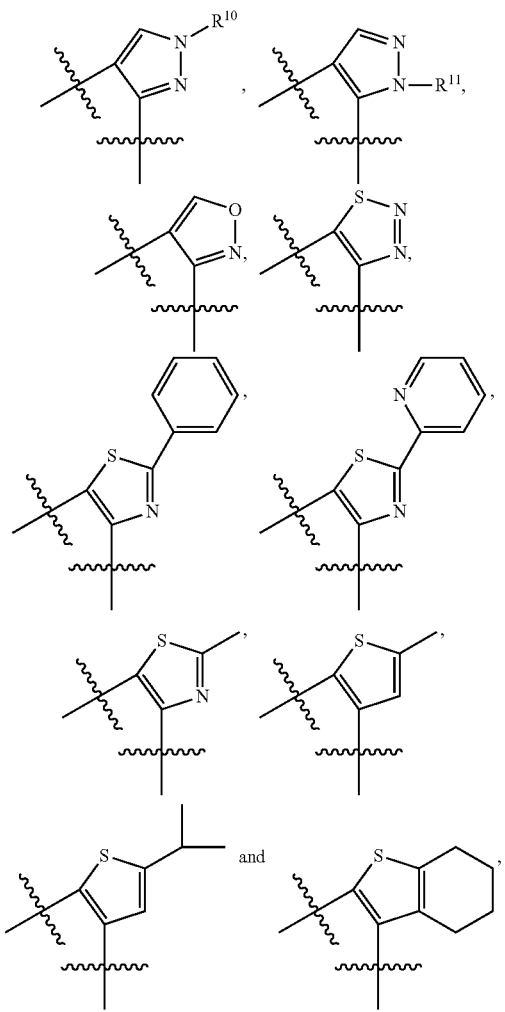

wherein
R¹⁰ is lower alkyl, lower-alkoxy-lower-alkyl, lower haloalkyl, aryl or heteroaryl, wherein said lower alkyl is optionally substituted by cycloalkyl; and R¹¹ is lower alkyl, lower-alkoxy-lower-alkyl, lower haloalkyl, lower hydroxyalkyl or heterocyclyl, wherein said lower alkyl is optionally substituted by cycloalkyl or heterocylyl.

6. The compound or a pharmaceutically acceptable salt thereof of claim 5, wherein
R¹⁰ is methyl, ethyl, cyclopropylmethyl, 2-methoxy-ethyl, 2,2,2-trifluoro-ethyl, 3,3,3-trifluoro-propyl, phenyl or pyridin-2-yl; and R¹¹ is methyl, ethyl, isopropyl, isobutyl, cyclopropylmethyl, oxetan-2-ylmethyl, tetrahydro-furan-2-ylmethyl, tetrahydro-furan-3-ylmethyl, 2-methoxy-ethyl, 2-hydroxy-ethyl, 2,2,2-trifluoro-ethyl, 3,3,3-trifluoro-propyl or tetrahydro-furan-3-yl.

7. The compound or a pharmaceutically acceptable salt thereof of claim 1, wherein R¹ is halogen, lower alkyl, lower alkoxy, lower hydroxyalkyl, lower-alkoxy-lower-alkyl, —C(O)-lower alkyl, —O-lower haloalkyl, cycloalkyl, heterocyclyl or amino, and wherein said heterocyclyl is optionally substituted by lower alkyl, and wherein said amino is substituted by 1 or 2 substituents independently selected from the group consisting of lower alkyl and lower-alkoxy-lower-alkyl.

8. The compound or a pharmaceutically acceptable salt thereof of claim 7, wherein R¹ is chloro, methyl, 1-hydroxy-ethyl, 1-hydroxy-1-methyl-ethyl, isopropyl, isobutyl, tert-butyl, methoxymethyl, methoxy, 2,2,2-trifluoro-ethoxy, acetyl, cyclopropyl, cyclobutyl, cyclohexyl, tetrahydrofuran-2-yl, tetrahydrofuran-3-yl, azetidin-1-yl, pyrrolidin-1-yl, morpholin-4-yl, 4-methyl-piperazin-1-yl, ethyl-methyl-amino or 2-methoxy-ethylamino.

9. The compound or a pharmaceutically acceptable salt thereof of claim 1,
wherein
R⁵ and R⁶ are independently hydrogen, lower alkyl, lower hydroxyalkyl, lower alkoxy, lower haloalkyl, lower-alkoxy-lower-alkyl, cycloalkyl or heterocyclyl, wherein said lower alkyl is optionally substituted by dimethylamino or heterocyclyl, and wherein said lower haloalkyl is optionally substituted by hydroxyl, and wherein said cycloalkyl is optionally substituted by hydroxyl, and wherein said heterocyclyl is optionally substituted by lower alkyl or —C(O)-lower alkoxy, or R⁵ and R⁶, together with the nitrogen atom to which they are attached, form an azetidine, pyrrolidine, piperidine, morpholine, piperazine, isoxazolidine or 2-oxa-6-aza-spiro[3.3]heptane ring, wherein each of said azetidine, pyrrolidine, piperidine, morpholine, piperazine, isoxazolidine or 2-oxa-6-aza-spiro[3.3]heptane ring is optionally substituted by 1 or 2 substituents independently selected from the group consisting of hydroxyl, halogen, lower alkyl, lower hydroxyalkyl, lower alkoxy, oxo and amino, and wherein said amino is substituted by 2 lower alkyl.

10. The compound or a pharmaceutically acceptable salt thereof of claim 9,
wherein
R⁵ and R⁶ are independently hydrogen, methyl, tetrahydrofuran-2-yl-methyl, ethyl, 2-methoxy-1-methyl-ethyl, 2-hydroxy-ethyl, 2-fluoro-ethyl, 2-hydroxy-1,1-dimethyl-ethyl, 2,2-difluoro-ethyl, 2,2,2-trifluoro-ethyl, 2,2,2-trifluoro-1-methyl-ethyl, 2-dimethylamino-ethyl, propyl, isopropyl, 2,3-dihydroxy-propyl, 3-hydroxy-propyl, 2-hydroxy-2-methyl-propyl, 3-hydroxy-2-methyl-propyl, 3-hydroxy-2,2-dimethyl-propyl, 2,2-difluoro-propyl, 3,3,3-trifluoro-2-hydroxy-propyl, 2-methoxy-2-methyl-propyl, butyl, isobutyl, 3-hydroxy-3-methyl-butyl, methoxy, cyclopropyl, cyclobutyl, cyclopentyl, 2-hydroxy-cyclopentyl, cyclohexyl, oxetan-3-yl, 3-methyl-oxetan-3-yl, tetrahydro-furan-3-yl, tetrahydro-pyran-4-yl, 1-methyl-azetidin-3-yl, pyrrolidin-3-yl, 1-methyl-pyrrolidin-3-yl, 1-(tert-butoxy-carbonyl)pyrrolidin-3-yl, 1-methyl-piperidin-3-yl or 1-methyl-piperidin-4-yl, or $R^5$ and $R^6$, together with the nitrogen atom to which they are attached, form an optionally substituted heterocyclyl or spiro-heterocyclyl ring selected from the group consisting of azetidin-1-yl, 3-hydroxy-azetidin-1-yl, 3-fluoro-azetidin-1-yl, 3,3-difluoro-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, piperidin-1-yl, 2-methyl-piperidin-1-yl, isoxazolidin-2-yl, morpholin-4-yl, 3-oxo-piperazin-1-yl and 2-oxa-6-aza-spiro[3.3]heptan-6-yl.

11. The compound of claim 1, selected from the group consisting of:

6-Cyclopropyl-3-(pyrimidin-5-ylamino)-pyridine-2-carboxylic acid (3-dimethylcarbamoyl-1-methyl-1H-pyrazol-4-yl)-amide, 6-Cyclopropyl-3-(pyrimidin-5-ylamino)-pyridine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid (3-carbamoyl-1-methyl-1H-pyrazol-4-yl)-amide, 6-Cyclopropyl-3-(pyrimidin-5-ylamino)-pyridine-2-carboxylic acid [3-dimethylcarbamoyl-1-(2-methoxy-ethyl)-1H-pyrazol-4-yl]-amide, 6-Cyclopropyl-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid [5-dimethylcarbamoyl-1-(2-methoxy-ethyl)-1H-pyrazol-4-yl]-amide, 6-Cyclopropyl-3-(pyrimidin-5-ylamino)-pyridine-2-carboxylic acid [3-dimethylcarbamoyl-1-(2,2,2-trifluoro-ethyl)-1H-pyrazol-4-yl]-amide, 6-Cyclopropyl-3-(pyrimidin-5-ylamino)-pyridine-2-carboxylic acid [3-methylcarbamoyl-1-(2,2,2-trifluoro-ethyl)-1H-pyrazol-4-yl]-amide, 6-Cyclopropyl-3-(pyrimidin-5-ylamino)-pyridine-2-carboxylic acid [3-methylcarbamoyl-1-(3,3,3-trifluoro-propyl)-1H-pyrazol-4-yl]-amide, and 6-Cyclopropyl-3-(pyrimidin-5-ylamino)-pyridine-2-carboxylic acid [5-methylcarbamoyl-1-(3,3,3-trifluoro-propyl)-1H-pyrazol-4-yl]-amide, or a pharmaceutically acceptable salt thereof.

12. The compound of claim 1, selected from the group consisting of:

6-Cyclopropyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-3-(pyrimidin-5-ylamino)-pyridine-2-carboxylic acid (1-cyclopropylmethyl-3-methylcarbamoyl-1H-pyrazol-4-yl)-amide, 6-Cyclopropyl-3-(pyrimidin-5-ylamino)-pyridine-2-carboxylic acid (1-cyclopropylmethyl-5-methylcarbamoyl-1H-pyrazol-4-yl)-amide, 6-Cyclopropyl-3-(pyrimidin-5-ylamino)-pyridine-2-carboxylic acid [1-methyl-3-(morpholine-4-carbonyl)-1H-pyrazol-4-yl]-amide, 6-Cyclopropyl-3-(pyrimidin-5-ylamino)-pyridine-2-carboxylic acid [3-(cyclopropyl-methyl-carbamoyl)-1-methyl-1H-pyrazol-4-yl]-amide, 6-Cyclopropyl-3-(pyrimidin-5-ylamino)-pyridine-2-carboxylic acid [1-methyl-3-(piperidine-1-carbonyl)-1H-pyrazol-4-yl]-amide, 6-Cyclopropyl-3-(pyrimidin-5-ylamino)-pyridine-2-carboxylic acid [3-(cyclohexyl-methyl-carbamoyl)-1-methyl-1H-pyrazol-4-yl]-amide, 6-Cyclopropyl-3-(pyrimidin-5-ylamino)-pyridine-2-carboxylic acid [1-(2-methoxy-ethyl)-3-methylcarbamoyl-1H-pyrazol-4-yl]-amide, 6-Cyclopropyl-3-(pyrimidin-5-ylamino)-pyridine-2-carboxylic acid [3-(cyclopentyl-methyl-carbamoyl)-1-methyl-1H-pyrazol-4-yl]-amide, and 6-Cyclopropyl-3-(pyrimidin-5-ylamino)-pyridine-2-carboxylic acid [3-(isopropyl-methyl-carbamoyl)-1-methyl-1H-pyrazol-4-yl]-amide, or a pharmaceutically acceptable salt thereof.

13. The compound of claim 1, selected from the group consisting of:

6-Cyclopropyl-3-(pyrimidin-5-ylamino)-pyridine-2-carboxylic acid [1-methyl-3-(pyrrolidine-1-carbonyl)-1H-pyrazol-4-yl]-amide, 6-Cyclopropyl-3-(pyrimidin-5-ylamino)-pyridine-2-carboxylic acid (3-methylcarbamoyl-1-phenyl-1H-pyrazol-4-yl)-amide, 6-Methoxymethyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-N-[1-methyl-3-(2-methyl-pyrrolidine-1-carbonyl)-1H-pyrazol-4-yl]-3-(pyrimidin-5-ylamino)-pyridine-2-carboximidic acid, N-(3-Cyclohexylcarbamoyl-1-methyl-1H-pyrazol-4-yl)-6-cyclopropyl-3-(pyrimidin-5-ylamino)-pyridine-2-carboximidic acid, N-[3-(Azetidine-1-carbonyl)-1-methyl-1H-pyrazol-4-yl]-6-cyclopropyl-3-(pyrimidin-5-ylamino)-pyridine-2-carboximidic acid, 6-Cyclopropyl-N-(3-cyclopropylcarbamoyl-1-methyl-1H-pyrazol-4-yl)-3-(pyrimidin-5-ylamino)-pyridine-2-carboximidic acid, 6-Cyclopropyl-N-[3-(3,3-dimethyl-pyrrolidine-1-carbonyl)-1-methyl-1H-pyrazol-4-yl]-3-(pyrimidin-5-ylamino)-pyridine-2-carboximidic acid, N-(3-Cyclobutylcarbamoyl-1-methyl-1H-pyrazol-4-yl)-6-cyclopropyl-3-(pyrimidin-5-ylamino)-pyridine-2-carboximidic acid, and N-(3-Cyclopentylcarbamoyl-1-methyl-1H-pyrazol-4-yl)-6-cyclopropyl-3-(pyrimidin-5-ylamino)-pyridine-2-carboximidic acid, or a pharmaceutically acceptable salt thereof.

14. The compound of claim 1, selected from the group consisting of:

6-Cyclopropyl-N-[3-(2,5-dimethyl-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3,3-difluoro-pyrrolidine-1-carbonyl)-1-methyl-1H-pyrazol-4-yl]-3-(pyrimidin-5-ylamino)-pyridine-2-carboximidic acid, 6-Cyclopropyl-N-[3-(3-dimethylamino-pyrrolidine-1-carbonyl)-1-methyl-1H-pyrazol-4-yl]-3-(pyrimidin-5-ylamino)-pyridine-2-carboximidic acid, 6-Cyclopropyl-N-{3-[(3-hydroxy-propyl)-methyl-carbamoyl]-1-methyl-1H-pyrazol-4-yl}-3-(pyrimidin-5-ylamino)-pyridine-2-carboximidic acid, 6-Cyclopropyl-N-[3-(2-hydroxy-ethylcarbamoyl)-1-methyl-1H-pyrazol-4-yl]-3-(pyrimidin-5-ylamino)-pyridine-2-carboximidic acid, 6-Cyclopropyl-N-{3-[(2-hydroxy-ethyl)-methyl-carbamoyl]-1-methyl-1H-pyrazol-4-yl}-3-(pyrimidin-5-ylamino)-pyridine-2-carboximidic acid,
6-Cyclopropyl-N-[3-(2-methoxy-1-methyl-ethylcarbamoyl)-1-methyl-1H-pyrazol-4-yl]-3-(pyrimidin-5-ylamino)-pyridine-2-carboximidic acid,
6-Cyclopropyl-N-[3-(2,3-dihydroxy-propylcarbamoyl)-1-methyl-1H-pyrazol-4-yl]-3-(pyrimidin-5-ylamino)-pyridine-2-carboximidic acid,
6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid, and
6-Cyclopropyl-N-[3-(3-hydroxy-pyrrolidine-1-carbonyl)-1-methyl-1H-pyrazol-4-yl]-3-(pyrimidin-5-ylamino)-pyridine-2-carboximidic acid,
or a pharmaceutically acceptable salt thereof.

15. The compound of claim 1, selected from the group consisting of:
6-Cyclopropyl-N-[3-(2-hydroxy-1-methyl-ethylcarbamoyl)-1-methyl-1H-pyrazol-4-yl]-3-(pyrimidin-5-ylamino)-pyridine-2-carboximidic acid,
6-Cyclopropyl-N-{3-[(2,3-dihydroxy-propyl)-methyl-carbamoyl]-1-methyl-1H-pyrazol-4-yl}-3-(pyrimidin-5-ylamino)-pyridine-2-carboximidic acid,
6-Cyclopropyl-N-[3-(5-hydroxy-3,6-dihydro-2H-pyrazine-1-carbonyl)-1-methyl-1H-pyrazol-4-yl]-3-(pyrimidin-5-ylamino)-pyridine-2-carboximidic acid,
6-Cyclopropyl-N-[3-(3-methoxy-pyrrolidine-1-carbonyl)-1-methyl-1H-pyrazol-4-yl]-3-(pyrimidin-5-ylamino)-pyridine-2-carboximidic acid,
6-Cyclopropyl-N-[3-(2-hydroxymethyl-pyrrolidine-1-carbonyl)-1-methyl-1H-pyrazol-4-yl]-3-(pyrimidin-5-ylamino)-pyridine-2-carboximidic acid,
6-Cyclopropyl-N-[3-(3-hydroxy-azetidine-1-carbonyl)-1-methyl-1H-pyrazol-4-yl]-3-(pyrimidin-5-ylamino)-pyridine-2-carboximidic acid,
6-Cyclopropyl-N-[1-methyl-3-(2-oxa-6-aza-spiro[3.3]heptane-6-carbonyl)-1H-pyrazol-4-yl]-3-(pyrimidin-5-ylamino)-pyridine-2-carboximidic acid,
6-Cyclopropyl-N-[3-(2,2-dimethyl-pyrrolidine-1-carbonyl)-1-methyl-1H-pyrazol-4-yl]-3-(pyrimidin-5-ylamino)-pyridine-2-carboximidic acid,
6-Cyclopropyl-3-(pyrimidin-5-ylamino)-pyridine-2-carboxylic acid (4-methylcarbamoyl-[1,2,3]thiadiazol-5-yl)-amide, and
6-Cyclopropyl-3-(pyrimidin-5-ylamino)-pyridine-2-carboxylic acid (4-methylcarbamoyl-2-phenyl-thiazol-5-yl)-amide,
or a pharmaceutically acceptable salt thereof.

16. The compound of claim 1, selected from the group consisting of:
6-Cyclopropyl-3-(pyrimidin-5-ylamino)-pyridine-2-carboxylic acid (4-methylcarbamoyl-2-pyridin-2-yl-thiazol-5-yl)-amide,
6-Cyclopropyl-3-(pyrimidin-5-ylamino)-pyridine-2-carboxylic acid (3-dimethylcarbamoyl-1-pyridin-2-yl-1H-pyrazol-4-yl)-amide,
2-Isopropyl-5-(pyrimidin-5-ylamino)-pyrimidine-4-carboxylic acid (1-methyl-3-methylcarbamoyl-1H-pyrazol-4-yl)-amide,
2-Cyclopropyl-5-(pyrimidin-5-ylamino)-pyrimidine-4-carboxylic acid (1-methyl-3-methylcarbamoyl-1H-pyrazol-4-yl)-amide,
2-tert-Butyl-5-(pyrimidin-5-ylamino)-pyrimidine-4-carboxylic acid (1-methyl-3-methylcarbamoyl-1H-pyrazol-4-yl)-amide,
2-Isobutyl-5-(pyrimidin-5-ylamino)-pyrimidine-4-carboxylic acid (1-methyl-3-methylcarbamoyl-1H-pyrazol-4-yl)-amide,
2-Cyclohexyl-5-(pyrimidin-5-ylamino)-pyrimidine-4-carboxylic acid (1-methyl-3-methylcarbamoyl-1H-pyrazol-4-yl)-amide,
6-Cyclopropyl-3-(pyrimidin-5-ylamino)-pyridine-2-carboxylic acid (3-cyclopropylcarbamoyl-thiophen-2-yl)-amide,
6-Cyclopropyl-3-(pyrimidin-5-ylamino)-pyridine-2-carboxylic acid [3-(morpholine-4-carbonyl)-thiophen-2-yl]-amide, and
6-Cyclopropyl-3-(pyrimidin-5-ylamino)-pyridine-2-carboxylic acid [5-isopropyl-3-(morpholine-4-carbonyl)-thiophen-2-yl]-amide,
or a pharmaceutically acceptable salt thereof.

17. The compound of claim 1, selected from the group consisting of:
6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide,
N-(1-methyl-3-(methylcarbamoyl)-1H-pyrazol-4-yl)-3-(pyrimidin-5-ylamino)-6-(tetrahydrofuran-2-yl)pyrazine-2-carboxamide,
N-(1-methyl-3-(methylcarbamoyl)-1H-pyrazol-4-yl)-3-(pyrimidin-5-ylamino)-6-(tetrahydro furan-3-yl)pyrazine-2-carboxamide,
N-(1-methyl-3-(methylcarbamoyl)-1H-pyrazol-4-yl)-3-(pyrimidin-5-ylamino)-6-(tetrahydrofuran-2-yl)picolinamide,
6-isobutyl-N-(1-methyl-3-(methylcarbamoyl)-1H-pyrazol-4-yl)-3-(pyrimidin-5-ylamino)pyrazine-2-carboxamide,
6-cyclopropyl-N-(1-ethyl-3-(methylcarbamoyl)-1H-pyrazol-4-yl)-3-(pyrimidin-5-ylamino)pyrazine-2-carboxamide,
6-cyclopropyl-N-(1-ethyl-3-((tetrahydrofuran-2-yl)methylcarbamoyl)-1H-pyrazol-4-yl)-3-(pyrimidin-5-ylamino)pyrazine-2-carboxamide,
6-cyclopropyl-N-(1-methyl-3-((tetrahydrofuran-2-yl)methylcarbamoyl)-1H-pyrazol-4-yl)-3-(pyrimidin-5-ylamino)pyrazine-2-carboxamide,
6-cyclopropyl-N-(3-((2-hydroxy-2-methylpropyl)(methyl)carbamoyl)-1-methyl-1H-pyrazol-4-yl)-3-(pyrimidin-5-ylamino)pyrazine-2-carboxamide, and
N-(3-(2-hydroxy-2-methylpropylcarbamoyl)-1-methyl-1H-pyrazol-4-yl)-2-methyl-5-(pyrimidin-5-ylamino)pyrimidine-4-carboxamide,
or a pharmaceutically acceptable salt thereof.

18. The compound of claim 1, selected from the group consisting of:
6-(1-Hydroxy-ethyl)-3-(pyrimidin-5-ylamino)-pyrazine-2-carboxylic acid (1-methyl-3-methylcarbamoyl-1H-pyrazol-4-yl)-amide,
6-Cyclopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide,
2-(2-Methoxy-ethylamino)-5-(pyrimidin-5-ylamino)-pyrimidine-4-carboxylic acid (1-methyl-3-methylcarbamoyl-1H-pyrazol-4-yl)-amide,
3-(Pyrimidin-5-ylamino)-6-(tetrahydro-furan-3-yl)-pyridine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (2-methyl-4-methylcarbamoyl-thiazol-5-yl)-amide,
6-Isopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-ethyl-5-(2-hydroxy-2-methyl-propylcarbamoyl)-1H-pyrazol-4-yl]-amide,
6-Cyclopropyl-3-(pyrimidin-5-ylamino)-pyrazine-2-carboxylic acid (1-ethyl-5-methylcarbamoyl-1H-pyrazol-4-yl)-amide, and
6-Cyclopropyl-3-(pyrimidin-5-ylamino)-pyrazine-2-carboxylic acid [5-(2-hydroxy-2-methyl-propylcarbamoyl)-1-isobutyl-1H-pyrazol-4-yl]-amide, or a pharmaceutically acceptable salt thereof.

19. The compound of claim 1, selected from the group consisting of:
6-Cyclopropyl-3-(pyrimidin-5-ylamino)-pyrazine-2-carboxylic acid [1-methyl-5-(oxetan-3-ylcarbamoyl)-1H-pyrazol-4-yl]-amide,
6-Cyclopropyl-3-(pyrimidin-5-ylamino)-pyrazine-2-carboxylic acid [1-methyl-5-(3-methyl-oxetan-3-ylcarbamoyl)-1H-pyrazol-4-yl]-amide,
6-Cyclopropyl-3-(pyrimidin-5-ylamino)-pyrazine-2-carboxylic acid (1-isobutyl-5-methylcarbamoyl-1H-pyrazol-4-yl)-amide,
6-Cyclopropyl-3-(pyrimidin-5-ylamino)-pyrazine-2-carboxylic acid [5-(2-hydroxy-2-methyl-propylcarbamoyl)-1-isopropyl-1H-pyrazol-4-yl]-amide,
6-Cyclopropyl-3-(pyrimidin-5-ylamino)-pyrazine-2-carboxylic acid (1-isopropyl-5-methylcarbamoyl-1H-pyrazol-4-yl)-amide,
6-Cyclopropyl-3-(pyrimidin-5-ylamino)-pyrazine-2-carboxylic acid [5-(3-hydroxy-3-methyl-butylcarbamoyl)-1-methyl-1H-pyrazol-4-yl]-amide,
6-Cyclopropyl-3-(pyrimidin-5-ylamino)-pyrazine-2-carboxylic acid [1-methyl-5-(tetrahydro-furan-3-ylcarbamoyl)-1H-pyrazol-4-yl]-amide,
6-Cyclopropyl-3-(pyrimidin-5-ylamino)-pyrazine-2-carboxylic acid [5-(3-hydroxy-2,2-dimethyl-propylcarbamoyl)-1-methyl-1H-pyrazol-4-yl]-amide,
6-Cyclopropyl-3-(pyrimidin-5-ylamino)-pyrazine-2-carboxylic acid [5-(3,3-difluoro-azetidine-1-carbonyl)-1-methyl-1H-pyrazol-4-yl]-amide, and
6-Cyclopropyl-3-(pyrimidin-5-ylamino)-pyrazine-2-carboxylic acid [1-methyl-5-(2,2,2-trifluoro-ethylcarbamoyl)-1H-pyrazol-4-yl]-amide, or a pharmaceutically acceptable salt thereof.

20. The compound of claim 1, selected from the group consisting of:
6-Cyclopropyl-3-(pyrimidin-5-ylamino)-pyrazine-2-carboxylic acid [5-(2,2-difluoro-ethylcarbamoyl)-1-methyl-1H-pyrazol-4-yl]-amide,
6-Cyclopropyl-3-(pyrimidin-5-ylamino)-pyrazine-2-carboxylic acid [1-methyl-5-(3,3,3-trifluoro-2-hydroxy-propylcarbamoyl)-1H-pyrazol-4-yl]-amide,
6-Cyclopropyl-3-(pyrimidin-5-ylamino)-pyrazine-2-carboxylic acid [1-(2-methoxy-ethyl)-5-methylcarbamoyl-1H-pyrazol-4-yl]-amide,
6-Cyclopropyl-3-(pyrimidin-5-ylamino)-pyridine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(3-hydroxy-2-methyl-propylcarbamoyl)-1-methyl-1H-pyrazol-4-yl]-amide,
6-Cyclopropyl-3-(pyrimidin-5-ylamino)-pyrazine-2-carboxylic acid (5-carbamoyl-1-methyl-1H-pyrazol-4-yl)-amide,
6-Cyclopropyl-3-(pyrimidin-5-ylamino)-pyrazine-2-carboxylic acid [5-(2-methoxy-2-methyl-propylcarbamoyl)-1-methyl-1H-pyrazol-4-yl]-amide,
6-Cyclopropyl-3-(pyrimidin-5-ylamino)-pyrazine-2-carboxylic acid [5-(2-hydroxy-1,1-dimethyl-ethylcarbamoyl)-1-methyl-1H-pyrazol-4-yl]-amide,
6-Cyclopropyl-3-(pyrimidin-5-ylamino)-pyrazine-2-carboxylic acid {5-[(2-hydroxy-2-methyl-propyl)-methyl-carbamoyl]-1-methyl-1H-pyrazol-4-yl}-amide, and
2-tert-Butyl-5-(pyrimidin-5-ylamino)-pyrimidine-4-carboxylic acid (1-methyl-5-methylcarbamoyl-1H-pyrazol-4-yl)-amide, or a pharmaceutically acceptable salt thereof.

21. The compound of claim 1, selected from the group consisting of:
6-Cyclopropyl-3-(pyrimidin-5-ylamino)-pyrazine-2-carboxylic acid [5-(azetidine-1-carbonyl)-1-methyl-1H-pyrazol-4-yl]-amide,
6-Cyclopropyl-3-(pyrimidin-5-ylamino)-pyrazine-2-carboxylic acid [1-methyl-5-(pyrrolidine-1-carbonyl)-1H-pyrazol-4-yl]-amide,
6-Cyclopropyl-3-(pyrimidin-5-ylamino)-pyrazine-2-carboxylic acid (5-dimethylcarbamoyl-1-methyl-1H-pyrazol-4-yl)-amide,
3-(Pyrimidin-5-ylamino)-6-(tetrahydro-furan-3-yl)-pyrazine-2-carboxylic acid (1-methyl-5-methylcarbamoyl-1H-pyrazol-4-yl)-amide,
2-Isopropyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-5-(tetrahydro-furan-2-yl)-pyrazine-2-carboxylic acid [5-(2-fluoro-ethylcarbamoyl)-1-methyl-1H-pyrazol-4-yl]-amide,
6-Cyclopropyl-3-(pyrimidin-5-ylamino)-pyrazine-2-carboxylic acid (3-cyclopropylcarbamoyl-isoxazol-4-yl)-amide,
6-Cyclopropyl-3-(pyrimidin-5-ylamino)-pyrazine-2-carboxylic acid [1-methyl-5-(2,2,2-trifluoro-1-methyl-ethylcarbamoyl)-1H-pyrazol-4-yl]-amide,
6-Cyclopropyl-3-(pyrimidin-5-ylamino)-pyrazine-2-carboxylic acid [5-(2,2-difluoro-propylcarbamoyl)-1-methyl-1H-pyrazol-4-yl]-amide, and
6-Chloro-3-(pyrimidin-5-ylamino)-pyridine-2-carboxylic acid (1-methyl-5-methylcarbamoyl-1H-pyrazol-4-yl)-amide, or a pharmaceutically acceptable salt thereof.

22. The compound of claim 1, selected from the group consisting of:
6-Cyclopropyl-3-(pyrimidin-5-ylamino)-pyrazine-2-carboxylic acid (5-isobutylcarbamoyl-1-methyl-1H-pyrazol-4-yl)-amide,
6-Cyclopropyl-3-(pyrimidin-5-ylamino)-pyrazine-2-carboxylic acid [1-methyl-5-(piperidine-1-carbonyl)-1H-pyrazol-4-yl]-amide,
6-Cyclopropyl-3-(pyrimidin-5-ylamino)-pyrazine-2-carboxylic acid (5-dimethylcarbamoyl-1-ethyl-1H-pyrazol-4-yl)-amide,
6-Cyclopropyl-3-(pyrimidin-5-ylamino)-pyrazine-2-carboxylic acid [1-ethyl-5-(morpholine-4-carbonyl)-1H-pyrazol-4-yl]-amide,
6-Cyclopropyl-3-(pyrimidin-5-ylamino)-pyrazine-2-carboxylic acid [5-(2-fluoro-ethylcarbamoyl)-1-methyl-1H-pyrazol-4-yl]-amide, 6-Cyclopropyl-3-(pyrimidin-5-ylamino)-pyrazine-2-carboxylic acid [5-(2-hydroxy-2-methyl-propylcarbamoyl)-1-(3,3,3-trifluoro-propyl)-1H-pyrazol-4-yl]-amide, 6-Cyclopropyl-3-(pyrimidin-5-ylamino)-pyrazine-2-carboxylic acid [5-methylcarbamoyl-1-(3,3,3-trifluoro-propyl)-1H-pyrazol-4-yl]-amide, 6-Cyclopropyl-3-(pyrimidin-5-ylamino)-pyrazine-2-carboxylic acid [5-(3-fluoro-azetidine-1-carbonyl)-1-methyl-1H-pyrazol-4-yl]-amide, 6-Cyclopropyl-3-(pyrimidin-5-ylamino)-pyrazine-2-carboxylic acid [5-(2-hydroxy-2-methyl-propylcarbamoyl)-1-(2,2,2-trifluoro-ethyl)-1H-pyrazol-4-yl]-amide, and 6-Cyclopropyl-3-(pyrimidin-5-ylamino)-pyrazine-2-carboxylic acid [5-methylcarbamoyl-1-(2,2,2-trifluoro-ethyl)-1H-pyrazol-4-yl]-amide, or a pharmaceutically acceptable salt thereof.

23. The compound of claim 1, selected from the group consisting of:

6-Cyclopropyl-3-(pyrimidin-5-ylamino)-pyrazine-2-carboxylic acid [1-methyl-5-(morpholine-4-carbonyl)-1-pyrazol-4-yl]-amide, 6-Acetyl-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid (3-ethylcarbamoyl-4,5,6,7-tetrahydro-benzo[b]thiophen-2-yl)-amide, 2-Isopropyl-5-(pyridin-3-ylamino)-pyrimidine-4-carboxylic acid (1-methyl-5-methylcarbamoyl-1H-pyrazol-4-yl)-amide, 6-(1-Hydroxy-ethyl)-3-(pyrimidin-5-ylamino)-pyrazine-2-carboxylic acid (1-methyl-5-methylcarbamoyl-1H-pyrazol-4-yl)-amide, 5-(3-Fluoro-phenylamino)-2-isopropyl-pyrimidine-4-carboxylic acid (1-methyl-5-methylcarbamoyl-1H-pyrazol-4-yl)-amide, 6-Methoxymethyl-3-(pyrimidin-5-ylamino)-pyridine-2-carboxylic acid (1-methyl-5-methylcarbamoyl-1H-pyrazol-4-yl)-amide, 5-(5-Fluoro-pyridin-3-ylamino)-2-isopropyl-pyrimidine-4-carboxylic acid (1-methyl-5-methylcarbamoyl-1H-pyrazol-4-yl)-amide, 5-(4-Fluoro-phenylamino)-2-isopropyl-pyrimidine-4-carboxylic acid (1-methyl-5-methylcarbamoyl-1H-pyrazol-4-yl)-amide, and 2-Cyclobutyl-5-(pyrimidin-5-ylamino)-pyrimidine-4-carboxylic acid (1-methyl-5-methylcarbamoyl-1H-pyrazol-4-yl)-amide, or a pharmaceutically acceptable salt thereof.

24. The compound of claim 1, selected from the group consisting of:

6-Cyclopropyl-3-(pyrimidin-5-ylamino)-pyrazine-2-carboxylic acid (5-ethylcarbamoyl-1-methyl-1H-pyrazol-4-yl)-amide, 6-Cyclopropyl-3-(pyrazin-2-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid (1-ethyl-5-ethylcarbamoyl-1H-pyrazol-4-yl)-amide, 6-Cyclopropyl-3-(pyrimidin-5-ylamino)-pyrazine-2-carboxylic acid (1-ethyl-5-isobutylcarbamoyl-1H-pyrazol-4-yl)-amide, 6-Cyclopropyl-3-(pyrimidin-5-ylamino)-pyrazine-2-carboxylic acid [5-(ethyl-methyl-carbamoyl)-1-methyl-1H-pyrazol-4-yl]-amide, 6-Cyclopropyl-3-(pyridin-3-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid (5-dipropylcarbamoyl-1-methyl-1H-pyrazol-4-yl)-amide, 6-Cyclopropyl-3-(pyrimidin-5-ylamino)-pyrazine-2-carboxylic acid [5-(butyl-methyl-carbamoyl)-1-methyl-1H-pyrazol-4-yl]-amide, 6-Cyclopropyl-3-(pyrimidin-5-ylamino)-pyrazine-2-carboxylic acid {5-[(2-hydroxy-ethyl)-methyl-carbamoyl]-1-methyl-1H-pyrazol-4-yl}-amide, and 6-Cyclopropyl-3-(pyrimidin-5-ylamino)-pyrazine-2-carboxylic acid [5-(isopropyl-methyl-carbamoyl)-1-methyl-1H-pyrazol-4-yl]-amide, or a pharmaceutically acceptable salt thereof.

25. The compound of claim 1, selected from the group consisting of:

6-Cyclopropyl-3-(pyrimidin-5-ylamino)-pyrazine-2-carboxylic acid (5-diethylcarbamoyl-1-methyl-1H-pyrazol-4-yl)-amide, 6-Cyclopropyl-3-(pyrimidin-5-ylamino)-pyrazine-2-carboxylic acid [1-methyl-5-(methyl-propyl-carbamoyl)-1H-pyrazol-4-yl]-amide, 6-Cyclopropyl-3-(pyrimidin-5-ylamino)-pyrazine-2-carboxylic acid {5-[ethyl-(2-hydroxy-ethyl)-carbamoyl]-1-methyl-1H-pyrazol-4-yl}-amide, 6-Cyclopropyl-3-(pyrimidin-5-ylamino)-pyrazine-2-carboxylic acid {1-methyl-5-[methyl-(tetrahydro-pyran-4-yl)-carbamoyl]-1H-pyrazol-4-yl}-amide, 6-Cyclopropyl-3-(pyrimidin-5-ylamino)-pyrazine-2-carboxylic acid {1-methyl-5-[(tetrahydro-furan-2-ylmethyl)-carbamoyl]-1H-pyrazol-4-yl}-amide, 6-Cyclopropyl-3-(pyrimidin-5-ylamino)-pyrazine-2-carboxylic acid {1-ethyl-5-[(tetrahydro-furan-2-ylmethyl)-carbamoyl]-1H-pyrazol-4-yl}-amide, 6-Cyclopropyl-3-(pyridin-3-ylamino)-pyrazine-2-carboxylic acid [5-(azetidine-1-carbonyl)-1-methyl-1H-pyrazol-4-yl]-amide, 6-Cyclopropyl-3-(pyrimidin-5-ylamino)-pyrazine-2-carboxylic acid [1-methyl-5-(2-methyl-piperidine-1-carbonyl)-1H-pyrazol-4-yl]-amide, 3-[(4-{[6-Cyclopropyl-3-(pyrimidin-5-ylamino)-pyrazine-2-carbonyl]-amino}-2-methyl-2H-pyrazole-3-carbonyl)-amino]-pyrrolidine-1-carboxylic acid tert-butyl ester, and 6-Cyclopropyl-3-(pyrimidin-5-ylamino)-pyrazine-2-carboxylic acid {1-methyl-5-[methyl-(2,2,2-trifluoro-ethyl)-carbamoyl]-1H-pyrazol-4-yl}-amide, or a pharmaceutically acceptable salt thereof.

26. The compound of claim 1, selected from the group consisting of:

6-Cyclopropyl-3-(pyrimidin-5-ylamino)-pyrazine-2-carboxylic acid [5-(cyclopropyl-methyl-carbamoyl)-1-methyl-1H-pyrazol-4-yl]-amide, 6-Cyclopropyl-3-(pyrimidin-5-ylamino)-pyrazine-2-carboxylic acid [1-methyl-5-(2-methyl-pyrrolidine-1-carbonyl)-1H-pyrazol-4-yl]-amide, 6-Cyclopropyl-3-(pyrimidin-5-ylamino)-pyrazine-2-carboxylic acid [1-methyl-5-(methyl-oxetan-3-yl-carbamoyl)-1H-pyrazol-4-yl]-amide, 6-Cyclopropyl-3-(pyrimidin-5-ylamino)-pyrazine-2-carboxylic acid [1-methyl-5-(1-methyl-piperidin-3-ylcarbamoyl)-1H-pyrazol-4-yl]-amide, 6-Cyclopropyl-3-(pyrimidin-5-ylamino)-pyrazine-2-carboxylic acid [1-methyl-5-(1-methyl-piperidin-4-ylcarbamoyl)-1H-pyrazol-4-yl]-amide, 6-Cyclopropyl-3-(pyrimidin-5-ylamino)-pyrazine-2-carboxylic acid [5-methylcarbamoyl-1-(tetrahydro-furan-2-ylmethyl)-1H-pyrazol-4-yl]-amide, 6-Cyclopropyl-3-(pyrimidin-5-ylamino)-pyrazine-2-carboxylic acid [5-(2-hydroxy-2-methyl-propylcarbamoyl)-1-(tetrahydro-furan-2-ylmethyl)-1H-pyrazol-4-yl]-amide, 6-Cyclopropyl-3-(pyrimidin-5-ylamino)-pyrazine-2-carboxylic acid {5-[(2-fluoro-ethyl)-methyl-carbamoyl]-1-methyl-1H-pyrazol-4-yl}-amide, 6-Cyclopropyl-3-(pyrimidin-5-ylamino)-pyrazine-2-carboxylic acid {1-methyl-5-[methyl-(1-methyl-pyrrolidin-3-yl)-carbamoyl]-1H-pyrazol-4-yl}-amide, and 6-Cyclopropyl-3-(pyrimidin-5-ylamino)-pyrazine-2-carboxylic acid [5-methylcarbamoyl-1-(tetrahydro-furan-3-yl)-1H-pyrazol-4-yl]-amide, or a pharmaceutically acceptable salt thereof.

27. The compound of claim 1, selected from the group consisting of:

6-Cyclopropyl-3-(pyrimidin-5-ylamino)-pyrazine-2-carboxylic acid [1-methyl-5-(pyrrolidin-3-ylcarbamoyl)-1H-pyrazol-4-yl]-amide, 6-Cyclopropyl-3-(pyrimidin-5-ylamino)-pyrazine-2-carboxylic acid (1-methyl-5-{[(S)-1-(tetrahydro-furan-2-yl)methyl]-carbamoyl}-1H-pyrazol-4-yl)-amide, 6-Cyclopropyl-3-(pyrimidin-5-ylamino)-pyrazine-2-carboxylic acid (1-methyl-5-{[(R)-1-(tetrahydro-furan-2-yl)methyl]-carbamoyl}-1H-pyrazol-4-yl)-amide, 6-Cyclopropyl-3-(pyrimidin-5-ylamino)-pyrazine-2-carboxylic acid {1-methyl-5-[methyl-(tetrahydro-furan-2-ylmethyl)-carbamoyl]-1H-pyrazol-4-yl}-amide, 6-Methoxy-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [1-(2-hydroxy-ethyl)-5-methylcarbamoyl-1H-pyrazol-4-yl]-amide, 3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide, 3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid {1-methyl-5-[(S)-(tetrahydro-furan-3-yl)carbamoyl]-1H-pyrazol-4-yl}-amide, and 6-Cyclopropyl-3-(pyrimidin-5-ylamino)-pyrazine-2-carboxylic acid {1-methyl-5-[(R)-(tetrahydro-furan-3-yl)carbamoyl]-1H-pyrazol-4-yl}-amide, or a pharmaceutically acceptable salt thereof.

28. The compound of claim 1, selected from the group consisting of:

6-Cyclopropyl-3-(pyrimidin-5-ylamino)-pyrazine-2-carboxylic acid (5-methylcarbamoyl-1-oxetan-2-ylmethyl-1H-pyrazol-4-yl)-amide, 6-Cyclopropyl-3-(pyrimidin-5-ylamino)-pyrazine-2-carboxylic acid [5-(2-hydroxy-2-methyl-propylcarbamoyl)-1-oxetan-2-ylmethyl-1H-pyrazol-4-yl]-amide, 6-Cyclopropyl-3-(pyrimidin-5-ylamino)-pyrazine-2-carboxylic acid [5-methylcarbamoyl-1-(tetrahydro-furan-3-ylmethyl)-1H-pyrazol-4-yl]-amide, 6-Cyclopropyl-3-(pyrimidin-5-ylamino)-pyrazine-2-carboxylic acid [5-(2-hydroxy-2-methyl-propylcarbamoyl)-1-(tetrahydro-furan-3-ylmethyl)-1H-pyrazol-4-yl]-amide, 3-(Pyrimidin-5-ylamino)-6-pyrrolidin-1-yl-pyrazine-2-carboxylic acid (1-methyl-5-methylcarbamoyl-1H-pyrazol-4-yl)-amide, 6-Morpholin-4-yl-3-(pyrimidin-5-ylamino)-pyrazine-2-carboxylic acid (1-methyl-5-methylcarbamoyl-1H-pyrazol-4-yl)-amide, 6-Azetidin-1-yl-3-(pyrimidin-5-ylamino)-pyrazine-2-carboxylic acid (1-methyl-5-methylcarbamoyl-1H-pyrazol-4-yl)-amide, 6-(Ethyl-methyl-amino)-3-(pyrimidin-5-ylamino)-pyrazine-2-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [5-(2-dimethylamino-ethylcarbamoyl)-1-methyl-1H-pyrazol-4-yl]-amide, and 2-Cyclopropyl-5-(pyrimidin-5-ylamino)-pyrimidine-4-carboxylic acid (1-methyl-5-methylcarbamoyl-1H-pyrazol-4-yl)-amide, or a pharmaceutically acceptable salt thereof.

29. The compound of claim 1, selected from the group consisting of:

6-Cyclopropyl-3-(pyrimidin-5-ylamino)-pyrazine-2-carboxylic acid [1-methyl-5-(1-methyl-azetidin-3-ylcarbamoyl)-1H-pyrazol-4-yl]-amide, 2-Isobutyl-5-(pyrimidin-5-ylamino)-pyrimidine-4-carboxylic acid (1-methyl-5-methylcarbamoyl-1H-pyrazol-4-yl)-amide, 4-Methyl-5'-(pyrimidin-5-ylamino)-3,4,5,6-tetrahydro-2H-[1,2]bipyrazinyl-6'-carboxylic acid (1-methyl-5-methylcarbamoyl-1H-pyrazol-4-yl)-amide, 6-Cyclopropyl-3-(pyrimidin-5-ylamino)-pyrazine-2-carboxylic acid [5-(methoxy-methyl-carbamoyl)-1-methyl-1H-pyrazol-4-yl]-amide, 6-Cyclopropyl-3-(pyrimidin-5-ylamino)-pyrazine-2-carboxylic acid [5-(isoxazolidine-2-carbonyl)-1-methyl-1H-pyrazol-4-yl]-amide, 6-Cyclopropyl-3-(pyrimidin-5-ylamino)-pyrazine-2-carboxylic acid [5-(2-hydroxy-cyclopentylcarbamoyl)-1-methyl-1H-pyrazol-4-yl]-amide, 5-(Pyrimidin-5-ylamino)-2-(2,2,2-trifluoro-ethoxy)-pyrimidine-4-carboxylic acid (1-methyl-5-methylcarbamoyl-1H-pyrazol-4-yl)-amide, 3-(Pyrimidin-5-ylamino)-6-(2,2,2-trifluoro-ethoxy)-pyrazine-2-carboxylic acid (1-methyl-5-methylcarbamoyl-1H-pyrazol-4-yl)-amide, 2-(1-Hydroxy-1-methyl-ethyl)-5-(pyrimidin-5-ylamino)-pyrimidine-4-carboxylic acid (1-methyl-5-methylcarbamoyl-1H-pyrazol-4-yl)-amide, and 6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide, or a pharmaceutically acceptable salt thereof.

30. The compound of claim 1, selected from the group consisting of:

6-Cyclopropyl-3-(pyrimidin-5-ylamino)-pyridine-2-carboxylic acid (1-methyl-3-methylcarbamoyl-1H-pyrazol-4-yl)-amide, 6-Cyclopropyl-3-(pyrimidin-5-ylamino)-pyrazine-2-carboxylic acid (1-methyl-3-methylcarbamoyl-1H-pyrazol-4-yl)-amide, 6-Cyclopropyl-3-(pyrimidin-5-ylamino)-pyridine-2-carboxylic acid [1-(2-methoxy-ethyl)-5-methylcarbamoyl-1H-pyrazol-4-yl]-amide, 6-Cyclopropyl-N-[3-(2-hydroxy-2-methyl-propylcarbamoyl)-1-methyl-1H-pyrazol-4-yl]-3-(pyrimidin-5-ylamino)-pyridine-2-carboximidic acid,
2-Isopropyl-5-(pyrimidin-5-ylamino)-pyrimidine-4-carboxylic acid (1-methyl-3-methylcarbamoyl-1H-pyrazol-4-yl)-amide,
2-Isobutyl-5-(pyrimidin-5-ylamino)-pyrimidine-4-carboxylic acid (1-methyl-3-methylcarbamoyl-1H-pyrazol-4-yl)-amide,
6-Cyclopropyl-3-(pyrimidin-5-ylamino)-pyridine-2-carboxylic acid [3-(morpholine-4-carbonyl)-thiophen-2-yl]-amide,
6-cyclopropyl-N-(3-(2-hydroxy-2-methylpropylcarbamoyl)-1-methyl-1H-pyrazol-4-yl)-3-(pyrimidin-5-ylamino)pyrazine-2-carboxamide,
6-isobutyl-N-(1-methyl-3-(methylcarbamoyl)-1H-pyrazol-4-yl)-3-(pyrimidin-5-ylamino)pyrazine-2-carboxamide, and
6-Cyclopropyl-3-(pyrimidin-5-ylamino)-pyrazine-2-carboxylic acid (1-methyl-5-methylcarbamoyl-1H-pyrazol-4-yl)-amide
or a pharmaceutically acceptable salt thereof.

31. The compound of claim 1, selected from the group consisting of:
6-Cyclopropyl-3-(pyrimidin-5-ylamino)-pyrazine-2-carboxylic acid [5-(2-hydroxy-2-methyl-propylcarbamoyl)-1-methyl-1H-pyrazol-4-yl]-amide,
6-Isopropyl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-methyl-5-(3-methyl-oxetan-3-ylcarbamoyl)-1H-pyrazol-4-yl]-amide,
6-Cyclopropyl-3-(pyrimidin-5-ylamino)-pyrazine-2-carboxylic acid [5-(2,2-difluoro-ethylcarbamoyl)-1-methyl-1H-pyrazol-4-yl]-amide,
2-tert-Butyl-5-(pyrimidin-5-ylamino)-pyrimidine-4-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [5-(azetidine-1-carbonyl)-1-methyl-1H-pyrazol-4-yl]-amide,
3-(Pyrimidin-5-ylamino)-6-(tetrahydro-furan-3-yl)-pyrazine-2-carboxylic acid (1-methyl-5-methylcarbamoyl-1H-pyrazol-4-yl)-amide,
2-Isopropyl-5-(pyrimidin-5-ylamino)-pyrimidine-4-carboxylic acid (1-methyl-5-methylcarbamoyl-1H-pyrazol-4-yl)-amide,
2-Isopropyl-5-(pyridin-3-ylamino)-pyrimidine-4-carboxylic acid (1-methyl-5-methylcarbamoyl-1H-pyrazol-4-yl)-amide, and
5-(5-Fluoro-pyridin-3-ylamino)-2-isopropyl-pyrimidine-4-carboxylic acid (1-methyl-5-methylcarbamoyl-1H-pyrazol-4-yl)-amide
or a pharmaceutically acceptable salt thereof.

32. The compound of claim 1, selected from the group consisting of:
6-Cyclopropyl-3-(pyrimidin-5-ylamino)-pyrazine-2-carboxylic acid (5-ethylcarbamoyl-1-methyl-1H-pyrazol-4-yl)-amide,
6-Cyclopropyl-3-(pyrimidin-5-ylamino)-pyrazine-2-carboxylic acid [5-(ethyl-methyl-carbamoyl)-1-methyl-1H-pyrazol-4-yl]-amide,
3-(Pyrimidin-5-ylamino)-6-(R)-tetrahydro-furan-3-yl-pyrazine-2-carboxylic acid (1-methyl-5-methylcarbamoyl-1H-pyrazol-4-yl)-amide,
3-(Pyrimidin-5-ylamino)-6-(S)-tetrahydro-furan-3-yl-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid {1-methyl-5-[(S)-(tetrahydro-furan-3-yl)carbamoyl]-1H-pyrazol-4-yl}-amide,
6-Cyclopropyl-3-(pyrimidin-5-ylamino)-pyrazine-2-carboxylic acid {1-methyl-5-[(R)-(tetrahydro-furan-3-yl)carbamoyl]-1H-pyrazol-4-yl}-amide,
6-Morpholin-4-yl-3-(pyrimidin-5-ylamino)-pyrazine-2-carboxylic acid (1-methyl-5-methylcarbamoyl-1H-pyrazol-4-yl)-amide,
6-Cyclopropyl-3-(pyrimidin-5-ylamino)-pyrazine-2-carboxylic acid [1-methyl-5-(1-methyl-azetidin-3-ylcarbamoyl)-1H-pyrazol-4-yl]-amide,
6-Cyclopropyl-3-(pyrimidin-5-ylamino)-pyrazine-2-carboxylic acid [5-(isoxazolidine-2-carbonyl)-1-methyl-1H-pyrazol-4-yl]-amide,
6-Cyclopropyl-3-(pyrimidin-5-ylamino)-pyrazine-2-carboxylic acid [5-(2-hydroxy-cyclopentylcarbamoyl)-1-methyl-1H-pyrazol-4-yl]-amide, and
6-(1-Hydroxy-1-methyl-ethyl)-3-(pyrimidin-5-ylamino)-pyrazine-2-carboxylic acid (1-methyl-5-methylcarbamoyl-1H-pyrazol-4-yl)-amide,
or a pharmaceutically acceptable salt thereof.

33. The compound or a pharmaceutically acceptable salt thereof of claim 1, wherein

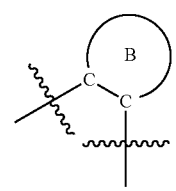

is selected from the group consisting of:

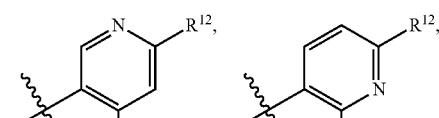

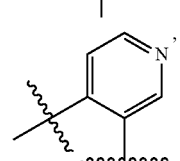

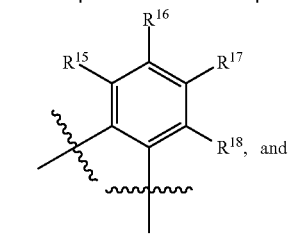

-continued

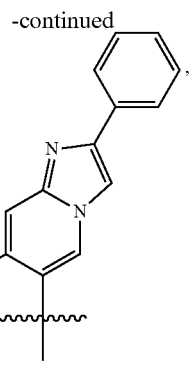

wherein
$R^{12}$ is hydrogen or halogen;
$R^{13}$ is hydrogen, lower alkyl, lower-alkoxy-lower-alkyl, cycloalkyl or tetrahydrofuranyl;
$R^{14}$ is hydrogen or lower alkyl;
$R^{15}$ is hydrogen or halogen;
$R^{16}$ is hydrogen, halogen or diethylaminocarbonyl;
$R^{17}$ is hydrogen, halogen, lower alkyl, lower alkoxy, lower haloalkyl, cyano, 2-hydroxy-ethoxy, 2-methoxy-ethoxy, 2-hydroxy-2-methyl-propoxy, 2-(hydroxycarbonyl)ethyl, 2-ethoxycarbonyl-ethyl, methylcarbamoylmethoxy or acetylamino; and
$R^{18}$ is hydrogen, halogen, lower alkyl or lower alkoxy.

34. The compound or a pharmaceutically acceptable salt thereof of claim 1, wherein $R^1$ is lower alkyl or cycloalkyl.

35. The compound or a pharmaceutically acceptable salt thereof of claim 14, wherein $R^1$ is isopropyl, isobutyl, tert-butyl or cyclopropyl.

36. The compound or a pharmaceutically acceptable salt thereof of claim 1,
wherein
$R^5$ and $R^6$ are independently hydrogen, lower alkyl, lower hydroxyalkyl, lower haloalkyl, lower-alkoxy-lower-alkyl, cycloalkyl or heterocyclyl, wherein said lower alkyl is optionally substituted by heterocyclyl, and wherein said heterocyclyl is optionally substituted by lower alkyl or
$R^5$ and $R^6$, together with the nitrogen atom to which they are attached, form an azetidine, pyrrolidine, piperidine, piperazine or 2-oxa-6-aza-spiro[3.3]heptane ring, wherein each of said azetidine, pyrrolidine, piperazine or 2-oxa-6-aza-spiro[3.3]heptane ring is optionally substituted by 1 or 2 substituents independently selected from the group consisting of hydroxyl, halogen, lower alkyl, lower hydroxyalkyl, lower alkoxy, oxo and amino, and wherein said amino is substituted by 2 lower alkyl.

37. The compound or a pharmaceutically acceptable salt thereof of claim 16,
wherein
$R^5$ and $R^6$ are independently hydrogen, methyl, tetrahydrofuran-2-yl-methyl, ethyl, 2-hydroxy-1-methyl-ethyl, 2-hydroxy-1,1-dimethyl-ethyl, 2-methoxyethyl, 2-methoxy-1-methyl-ethyl, 2-hydroxy-ethyl, 2-isopropoxy-ethyl, 2,2,2,-trifluoro-ethyl, isopropyl, 2,3-dihydroxy-propyl, 3-hydroxy-propyl, 2-hydroxy-2-methyl-propyl, 2-methoxy-2-methyl-propyl, 3-methoxy-2,2-dimethyl-propyl, cyclopropyl, cyclobutyl, cyclopentyl, cyclohexyl, tetrahydrofuran-3-yl, oxetan-3-yl, 3-methyl-oxetan-3-yl or tetrahydro-pyran-4-yl, or
$R^5$ and $R^6$, together with the nitrogen atom to which they are attached, form an optionally substituted heterocyclyl or spiro-heterocyclyl ring selected from the group consisting of azetidin-1-yl, 3-hydroxy-azetidin-1-yl, 3,3-difluoro-azetidin-1-yl, pyrrolidin-1-yl, 2-methyl-pyrrolidin-1-yl, 3-hydroxy-pyrrolidin-1-yl, 3-methoxy-pyrrolidin-1-yl, 2-hydroxymethyl-pyrrolidin-1-yl, 3-dimethylamino-pyrrolidin-1-yl, 2,5-dimethyl-pyrrolidin-1-yl, 2,2-dimethyl-pyrrolidin-1-yl, 3,3-dimethyl-pyrrolidin-1-yl, 3,3-difluoro-pyrrolidin-1-yl, piperidin-1-yl, 2-methyl-piperidin-1-yl, 3-oxo-piperazin-1-yl, 3-methyl-morpholin-4-yl and 2-oxa-6-aza-spiro[3.3]heptan-6-yl.

38. The compound of claim 1, selected from the group consisting of:
6-Cyclopropyl-3-(pyrimidin-5-ylamino)-pyridine-2-carboxylic acid [4-(pyrrolidine-1-carbonyl)-pyridin-3-yl]-amide,
6-Cyclopropyl-3-(pyrimidin-5-ylamino)-pyridine-2-carboxylic acid (4-dimethylcarbamoyl-pyridin-3-yl)-amide,
6-Cyclopropyl-3-(pyrimidin-5-ylamino)-pyridine-2-carboxylic acid (4-methylcarbamoyl-pyridin-3-yl)-amide,
6-Cyclopropyl-3-(pyrimidin-5-ylamino)-pyridine-2-carboxylic acid (2-methylcarbamoyl-phenyl)-amide,
6-Cyclopropyl-N-[4-(3-dimethylamino-pyrrolidine-1-carbonyl)-pyridin-3-yl]-3-(pyrimidin-5-ylamino)-pyridine-2-carboximidic acid,
6-Cyclopropyl-N-[4-(2-methyl-pyrrolidine-1-carbonyl)-pyridin-3-yl]-3-(pyrimidin-5-ylamino)-pyridine-2-carboximidic acid,
6-Cyclopropyl-N-[4-(3,3-difluoro-pyrrolidine-1-carbonyl)-pyridin-3-yl]-3-(pyrimidin-5-ylamino)-pyridine-2-carboximidic acid,
6-Cyclopropyl-N-(4-cyclopropylcarbamoyl-pyridin-3-yl)-3-(pyrimidin-5-ylamino)-pyridine-2-carboximidic acid,
N-(4-Cyclobutylcarbamoyl-pyridin-3-yl)-6-cyclopropyl-3-(pyrimidin-5-ylamino)-pyridine-2-carboximidic acid, and
6-Cyclopropyl-N-[4-(2,5-dimethyl-pyrrolidine-1-carbonyl)-pyridin-3-yl]-3-(pyrimidin-5-ylamino)-pyridine-2-carboximidic acid,
or a pharmaceutically acceptable salt thereof.

39. The compound of claim 1, selected from the group consisting of:
6-Cyclopropyl-N-[4-(5-hydroxy-3,6-dihydro-2H-pyrazine-1-carbonyl)-pyridin-3-yl]-3-(pyrimidin-5-ylamino)-pyridine-2-carboximidic acid,
N-(4-Cyclopentylcarbamoyl-pyridin-3-yl)-6-cyclopropyl-3-(pyrimidin-5-ylamino)-pyridine-2-carboximidic acid,
6-Cyclopropyl-N-[4-(3-methoxy-pyrrolidine-1-carbonyl)-pyridin-3-yl]-3-(pyrimidin-5-ylamino)-pyridine-2-carboximidic acid,
6-Cyclopropyl-N-[4-(3,3-dimethyl-pyrrolidine-1-carbonyl)-pyridin-3-yl]-3-(pyrimidin-5-ylamino)-pyridine-2-carboximidic acid,
6-Cyclopropyl-N-[4-(2-hydroxy-1-methyl-ethylcarbamoyl)-pyridin-3-yl]-3-(pyrimidin-5-ylamino)-pyridine-2-carboximidic acid,
N-[4-(Azetidine-1-carbonyl)-pyridin-3-yl]-6-cyclopropyl-3-(pyrimidin-5-ylamino)-pyridine-2-carboximidic acid,
6-Cyclopropyl-N-[4-(2-hydroxy-ethylcarbamoyl)-pyridin-3-yl]-3-(pyrimidin-5-ylamino)-pyridine-2-carboximidic acid, 6-Cyclopropyl-N-[4-(2,3-dihydroxy-propylcarbamoyl)-pyridin-3-yl]-3-(pyrimidin-5-ylamino)-pyridine-2-carboximidic acid, 6-Cyclopropyl-N-[4-(2-hydroxy-2-methyl-propylcarbamoyl)-pyridin-3-yl]-3-(pyrimidin-5-ylamino)-pyridine-2-carboximidic acid, and 6-Cyclopropyl-N-{4-[(3-hydroxy-propyl)-methyl-carbamoyl]-pyridin-3-yl}-3-(pyrimidin-5-ylamino)-pyridine-2-carboximidic acid or a pharmaceutically acceptable salt thereof.

40. The compound of claim 1, selected from the group consisting of:

6-Cyclopropyl-N-[4-(2-methoxy-1-methyl-ethylcarbamoyl)-pyridin-3-yl]-3-(pyrimidin-5-ylamino)-pyridine-2-carboximidic acid, 6-Cyclopropyl-N-{4-[(2-hydroxy-ethyl)-methyl-carbamoyl]-pyridin-3-yl}-3-(pyrimidin-5-ylamino)-pyridine-2-carboximidic acid, N-(4-Cyclohexylcarbamoyl-pyridin-3-yl)-6-cyclopropyl-3-(pyrimidin-5-ylamino)-pyridine-2-carboximidic acid, 6-Cyclopropyl-N-[4-(3,3-difluoro-azetidine-1-carbonyl)-pyridin-3-yl]-3-(pyrimidin-5-ylamino)-pyridine-2-carboximidic acid, 6-Cyclopropyl-N-[4-(2-hydroxymethyl-pyrrolidine-1-carbonyl)-pyridin-3-yl]-3-(pyrimidin-5-ylamino)-pyridine-2-carboximidic acid, 7-{[6-Cyclopropyl-3-(pyrimidin-5-ylamino)-pyridine-2-carbonyl]-amino}-2-phenyl-imidazo[1,2-a]pyridine-6-carboxylic acid methylamide, 6-Cyclopropyl-N-[4-(3-hydroxy-azetidine-1-carbonyl)-pyridin-3-yl]-3-(pyrimidin-5-ylamino)-pyridine-2-carboximidic acid, 6-Cyclopropyl-N-[4-(2,2-dimethyl-pyrrolidine-1-carbonyl)-pyridin-3-yl]-3-(pyrimidin-5-ylamino)-pyridine-2-carboximidic acid, 6-Cyclopropyl-N-{4-[(2,3-dihydroxy-propyl)-methyl-carbamoyl]-pyridin-3-yl}-3-(pyrimidin-5-ylamino)-pyridine-2-carboximidic acid, and 6-Cyclopropyl-N-[4-(3-hydroxy-pyrrolidine-1-carbonyl)-pyridin-3-yl]-3-(pyrimidin-5-ylamino)-pyridine-2-carboximidic acid or a pharmaceutically acceptable salt thereof.

41. The compound of claim 1, selected from the group consisting of:

6-Cyclopropyl-N-[4-(2-oxa-6-aza-spiro[3.3]heptane-6-carbonyl)-pyridin-3-yl]-3-(pyrimidin-5-ylamino)-pyridine-2-carboximidic acid, 2-Isopropyl-5-(pyrimidin-5-ylamino)-pyrimidine-4-carboxylic acid [4-(2-hydroxy-2-methyl-propylcarbamoyl)-pyridin-3-yl]-amide, 2-tert-Butyl-5-(pyrimidin-5-ylamino)-pyrimidine-4-carboxylic acid [4-(2-hydroxy-2-methyl-propylcarbamoyl)-pyridin-3-yl]-amide, 2-(2-tert-butyl-5-(pyrimidin-5-ylamino)pyrimidine-4-carboxamido)-N4,N4-diethyl-N1-methylterephthalamide, 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide, 6-Cyclopropyl-3-(pyrimidin-5-ylamino)-pyrazine-2-carboxylic acid [2-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-isopropoxy-ethylcarbamoyl)-pyridin-3-yl]-amide, 6-Cyclopropyl-3-(pyrimidin-5-ylamino)-pyrazine-2-carboxylic acid [4-(tetrahydro-furan-3-ylcarbamoyl)-pyridin-3-yl]-amide, 6-Cyclopropyl-3-(pyrimidin-5-ylamino)-pyrazine-2-carboxylic acid {4-[(tetrahydro-furan-2-ylmethyl)-carbamoyl]-pyridin-3-yl}-amide, and 6-Cyclopropyl-3-(pyrimidin-5-ylamino)-pyrazine-2-carboxylic acid [4-(2-hydroxy-2-methyl-propylcarbamoyl)-pyridin-3-yl]-amide or a pharmaceutically acceptable salt thereof.

42. The compound of claim 1, selected from the group consisting of:

6-Cyclopropyl-3-(pyrimidin-5-ylamino)-pyrazine-2-carboxylic acid [4-(oxetan-3-ylcarbamoyl)-pyridin-3-yl]-amide, 6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide, 6-Cyclopropyl-3-(pyrimidin-5-ylamino)-pyrazine-2-carboxylic acid [4-(2-methoxy-2-methyl-propylcarbamoyl)-pyridin-3-yl]-amide, 6-Cyclopropyl-3-(pyrimidin-5-ylamino)-pyrazine-2-carboxylic acid [4-(3-methoxy-2,2-dimethyl-propylcarbamoyl)-pyridin-3-yl]-amide, 6-cyclopropyl-N-(2-((2-methoxyethyl)(methyl)carbamoyl)pyridin-3-yl)-3-(pyrimidin-5-ylamino)pyrazine-2-carboxamide, 5-(6-cyclopropyl-3-(pyrimidin-5-ylamino)pyrazine-2-carboxamido)-N-(2-methoxyethyl)-N-methylpyrimidine-4-carboxamide, 6-cyclopropyl-N-(3-(2-hydroxy-2-methylpropylcarbamoyl)pyridin-4-yl)-3-(pyrimidin-5-ylamino)pyrazine-2-carboxamide, 6-Cyclopropyl-3-(pyrimidin-5-ylamino)-pyrazine-2-carboxylic acid [4-(3-methyl-oxetan-3-ylcarbamoyl)-pyridin-3-yl]-amide, 5-(6-cyclopropyl-3-(pyrimidin-5-ylamino)pyrazine-2-carboxamido)-N-(2-hydroxy-2-methylpropyl)-N-methylpyrimidine-4-carboxamide, and 6-cyclopropyl-N-(2-((2-hydroxy-2-methylpropyl)(methyl)carbamoyl)pyridin-3-yl)-3-(pyrimidin-5-ylamino)pyrazine-2-carboxamide or a pharmaceutically acceptable salt thereof.

43. The compound of claim 1, selected from the group consisting of:

6-Cyclopropyl-3-(pyrimidin-5-ylamino)-pyrazine-2-carboxylic acid (4-methylcarbamoyl-pyridin-3-yl)-amide, 6-Cyclopropyl-3-(pyrimidin-5-ylamino)-pyrazine-2-carboxylic acid [4-(2-hydroxy-1,1-dimethyl-ethylcarbamoyl)-pyridin-3-yl]-amide, 6-Cyclopropyl-3-(pyrimidin-5-ylamino)-pyrazine-2-carboxylic acid (2-methylcarbamoyl-pyridin-3-yl)-amide, 6-Cyclopropyl-3-(pyrimidin-5-ylamino)-pyrazine-2-carboxylic acid (2-dimethylcarbamoyl-pyridin-3-yl)-amide, 6-Cyclopropyl-3-(pyrimidin-5-ylamino)-pyrazine-2-carboxylic acid (6-cyclopropyl-2-methylcarbamoyl-pyridin-3-yl)-amide, 6-Cyclopropyl-3-(pyrimidin-5-ylamino)-pyrazine-2-carboxylic acid [6-cyclopropyl-2-(2-hydroxy-2-methyl-propylcarbamoyl)-pyridin-3-yl]-amide, 6-Cyclopropyl-3-(pyrimidin-5-ylamino)-pyrazine-2-carboxylic acid [2-methylcarbamoyl-6-(tetrahydro-furan-2-yl)-pyridin-3-yl]-amide, 6-Cyclopropyl-3-(pyrimidin-5-ylamino)-pyrazine-2-carboxylic acid [2-(2-hydroxy-2-methyl-propylcarbamoyl)-6-(tetrahydro-furan-2-yl)-pyridin-3-yl]-amide, 6-Cyclopropyl-3-(pyrimidin-5-ylamino)-pyrazine-2-carboxylic acid (6-ethyl-2-methylcarbamoyl-pyridin-3-yl)-amide, and
6-Cyclopropyl-3-(pyrimidin-5-ylamino)-pyrazine-2-carboxylic acid [6-ethyl-2-(2-hydroxy-2-methyl-propylcarbamoyl)-pyridin-3-yl]-amide or a pharmaceutically acceptable salt thereof.

44. The compound of claim 1, selected from the group consisting of:
    6-Cyclopropyl-3-(pyrimidin-5-ylamino)-pyrazine-2-carboxylic acid (6-methyl-2-methylcarbamoyl-pyridin-3-yl)-amide,
    6-Cyclopropyl-3-(pyrimidin-5-ylamino)-pyrazine-2-carboxylic acid [2-(2-hydroxy-2-methyl-propylcarbamoyl)-6-methyl-pyridin-3-yl]-amide,
    6-Cyclopropyl-3-(pyrimidin-5-ylamino)-pyrazine-2-carboxylic acid (3-methoxy-2-methylcarbamoyl-phenyl)-amide,
    6-Cyclopropyl-3-(pyrimidin-5-ylamino)-pyrazine-2-carboxylic acid [2-(azetidine-1-carbonyl)-pyridin-3-yl]-amide,
    6-Cyclopropyl-3-(pyrimidin-5-ylamino)-pyrazine-2-carboxylic acid [2-(piperidine-1-carbonyl)-pyridin-3-yl]-amide,
    6-Cyclopropyl-3-(pyrimidin-5-ylamino)-pyrazine-2-carboxylic acid (3-chloro-2-methylcarbamoyl-phenyl)-amide,
    6-Cyclopropyl-3-(pyrimidin-5-ylamino)-pyrazine-2-carboxylic acid [2-(pyrrolidine-1-carbonyl)-pyridin-3-yl]-amide,
    6-Cyclopropyl-3-(pyrimidin-5-ylamino)-pyrazine-2-carboxylic acid [2-(ethyl-methyl-carbamoyl)-pyridin-3-yl]-amide,
    5-{[6-Cyclopropyl-3-(pyrimidin-5-ylamino)-pyrazine-2-carbonyl]-amino}-pyrimidine-4-carboxylic acid ethyl-methyl-amide, and
    5-{[6-Cyclopropyl-3-(pyrimidin-5-ylamino)-pyrazine-2-carbonyl]-amino}-pyrimidine-4-carboxylic acid dimethylamide, or a pharmaceutically acceptable salt thereof.

45. The compound of claim 1, selected from the group consisting of:
    6-Cyclopropyl-3-(pyrimidin-5-ylamino)-pyrazine-2-carboxylic acid (2-dimethylcarbamoyl-3-methoxy-phenyl)-amide,
    6-Cyclopropyl-3-(pyrimidin-5-ylamino)-pyrazine-2-carboxylic acid [2-(2-hydroxy-2-methyl-propylcarbamoyl)-4-isopropyl-phenyl]-amide,
    6-Cyclopropyl-3-(pyrimidin-5-ylamino)-pyrazine-2-carboxylic acid (4-isopropyl-2-methylcarbamoyl-phenyl)-amide,
    6-Cyclopropyl-3-(pyrimidin-5-ylamino)-pyrazine-2-carboxylic acid (6-methoxymethyl-2-methylcarbamoyl-pyridin-3-yl)-amide,
    6-Cyclopropyl-3-(pyrimidin-5-ylamino)-pyrazine-2-carboxylic acid [2-(2-hydroxy-2-methyl-propylcarbamoyl)-6-methoxymethyl-pyridin-3-yl]-amide,
    6-Cyclopropyl-3-(pyrimidin-5-ylamino)-pyrazine-2-carboxylic acid [4-(azetidine-1-carbonyl)-pyrimidin-5-yl]-amide,
    6-Cyclopropyl-3-(pyrimidin-5-ylamino)-pyrazine-2-carboxylic acid [4-(piperidine-1-carbonyl)-pyrimidin-5-yl]-amide,
    6-Cyclopropyl-3-(pyrimidin-5-ylamino)-pyrazine-2-carboxylic acid [2-(2-hydroxy-2-methyl-propylcarbamoyl)-4-(2-methoxy-ethoxy)-phenyl]-amide,
    6-Cyclopropyl-3-(pyrimidin-5-ylamino)-pyrazine-2-carboxylic acid [4-(2-methoxy-ethoxy)-2-methylcarbamoyl-phenyl]-amide, and
    6-Cyclopropyl-3-(pyrimidin-5-ylamino)-pyrazine-2-carboxylic acid [4-(2-hydroxy-ethoxy)-2-(2-hydroxy-2-methyl-propylcarbamoyl)-phenyl]-amide, or a pharmaceutically acceptable salt thereof.

46. The compound of claim 1, selected from the group consisting of:
    6-Cyclopropyl-3-(pyrimidin-5-ylamino)-pyrazine-2-carboxylic acid [4-(2-hydroxy-ethoxy)-2-methylcarbamoyl-phenyl]-amide,
    5-{[6-Cyclopropyl-3-(pyrimidin-5-ylamino)-pyrazine-2-carbonyl]-amino}-pyrimidine-4-carboxylic acid methylamide,
    6-Cyclopropyl-3-(pyrimidin-5-ylamino)-pyrazine-2-carboxylic acid [4-(pyrrolidine-1-carbonyl)-pyrimidin-5-yl]-amide,
    6-Cyclopropyl-3-(pyrimidin-5-ylamino)-pyrazine-2-carboxylic acid (2-ethylcarbamoyl-pyridin-3-yl)-amide,
    6-Cyclopropyl-3-(pyrimidin-5-ylamino)-pyrazine-2-carboxylic acid (2-isopropylcarbamoyl-pyridin-3-yl)-amide,
    6-Cyclopropyl-3-(pyrimidin-5-ylamino)-pyrazine-2-carboxylic acid (3-methyl-2-methylcarbamoyl-phenyl)-amide,
    6-Cyclopropyl-3-(pyrimidin-5-ylamino)-pyrazine-2-carboxylic acid (4-methoxy-2-methylcarbamoyl-phenyl)-amide,
    6-Cyclopropyl-3-(pyrimidin-5-ylamino)-pyrazine-2-carboxylic acid {2-[methyl-(tetrahydro-pyran-4-yl)-carbamoyl]-pyridin-3-yl}-amide,
    6-Cyclopropyl-3-(pyrimidin-5-ylamino)-pyrazine-2-carboxylic acid {2-[methyl-(2,2,2-trifluoro-ethyl)-carbamoyl]-pyridin-3-yl}-amide, and
    6-Cyclopropyl-3-(pyrimidin-5-ylamino)-pyrazine-2-carboxylic acid [2-(cyclopropyl-methyl-carbamoyl)-pyridin-3-yl]-amide, or a pharmaceutically acceptable salt thereof.

47. The compound of claim 1, selected from the group consisting of:
    6-Cyclopropyl-3-(pyrimidin-5-ylamino)-pyrazine-2-carboxylic acid [2-(2-methyl-pyrrolidine-1-carbonyl)-pyridin-3-yl]-amide,
    6-Cyclopropyl-3-(pyrimidin-5-ylamino)-pyrazine-2-carboxylic acid [2-(2-methyl-piperidine-1-carbonyl)-pyridin-3-yl]-amide,
    6-Cyclopropyl-3-(pyrimidin-5-ylamino)-pyrazine-2-carboxylic acid [2-(3-methyl-morpholine-4-carbonyl)-pyridin-3-yl]-amide,
    6-Cyclopropyl-3-(pyrimidin-5-ylamino)-pyrazine-2-carboxylic acid (6-chloro-4-methylcarbamoyl-pyridin-3-yl)-amide,
    6-Cyclopropyl-3-(pyrimidin-5-ylamino)-pyrazine-2-carboxylic acid [6-chloro-4-(2-hydroxy-2-methyl-propylcarbamoyl)-pyridin-3-yl]-amide,
    6-Cyclopropyl-3-(pyrimidin-5-ylamino)-pyrazine-2-carboxylic acid (4-cyano-2-methylcarbamoyl-phenyl)-amide,
    6-Cyclopropyl-3-(pyrimidin-5-ylamino)-pyrazine-2-carboxylic acid [4-cyano-2-(2-hydroxy-2-methyl-propylcarbamoyl)-phenyl]-amide,
    6-Cyclopropyl-3-(pyrimidin-5-ylamino)-pyrazine-2-carboxylic acid (3,4-dimethyl-2-methylcarbamoyl-phenyl)-amide, 6-Cyclopropyl-3-(pyrimidin-5-ylamino)-pyrazine-2-carboxylic acid (6-cyclopropyl-2-dimethylcarbamoyl-pyridin-3-yl)-amide, and 6-Cyclopropyl-3-(pyrimidin-5-ylamino)-pyrazine-2-carboxylic acid (2-dimethylcarbamoyl-6-methyl-pyridin-3-yl)-amide, or a pharmaceutically acceptable salt thereof.

48. The compound of claim 1, selected from the group consisting of:

6-Cyclopropyl-3-(pyrimidin-5-ylamino)-pyrazine-2-carboxylic acid {2-[(2-hydroxy-ethyl)-methyl-carbamoyl]-pyridin-3-yl}-amide, 6-Cyclopropyl-3-(pyrimidin-5-ylamino)-pyrazine-2-carboxylic acid {2-[ethyl-(2-hydroxy-ethyl)-carbamoyl]-pyridin-3-yl}-amide, 6-Cyclopropyl-3-(pyrimidin-5-ylamino)-pyrazine-2-carboxylic acid [2-(2-hydroxy-ethylcarbamoyl)-pyridin-3-yl]-amide, 6-Cyclopropyl-3-(pyrimidin-5-ylamino)-pyrazine-2-carboxylic acid [2-(azetidine-1-carbonyl)-6-cyclopropyl-pyridin-3-yl]-amide, 6-Cyclopropyl-3-(pyrimidin-5-ylamino)-pyrazine-2-carboxylic acid [2-(2-hydroxy-1,1-dimethyl-ethylcarbamoyl)-pyridin-3-yl]-amide, 6-Cyclopropyl-3-(pyrimidin-5-ylamino)-pyrazine-2-carboxylic acid (4-acetylamino-2-methylcarbamoyl-phenyl)-amide, 6-Cyclopropyl-3-(pyrimidin-5-ylamino)-pyrazine-2-carboxylic acid [2-(3-methyl-oxetan-3-ylcarbamoyl)-pyridin-3-yl]-amide, 6-Cyclopropyl-3-(pyrimidin-5-ylamino)-pyrazine-2-carboxylic acid {2-[methyl-(tetrahydro-furan-2-ylmethyl)-carbamoyl]-pyridin-3-yl}-amide, 6-Cyclopropyl-3-(pyrimidin-5-ylamino)-pyrazine-2-carboxylic acid [2-(oxetan-3-ylcarbamoyl)-pyridin-3-yl]-amide, and 6-Cyclopropyl-3-(pyrimidin-5-ylamino)-pyrazine-2-carboxylic acid [2-(azetidine-1-carbonyl)-6-methyl-pyridin-3-yl]-amide, or a pharmaceutically acceptable salt thereof.

49. The compound of claim 1, selected from the group consisting of:

5-{[6-Cyclopropyl-3-(pyrimidin-5-ylamino)-pyrazine-2-carbonyl]-amino}-2-methyl-pyrimidine-4-carboxylic acid (2-hydroxy-2-methyl-propyl)-amide, 6-Cyclopropyl-3-(pyrimidin-5-ylamino)-pyrazine-2-carboxylic acid (2-dimethylcarbamoyl-4,5-difluoro-phenyl)-amide, 5-{[6-Cyclopropyl-3-(pyrimidin-5-ylamino)-pyrazine-2-carbonyl]-amino}-2-methyl-pyrimidine-4-carboxylic acid methylamide, 6-Cyclopropyl-3-(pyrimidin-5-ylamino)-pyrazine-2-carboxylic acid (4,5-difluoro-2-methylcarbamoyl-phenyl)-amide, 6-Cyclopropyl-3-(pyrimidin-5-ylamino)-pyrazine-2-carboxylic acid (2-fluoro-6-methylcarbamoyl-phenyl)-amide, 6-Cyclopropyl-3-(pyrimidin-5-ylamino)-pyrazine-2-carboxylic acid [2-(azetidine-1-carbonyl)-4,5-difluoro-phenyl]-amide, 6-Cyclopropyl-3-(pyrimidin-5-ylamino)-pyrazine-2-carboxylic acid (5-fluoro-2-methylcarbamoyl-phenyl)-amide, 6-Cyclopropyl-3-(pyrimidin-5-ylamino)-pyrazine-2-carboxylic acid [2-fluoro-6-(2-hydroxy-2-methyl-propylcarbamoyl)-phenyl]-amide, 6-Cyclopropyl-3-(pyrimidin-5-ylamino)-pyrazine-2-carboxylic acid (2-dimethylcarbamoyl-5-fluoro-phenyl)-amide, and 6-Cyclopropyl-3-(pyrimidin-5-ylamino)-pyrazine-2-carboxylic acid [2-(2-hydroxy-2-methyl-propylcarbamoyl)-4-trifluoromethyl-phenyl]-amide, or a pharmaceutically acceptable salt thereof.

50. The compound of claim 1, selected from the group consisting of:

6-Cyclopropyl-3-(pyrimidin-5-ylamino)-pyrazine-2-carboxylic acid (2-methylcarbamoyl-4-trifluoromethyl-phenyl)-amide, 6-Cyclopropyl-3-(pyrimidin-5-ylamino)-pyrazine-2-carboxylic acid (2-dimethylcarbamoyl-4-fluoro-phenyl)-amide, 6-Cyclopropyl-3-(pyrimidin-5-ylamino)-pyrazine-2-carboxylic acid (3,5-difluoro-2-methylcarbamoyl-phenyl)-amide, 6-Cyclopropyl-3-(pyrimidin-5-ylamino)-pyrazine-2-carboxylic acid (2-dimethylcarbamoyl-3,5-difluoro-phenyl)-amide, 6-Cyclopropyl-3-(pyrimidin-5-ylamino)-pyrazine-2-carboxylic acid [5-fluoro-2-(2-hydroxy-2-methyl-propylcarbamoyl)-phenyl]-amide, 6-Cyclopropyl-3-(pyrimidin-5-ylamino)-pyrazine-2-carboxylic acid [2-(azetidine-1-carbonyl)-5-fluoro-phenyl]-amide, 6-Cyclopropyl-3-(pyrimidin-5-ylamino)-pyrazine-2-carboxylic acid (2-dimethylcarbamoyl-6-fluoro-phenyl)-amide, 6-Cyclopropyl-3-(pyrimidin-5-ylamino)-pyrazine-2-carboxylic acid [2-(azetidine-1-carbonyl)-4-fluoro-phenyl]-amide, 6-Cyclopropyl-3-(pyrimidin-5-ylamino)-pyrazine-2-carboxylic acid [4-fluoro-2-(2-hydroxy-2-methyl-propylcarbamoyl)-phenyl]-amide, and 6-Cyclopropyl-3-(pyrimidin-5-ylamino)-pyrazine-2-carboxylic acid (3-fluoro-2-methylcarbamoyl-phenyl)-amide, or a pharmaceutically acceptable salt thereof.

51. The compound of claim 1, selected from the group consisting of:

6-Cyclopropyl-3-(pyrimidin-5-ylamino)-pyrazine-2-carboxylic acid (2-dimethylcarbamoyl-3-fluoro-phenyl)-amide, 6-Cyclopropyl-3-(pyrimidin-5-ylamino)-pyrazine-2-carboxylic acid [2-(azetidine-1-carbonyl)-3-fluoro-phenyl]-amide, 6-Cyclopropyl-3-(pyrimidin-5-ylamino)-pyrazine-2-carboxylic acid [3-fluoro-2-(2-hydroxy-2-methyl-propylcarbamoyl)-phenyl]-amide, 6-Cyclopropyl-3-(pyrimidin-5-ylamino)-pyrazine-2-carboxylic acid (4-fluoro-2-methylcarbamoyl-phenyl)-amide, 6-Cyclopropyl-3-(pyrimidin-5-ylamino)-pyrazine-2-carboxylic acid (2-dimethylcarbamoyl-3,4-difluoro-phenyl)-amide, 6-Cyclopropyl-3-(pyrimidin-5-ylamino)-pyrazine-2-carboxylic acid (3,4-difluoro-2-methylcarbamoyl-phenyl)-amide, 6-Cyclopropyl-3-(pyrimidin-5-ylamino)-pyrazine-2-carboxylic acid [3,4-difluoro-2-(2-hydroxy-2-methyl-propylcarbamoyl)-phenyl]-amide, 6-Cyclopropyl-3-(pyrimidin-5-ylamino)-pyrazine-2-carboxylic acid [2-(azetidine-1-carbonyl)-3,4-difluoro-phenyl]-amide, 6-Cyclopropyl-3-(pyrimidin-5-ylamino)-pyrazine-2-carboxylic acid [6-(azetidine-1-carbonyl)-2,3-difluorophenyl]-amide, and 3-(4-{[6-Cyclopropyl-3-(pyrimidin-5-ylamino)-pyrazine-2-carbonyl]-amino}-3-methylcarbamoyl-phenyl)-propionic acid ethyl ester, or a pharmaceutically acceptable salt thereof.

52. The compound of claim 1, selected from the group consisting of:

6-Cyclopropyl-3-(pyrimidin-5-ylamino)-pyrazine-2-carboxylic acid (2-methylcarbamoyl-4-methylcarbamoylmethoxy-phenyl)-amide, 6-Cyclopropyl-3-(pyrimidin-5-ylamino)-pyrazine-2-carboxylic acid [2-(azetidine-1-carbonyl)-3,5-difluorophenyl]-amide, 6-Cyclopropyl-3-(pyrimidin-5-ylamino)-pyrazine-2-carboxylic acid [3,5-difluoro-2-(2-hydroxy-2-methyl-propylcarbamoyl)-phenyl]-amide, 6-Cyclopropyl-3-(pyrimidin-5-ylamino)-pyrazine-2-carboxylic acid (6-dimethylcarbamoyl-2,3-difluoro-phenyl)-amide, 6-Cyclopropyl-3-(pyrimidin-5-ylamino)-pyrazine-2-carboxylic acid [2,3-difluoro-6-(2-hydroxy-2-methyl-propylcarbamoyl)-phenyl]-amide, 6-Cyclopropyl-3-(pyrimidin-5-ylamino)-pyrazine-2-carboxylic acid (2,3-difluoro-6-methylcarbamoyl-phenyl)-amide, 3-(4-{[6-Cyclopropyl-3-(pyrimidin-5-ylamino)-pyrazine-2-carbonyl]-amino}-3-methylcarbamoyl-phenyl)-propionic acid, 2-Isopropyl-5-(pyrimidin-5-ylamino)-pyrimidine-4-carboxylic acid [2-(2-hydroxy-2-methyl-propylcarbamoyl)-pyridin-3-yl]-amide, 2-tert-Butyl-5-(pyrimidin-5-ylamino)-pyrimidine-4-carboxylic acid [2-(2-hydroxy-2-methyl-propylcarbamoyl)-pyridin-3-yl]-amide, 2-Isobutyl-5-(pyrimidin-5-ylamino)-pyrimidine-4-carboxylic acid [2-(2-hydroxy-2-methyl-propylcarbamoyl)-pyridin-3-yl]-amide, and 6-Cyclopropyl-3-(pyrimidin-5-ylamino)-pyrazine-2-carboxylic acid [4-(2-hydroxy-2-methyl-propoxy)-2-methylcarbamoyl-phenyl]-amide, or a pharmaceutically acceptable salt thereof.

53. The compound of claim 1, selected from the group consisting of:

6-Cyclopropyl-N-(4-cyclopropylcarbamoyl-pyridin-3-yl)-3-(pyrimidin-5-ylamino)-pyridine-2-carboximidic acid, 6-Cyclopropyl-N-[4-(2-hydroxy-2-methyl-propylcarbamoyl)-pyridin-3-yl]-3-(pyrimidin-5-ylamino)-pyridine-2-carboximidic acid, 6-Cyclopropyl-N-[4-(2-methoxy-1-methyl-ethylcarbamoyl)-pyridin-3-yl]-3-(pyrimidin-5-ylamino)-pyridine-2-carboximidic acid, 5-{[6-Cyclopropyl-3-(pyrimidin-5-ylamino)-pyrazine-2-carbonyl]-amino}-pyrimidine-4-carboxylic acid (2-hydroxy-2-methyl-propyl)-amide, 6-Cyclopropyl-3-(pyrimidin-5-ylamino)-pyrazine-2-carboxylic acid [2-(2-hydroxy-2-methyl-propylcarbamoyl)-pyridin-3-yl]-amide, 6-Cyclopropyl-3-(pyrimidin-5-ylamino)-pyrazine-2-carboxylic acid [4-(2-hydroxy-2-methyl-propylcarbamoyl)-pyridin-3-yl]-amide, 6-Cyclopropyl-3-(pyrimidin-5-ylamino)-pyrazine-2-carboxylic acid [4,5-difluoro-2-(2-hydroxy-2-methyl-propylcarbamoyl)-phenyl]-amide, 6-Cyclopropyl-3-(pyrimidin-5-ylamino)-pyrazine-2-carboxylic acid [4-(2-methoxy-2-methyl-propylcarbamoyl)-pyridin-3-yl]-amide, 6-cyclopropyl-N-(2-((2-hydroxy-2-methylpropyl)(methyl)carbamoyl)pyridin-3-yl)-3-(pyrimidin-5-ylamino)pyrazine-2-carboxamide, and 6-Cyclopropyl-3-(pyrimidin-5-ylamino)-pyrazine-2-carboxylic acid (6-cyclopropyl-2-methylcarbamoyl-pyridin-3-yl)-amide, 6-Cyclopropyl-3-(pyrimidin-5-ylamino)-pyrazine-2-carboxylic acid [2-(2-hydroxy-2-methyl-propylcarbamoyl)-6-methyl-pyridin-3-yl]-amide, 2-Isopropyl-5-(pyrimidin-5-ylamino)-pyrimidine-4-carboxylic acid [2-(2-hydroxy-2-methyl-propylcarbamoyl)-pyridin-3-yl]-amide, and 2-tert-Butyl-5-(pyrimidin-5-ylamino)-pyrimidine-4-carboxylic acid [2-(2-hydroxy-2-methyl-propylcarbamoyl)-pyridin-3-yl]-amide, or a pharmaceutically acceptable salt thereof.

54. A pharmaceutical composition comprising a therapeutically effective amount of a compound of formula I

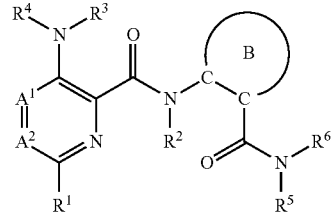

(I)

wherein $A^1$ is selected from the group consisting of CH and N;

$A^2$ is selected from the group consisting of $CR^{19}$ and N, provided that $A^1$ and $A^2$ are not N simultaneously;

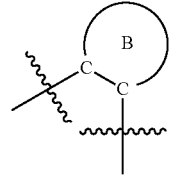

is aryl or heteroaryl, wherein said aryl and said heteroaryl are optionally substituted by 1 to 3 substituents independently selected from the group consisting of lower alkyl, lower alkoxy, lower hydroxyalkyl, lower haloalkyl, lower-alkoxy-lower-alkyl, lower alkyl-C(O)—, —C(O)—N($R^8$)$_2$, —N($R^8$)—C(O)-lower alkyl, cyano, halogen, $R^9$ and amino, and wherein said lower alkyl is optionally substituted by oxo, —C(O)OH, lower alkoxy-C(O)— or $R^7$, and wherein said lower alkoxy is optionally substituted by hydroxyl, lower alkoxy or —C(O)—N($R^8$)$_2$, and wherein said amino is optionally substituted by 1 or 2 substituents independently selected from the group consisting of lower alkyl, lower hydroxyalkyl, lower-alkoxy-lower-alkyl and lower alkyl-C(O)—;

$R^1$ is lower alkyl, lower alkoxy, lower hydroxyalkyl, lower haloalkyl, lower-alkoxy-lower-alkyl, lower alkyl-C(O)—, —O-lower haloalkyl, cyano, halogen, $R^7$ or amino, wherein said lower alkyl is optionally substituted by $R^7$, and wherein said amino is optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is aryl or heteroaryl, wherein said aryl and said heteroaryl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino, and wherein said amino is optionally substituted by 1 or 2 substituents independently selected from the group consisting of lower alkyl and lower-alkoxy-lower-alkyl;

$R^5$ and $R^6$ are independently hydrogen, lower alkyl, lower alkoxy, lower haloalkyl, lower cyanoalkyl, lower hydroxyalkyl, lower-alkoxy-lower-alkyl, cycloalkyl or heterocyclyl, wherein said lower alkyl is optionally substituted by oxo, $R^7$ or —$N(R^8)_2$, and wherein said lower haloalkyl is optionally substituted by hydroxyl, and wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano, —C(O)-lower alkoxy and —$N(R^8)_2$, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino, and wherein said amino is optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl;

$R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl; and $R^{19}$ is hydrogen or tetrahydrofuran-2-yl;

or a pharmaceutically acceptable salt thereof
and a pharmaceutically acceptable carrier.

55. A pharmaceutical composition comprising a therapeutically effective amount of a compound of formula (I)

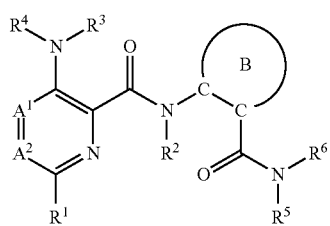

(I)

wherein $A^1$ and $A^2$ are independently selected from the group consisting of CH and N, provided that $A^1$ and $A^2$ are not N simultaneously;

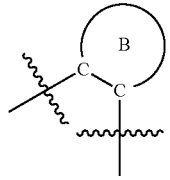

is aryl or heteroaryl, wherein said aryl and said heteroaryl are optionally substituted by 1 or 2 substituents independently selected from the group consisting of lower alkyl optionally substituted by oxo or $R^7$, lower alkoxy, lower hydroxyalkyl, lower haloalkyl, lower-alkoxy-lower-alkyl, lower alkyl-C(O)—, —C(O)—$N(R^8)_2$, —$N(R^8)$—C(O)-lower alkyl, cyano, halogen, $R^9$ and amino optionally substituted by 1 or 2 substituents independently selected from the group consisting of lower alkyl, lower hydroxyalkyl and lower-alkoxy-lower-alkyl;

$R^1$ is lower alkyl optionally substituted by $R^7$, lower alkoxy, lower hydroxyalkyl, lower haloalkyl, lower-alkoxy-lower-alkyl, lower alkyl-C(O)—, cyano, halogen, $R^7$ or amino optionally substituted by 1 or 2 substituents independently selected from the group consisting of lower alkyl and lower-alkoxy-lower-alkyl;

$R^2$ and $R^3$ are independently hydrogen or lower alkyl;

$R^4$ is heteroaryl optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano and amino optionally substituted by 1 or 2 substituents independently selected from the group consisting of lower alkyl and lower-alkoxy-lower-alkyl;

$R^5$ and $R^6$ are independently hydrogen, lower alkyl optionally substituted by oxo or $R^7$, lower haloalkyl, lower cyanoalkyl, lower hydroxyalkyl, lower-alkoxy-lower-alkyl, cycloalkyl or heterocyclyl, wherein said cycloalkyl and said heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, acetyl, cyano and amino optionally substituted by 1 or 2 substituents independently selected from the group consisting of lower alkyl and lower-alkoxy-lower-alkyl, or $R^5$ and $R^6$, together with the nitrogen atom to which they are attached, form a heterocyclyl or spiro-heterocyclyl, wherein said heterocyclyl and said spiro-heterocyclyl are optionally substituted by 1 to 3 substituents independently selected from the group consisting of hydroxyl, halogen, lower alkyl, lower alkoxy, lower hydroxyalkyl, lower haloalkyl, lower-alkoxy-lower-alkyl, lower alkyl-C(O)—, cyano, oxo and amino optionally substituted by 1 or 2 substituents independently selected from the group consisting of lower alkyl, lower hydroxyalkyl and lower-alkoxy-lower-alkyl;

$R^7$ is cycloalkyl or heterocyclyl, wherein said cycloalkyl and said heterocyclyl are optionally substituted by 1 or 2 substituents independently selected from the group consisting of lower alkyl, lower hydroxyalkyl, lower-alkoxy-lower-alkyl, halogen and lower haloalkyl;

$R^8$ is independently selected from the group consisting of hydrogen, lower alkyl, lower hydroxyalkyl and lower-alkoxy-lower-alkyl; and $R^9$ is cycloalkyl, heterocyclyl, aryl or heteroaryl, wherein said cycloalkyl, said heterocyclyl, said aryl and said heteroaryl are optionally substituted by 1 or 2 substituents independently selected from the group consisting of lower alkyl, lower hydroxyalkyl, lower-alkoxy-lower-alkyl, halogen and lower haloalkyl;

or a pharmaceutically acceptable salt thereof and a pharmaceutically acceptable carrier.

\* \* \* \* \*